United States Patent
Nacharaju et al.

(10) Patent No.: US 10,407,528 B2
(45) Date of Patent: Sep. 10, 2019

(54) UV-ABSORBING POLYMERS AND FORMULATIONS THEREOF

(71) Applicant: ISP INVESTMENTS LLC, Wilmington, DE (US)

(72) Inventors: Krishnamurthy Nacharaju, Hilliard, OH (US); Osama M. Musa, Bedminster, NJ (US); Michael A. Tallon, Aberdeen, NJ (US)

(73) Assignee: ISP INVESTMENTS LLC, Wilmington, DE (US)

(*) Notice: Subject to any disclaimer, the term of this patent is extended or adjusted under 35 U.S.C. 154(b) by 0 days.

(21) Appl. No.: 15/925,042

(22) Filed: Mar. 19, 2018

(65) Prior Publication Data

US 2018/0208695 A1    Jul. 26, 2018

Related U.S. Application Data

(60) Division of application No. 15/400,271, filed on Jan. 6, 2017, now Pat. No. 9,920,152, which is a continuation of application No. 14/769,388, filed as application No. PCT/US2014/018021 on Feb. 24, 2014, now Pat. No. 9,540,474.

(60) Provisional application No. 61/789,582, filed on Mar. 15, 2013.

(51) Int. Cl.
| | |
|---|---|
| C08F 265/02 | (2006.01) |
| A61K 47/32 | (2006.01) |
| C08F 255/08 | (2006.01) |
| C08F 255/10 | (2006.01) |
| C08F 257/02 | (2006.01) |
| C08F 261/06 | (2006.01) |
| A61K 9/00 | (2006.01) |
| A61Q 17/04 | (2006.01) |
| A61Q 19/00 | (2006.01) |
| A61K 8/81 | (2006.01) |
| A61Q 5/06 | (2006.01) |

(52) U.S. Cl.
CPC .......... *C08F 265/02* (2013.01); *A61K 8/8164* (2013.01); *A61K 9/0014* (2013.01); *A61K 47/32* (2013.01); *A61Q 5/06* (2013.01); *A61Q 17/04* (2013.01); *A61Q 19/00* (2013.01); *C08F 255/08* (2013.01); *C08F 255/10* (2013.01); *C08F 257/02* (2013.01); *C08F 261/06* (2013.01); *A61K 2800/10* (2013.01)

(58) Field of Classification Search
CPC .... C08F 265/02; C08F 255/08; C08F 255/10; C08F 257/02; C08F 261/06; A61K 8/8164; A61K 9/0014; A61K 47/32; A61K 2800/10; A61Q 5/06; A61Q 17/04; A61Q 19/00
USPC ....................................................... 525/150
See application file for complete search history.

(56) References Cited

U.S. PATENT DOCUMENTS

| | | |
|---|---|---|
| 5,725,994 A | 3/1998 | Kondo |
| 5,827,508 A | 10/1998 | Tanner et al. |
| 6,001,337 A | 12/1999 | Keller et al. |
| 6,255,405 B1 | 7/2001 | Kang et al. |
| 6,328,981 B1 | 12/2001 | Boussouira et al. |
| 6,329,117 B1 | 12/2001 | Padmanaban et al. |
| 6,548,597 B2 | 4/2003 | Hood et al. |
| 2003/0065178 A1 | 4/2003 | Gupta et al. |
| 2005/0019281 A1* | 1/2005 | Fletcher ............... A61K 8/4966 424/59 |
| 2005/0075465 A1 | 4/2005 | Bolle et al. |
| 2008/0305058 A1 | 12/2008 | Richard |
| 2010/0189661 A1 | 7/2010 | Musa et al. |
| 2011/0311786 A1 | 12/2011 | Cunningham et al. |

FOREIGN PATENT DOCUMENTS

| | | |
|---|---|---|
| WO | WO2001026620 A1 | 4/2001 |
| WO | WO2007048486 A1 | 5/2007 |
| WO | WO2011126978 A1 | 10/2011 |

OTHER PUBLICATIONS

International Search Report, PCT/US2014/018021 published on Sep. 25, 2014.

* cited by examiner

*Primary Examiner* — William K Cheung
(74) *Attorney, Agent, or Firm* — William J. Davis; Nathalie Tietcheu

(57) ABSTRACT

UV-absorbing polymers are provided that have at least one anhydride repeating unit that is covalently attached to at least one UV-absorbing moiety selected from the group consisting of functionalized dibenzoylmethanes, benzophenone sulfonamides, triphenyl triazines, and combinations thereof. Also provided are formulations comprising the UV-absorbing polymers.

11 Claims, No Drawings

UV-ABSORBING POLYMERS AND FORMULATIONS THEREOF

CROSS-REFERENCE

This application is a divisional of U.S. application Ser. No. 15/400,271 filed on Jan. 6, 2017, now allowed (granted as U.S. Pat. No. 9,920,152) which is a continuation of application Ser. No. 14/769,388 filed on Aug. 20, 2015 now patented (granted as U.S. Pat. No. 9,540,474), which is a national stage of PCT Application No. PCT/US2014/018021 filed Feb. 24, 2014, which claims priority of the provisional application No. 61/789,582 filed Mar. 15, 2013, the entire contents of these applications being incorporated by reference herein.

BACKGROUND

Field of the Invention

The invention provides UV-absorbing polymers. The invention further provides a wide variety of formulations comprising the UV-absorbing polymers.

Description of Related Art

It is now generally accepted that ultraviolet (UV) radiation can be a serious health hazard. Even a limited exposure to solar radiation can cause short- and long-term skin damage, such as erythema, burns, wrinkles, lentigo ("liver spots"), skin cancers, keratotic lesions, and other cellular changes. There is a greater risk for developing such conditions for those who send prolonged time in the sun, such as for their occupation or during recreation.

UV radiation is just one portion of the electromagnetic spectrum with wavelengths from about 100 nm and about 400 nm, and is further divided into three subregions. UV-A radiation, from about 320 nm to about 400 nm, has the longest wavelength within the UV spectrum, and consequently is the least energetic. While UV-A rays can induce skin tanning, they are liable to induce adverse changes as well, especially in the case of sensitive skin or of skin which is continually exposed to solar radiation. In particular UV-A rays cause a loss of skin elasticity and the appearance of wrinkles, leading to premature skin aging. UV-B rays have shorter wavelengths, from about 290 nm to about 320 nm, and their higher energy can cause erythema and skin burns which may be harmful. The third subgroup, UV-C has the shortest wavelengths, from about 200 nm to about 290 nm, and the highest energy. The Earth's ozone layer effectively filters much UV-C radiation from reaching the ground. Nonetheless, UV-C rays can be generated from tanning bed devices.

In addition to harming the skin, UV radiation can injure the hair, resulting in color changes (especially for color-treated hair), embrittlement, and a loss in aesthetics (e.g., shine, manageability).

UV radiation damage is not limited to the skin and hair, as inanimate objects exposed to solar radiation can experience changes related to color, hardness, and structural integrity, which can contribute to aesthetical and functional deterioration. Thus, there is the very real and demanding need for compositions that protect the skin, hair, and objects from UV rays, especially UV-A and UV-B radiation. Of special interest are compositions that provide broad UV-spectrum protection from both UV-A and UV-B radiation.

Broadly speaking, para-aminobenzoic acid (PABA) exhibits a common trait shared with many UV absorbers/filters. The molecule possesses both electron withdrawing and electron accepting groups, providing resonance delocalization that coincides with the absorbed energy of UV radiation:

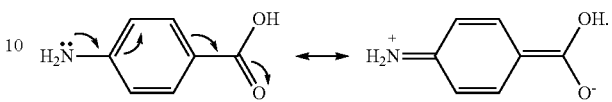

However, PABA is a highly polar molecule, making it water soluble, and giving it low persistence, meaning that it is not highly retained on the skin after swimming or perspiring. In addition, due to extensive intermolecular bonding, PABA exists as a solid, which may further complicate its formulation. Thus, there exists the need to improve the persistence of UV absorbers, especially those that are water-soluble, and to provide formulation flexibility.

UV absorbers may exhibit photolability, in which the absorbed energy causes photodegradation and/or photoreactivity, and thus reduce its efficacy. Such photolability may result from irreversible isomerisms (i.e., keto-enol tautomerism and cis-trans isomerism), photocleavage, and/or photoaddition, and may be formulation sensitive, (e.g., blends of avobenzone and octinoxate). Examples of photolabile UV absorber include, without limitation: avobenzone, PABA derivatives, cinnamates, and dibenzoyl methane derivatives, all of which degrades over time, and reduce UV protection. Hence, there exists a need to stabilize UV absorbers from photodegradative effects.

Additionally, there exists the need to enhance the efficacy of UV absorbers without increasing their content in the formula, since a maximum addition level frequently is regulated. This efficacy need is especially important for avobenzone, a highly effective UV-A absorber. Avobenzone is subject to keto-enol isomerization due to formulation dependencies (e.g., solvent, other UV absorbers):

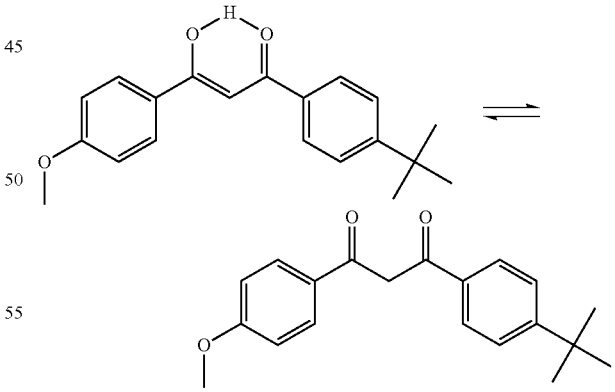

The enol tautomer (left) has its maximum absorbance at 357 nm, which identifies it as a UV-A absorber. Unfortunately, avobenzone is subject to bimolecular reactions (viz, via cleavage mechanisms) that alter the molecule's structure and decrease its effectiveness as an UV absorber. Hence, an effective method is needed for stabilizing labile chromophores like avobenzone in order to enhance their efficacy without increasing their addition level.

Methods for stabilizing chromophores, and in particular UV absorbers, are known in the prior art. For example, Japanese patent 1971/26,860 describes UV stabilizers having amino, hydroxyl, or isocyanate groups attached to cross-linked polymers, being crosslinked glycidyl methacrylate-divinylbenzene copolymers or crosslinked styrene-maleic anhydride-divinylbenzene copolymers.

U.S. Pat. No. 4,868,246 teaches polymer chemistries having UV absorbers bonded to recurring units:

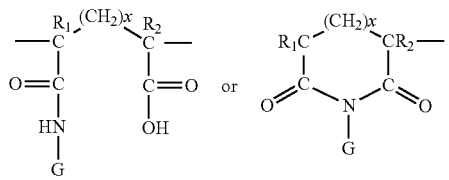

in the polymer backbone, on grafted side chains, as pendant units, or as combinations thereof. The group N-G is the residue of a primary amino or hydrazido substituted stabilizer group selected from (a) 2-hydroxybenzophenones, (b) 2-(2-hydroxyphenyl)-2H-benzotriazoles, (c) aryl salicylates, or (d) oxalic acid amides. The polymeric stabilizers are directed for use in other polymeric systems which are normally subject to actinic light degradation, for example polypropylene. No mention is made of their use in personal care compositions.

A similar approach is taught in U.S. Pat. No. 4,857,596 for thermally stabilizing antioxidants.

Polymer-bound light stabilizers are disclosed in U.S. Pat. No. 4,975,494 that are prepared from a preformed polymer having two different types of reactive groups and a light stabilizer having hydrazido functionality.

U.S. Pat. No. 6,569,531 teaches additive-containing resins having a bi- or multifunctional additive linking a polyester resin with an additive, such as a UV absorber.

U.S. Pat. No. 7,648,697 teaches compounds derived from polyanhydride resins with film-forming, UV-absorbing, and photostabilizing properties.

Japanese patent 1985/84,378 provides 2-hydroxy-4-(2-hydroxyethoxy)benzophenone reacted with maleic anhydride-grafted polyethylene to form a polyethylene-bound 2-hydroxybenzophonone semi-ester.

Two radiation-absorbing polymer chemistries are taught in U.S. Pat. No. 6,255,405. The '405 patent is directed toward radiation-absorbing compositions and coatings, particular for "forming a bottom anti-reflective coating upon producing an integrated circuit." The polymeric compositions comprise two recurring units, the first having the formula:

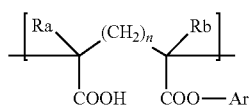

wherein $R_a$ and $R_b$ may be the same or different and represent hydrogen, an alkyl group or other organic groups, Ar represents an organic chromophore, and n represents 0 or an integer of 1 or more; and the second recurring unit having the formula:

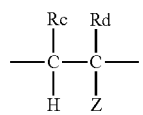

wherein $R_c$ and $R_d$ may be the same or different and each represents hydrogen, an alkyl group, a carboxyl group, or other organic groups, and Z represents hydrogen, a substituted or non-substituted alkoxyl group, a substituted or non-substituted alkyl group, a halogen atom, —CN, an alkylcarbonyloxy group, an imide group, a substituted or non-substituted carbamoyl group, a substituted or non-substituted oxycarbonyl group, or a substituted or non-substituted phenyl group.

U.S. Pat. No. 6,492,455 discloses compositions comprising the reaction product of a $C_6+$ alpha olefin/maleic anhydride copolymer with a polyfunctionalized secondary or tertiary amine. The resulting copolymer is an alternating copolymer of an olefinic monomer and a maleic anhydride with a polyfunctionalized secondary or tertiary amine. Uses includes hair spray and water-proof sunscreen compositions U.S. Pat. No. 7,361,710 describes compositions comprising the reaction of (a) an unsaturated vegetable oil and an enophile or dienophile having acid, ester, or anhydride functionality and (b) a functional vinyl monomer. For example, soybean oil is reacted with maleic anhydride, to yield a maleated vegetable oil:

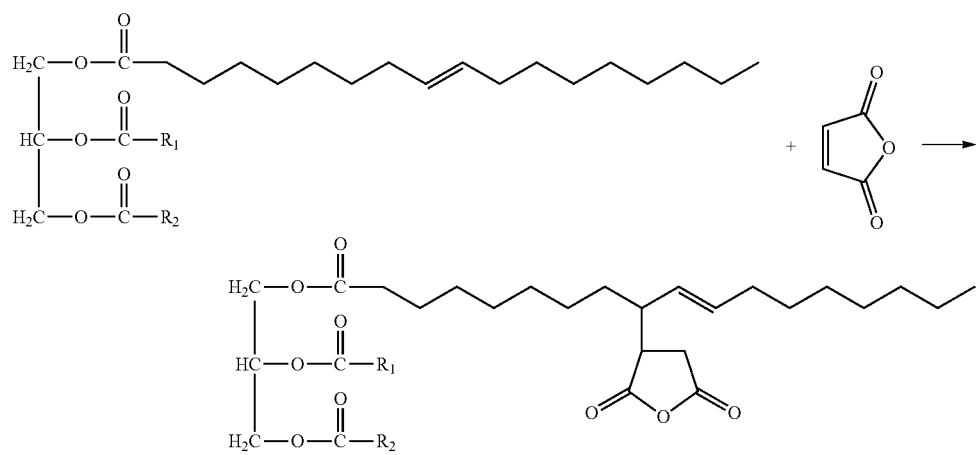

The maleated oil is reacted with hydroxyethyl methacrylate, 2-(tert-butylamino)ethyl methacrylate, or glycidyl methacrylate.

Another maleated oil is described in U.S. Pat. No. 3,428,589, which is directed to polycarboxylic acid anhydride resins of high viscosity, and for such resins of voltage capabilities. This invention discloses the heating (1) of a dry oil, a modified drying oil, or a mixture thereof, and (2) and alpha, beta-ethylenically unsaturated dicarboxylic acid anhydride, which is heated until a polycarboxylic acid anhydride resin product (i.e., an adduct) with a desirably high viscosity is obtained. The polycarboxylic acid anhydride resin is then reacted with an organic aromatic primary or secondary amine, as represented in the following reaction:

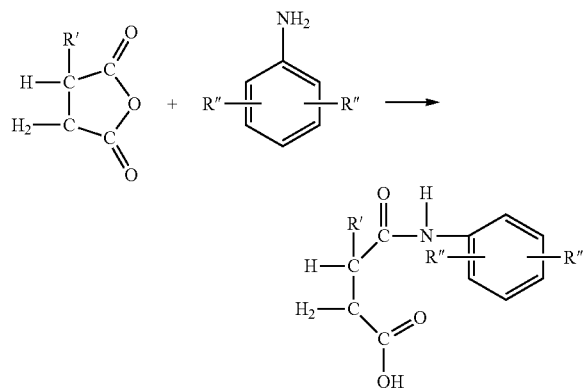

wherein R' represented the drying oil portion of the adduct, and R'' is hydrogen or alkyl. The '589 patent specifies that the organic aromatic primary or secondary amine has from 1 to 20 carbon atoms, preferably from 1 to 10 carbon atoms. The '589 patent discloses compositions for electrocoating baths, compositions with high throwing power, and of excellent intermediate voltage capacity.

Additional disclosure related to anhydride-functionalized vegetable oils is provided by Aydin, S., et al., *Prog Org Coat,* 51, 273-279, 2004; and by Guner, F. S., et al., *Prog Polym Sci,* 31, 633-670, 2006, both of which are incorporated in their entirety by reference. While these works describe methods to graft anhydride functional groups onto vegetable oils, they do not teach subsequent grafting of UV absorbers onto the anhydride moiety.

Functionalized poly(alpha olefin-maleic anhydride) polymers are the subject of application WO 2007/096400A1. This functionalized copolymer has the structure:

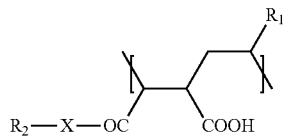

wherein X is —O— or —NH—, and —X—$R_2$— is a functional radical selected from a group that includes natural molecules that are UV absorbers, such as tannins, flavonoids, thymol, caffeic acid esters, and vitamin E.

UV absorbers bound to polymers in personal care compositions are taught in US 2010/0189661, the contents of which are incorporated in their entirety by reference.

Despite advances in UV-absorbers, there remains a commercial demand for UV-absorbing polymers with enhanced performance.

SUMMARY

In one aspect, the invention provides UV-absorbing polymers. In a first embodiment, a UV-absorbing polymer comprises a first repeating unit selected from the group consisting of:

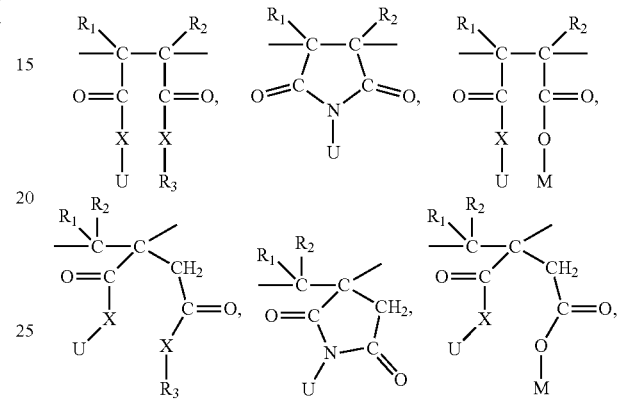

and combinations thereof, wherein each X is independently selected from the group consisting of O, $NR_1$, and combinations thereof; each $R_1$ and $R_2$ is independently selected from the group consisting of hydrogen, halogen, and functionalized and unfunctionalized hydrocarbyl optionally having one or more heteroatoms; each $R_3$ is independently selected from the group consisting of hydrogen, U, and functionalized and unfunctionalized hydrocarbyl optionally having one or more heteroatoms; each M is independently selected from the group consisting of alkali metal ion, alkaline earth metal ion, ammonium ion, and combinations thereof; each U has a structure independently selected from the group consisting of:

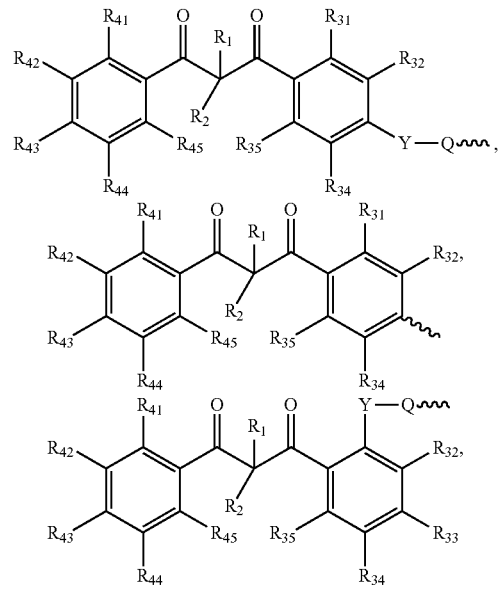

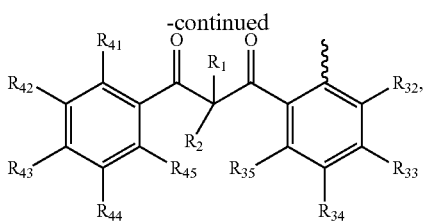

and combinations thereof, wherein each $R_{31}$, $R_{32}$, $R_{33}$, $R_{34}$, $R_{35}$, $R_{41}$, $R_{42}$, $R_{43}$, $R_{44}$ and $R_{45}$ is independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof; each Y is independently selected from the group consisting of O, $NR_1$, S, and combinations thereof; each Q is independently selected from the group consisting of functionalized and unfunctionalized hydrocarbylene optionally having one or more heteroatoms; and each ∿∿ (wavy bond) indicates the point of attachment for each U.

In a second embodiment, a UV-absorbing polymer comprises a first repeating unit selected from the group consisting of:

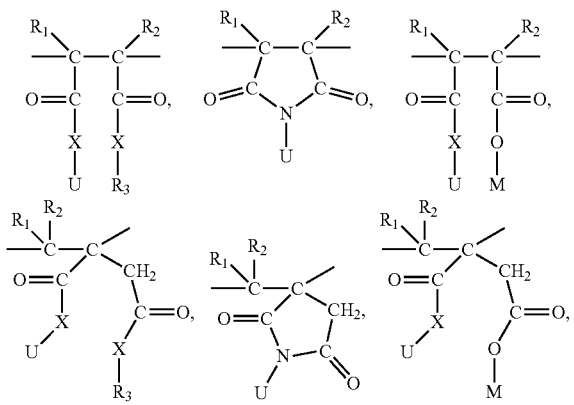

and combinations thereof, wherein each X is independently selected from the group consisting of O, $NR_1$, and combinations thereof; each $R_1$ and $R_2$ is independently selected from the group consisting of hydrogen, halogen, and functionalized and unfunctionalized hydrocarbyl optionally having one or more heteroatoms; each $R_3$ is independently selected from the group consisting of hydrogen, U, and functionalized and unfunctionalized hydrocarbyl optionally having one or more heteroatoms; each M is independently selected from the group consisting of alkali metal ion, alkaline earth metal ion, ammonium ion, and combinations thereof; each U has a structure independently selected from the group consisting of:

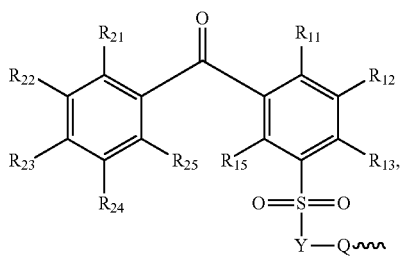

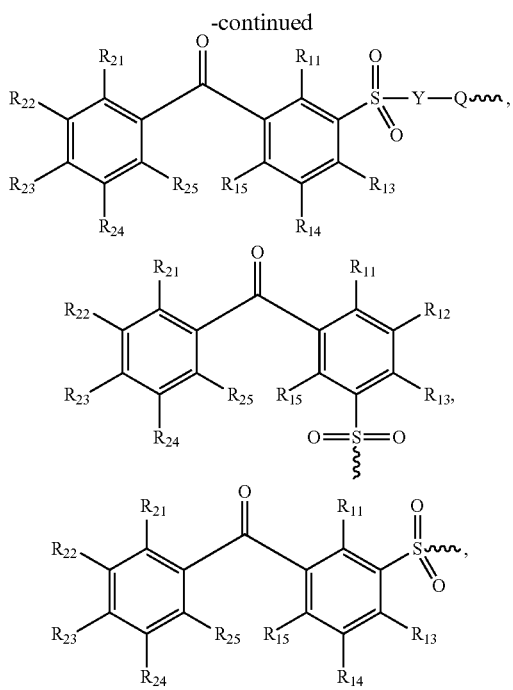

and combinations thereof, wherein each $R_{11}$, $R_{12}$, $R_{13}$, $R_{14}$, $R_{15}$, $R_{21}$, $R_{22}$, $R_{23}$, $R_{24}$ and $R_{25}$ is independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof; each Y is independently selected from the group consisting of O, $NR_1$, S, and combinations thereof; each Q is independently selected from the group consisting of functionalized and unfunctionalized hydrocarbylene optionally having one or more heteroatoms; and each ∿∿ (wavy bond) indicates the point of attachment for each U.

In a third embodiment, a UV-absorbing polymer comprises a first repeating unit selected from the group consisting of:

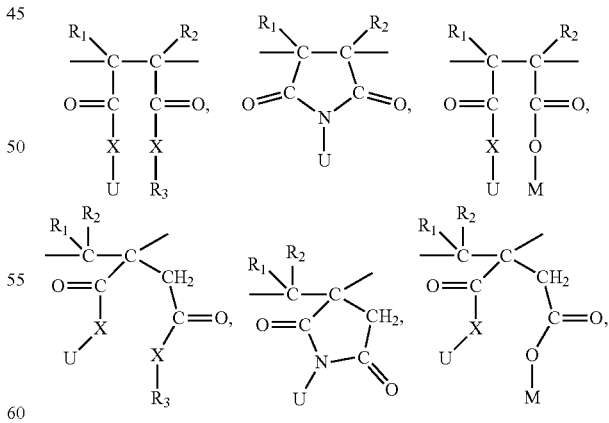

and combinations thereof, wherein each X is independently selected from the group consisting of O, $NR_1$, and combinations thereof; each $R_1$ and $R_2$ is independently selected from the group consisting of hydrogen, halogen, and functionalized and unfunctionalized hydrocarbyl optionally having one or more heteroatoms; each $R_3$ is independently selected from the group consisting of hydrogen, U, and functionalized and unfunctionalized hydrocarbyl optionally having one or more heteroatoms; each M is independently selected from the group consisting of alkali metal ion, alkaline earth metal ion, ammonium ion, and combinations thereof; each U has a structure independently selected from the group consisting of:

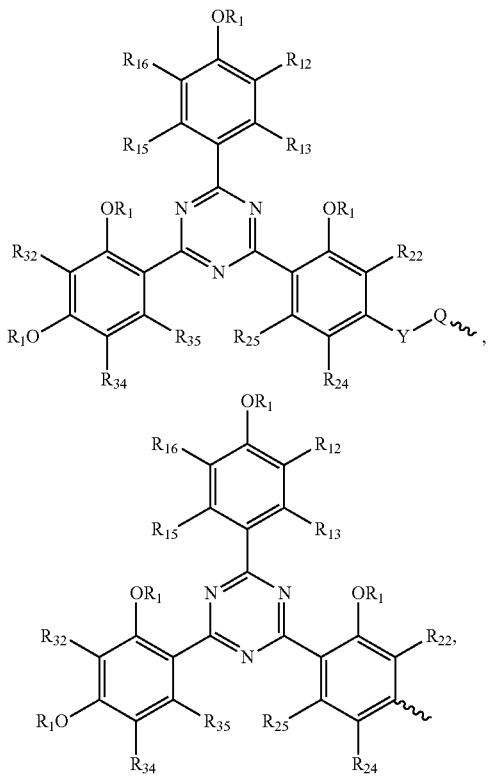

and combinations thereof, wherein each $R_{12}$, $R_{13}$, $R_{15}$, $R_{16}$, $R_{22}$, $R_{24}$, $R_{25}$, $R_{32}$, $R_{34}$ and $R_{35}$ is independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof; each Y is independently selected from the group consisting of O, $NR_1$, S, and combinations thereof; each Q is independently selected from the group consisting of functionalized and unfunctionalized hydrocarbylene optionally having one or more heteroatoms; and each ⌇ (wavy bond) indicates the point of attachment for each U.

In a fourth embodiment, a UV-absorbing polymer comprises a first repeating unit selected from the group consisting of:

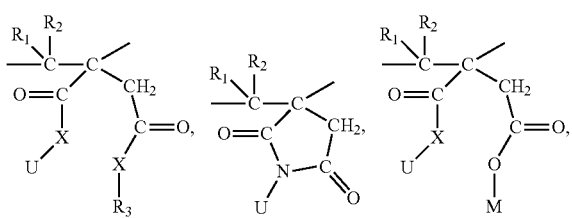

and combinations thereof, wherein each X is independently selected from the group consisting of O, $NR_1$, and combinations thereof; each $R_1$ and $R_2$ is independently selected from the group consisting of hydrogen, halogen, and functionalized and unfunctionalized hydrocarbyl optionally having one or more heteroatoms; $R_3$ is selected from the group consisting of hydrogen, U, and functionalized and unfunctionalized hydrocarbyl optionally having one or more heteroatoms; M is independently selected from the group consisting of alkali metal ion, alkaline earth metal ion, ammonium ion, and combinations thereof; each U has a structure independently selected from the group consisting of:

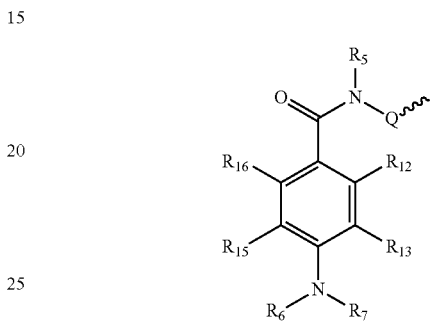

and combinations thereof, wherein each $R_{12}$, $R_{13}$, $R_{15}$, and $R_{16}$ is independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof; each $R_5$ is independently selected from the group consisting of hydrogen and functionalized and unfunctionalized hydrocarbyl optionally having one or more heteroatoms; each $R_6$ and $R_7$ is independently selected from the group consisting of functionalized and unfunctionalized hydrocarbyl optionally having one or more heteroatoms; each Q is independently selected from the group consisting of functionalized and unfunctionalized hydrocarbylene optionally having one or more heteroatoms; and each ⌇ (wavy bond) indicates the point of attachment for each U.

In another aspect, the invention provides a wide variety of formulations comprising the UV-absorbing polymers described herein. Such formulations include, but are not limited to personal care (e.g., hair care, sun care, sunscreen, skin care, color cosmetic, and oral care) formulations, adhesives, coatings, paints, electronics, Household, Industrial and Institutional (HI&I) formulations, inks, membranes, metal working fluids, oilfield formulations, plastics and plasticizers, paper, construction formulations, textiles, industrial products, biocides, pharmaceuticals, food, and agrochemical formulations.

DETAILED DESCRIPTION

The terms "ultraviolet" and "UV" are taken to mean electromagnetic radiation, especially solar electromagnetic radiation, with a wavelength from about 100 nm to about 400 nm, and includes the UV-A, UV-B, and UV-C sub-classifications of such radiation.

The term "UV-A" means ultraviolet electromagnetic radiation with a wavelength from about 320 nm to about 400 nm, and includes UV-A1 (from about 340 nm to about 400 nm) and UV-A2 (from about 320 nm to about 340 nm).

The term "UV-B" means ultraviolet electromagnetic radiation with a wavelength from about 290 nm to about 320 nm.

The term "UV-C" means ultraviolet electromagnetic radiation with a wavelength from about 200 nm to about 290 nm.

The term "UV-absorber" is taken to mean a chemical entity that absorbs, scatters, and/or reflects UV radiation.

The term "each independently selected from the group consisting of" means when a group appears more than once in a structure, that group may be selected independently each time it appears.

The term "functionalized" refers to replacing one or more hydrogens with one or more non-hydrogen groups, for e.g., alkyl, alkoxyl, cycloalkyl, alkenyl, cycloalkenyl, alkynyl, and/or aryl groups. Alkyl, alkenyl and/or alkynyl groups include $C_1$-$C_{60}$, more particularly $C_1$-$C_{36}$, and most particularly $C_1$-$C_{18}$ groups. Cycloalkyl groups include cyclopentane, cyclohexane, cycloheptane, and the like. Alkoxy groups include methoxy, ethoxy, n-propoxy, isopropoxy, and the like. Aryl groups include benzenes, naphthalenes (2 rings), anthracenes (3 rings), and the like.

The term "hydrocarbyl" refers to straight-chain and/or branched-chain groups comprising carbon and hydrogen atoms with optional heteroatom(s). Particularly, the hydrocarbyl group includes $C_1$-$C_{60}$, more particularly $C_1$-$C_{36}$, and most particularly $C_1$-$C_{18}$ alkyl and alkenyl groups optionally having one or more hetero atoms. The hydrocarbyl group may be mono-, di- or polyvalent. The divalent hydrocarbyl group is termed as "hydrocarbylene".

The term "heteroatom" refers to oxygen, nitrogen, sulfur, silicon, and/or phosphorous. The heteroatom may be present as a part of one or more functional groups on the hydrocarbyl chain and/or as a part of the hydrocarbyl chain itself.

The term "halogen" refers to chloro, bromo, iodo and/or fluoro.

The term "residue of" refers to a fragment of a reactant that remains after a reaction with another reactant(s). The residue may be mono-, di- or polyvalent.

The term "lower molecular weight alcohol" refers to any alcohol having from one to 4 carbon atoms, and includes: methanol, ethanol, 1-propanol, 2-propanol, allyl alcohol, propargyl alcohol, 2-aminoethanol, ethylene glycol, methylpropargyl alcohol, 1-butyn-4-ol, 2-butyn-1-ol, 2-buten-1-ol, 2-butanol, 2-methyl-2-propanol, and t-butanol. In various aspects of the invention the lower molecular weight alcohol may be methanol, ethanol, 1-propanol, 2-propanol, and t-butanol.

The term "monomer" refers to a small molecule that chemically bonds during polymerization to one or more monomers of the same or different kind to form a polymer.

The term "polymer" refers to a large molecule comprising one or more types of monomer residues (repeating units) connected by covalent chemical bonds. By this definition polymer encompasses molecules wherein the number of monomer units ranges from very few, which more commonly may be called oligomers, to very many. Non-limiting examples of polymers include homopolymers, non-homopolymers, copolymers, terpolymers, tetramers, and the like, wherein the polymer may be a random, block, or alternating polymer.

The term "homopolymer" refers to a polymer that consists essentially of a single monomer type.

The term "non-homopolymer" refers to a polymer that comprises more than one monomer types.

The term "copolymer" refers to a non-homopolymer that comprises two different monomer types.

The term "terpolymer" refers to a non-homopolymer that comprises three different monomer types.

The term "branched" refers to any non-linear molecular structure. To avoid any arbitrary delineation, the term "branched" describes both branched and hyperbranched structures.

The term "polymer-bound UV absorber" refers to a polymer molecule having at least one UV absorber covalently-bonded to the polymer backbone and/or side chain.

The term "free radical addition polymerization initiator" refers to a compound used in a catalytic amount to initiate a free radical addition polymerization. The choice of initiator depends mainly upon its solubility and its decomposition temperature.

The term "1-(4-hydroxyphenyl)-3-(4-methylphenyl)-1,3-propanedione," also known as "JT-benzone" refers to a compound having the structure:

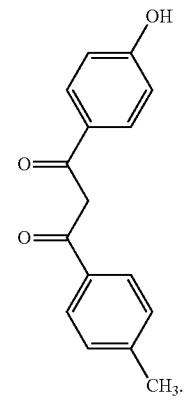 [SMILES: Cc1ccc(C(=O)CC(=O)c2ccc(O)cc2)cc1]

The term "1-(4-hydroxyethylphenyl)-3-(4-methylphenyl)-1,3-propanedione," also known as "HE-JT benzone," refers to a compound having the structure:

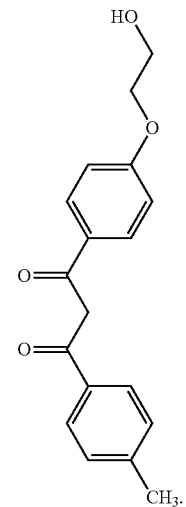 [SMILES: Cc1ccc(C(=O)CC(=O)c2ccc(OCCO)cc2)cc1]

The term "577-sulfanamide-ethanolamine" refers to a compound having the structure:

The term "577-sulfanamide-propylenediamine" refers to a compound having the structure:

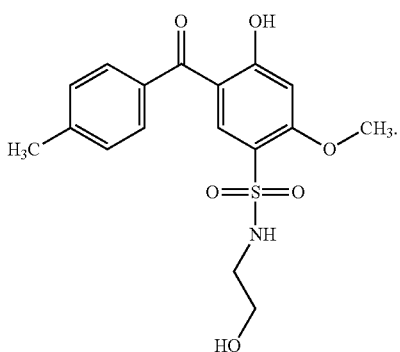 [SMILES: COc1cc(O)c(C(=O)c2ccc(C)cc2)cc1S(=O)(=O)NCCO]

The term "577-sulfanamide-hexylenediamine" refers to a compound having the structure:

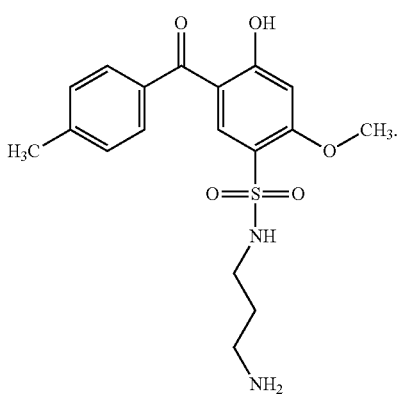 [SMILES: COc1cc(O)c(C(=O)c2ccc(C)cc2)cc1S(=O)(=O)NCCCN]

The term "p-dimethylaminobenzamido ethanolamine," which is abbreviated as DMABEA, refers to a compound having the structure:

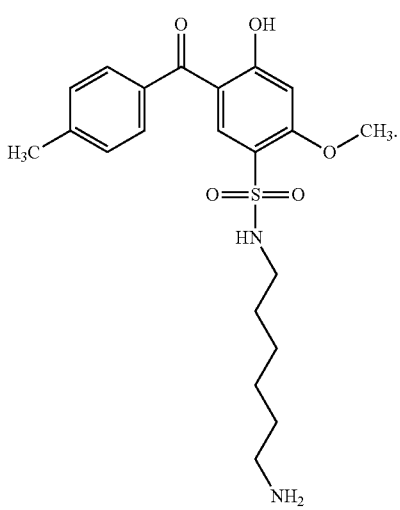 [SMILES: COc1cc(O)c(C(=O)c2ccc(C)cc2)cc1S(=O)(=O)NCCCCCCN]

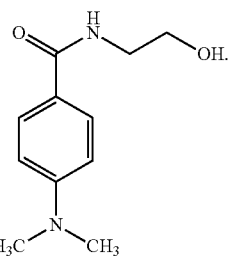

The term "p-dimethylaminobenzyl propylenediamine," which is abbreviated as DMABPD, refers to a compound having the structure:

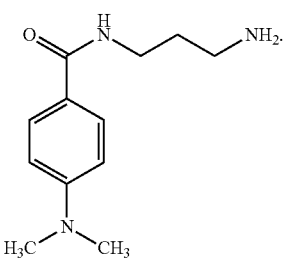 [SMILES: CN(C)c1ccc(C(=O)NCCCN)cc1]

The term "p-dimethylaminobenzamido hexylenediamine" which is abbreviated as DMABHD, refers to a compound having the structure:

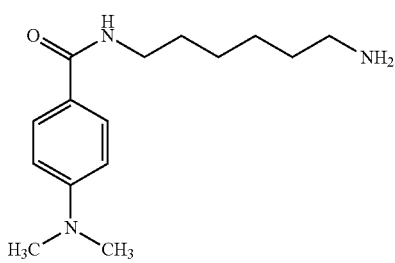 [SMILES: CN(C)c1ccc(C(=O)NCCCCCCN)cc1]

The terms "personal care formulation" and "cosmetics" refer to compositions intended for use on or in the human body, such as skin, sun, oil, hair, cosmetic, and preservative compositions, including those to alter the color and appearance of the skin and hair. Potential personal care compositions include, but are not limited to, compositions for increased flexibility in styling, durable styling, increased humidity resistance for hair, skin, and color cosmetics, sun care water-proof/resistance, wear-resistance, and thermal protecting/enhancing compositions.

The term "sun-care formulation" means personal care and/or pharmaceutical compositions and formulations comprising an effective amount of UV-absorber. Sun-care formulations include beach and non-beach products that are applied to the face, décolleté, lips, and skin to treat and/or protect against erythema, burns, wrinkles, lentigo ("liver spots"), skin cancers, keratotic lesions, and cellular changes of the skin; and to hair to treat and/or protect against color changes, lack of luster, tangles, split ends, unmanageability, and embrittlement.

The term "performance chemicals formulation" refers to any non-personal care formulation. Performance chemicals formulations serve a broad spectrum of arts, and include non-limiting compositions such as: adhesives, agricultural, biocides, coatings, electronics, household-industrial-institutional (HI&I), inks, membranes, metal fluids, oilfield, paper, paints, plastics, printing, construction, and wood-care formulations.

The term "oilfield formulation" refers to a composition that may be used in the exploration, extraction, recovery, or completion of any hydrocarbon-based fuel. Non-limiting examples of oilfield formulations include anti-agglomerants, emulsifiers, de-emulsifiers, gas hydrate inhibitors, kinetic hydrate inhibitors, shale swelling inhibitors, drilling fluids, drilling muds, friction reducers, rheology modifier, fracturing fluids, and/or scale inhibitors.

The term "coating formulation" refers to any composition suitable for application on a substrate in order to provide one or more desired functions, including, but not limited to protecting, smoothing, strengthening, decorating, color enhancing/altering, substrate preparing and/or texturizing. The substrate for a coating formulation may include, without limitation, paper, paper board, wood, inorganic substrate, woven and non-woven textiles, metal, leather, powder, plastic, polymer, glass, cement, ceramic, traffic, tile, rubber, sealant, cable, concrete, plasterboard, adhesives, fillers, primers, inks, fertilizers, pharmaceuticals, structural materials, molding, printing, inks, and the like. Examples of coating formulations include, without limitation, the following: paints, primers, stains, sealers, varnishes/polyurethanes, adhesives, waterproofers, wood hardeners. Coating formulations may be applied by brush, dauber, roll, strip/sheet, and/or trowel, or may be atomized and applied as a spray, mist, or droplet.

A "paint formulation" is a non-limiting, specific type of a "coating formulation". Paints may be water based or non-water based (i.e., solvent based). Paint formulations may be designed for any number of substrates, including wood, siding, dry wall, plaster, plastics, masonry, brick, tile, particle board, glass, stucco, concrete, and the like. Non-limiting examples of paints include exterior paints, interior paints, architectural paints, and automotive paints.

All percentages, ratio, and proportions used herein are based on a weight basis unless other specified.

In a first embodiment, the invention provides a UV-absorbing polymer comprising a first repeating unit selected from the group consisting of:

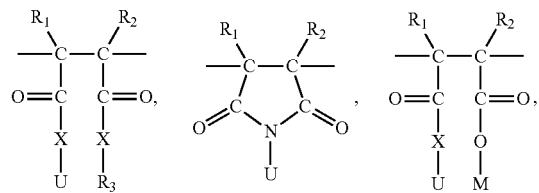

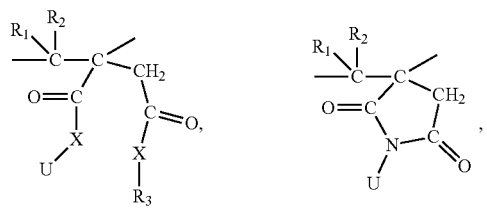

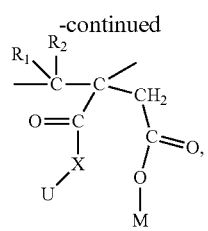

and combinations thereof, wherein each X may be independently selected from the group consisting of O, $NR_1$, and combinations thereof; each $R_1$ and $R_2$ may be independently selected from the group consisting of hydrogen, halogen, and functionalized and unfunctionalized hydrocarbyl optionally having one or more heteroatoms; each $R_3$ may be independently selected from the group consisting of hydrogen, U, and functionalized and unfunctionalized hydrocarbyl optionally having one or more heteroatoms; each M may be independently selected from the group consisting of alkali metal ion, alkaline earth metal ion, ammonium ion, and combinations thereof; each U has a structure independently selected from the group consisting of:

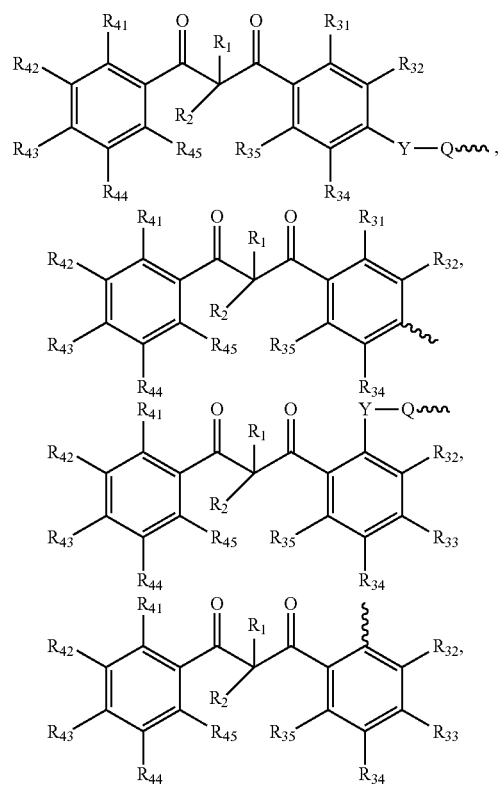

and combinations thereof, wherein each $R_{31}$, $R_{32}$, $R_{33}$, $R_{34}$, $R_{35}$, $R_{41}$, $R_{42}$, $R_{43}$, $R_{44}$ and $R_{45}$ may be independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof; each Y may be independently selected from the group consisting of O, $NR_1$, S, and combinations thereof; each Q may be independently selected from the group consisting of functionalized and unfunctionalized hydrocarbylene optionally having one or more heteroatoms; and each ⌇ (wavy bond) indicates the point of attachment for each U.

Particularly, a first repeating unit may be selected from the group consisting of:

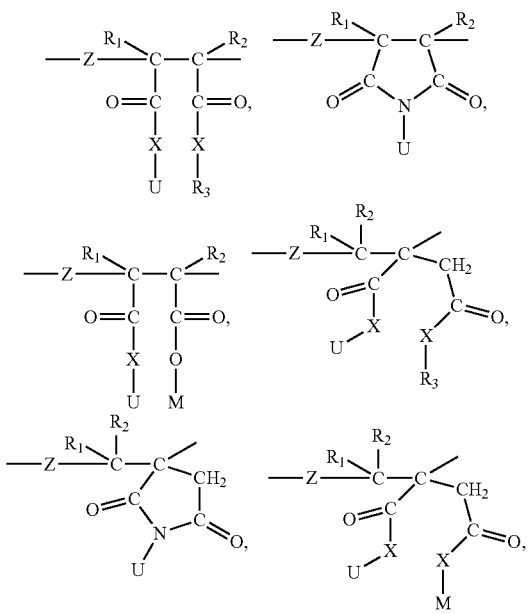

and combinations thereof, wherein each Z may be a residue of a monomer independently selected from the group consisting of functionalized and unfunctionalized: alpha-olefins, maleimides, maleamic acids, maleic anhydride, 4-vinyl-1,2,3-triazoles, 5-vinyl-1,2,3-triazoles, (meth) acrylamides, (meth)acrylates, vinyls, allyls, α-β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, allyl ethers, and combinations thereof, and wherein X, Y, Q, $R_1$, $R_2$, $R_3$, M, U, $R_{31}$, $R_{32}$, $R_{33}$, $R_{34}$, $R_{35}$, $R_{41}$, $R_{42}$, $R_{43}$, $R_{44}$, and $R_{45}$ retain the aforementioned definitions.

Non-limiting examples of vinyl ethers include one or more alkyl vinyl ethers such as methyl vinyl ether, ethyl vinyl ether, isobutyl vinyl ether, octyl vinyl ether, ethyl hexyl vinyl ether, decyl vinyl ether, dodecyl vinyl ether, tetradecyl vinyl ether, hexadecyl vinyl ether, octadecyl vinyl ether, and combinations thereof.

Non-limiting examples of alpha-olefins include isobutylene, styrene, octadecene, and combinations thereof.

In a particular embodiment, Q may be a $C_1$-$C_{60}$ alkylene. More particularly, Q may be a residue of a compound selected from the group consisting of diols, diamines, thio alcohols, amino alcohols, polyols, polyether polyols, polyacetal polyethers, polyalkylene polyamines, polyetheramines, polyalkylene imines, polysaccharides, and combinations thereof. Even more particularly, Q may be a residue of a diol, an amino alcohol, or a diamine.

Non-limiting examples of diols include ethylene glycol, propylene glycol, diethylene glycol, triethylene glycol, tetraethylene glycol, dipropylene glycol, 2-butyl-2-ethyl-1,3-propanediol, 2,2-dimethyl-1,3-propanediol, 1,1-bis(hydroxymethyl)cyclopropane, 1,2-butanediol, 2,3-butanediol, 1,4-butanediol, 3-methyl-1,3-butanediol, 1,2-cyclopentanediol, 1,3-cyclopentanediol, 1,4-pentanediol, 1,5-pentanediol, 2,4-pentanediol, 3-methyl-1,5-pentanediol, 1,2-cyclohexanediol, 1,3-cyclohexanediol, 1,4-cyclohexanediol, 1,2-hexanediol, 1,5-hexanediol, 1,6-hexanediol, 2,5-hexanediol, 1,8-octanediol, and 3,6-dithiaoctane-1,8-diol.

Non-limiting examples of amino alcohols include ethanol amine, propanol amine, 2-(methylamino)ethanol, 1-amino-2-propanol, 2-(ethylamino)ethanol, 2-amino-2-methyl-1-propanol, 4-amino-1-butanol, 4-amino-2-butanol, 2-(2-aminoethoxy)ethanol, 2-aminocyclopentanol, 2-(isopropylamino)ethanol, 2-amino-3-methyl-1-butanol, 5-amino-1-pentanol, 2-amino-1-pentanol, 1-amino-1-cyclopentanemethanol, 2-aminocyclohexanol, 4-aminocyclohexanol, 6-amino-1-hexanol, 2-amino-1-hexanol, 2-(aminomethyl)cyclohexanol, 5-amino-2,2-dimethylpentanol, 2-amino-1-phenylethanol, 4-chlorophenylalaninol, 2-benzylaminoethanol, 6-amino-1-hexanol, 8-amino-1-octanol, and 3-amino-1-adamantanol.

Non-limiting examples of diamines include ethylene diamine, diphenylethylenediamine, 1,3-diaminopropane, diaminocyclopropane, 1,4-diaminobutane, 1,5-diaminopentane, diaminocyclopentane, hexamethylenediamine, and diaminocyclohexane.

Particularly, a U group has a structure independently selected from the group consisting of:

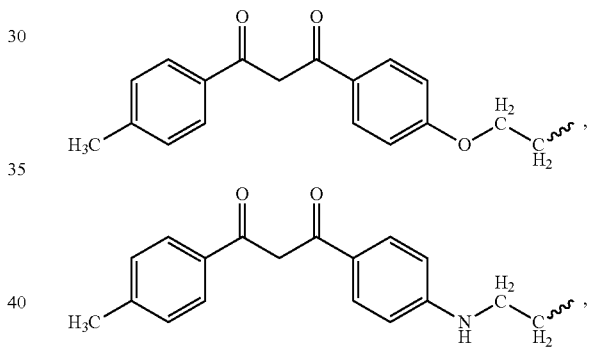

and combinations thereof, wherein each ⁓ (wavy bond) indicates the point of attachment for each U.

In a second embodiment, the invention provides a UV-absorbing polymer comprising a first repeating unit selected from the group consisting of:

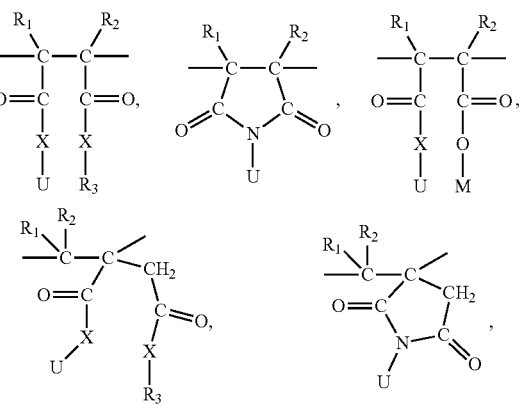

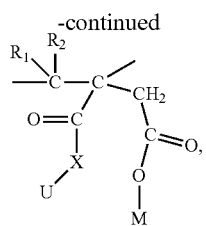

and combinations thereof, wherein each X may be independently selected from the group consisting of O, $NR_1$, and combinations thereof; each $R_1$ and $R_2$ may be independently selected from the group consisting of hydrogen, halogen, and functionalized and unfunctionalized hydrocarbyl optionally having one or more heteroatoms; each $R_3$ is independently selected from the group consisting of hydrogen, U, and functionalized and unfunctionalized hydrocarbyl optionally having one or more heteroatoms; each M may be independently selected from the group consisting of alkali metal ion, alkaline earth metal ion, ammonium ion, and combinations thereof; each U has a structure independently selected from the group consisting of:

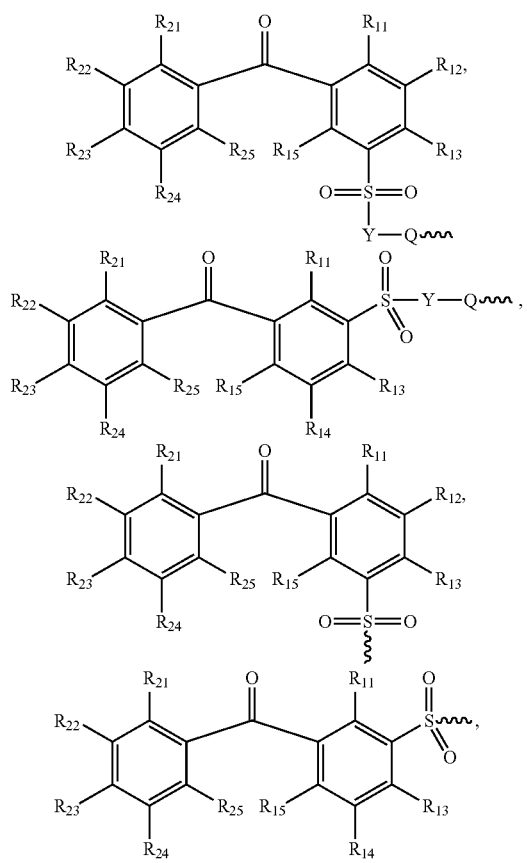

and combinations thereof, wherein each $R_{11}$, $R_{12}$, $R_{13}$, $R_{14}$, $R_{15}$, $R_{21}$, $R_{22}$, $R_{23}$, $R_{24}$ and $R_{25}$ may be independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof; each Y may be independently selected from the group consisting of O, $NR_1$, S, and combinations thereof; each Q may be independently selected from the group consisting of functionalized and unfunctionalized hydrocarbylene optionally having one or more heteroatoms; and each ⌇ (wavy bond) indicates the point of attachment for U.

Particularly, the first repeating unit may be selected from the group consisting of:

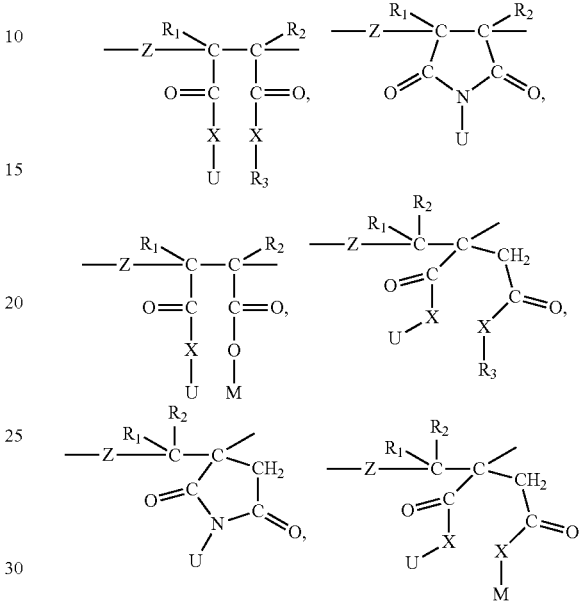

and combinations thereof, wherein each Z may be a residue of a monomer independently selected from the group consisting of functionalized and unfunctionalized: alpha-olefins, maleimides, maleamic acids, maleic anhydride, 4-vinyl-1,2,3-triazoles, 5-vinyl-1,2,3-triazoles, (meth)acrylamides, (meth)acrylates, vinyls, allyls, α-β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, allyl ethers, and combinations thereof, and wherein X, Y, Q, $R_1$, $R_2$, $R_3$, M, U, $R_{11}$, $R_{12}$, $R_{13}$, $R_{14}$, $R_{15}$, $R_{21}$, $R_{22}$, $R_{23}$, $R_{24}$ and $R_{25}$ retain the aforementioned definitions.

Non-limiting examples of vinyl ethers include one or more alkyl vinyl ethers such as methyl vinyl ether, ethyl vinyl ether, isobutyl vinyl ether, octyl vinyl ether, ethyl hexyl vinyl ether, decyl vinyl ether, dodecyl vinyl ether, tetradecyl vinyl ether, hexadecyl vinyl ether, octadecyl vinyl ether, and combinations thereof.

Non-limiting examples of alpha-olefins include isobutylene, styrene, octadecene, and combinations thereof.

In a particular embodiment, Q may be a $C_1$-$C_{60}$ alkylene. More particularly, Q may be a residue of a compound selected from the group consisting of diols, diamines, thio alcohols, amino alcohols, polyols, polyether polyols, polyacetal polyethers, polyalkylene polyamines, polyetheramines, polyalkylene imines, polysaccharides, and combinations thereof. Even more particularly, Q may be a residue of a diol, an amino alcohol, or a diamine.

Non-limiting examples of diols include ethylene glycol, propylene glycol, diethylene glycol, triethylene glycol, tetraethylene glycol, dipropylene glycol, 2-butyl-2-ethyl-1,3-propanediol, 2,2-dimethyl-1,3-propanediol, 1,1-bis(hydroxymethyl)cyclopropane, 1,2-butanediol, 2,3-butanediol, 1,4-butanediol, 3-methyl-1,3-butanediol, 1,2-cyclopentanediol, 1,3-cyclopentanediol, 1,4-pentanediol, 1,5-pentanediol, 1,5-pentanediol, 2,4-pentanediol, 3-methyl-1,5-pentanediol, 1,2-cyclohexanediol, 1,3-cyclohexanediol, 1,4-cyclohexanediol, 1,2-hexanediol, 1,5-hexanediol, 1,6-hexanediol, 2,5-hexanediol, 1,8-octanediol, and 3,6-dithiaoctane-1,8-diol.

Non-limiting examples of amino alcohols include ethanol amine, propanol amine, 2-(methylamino)ethanol, 1-amino-2-propanol, 2-(ethylamino)ethanol, 2-amino-2-methyl-1-propanol, 4-amino-1-butanol, 4-amino-2-butanol, 2-(2-aminoethoxy)ethanol, 2-aminocyclopentanol, 2-(isopropylamino)ethanol, 2-amino-3-methyl-1-butanol, 5-amino-1-pentanol, 2-amino-1-pentanol, 1-amino-1-cyclopentanemethanol, 2-aminocyclohexanol, 4-aminocyclohexanol, 6-amino-1-hexanol, 2-amino-1-hexanol, 2-(aminomethyl)cyclohexanol, 5-amino-2,2-dimethylpentanol, 2-amino-1-phenylethanol, 4-chlorophenylalaninol, 2-benzylaminoethanol, 6-amino-1-hexanol, 8-amino-1-octanol, and 3-amino-1-adamantanol.

Non-limiting examples of diamines include ethylene diamine, diphenylethylenediamine, 1,3-diaminopropane, diaminocyclopropane, 1,4-diaminobutane, 1,5-diaminopentane, diaminocyclopentane, hexamethylenediamine, and diaminocyclohexane.

Particularly, a U group has a structure independently selected from the group consisting of:

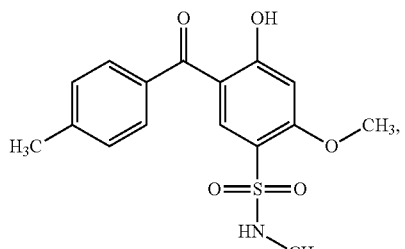

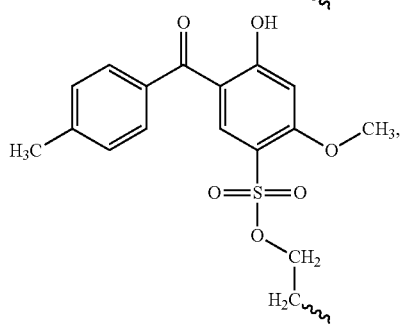

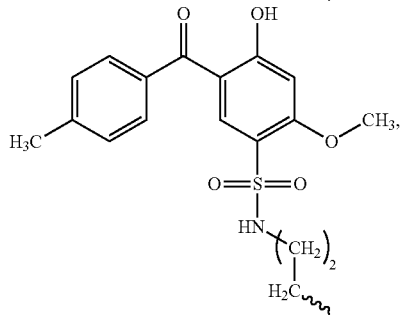

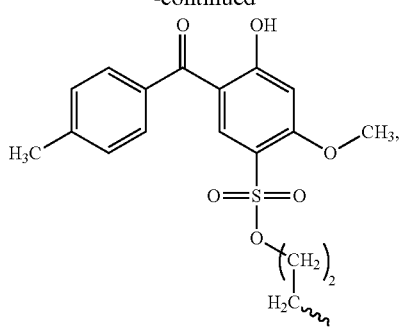

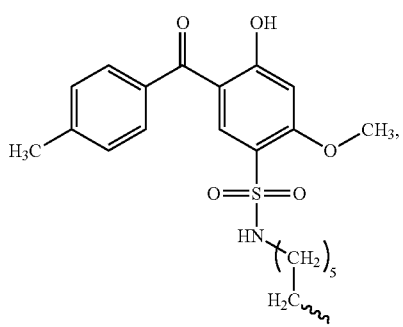

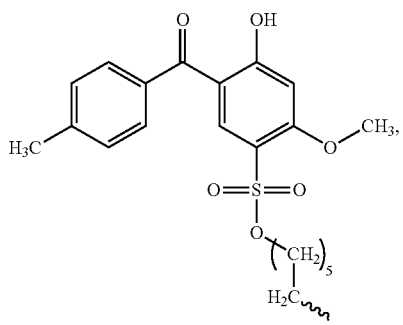

and combinations thereof, wherein each ⌇ (wavy bond) indicates the point of attachment for each U.

In a third embodiment, the invention provides a UV-absorbing polymer comprising a first repeating unit selected from the group consisting of:

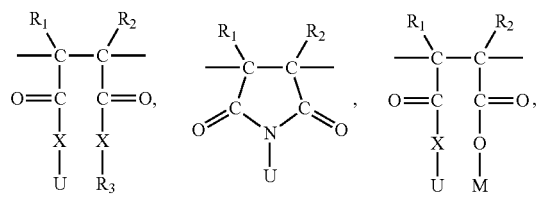

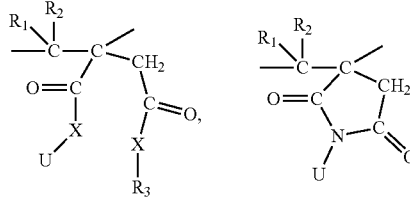

-continued

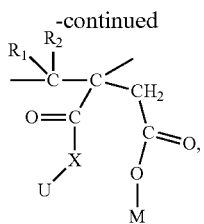

and combinations thereof, wherein each X may be independently selected from the group consisting of O, $NR_1$, and combinations thereof; each $R_1$ and $R_2$ may be independently selected from the group consisting of hydrogen, halogen, and functionalized and unfunctionalized hydrocarbyl optionally having one or more heteroatoms; each $R_3$ may be independently selected from the group consisting of hydrogen, U, and functionalized and unfunctionalized hydrocarbyl optionally having one or more heteroatoms; each M may be independently selected from the group consisting of alkali metal ion, alkaline earth metal ion, ammonium ion, and combinations thereof; each U has a structure independently selected from the group consisting of:

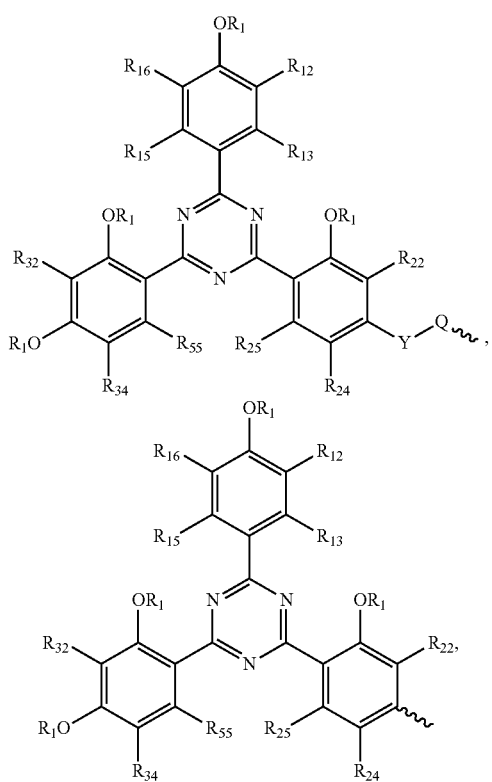

and combinations thereof, wherein each $R_{12}$, $R_{13}$, $R_{15}$, $R_{16}$, $R_{22}$, $R_{24}$, $R_{25}$, $R_{32}$, $R_{34}$ and $R_{35}$ may be independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof; each Y may be independently selected from the group consisting of O, $NR_1$, S, and combinations thereof; each Q may be independently selected from the group consisting of functionalized and unfunctionalized hydrocarbylene optionally having one or more heteroatoms; and wherein each ∿ (wavy bond) indicates the point of attachment for U.

Particularly, the first repeating unit may be selected from the group consisting of:

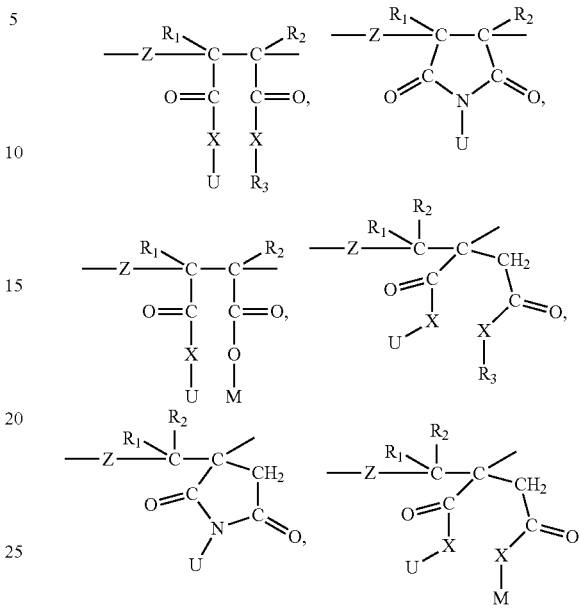

and combinations thereof, wherein each Z may be a residue of a monomer independently selected from the group consisting of functionalized and unfunctionalized: alpha-olefins, maleimides, maleamic acids, maleic anhydride, 4-vinyl-1,2,3-triazoles, 5-vinyl-1,2,3-triazoles, (meth)acrylamides, (meth)acrylates, vinyls, allyls, α-β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, allyl ethers, and combinations thereof, and wherein X, Y, Q, $R_1$, $R_2$, $R_3$, M, U, $R_{12}$, $R_{13}$, $R_{15}$, $R_{16}$, $R_{22}$, $R_{24}$, $R_{25}$, $R_{32}$, $R_{34}$ and $R_{35}$ retain the aforementioned definitions.

Non-limiting examples of vinyl ethers include one or more alkyl vinyl ethers such as methyl vinyl ether, ethyl vinyl ether, isobutyl vinyl ether, octyl vinyl ether, ethyl hexyl vinyl ether, decyl vinyl ether, dodecyl vinyl ether, tetradecyl vinyl ether, hexadecyl vinyl ether, octadecyl vinyl ether, and combinations thereof.

Non-limiting examples of alpha-olefins include isobutylene, styrene, octadecene, and combinations thereof.

In a particular embodiment, Q may be $C_1$-$C_{60}$ alkylene. More particularly, Q may be a residue of a compound selected from the group consisting of diols, diamines, thio alcohols, amino alcohols, polyols, polyether polyols, polyacetal polyethers, polyalkylene polyamines, polyetheramines, polyalkylene imines, polysaccharides, and combinations thereof. Even more particularly, Q may be a residue of a diol, an amino alcohol, or a diamine.

Non-limiting examples of diols include ethylene glycol, propylene glycol, diethylene glycol, triethylene glycol, tetraethylene glycol, dipropylene glycol, 2-butyl-2-ethyl-1,3-propanediol, 2,2-dimethyl-1,3-propanediol, 1,1-bis(hydroxymethyl)cyclopropane, 1,2-butanediol, 2,3-butanediol, 1,4-butanediol, 3-methyl-1,3-butanediol, 1,2-cyclopentanediol, 1,3-cyclopentanediol, 1,4-pentanediol, 1,5-pentanediol, 1,5-pentanediol, 2,4-pentanediol, 3-methyl-1,5- pentanediol, 1,2-cyclohexanediol, 1,3-cyclohexanediol, 1,4-cyclohexanediol, 1,2-hexanediol, 1,5-hexanediol, 1,6-hexanediol, 2,5-hexanediol, 1,8-octanediol, and 3,6-dithiaoctane-1,8-diol.

Non-limiting examples of amino alcohols include ethanol amine, propanol amine, 2-(methylamino)ethanol, 1-amino-2-propanol, 2-(ethylamino)ethanol, 2-amino-2-methyl-1-propanol, 4-amino-1-butanol, 4-amino-2-butanol, 2-(2-aminoethoxy)ethanol, 2-aminocyclopentanol, 2-(isopropylamino)ethanol, 2-amino-3-methyl-1-butanol, 5-amino-1-pentanol, 2-amino-1-pentanol, 1-amino-1-cyclopentanemethanol, 2-aminocyclohexanol, 4-aminocyclohexanol, 6-amino-1-hexanol, 2-amino-1-hexanol, 2-(aminomethyl)cyclohexanol, 5-amino-2,2-dimethylpentanol, 2-amino-1-phenylethanol, 4-chlorophenylalaninol, 2-benzylaminoethanol, 6-amino-1-hexanol, 8-amino-1-octanol, and 3-amino-1-adamantanol.

Non-limiting examples of diamines include ethylene diamine, diphenylethylenediamine, 1,3-diaminopropane, diaminocyclopropane, 1,4-diaminobutane, 1,5-diaminopentane, diaminocyclopentane, hexamethylenediamine, and diaminocyclohexane.

Particularly, each U group has an independently selected structure:

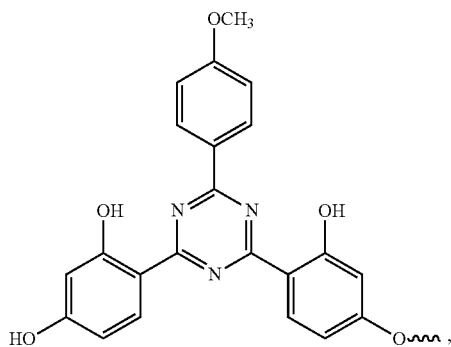

wherein ～ (wavy bond) indicates the point of attachment for U.

In a fourth embodiment, the invention provides a UV-absorbing polymer comprising a first repeating unit selected from the group consisting of:

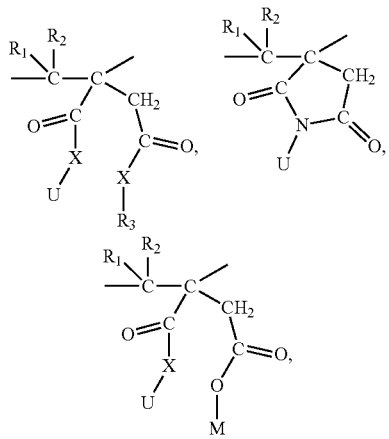

and combinations thereof, wherein each X may be independently selected from the group consisting of O, $NR_1$, and combinations thereof; each $R_1$ and $R_2$ may be independently selected from the group consisting of hydrogen, halogen, and functionalized and unfunctionalized hydrocarbyl optionally having one or more heteroatoms; $R_3$ may be selected from the group consisting of hydrogen, U and functionalized and unfunctionalized hydrocarbyl optionally having one or more heteroatoms; M may be independently selected from the group consisting of alkali metal ion, alkaline earth metal ion, ammonium ion, and combinations thereof; each U has a structure independently selected from the group consisting of:

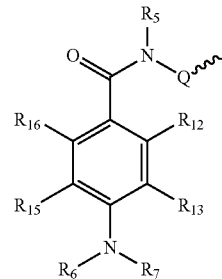

and combinations thereof, wherein each $R_{12}$, $R_{13}$, $R_{15}$, and $R_{16}$ may be independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof; each $R_5$ may be independently selected from the group consisting of hydrogen and functionalized and unfunctionalized hydrocarbyl optionally having one or more heteroatoms; each $R_6$ and $R_7$ may be independently selected from the group consisting of functionalized and unfunctionalized hydrocarbyl optionally having one or more heteroatoms; each Q may be independently selected from the group consisting of functionalized and unfunctionalized hydrocarbylene optionally having one or more heteroatoms; and each ～ (wavy bond) indicates the point of attachment for U.

Particularly, the first repeating unit may be selected from the group consisting of:

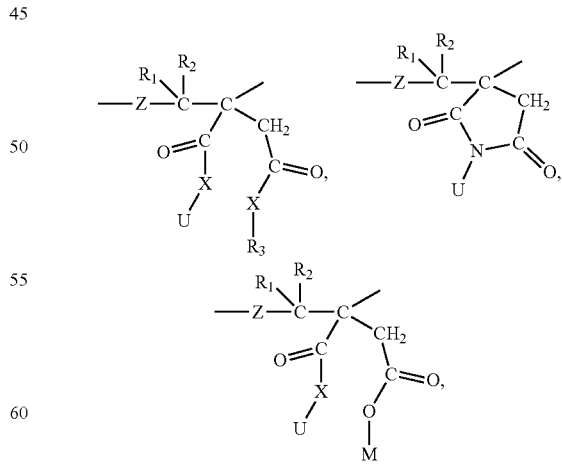

and combinations thereof, wherein each Z may be a residue of a monomer independently selected from the group consisting of functionalized and unfunctionalized: alpha-olefins, maleimides, maleamic acids, maleic anhydride, 4-vinyl-1,2,3-triazoles, 5-vinyl-1,2,3-triazoles, (meth) acrylamides, (meth)acrylates, vinyls, allyls, α-β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, allyl ethers, and combinations thereof, and wherein X, Q, $R_1$, $R_2$, $R_3$, M, U, $R_{12}$, $R_{13}$, $R_{15}$, $R_{16}$, $R_5$, $R_6$, and $R_7$ retain the aforementioned definitions.

Non-limiting examples of vinyl ethers include one or more alkyl vinyl ethers such as methyl vinyl ether, ethyl vinyl ether, isobutyl vinyl ether, octyl vinyl ether, ethyl hexyl vinyl ether, decyl vinyl ether, dodecyl vinyl ether, tetradecyl vinyl ether, hexadecyl vinyl ether, octadecyl vinyl ether, and combinations thereof.

Non-limiting examples of alpha-olefins include isobutylene, styrene, octadecene, and combinations thereof.

In a particular embodiment, Q may be $C_1$-$C_{60}$ alkylene. More particularly, Q may be a residue of a compound selected from the group consisting of diols, diamines, thio alcohols, amino alcohols, polyols, polyether polyols, polyacetal polyethers, polyalkylene polyamines, polyetheramines, polyalkylene imines, polysaccharides, and combinations thereof. Even more particularly, Q may be a residue of a diol, an amino alcohol, or a diamine.

Non-limiting examples of diols include ethylene glycol, propylene glycol, diethylene glycol, triethylene glycol, tetraethylene glycol, dipropylene glycol, 2-butyl-2-ethyl-1,3-propanediol, 2,2-dimethyl-1,3-propanediol, 1,1-bis(hydroxymethyl)cyclopropane, 1,2-butanediol, 2,3-butanediol, 1,4-butanediol, 3-methyl-1,3-butanediol, 1,2-cyclopentanediol, 1,3-cyclopentanediol, 1,4-pentanediol, 1,5-pentanediol, 1,5-pentanediol, 2,4-pentanediol, 3-methyl-1,5-pentanediol, 1,2-cyclohexanediol, 1,3-cyclohexanediol, 1,4-cyclohexanediol, 1,2-hexanediol, 1,5-hexanediol, 1,6-hexanediol, 2,5-hexanediol, 1,8-octanediol, and 3,6-dithiaoctane-1,8-diol.

Non-limiting examples of amino alcohols include ethanol amine, propanol amine, 2-(methylamino)ethanol, 1-amino-2-propanol, 2-(ethylamino)ethanol, 2-amino-2-methyl-1-propanol, 4-amino-1-butanol, 4-amino-2-butanol, 2-(2-aminoethoxy)ethanol, 2-aminocyclopentanol, 2-(isopropylamino)ethanol, 2-amino-3-methyl-1-butanol, 5-amino-1-pentanol, 2-amino-1-pentanol, 1-amino-1-cyclopentanemethanol, 2-aminocyclohexanol, 4-aminocyclohexanol, 6-amino-1-hexanol, 2-amino-1-hexanol, 2-(aminomethyl)cyclohexanol, 5-amino-2,2-dimethylpentanol, 2-amino-1-phenylethanol, 4-chlorophenylalaninol, 2-benzylaminoethanol, 6-amino-1-hexanol, 8-amino-1-octanol, and 3-amino-1-adamantanol.

Non-limiting examples of diamines include ethylene diamine, diphenylethylenediamine, 1,3-diaminopropane, diaminocyclopropane, 1,4-diaminobutane, 1,5-diaminopentane, diaminocyclopentane, hexamethylenediamine, and diaminocyclohexane.

Particularly, a U group has a structure independently selected from the group consisting of:

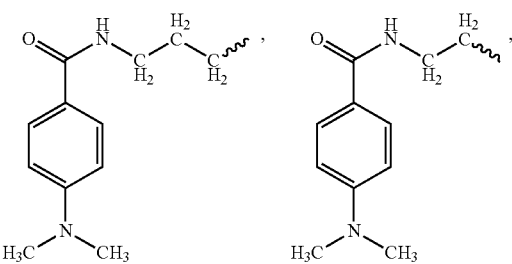

and combinations thereof, wherein each ⁓ (wavy bond) indicates the point of attachment for U.

The first repeating unit of UV-absorbing polymers described herein may be a residue of an anhydride monomer that may be functionalized by one or more UV-absorbing compound(s). Particularly, the anhydride monomer prior to functionalization may be selected from the group consisting of maleic anhydride, methyl maleic anhydride, dimethyl maleic anhydride, itaconic anhydride, citraconic anhydride, chloromaleic anhydride, bromomaleic anhydride, dichloromaleic anhydride, dibromomaleic anhydride, phenylmaleic anhydride, and combinations thereof. The functionalization of anhydride monomers by one or more UV-absorbing compound(s) results in formation of amic acid, amic acid salt, ester acid, ester acid salt, diester, diamide, ester amide, and/or imide moieties.

In one embodiment, the anhydride monomers may be functionalized by one or more UV-absorbing compound(s) followed by polymerization to yield UV-absorbing polymers. In an alternative embodiment, a polymer having one or more reactive anhydride, ester acid, amic acid, ester acid salt, amic acid salt, diester, diamide, ester amide, and/or imide moieties on the polymer backbone may be functionalized by post-polymerization modification reaction(s) to yield UV-absorbing polymers. The resulting UV-absorbing polymers include homopolymers, copolymers, terpolymers, and higher homologues.

The polymer backbone may be a homopolymer of an anhydride monomer, such as, poly(maleic anhydride), poly(dimethyl maleic anhydride), poly(methyl maleic anhydride), and poly(citaconic anhydride).

Alternatively, the polymer backbone may be provided by a copolymer. One non-limiting, exemplary member of this copolymer class may be poly(styrene-co-maleic anhydride), which are a general class of alternating copolymers of styrene and maleic anhydride, or the non-equimolar copolymers containing less than about 50 mole percent of the anhydride monomer. This copolymer may be defined by its generic chemical structure:

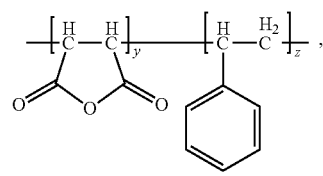

wherein the subscripts y and z represent the molar ratios of the repeating units. The styrene constituent in poly(styrene-co-maleic anhydride) may be replaced in whole or in part by other vinylaromatic monomers such as alpha-methylstyrene, nuclear methylstyrenes, ethylstyrene, iso-propylstyrene, tert-butylstyrene, chloro styrenes, dichlorostyrenes, bromo-styrenes, dibromostyrenes, vinylnaphthalene and the like. Similarly, the maleic anhydride can be replaced in whole or in part by another alpha, beta-unsaturated cyclic dicarboxylic acid anhydride such as citraconic, chloromaleic, itaconic, bromomaleic, dichloromaleic, dibromomaleic, phenylmaleic, and the like. Particularly, the alpha, beta-unsaturated cyclic anhydride may be maleic anhydride. Suitable poly(styrene-co-maleic anhydride) copolymers may be prepared by any of the several methods available for the preparation of styrene-maleic anhydride copolymers or they may be purchased commercially. Non-equimolar copolymers may be prepared by solution polymerization directly from the respective monomers by the incremental addition of the reactive monomer as taught by U.S. Pat. No. 2,971,939, by a continuous recycle polymerization process such as described in U.S. Pat. Nos. 2,769,804 and 2,989,517, by the suspension polymerization process described in U.S. Pat. No. 3,509,110, or by numerous known variations.

A second non-limiting example of a copolymer is a poly(alkyl vinyl ether-co-anhydride), such as poly(methyl vinyl ether-co-maleic anhydride):

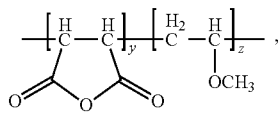

wherein the subscripts y and z represent the molar ratios of the repeating units.

Particularly, this copolymer may be predominantly alternating poly(methyl vinyl ether-co-maleic anhydride).

Poly(methyl vinyl ether-co-maleic anhydride) is offered for commercial sale as Gantrez™ AN by International Specialty Products (Wayne, N.J.).

Regardless of the synthesis approach, the imide forms can be created from the amic acid form through the application of heat, the use of a reaction catalyst, or the use of a reaction initiator, or combinations thereof.

The polymers and UV-bound polymers described herein may have a weight-average molecular weight from about 800 Da to about 5,000,000 Da, more particularly from about 10,000 Da to about 1,000,000 Da, and yet more particularly from about 20,000 Da to about 500,000 Da. The molecular weight may be controlled using methods known in the art, including strategies to control the reaction temperature and time, as well as the use of chain-transfer agents such as thiols (e.g., dodecyl mercaptan), and halocarbons (e.g., chlorinated compounds like carbon tetrachloride) families of compounds employed for such purposes.

In another aspect, the invention provides formulations comprising one or more UV-absorbing polymers described herein.

The UV-absorbing polymers according to the invention may be used alone or in combination with other ingredient(s) in various formulations and product forms. The amount of each ingredient in the composition varies depending on the type of composition, the function and/or physicochemical property of the ingredient, and the amount of other co-ingredients. The precise amount of each ingredient may be easily determined by any person skilled in the related arts. Such formulations include, but are not limited to personal care formulations, adhesives, coatings, paints, electronics, Household, Industrial and Institutional (HI&I) compositions, inks, paper, polish, printing, membranes, metal working fluids, oilfield formulations, construction formulations, plastics and plasticizers, textiles, industrial formulations, printing, lubricants, biocides, preservative, pharmaceuticals, food, agrochemical, and wood-care formulations.

The term "personal care formulation" refers to a composition intended for use on or in the human body. Non-limiting, but specific types of personal care formulations include hair care compositions (encompassing styling and non-styling compositions), sun care compositions (encompassing after-sun compositions), skin care compositions, and oral care compositions.

Non-limiting applications of the hair care compositions include: hair styling, hair setting, hair sculpting, hair curling, hair holding, hair waving, hair fixing, hair maintaining, hair shaping, hair straightening, hair volumizing, hair relaxing, shampooing, hair conditioning, hair cleansing, promoting hair style durability, imparting humidity resistance to hair and hair styles, enhancing hair shine, repairing split ends of hair, enhancing hair manageability such as lightness, smoothness, softness, disentangling and/or suppleness of hair, modulating hair stylability, protecting hair from thermal damage, hair dyeing, hair coloring, hair bleaching, oxidation dyeing of hair, limiting hair color bleeding, protecting hair color, hair treating (e.g., anti-dandruff), anti-hair fall, and protecting hair from UV radiation.

The hair care compositions of the invention may be particularly used in hair styling. More particularly, the hair care compositions may be used to improve the hair stiffness, curl retention, and/or hair conditioning.

In particular embodiments, the hair care compositions may comprise the polymer(s) described herein in an amount from about 0.1% to about 50% by weight of the composition. More particularly, the polymer(s) may be present in an amount from about 0.5% to about 20% by weight, most particularly from about 1% to about 10% by weight of the composition.

The hair care compositions may further comprise one or more additional ingredients. Particularly, the additional ingredients may be selected from the group consisting of: skin care or hair care agents, hair styling agents, hair fixative agents, film formers, structurants, gelling agents, surfactants, thickeners, preservatives, viscosity modifiers, electrolytes, pH adjusting agents, perfumes, dyes, organosilicon compounds, anti-dandruff agents, anti-foaming agents, anti-frizz agents, penetrants, vitamins, conditioning agents, chelating agents, antimicrobial agents, preservatives, UV absorbers, sunscreens, natural extracts, propellants, carriers, diluents, solvents, pharmaceutical actives, lubricants, combing aids, plasticizers, solubilizers, neutralizing agents, vapor pressure suppressants, bleaching agents, hydrating agents, moisturizers, cosmetic adjuvants and/or additives, protectants, and mixtures thereof.

The formulations according to the invention may further comprise one or more UV actives that is/are different from the UV-absorbing compounds described herein.

Non-limiting examples of such UV actives include 2,4-bis-(2,4-dihydroxyphenyl)-6-(4-methoxyphenyl)-s-triazine, aminobenzoic acid; 2-aminobenzophenone; amyl dimethyl PABA; bemotrizinol; benzophenone-3; benzophenone-4; benzophenone-9; 2-(2H-benzotriazole-2-yl)-4,6-di-tert-pentylphenol; 2-(2H-benzotriazole-2-yl)-4-methylphenol; 2-(2H-benzotriazole-2-yl)-4,6-bis(1-methyl-1-phenylethyl) phenol; bis-benzoxazoyl phenyl ethylhexyl amino triazine; 3-benzylidene camphor sulfonic acid; CAS number 152261-33-1; N,N'-bisformyl-N,N'-bis-(2,2,6,6-tetramethyl-4-piperidinyl)-hexamethylenediamine; bisoctrizole; 2-[(p-(tert-butylamido)-anilinol]-4,6,-bis[(p-(2'-ethylhexyl-1'-oxycarbonyl)-anilino]-1,3,5-triazine; 6-tert-butyl-2-(5- chloro-2H-benzotriazole-2-yl)-4-methylphenol; 2,4-di-tert-butyl-6-(5-chloro-2H-benzotriazole-2-yl)-phenol; camphor benzalkonium methosulfate; diethanolamine p-methoxycinnamate; diethylaminohydroxybenzoylhexylbenzoate; diethylhexyl butamido triazone; digalloyl trioleate; dioxybenzone; disodium phenyl dibenzimidazole tetrasulfonate; drometrizole trisiloxane; ecamsule; ensulizole; ethyl 4-bis(hydroxypropyl)aminobenzoate; ethylhexyl p-methoxycinnamate; 2-ethylhexyl salicylate; ethylhexyl triazone; beta-2-glucopyranoxypropylhydroxybenzophenone; glyceryl aminobenzoate; homomenthyl salicylate; [2-hydroxy-4-(octyloxy)phenyl](phenyl)methanone; 2-[bis(2-hydroxyethyl)amino]ethyl salicylate; (E)-3-(4-hydroxy-3-methoxyphenyl)prop-2-enoic acid; lawsone with dihydroxyacetone; meradimate; methoxycinnamido propyl hydroxy sultaine menthyl anthranilate; meradimate; methyl-2-aminobenzoate; oxybenzone; 2-phenylbenzimidazole-5-sulfonic acid (and its potassium, sodium and triethanolamine salts); sulisobenzone; bis-(2,2,6,6-tetramethyl-4-piperidyl)-sebacate; sterically hindered oligomeric amine, triethanolamine salicylate, and combinations thereof.

Non-limiting applications of the sun care compositions include: protecting skin and/or hair from UV radiation (including any or all of UV-A, UV-B and/or UV-C radiation), sun screening, skin anti-irritating, skin repairing, skin wrinkle masking, skin nourishing, skin moisturizing, skin relaxing, skin refreshing, skin cooling, skin soothing, skin tanning, skin tan prolonging, sun-less skin tanning, skin glowing, skin micro-glittering, skin shimmering, and skin anti-tanning.

Non-limiting applications of the skin care compositions include: protecting skin from UV radiation (including any or all of UV-A, UV-B and/or UV-C radiation), skin cleansing, face cleansing, body cleansing, insect repelling, antiperspirant, exfoliating skin, rejuvenating skin, influencing cell turnover, deodorant, astringent, imparting water resistance or water proofness to skin, decreasing and/or minimizing the appearance of skin wrinkles, decreasing and/or minimizing the appearance of skin blemishes (such as lentigo, skin discolorations, pimples, and/or acne), changing skin color (including skin lightening, skin brightening, skin color darkening, and color cosmetics for the face, cheeks, lips, eyelids, and/or eye lashes), skin iridescing, skin glossing, curling of eye lashes, eye lining, eye shadowing, mascara, removing facial and/or body hair, skin tightening, skin tanning, skin bronzing, skin blushing, prolonging skin tan, sun-less skin tanning, anti-tanning, skin anti-bacterial, skin anti-oxidant, skin anti-photoaging, skin anti-seborrheic, cell exchange and/or cell respiration activating of skin, skin conditioning, skin detoxifying, skin emollient, skin moisturizing, film forming on skin, skin healing-cicatrizing, skin immune-protecting, skin plumping, glossing, shading, plumping, and/or coloring of lips, skin revitalizing, skin energizing, skin re-sculpting, skin nourishing, skin smoothing, skin slimming, skin anti-irritating, and skin sanitizing.

Non-limiting applications of the oral care compositions include: tooth and/or mouth cleansing, providing denture adhesion, delivering and/or retaining actives to oral cavity, mouth washing, mouth refreshing, mouth rinsing, mouth gargling, providing oral hygiene, preventing, reducing, controlling, and/or removing tooth stain, preventing and/or controlling tooth decay, preventing and/or controlling tartar, tooth flossing, tooth whitening and/or bleaching, mouth treating, and tooth filling.

The polymers described herein also may be used alone or in combination with other ingredient(s) in pharmaceutical and/or nutritional compositions.

Non-limiting applications of the pharmaceutical and/or nutritional compositions include: providing anti-tack, binder, coating, disintegrating, dispersing, encapsulating, filling, film forming, lubricating, and solubilizing. Additional insight into how the polymers described herein find application in this art area may be found in the following publications by Ashland Specialty Ingredients: *Health and nutrition product guide—Performance enhancing products* (August 2008), *Plasdone™ povidones product overview* (April 2010), *Plasdone™ K-12 and K-17 povidones—Solubilizers for liquid softgel fill formulations* (September 2010), *Plasdone™ K-29/32 povidone—High efficiency binder for wet granulation* (April 2010), *Plasdone™ S-630 copovidone—Product Overview* (April 2010), *Polyplasdone™ Ultra and Ultra-10 crospovidones—Product overview* (September 2010), *Polyplasdone™ superdisintegrants—Product overview* (July 2010), *Polyplasdone™ crospovidone—Superdisinte grants for orally disintegrating and chewable tablets* (July 2010), *Polyplasdone™ crospovidone—Non-ionic superdisintegrant for improved dissolution of cationic drugs* (July 2009), *Polyplasdone™ crospovidone—The solution for poorly soluble drugs* (July 2009), *Polyplasdone™ crospovidone—Novel pelletization aid for extrusion spheronization* (July 2010), *PVP-Iodine povidone iodine antiseptic agent* (March 2004), and *Pharmaceutical technical bulletin—PVP-Iodine for prophylaxis and treatment of bovine mastitis* (December 2003). Each publication is hereby incorporated in its entirety by reference.

Any range in composition pH may be used. In embodiments wherein the composition may be applied to keratinous material, the pH may range from about 2 to 12. pH may be adjusted to a desired value by means of adding one or more acidifying or alkalinizing agents that are well-known in the state of the art. For example, the composition can contain at least one alkalizing or acidifying agent in amounts from about 0.01% to about 30% based on the total weight of the composition.

Non-limiting examples of acidifying or acidic pH adjusting agents include organic acids, such as citric acid, acetic acid, carboxylic acids, $\alpha$-hydroxyacids, $\beta$-hydroxyacids, $\alpha,\beta$-hydroxyacids, -hydroxyacids, salicylic acid, tartaric acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized.

Non-limiting examples of alkalizing or alkaline pH adjusting agents include ammonia, alkali metal hydroxides (such as sodium hydroxide and potassium hydroxide), ammonium hydroxide, alkanolamines (such as mono-, di- and triethanolamine), diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine, hydroxyalkylamines and ethoxylated and/or propoxylated ethylenediamines, alkali metal salts of inorganic acids, such as sodium borate (borax), sodium phosphate, sodium pyrophosphate, and the like, and mixtures thereof.

Non-limiting examples of alkalizing agent can be chosen from ammonia, alkali carbonates, alkanolamines, like mono-, di- and triethanolamines, as well as their derivatives, sodium or potassium hydroxides and compounds of the following formula:

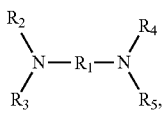

wherein $R_1$ may be a propylene residue that may be optionally substituted with an hydroxyl group or a C1-C4 alkyl radical; $R_2$, $R_3$, $R_4$ and $R_5$ are identical or different and represent a hydrogen atom, a C1-C4 alkyl radical or C1-C4 hydroxyalkyl radical.

The composition also may comprise one or more buffers. Suitable buffering agents include but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate. The personal care compositions may be formulated in any of the product forms known to a person of ordinary skill in the art. Non-limiting product forms are described below.

Product Forms

Non-limiting hair care product forms include: shampoos, conditioners, aerosols, mousses, sprays, mists, gels, waxes, creams, lotions, glues, pomades, spritzes, solutions, oils, liquids, solids, W/O emulsions, O/W emulsions, suspensions, multiple emulsions, microemulsions, microencapsulated products, sticks, balms, tonics, pastes, reconstitutable products, nanoemulsions, solid lipid nanoparticles, liposomes, cubosomes, neosomes, putties, lacquers, serums, perms, volumizers, packs, flakes, 2-in-1 shampoo/conditioner products, and 3-in-1 shampoo/conditioner/styling products.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

Non-limiting sun care product forms include: solutions, liquids, creams, powders, lotions, gels, pastes, waxes, aerosols, sprays, mists, roll-ons, sticks, milks, emulsions, and wipes.

Non-limiting skin care product forms include: solutions, oils, lotions, creams, ointments, liquids, gels, solids, W/O emulsions, O/W emulsions, milks, suspensions, microemulsions, dispersions, microencapsulated products, sticks, balms, tonics, pastes, mists, reconstitutable products, peels, soaps, aerosols, mousses, waxes, glues, pomades, spritzes, putties, lacquers, serums, perms, powders, pencils, flakes, blush, highlighters, bronzers, concealers, and 2-way cake products.

The compositions of the invention may also take the form of skin-washing compositions, and particularly in the form of solutions or gels for the bath or shower, or of make-up removal products.

The six skin care product categories that follow next may be considered a subset of the skin and sun care products:

(1) Eye Care

Non-limiting eye care product forms include: mascaras, eye liners, eye shadows, curlers of eye lashes, eyebrow pencils, and eye pencils.

(2) Lip Care

Non-limiting lip care product forms include: lipsticks, lip balms, lip pencils, lip glosses, lip sprays, transparent lip bases, tinted lip moisturizers, and multi-functional color sticks that can also be used for cheeks and eyes.

(3) Nail Care

Non-limiting nail care product forms include: nail polishes, nail varnishes, enamels, nail varnish removers, home-manicure products such as cuticle softeners and nail strengtheners, and artificial nails.

(4) Face Care

Non-limiting face care product forms include: creams, lotions, solutions, oils, liquids, peels, scrubs, emulsions, suspensions, microemulsions, microencapsulated product, pastes, econstitutable product, aerosols, mousses, gels, waxes, glues, pomades, spritzes, facial wet-wipes, putties, lacquers, serums, perms, powders, blush, highlighters, bronzers, masks, and concealers.

(5) Body Care

Non-limiting body care product forms include: foams, peels, masks, gels, sticks, aerosols, lotions, salts, oils, balls, liquids, powders, peels, pearls, bar soaps, liquid soaps, body washes, cleansers, scrubs, creams, flakes, other bath and shower products, shaving products, waxing products, and sanitizers.

(6) Foot Care

Non-limiting foot care product forms include: mousses, creams, lotions, powders, liquids, sprays, aerosols, gels, flakes, and scrubs.

Non-limiting oral care product forms include: toothpastes, adhesives, gums, gels, powders, creams, solutions, lotions, liquids, dispersions, suspensions, emulsions, tablets, capsules, rinses, flosses, aerosols, strips, films, pads, bandages, microencapsulated products, syrups, and lozenges.

Also contemplated are personal care compositions comprising polymer(s) described herein complexed with iodine. These compositions may be used in treating skin conditions, non-limiting examples of which include dermatitis, wounds, bacterial infections, burns, rashes, and herpes. These complexed compositions may be staining, substantially non-staining, or essentially non-staining.

Examples of related personal care compositions are disclosed in U.S. Pat. Nos. 5,599,800; 5,650,166; 5,916,549; and 6,812,192; U.S. patent application 2009/0317432; EP 556,660; 661,037; 661,038; 662,315; 676,194; 796,077; 970,682; 976383; 1,415,654; and 2,067,467; and WO 2005/032506; each of which is hereby incorporated in its entirety by reference.

It is also contemplated that the personal care compositions may be used in products for male and/or female personal grooming and/or toiletry such as: sanitary napkins, baby diapers, adult diapers, feminine products, products for incontinence, and other related products.

An array of additional personal care compositions, methods, and uses are contemplated. Disclosure of these compositions may be found in the following brochures by Ashland Specialty Ingredients, each of which is hereby incorporated in its entirety by reference: *Plasdone™ K-29/32, Advanced non-oxidative, non-abrasive teeth whitening in toothpastes, mouthwashes, and oral rinses* (2010), *Polymers for oral care, product and applications guide* (2002), *A formulation guide for excellent hair styling gels and lotions* (April 2003), *PVP (polyvinylpyrrolidone)* (no date provided), and *Textile chemicals, solutions for the most challenging product environment* (no date provided).

Also contemplated are additional personal care compositions that may comprise the polymers described herein. Disclosures on such compositions may be found in the publications listed below, each of which is hereby incorporated in its entirety by reference: (1) Prototype Formulations—Personal Care Products (2009) from Xiameter, Dow Corning. (2) Sun care formulations under the category "Refreshing Sun", "Younger Sun", "Sun for Men", and "Sunny Glow" from Dow Corning. (3) Cosmetic Nanotechnology, Polymers and Colloids in Cosmetics, 2007, ACS Symposium Series. (4) Review Paper: Lipid nanoparticles (SLN, NLC) in cosmetic and pharmaceutical dermal products, International Journal of Pharmaceutics, Volume 366, 2009.

Optional: Additional Composition Ingredients

It is also contemplated that the personal care compositions optionally may contain one or more additional ingredients.

Further, it is contemplated that the composition ingredients may be formulated in a single container, or the ingredients may be formulated in-part in two or more distinct containers of the same or different type, the contents of which may require mixing prior to use.

Furthermore, it also is contemplated that the compositions may be prepared in the form of concentrates that may be diluted by a suitable substance(s) prior to use. The concentrate may, in turn, be present in any of the forms as described under 'Product Forms' for the personal care compositions of the invention.

A non-limiting list of classes of additional ingredients that may optionally be present in different types of personal care compositions is provided below: conditioning agents, antimicrobials, protectives (for example, antiradical agents), abrasives, UV absorbers, emulsifiers (including, but not limited to ethoxylated fatty acids, ethoxylated glyceryl esters, ethoxylated oils, ethoxylated sorbitan esters, fatty esters, PEG esters, polyglycerol esters), antiperspirants (including, but not limited to aluminium chlorohydrates, aluminium zirconium chlorohydrates), antioxidants, vitamins and/or provitamins, botanicals, fixatives, oxidizing agents, reducing agents, dyes, cleansing agents, anionic, cationic, nonionic, and/or amphoteric surfactants, thickeners and/or gelling agents, perfumes, flavors, and/or fragrances, pearlizing agents, stabilizers, pH adjusters, filters, antimicrobial agents, preservatives and/or disinfectants, associative polymers, oils of vegetable, mineral, and/or synthetic origin, polyols, silicones, colorants, bleaching agents, highlighting agents, propellants (including, but not limited to hydrocarbons, dimethyl ether, fluorocarbons), styling polymers, benefit agents, skin tighteners (including, but not limited to arbutin and kojic acids), tanning agents (including, but not limited to dihydroxyacetone), solvents and/or cosolvents, diluents, essential oils, sequestrants and/or chelators, carriers, and natural extracts and/or natural products.

The amount of each ingredient in the composition varies depending on the type of composition, the function and/or physicochemical property of the ingredient, and the amount of other co-ingredients. The precise amount of each ingredient may be easily determined by any person skilled in the related arts.

It may be desirable to include one or more ingredients described in the prior art disclosures IPCOM000186541D, IPCOM000128968D, and IPCOM000109682D on www.ip.com, the contents of each of these disclosures are hereby incorporated in their entirety by reference.

Further reference to formulary co-ingredients and product forms include the disclosures in US 2010/0183532, paragraphs [0096]-[0162], and WO 2010/105050, paragraphs [0053]-[0069], the contents of which are hereby incorporated in their entirety by reference.

Non-limiting examples of structurants that may be used in the hair care compositions according to the invention include dextrin palmitate, trihydroxystearin, hydroxy stearic acid, hydrophilic or hydrophobic silica, hydrophobically modified clay selected from the group consisting of stearalkonium hectorite, quatemium-18 bentonite, quaternium-18 hectorite, disteardimonium hectorite, derivatives thereof, and mixtures thereof.

The hair care compositions of the invention may additionally comprise one or more hair styling agents, hair fixative agents, and/or film formers.

Particularly useful as styling agents are hair styling polymers. The hair styling polymers may be cationic, anionic, amphoteric or nonionic in nature. The polymers may be synthetic or naturally derived. Non-limiting examples of hair styling polymers include the following polymer products available for sale from Ashland Specialty Ingredients: (1) Cationic styling polymers with hair conditioning benefits—Styleze™ W Polymer, Styleze™ CC-10 (pseudo cationic), Gafquat™ 755 NP, and Gafquat™ 440; (2) Styling polymers with excellent high humidity curl retention—Styleze™ 2000, Allianz™ LT 120, Styleze™ W Polymer, and Advantage™ LCA; (3) Non-ionic styling polymers with broad ingredient compatibility—Polyvinylpyrrolidones such as PVP K-30, PVP K-60 and PVP K-90, Vinylpyrrolidone/vinyl acetate copolymers such as PVP/VA (E, I or W) 735, PVP/VA (E or W) 635, PVP/VA (E or I) 535, PVP/VA (E or I) 335 and PVP/VA S-630, and poly(vinylpyrrolidone/dimethylaminoethylmethacrylate) polymers such as Copolymer 845/937. Additional details on the aforementioned polymers and methods of use, or formulations thereof, may be found in a publication from Ashland Specialty Ingredients titled "*A Formulation Guide for Excellent Hair Styling Gels and Lotions*" (2002) that is hereby incorporated in its entirety by reference.

A non-limiting example of hair fixative agent that may be used in hair care compositions according to the invention includes a hair fixative polymer available for sale from Ashland Specialty Ingredients, AquaStyle™ 300 (INCI name Polyquaternium-69). A related publication from Ashland Specialty Ingredients titled "*Aquastyle® 300, A Fixative Polymer with Enhanced Styling Benefits*" (2007) is hereby incorporated in its entirety by reference.

Non-limiting examples of film formers that may be used in hair care compositions according to the invention include film forming polymers available for sale from Ashland Specialty Ingredients such as (1) Aquaflex™ FX 64, (2) AquaCat™ clear cationic solution, (3) Aqualon™ carboxymethylcellulose, (4) Klucel™ hydroxypropylcellulose, and (5) Primaflo™ HP22 polymer solution.

Further details on hair styling agents, hair fixative agents, and/or film formers may be found in U.S. Pat. Nos. 7,871,600, 7,205,271, 7,122,175, 7,041,281, 6,998,114, 6,749,836, 6,689,346, 6,599,999, 6,562,325, 6,413,505, 6,387,351, 6,228,352, 5,643,581, 5,922,312, 5,897,870, 5,879,669, 5,709,850, 5,753,216 and 5,632,977 each of which is hereby incorporated in its entirety by reference.

Non-limiting examples of anti-frizz agents that may be used in hair care compositions according to the invention include anti-frizz polymers available for sale from Ashland Specialty Ingredients such as AquaStyle™ 300 and Styleze™ XT3. Information on related anti-frizz agents may be found in U.S. Pat. No. 7,914,773, 7,785,575, and U.S. published application 2010/00093584, the disclosures of each of which is hereby incorporated in its entirety by reference.

One or more plasticizers or coalescing agents may be added to modify the film forming characteristics of hair care compositions according to the invention. Non-limiting examples of plasticizers include glycols, adipic esters, phthalate esters, isobutyrate esters, terephthalate esters, epoxidized butyl esters or fatty acids, epoxidized vegetable oils, glycerine, di-2-ethylhexyladipate or dioctyladipate (DOA), di-2-ethylhexyl phthalate or dioctyl phthalate (DOP), di-2-ethylhexyl terephthalate (DOTP), dicyclohexyl phthalate, diisononyl adipate, diisononylphthalate, n-butyl benzyl phthalate, 1,3-butylene glycol/adipic acid polyester, dialkyl adipate, dialkyl phthalate derivatives where the alkyl group is a $C_1$-$C_{12}$ alkyl group, di-n-hexylazelate, diphenylphthalate, tricresol phosphate, benzyl benzoate, dibutyl phosphate, tributyl phosphate, tributoxyethyl phosphate, triphenyl phosphate, butyl acetyl ricinoleate, glycerol acetyl ricinoleate, dibutyl phthalate, diethyl phthalate, dioctyl phthalate, dimethoxyethyl phthalate, diisobutyl phthalate, diamyl phthalate, dibutyl glycolate, butyl stearate, triethyl citrate, tributyl citrate, tributyl acetyl citrate, 2-hexyltriethylacetyl citrate, dibutyl tartarate, camphor, epoxidized butyl esters of linseed oil fatty acids, epoxidized linseed oil, epoxidized soya oil, propylene glycol adipate, 2,2,4-trimethyl-1,3-pentanediol diisobutyrate (TXIB), methyl abietate, cumyl acetate, dibutoxyethyl adipate, di-n-hexylazalate, glyceryl-tri-benzerate, tri-n-butylcitrate, dioctyl fumarate, triisonyl trimellitate, dioctyl isophthalate, butyl oleate, chlorinated paraffin, tricresolphosphate, dibutyl sebacate, dimethicone copolyol (Dow Corning 190), PEG-6 capric/caprylic glyceride (SOFTIGEN 767), DIACETIN, LAURAMIDE DEA (MONAMID 716), phenyl trimethicone (ABIL AV 20-1000), propylene glycol, dipropylene glycol, as well as polymeric plasticizers, and mixtures thereof. Non-limiting examples of coalescing solvents include acetone, methyl acetate, and di- or tri-propylene glycol methyl ethers, and mixtures thereof. Further examples of plasticizers may be found in U.S. Pat. Nos. 5,753,216 and 5,676,935, the disclosures of each of which are hereby incorporated in its entirety by reference.

Non-limiting examples of propellants that may be used in hair care compositions of the invention include trichlorofluoromethane, chlorodifluoromethane, 1,1-difluoroethane, dichlorotetrafluoroethane, monochlorodifluoromethane, trichlorotrifluoroethane, dimethyl ether, $C_1$-$C_4$ hydrocarbons such as methane, ethane, propane, n-butane, and isobutane, water-soluble gases such as, dimethyl ether, carbon dioxide, and/or nitrous oxide, and insoluble, compressed gases such as nitrogen, helium, and fully-fluorinated oxetanes and oxepanes, and mixtures thereof.

Non-limiting examples of penetrants that may be used in hair care compositions of the invention include lanolin compounds, protein hydrolysates, protein derivatives, and mixtures thereof.

Non-limiting examples of anti-foaming agents that may be used in hair care compositions of the invention include carrier oils, silicone oils, silicone foam inhibitors, hydrophobic silica, hydrophobic fat derivatives, waxes, water-insoluble polymers, amphiphilic components, emulsifiers, coupling agents, and mixtures thereof.

Any known conditioning agent may be used in the personal care compositions of the invention. An extensive discussion on conditioning agents may be found in the book *Conditioning Agents for Skin and Hair, Cosmetic Science and Technology Series*, Volume 21, 1999, Marcel Dekker Publishers. The contents of the book are hereby incorporated in its entirety by reference.

Conditioning agents may be chosen from synthetic oils, mineral oils, vegetable oils, fluorinated or perfluorinated oils, natural or synthetic waxes, silicones, cationic polymers, proteins and hydrolyzed proteins, cationic surfactants, ceramide type compounds, fatty amines, fatty acids and their derivatives, as well as mixtures of these different types of compounds.

Non-limiting examples of suitable synthetic oils include: polyolefins, e.g., poly-α-olefins, such as polybutenes, polyisobutenes, polydecenes, and blends thereof. The polyolefins may be hydrogenated.

Non-limiting examples of suitable mineral oils include hexadecane and oil of paraffin.

Non-limiting examples of suitable animal and vegetable oils include: sunflower oil, corn oil, soy oil, avocado oil, jojoba oil, squash oil, raisin seed oil, sesame seed oil, walnut oil, fish oil, glycerol tricaprocaprylate, purcellin oil, liquid jojoba, and blends thereof. Also suitable are natural oils such as oils of eucalyptus, lavender, vetiver, litsea cubeba, lemon, sandalwood, rosemary, chamomile, savory, nutmeg, cinnamon, hyssop, caraway, orange, geranium, cade, bergamot, and blends thereof.

The conditioning agent may be a fluorinated or a perfluorinated oil. The fluoridated oils may also be fluorocarbons such as fluoramines, e.g., perfluorotributylamine, fluoridated hydrocarbons such as perfluorodecahydronaphthalene, fluoroesters, fluoroethers, and blends thereof.

Non-limiting examples of suitable natural and synthetic waxes include: carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The conditioning agent may be any silicone known by those skilled in the art. Silicones include polyorganosiloxanes that are insoluble in the composition. The silicones may be present in the form of oils, waxes, resins, or gums. They may be volatile or non-volatile.

Non-limiting examples of suitable silicones include: polyalkyl siloxanes, polyaryl siloxanes, polyalkyl aryl siloxanes, silicone gums and resins, polyorgano siloxanes modified by organofunctional groups, and blends thereof.

Suitable polyalkyl siloxanes include polydimethyl siloxanes with terminal trimethyl silyl groups or terminal dimethyl silanol groups (dimethiconol) and polyalkyl (C1-C20) siloxanes. Suitable polyalkyl aryl siloxanes include polydimethyl methyl phenyl siloxanes and polydimethyl diphenyl siloxanes. The siloxanes can have a linear or branched structure.

Suitable silicone gums include polydiorganosiloxanes, such as those having a number-average molecular weight between 200,000 Da and 1,000,000 Da used alone or mixed with a solvent.

Non-limiting examples of suitable silicone gums include: polymethyl siloxane, polydimethyl siloxane/methyl vinyl siloxane gums, polydimethyl siloxane/diphenyl siloxane, polydimethyl siloxane/phenyl methyl siloxane, polydimethyl siloxane/diphenyl siloxane/methyl vinyl siloxane, and blends thereof.

Non-limiting examples of suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical, and grafted silicone polymers. The organo-modified silicones may be one from the amino functional silicone family.

The silicones may be used in the form of emulsions, nano-emulsions, or micro-emulsions.

The cationic polymers that may be used as conditioning agents according to the invention generally have a molecular weight (average number) from about 500 Da to about 5,000,000 Da, and particularly from about 1,000 Da to about 3,000,000 Da. The expression "cationic polymer" as used herein indicates any polymer having at least one cationic group.

The cationic polymers may be chosen from among polymers containing primary, secondary, tertiary amine, and/or quaternary ammonium groups that may form part of the main polymer backbone and/or side chain(s).

Non-limiting examples of suitable cationic polymers include polyamines, polyaminoamides, and quaternary polyammonium classes of polymers, such as:

(1) homopolymers and copolymers derived from acrylic or methacrylic esters or amides. The copolymers may contain one or more units derived from acrylamides, methacrylamides, diacetone acrylamides, acrylic or methacrylic acids or their esters, vinyllactams such as vinyl pyrrolidone or vinyl caprolactam, and vinyl esters. Non-limiting, specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone and dialkylaminoalkyl acrylate or methacrylate, optionally quaternized, such as the products sold under the name Gafquat™ by Ashland Specialty Ingredients; terpolymers of dimethyl amino ethyl methacrylate, vinyl caprolactam, and vinyl pyrrolidone such as the product sold under the name Gaffix™ VC 713 by Ashland Specialty Ingredients; the vinyl pyrrolidone/methacrylamidopropyl dimethylamine copolymer, marketed under the name Styleze™ CC 10 by Ashland Specialty Ingredients; and the vinyl pyrrolidone/quaternized dimethyl amino propyl methacrylamide copolymers such as the product sold under the name Gafquat™ HS 100 by Ashland Specialty Ingredients (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as hydroxy alkyl cellulose, and hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups, and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers include those described in U.S. Pat. Nos. 3,227,615 and 2,961,347.

(9) cyclopolymers of alkyl diallyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride.

(11) quaternary polyammonium polymers, including, for example, Mirapol® A 15, Mirapol® AD1, Mirapol® AZ1, and Mirapol® 175 products sold by Miranol.

(12) quaternary polymers of vinyl pyrrolidone and vinyl imidazole such as the products sold under the names Luviquat® FC 905, FC 550, and FC 370 by BASF Corporation.

(13) quaternary polyamines.

(14) reticulated polymers known in the art.

Other cationic polymers that may be used include cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The conditioning agent may comprise a protein or hydrolyzed cationic or non-cationic protein. Non-limiting examples of suitable compounds include: hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl, and blends thereof.

Non-limiting examples of suitable hydrolyzed cationic proteins include: Croquat® L, in which the quaternary ammonium groups include a C12 alkyl group, Croquat® M, in which the quaternary ammonium groups include C10-C18 alkyl groups, Croquat® S in which the quaternary ammonium groups include a C18 alkyl group, Crotein® Q in which the quaternary ammonium groups include at least one C1-C18 alkyl group, and blends thereof. These products are sold by Croda.

The conditioning agent may also comprise quaternized vegetable protein(s) such as wheat, corn, or soy proteins, non-limiting examples of which include: cocodimonium hydrolyzed wheat protein, laurdimonium hydrolyzed wheat protein, steardimonium hydrolyzed wheat protein, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, n-stearoyl phytosphingosine, 2-N-palmitoyl amino-hexadecane-1,3-diol, bis-(N-hydroxy ethyl n-cetyl) malonamide, n-(2-hydroxy ethyl)-N-(3-cetoxyl-2-hydroxy propyl)amide of cetylic acid, n-docosanoyl n-methyl-D-glucamine, and blends thereof.

The conditioning agent may also comprise a cationic surfactant such as a salt of a primary, secondary, or tertiary fatty amine, optionally polyoxyalkylenated, a quaternary ammonium salt, a derivative of imadazoline, or an amine oxide. Conditioning agents may also be selected from the group consisting of: mono-, di-, and tri-alkyl amines, and quaternary ammonium compounds with a counterion such as a chloride, a methosulfate, a tosylate, etc. Non-limiting examples of suitable amines include: cetrimonium chloride, dicetyldimonium chloride, behentrimonium methosulfate, and blends thereof.

The conditioning agent may comprise a fatty amine. Non-limiting examples of suitable fatty amines include: dodecyl amines, cetyl amines, stearyl amines such as stearamidopropyl dimethylamine, and blends thereof.

The conditioning agent may comprise a fatty acid or derivative(s) thereof. Non-limiting examples of suitable fatty acids include: myristic acid, palmitic acid, stearic acid, behenic acid, oleic acid, linoleic acid, isostearic acid, and blends thereof. The derivatives of fatty acids include carboxylic ester acids including mono-, di-, tri- and tetra-carboxylic acids esters, amides, anhydrides, esteramides, imides, and mixtures of these functional groups.

Also suitable as conditioning agents are the following commercial products:

(1) Aquacat™ Clear Cationic Solution (INCI Name: guar hydroxypropyltrimonium Chloride), n-Hance™ SP-100 (INCI Name: acrylamidopropyl trimonium chloride/acrylamide copolymer), and n-Hance™ cationic guar (INCI Name: guar hydroxypropyltrimonium chloride) from Ashland Specialty Ingredients (2) Salcare® from BASF Corp.

(3) Softcat™ Polymers from The Dow Chemical Company.

(4) Jaguar® C500, Polycare® Boost, Mackconditioner™ Brite, and Mackine® 301 from Rhodia.

(5) Stepanquat® ML, Stepanquat® GA-90, Ninol®, and Ammonyx® from Stepan Company.

(6) Conditioneze™ 7 and Conditioneze™ NT-20 from Ashland Specialty Ingredients (Wayne, N.J.).

Of course, mixtures of two or more conditioning agents may be used.

The conditioning agent(s) may be present in an amount from about 0.001% to about 20%, particularly from about 0.01% to about 10%, and even more particularly from about 0.1% to about 3% by weight of the composition.

Personal care compositions may optionally comprise antimicrobial agent(s).

Non-limiting examples of suitable water insoluble, non-cationic antimicrobial agents include: halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, halogenated carbanilides, and blends thereof.

Non-limiting examples of suitable water soluble antimicrobial agents include: quaternary ammonium salts, bis-biquanide salts, triclosan monophosphate, and blends thereof.

The quaternary ammonium agents include those in which one or two of the substituents on the quaternary nitrogen has a carbon chain length (typically alkyl group) from about 8 to about 20, typically from about 10 to about 18 carbon atoms, while the remaining substituents (typically alkyl or benzyl group) have a lower number of carbon atoms, such as from about 1 to about 7 carbon atoms, typically methyl or ethyl groups.

Non-limiting examples of suitable quaternary ammonium antibacterial agents include: Dodecyl trimethyl ammonium bromide, tetradecylpyridinium chloride, domiphen bromide, n-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methyl hexahydropyrimidine, benzalkonium chloride, benzethonium chloride, methyl benzethonium chloride, and blends thereof.

Other antimicrobial compounds are bis[4-(R-amino)-1-pyridinium]alkanes as disclosed in U.S. Pat. No. 4,206,215. Other antimicrobials such as copper salts, zinc salts and/or stannous salts may also be included. Also useful are enzymes, including endoglycosidase, papain, dextranase, mutanase, and blends thereof. Such antimicrobial agents are disclosed in U.S. Pat. Nos. 2,946,725 and 4,051,234. The antimicrobial agents may also comprise chlorhexidine, triclosan, and flavor oils such as thymol. Triclosan and other agents are disclosed in U.S. Pat. Nos. 5,015,466 and 4,894,220.

In particular embodiments, one or more preservatives may be included.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof.

In particular embodiments, preservative boosters/solvents may be incorporated, non-limiting examples of which include: caprylyl glycol, hexylene glycol, pentylene glycol, ethylhexylglycerin, caprylhydroxamic acid, caprylohydroxamic acid, glyceryl caprylate, and blends thereof.

Polysaccharides, such as gum Arabic, may be included as well.

Personal care compositions may comprise liquid or liquid-like carrier(s) that help to distribute, disperse, and/or dissolve the ingredients.

Non-limiting examples of suitable liquid carriers include: water, alcohols, oils, esters, and blends thereof.

The compositions of the invention may also be in the form of aqueous or hydro-alcoholic solutions.

The physiological and cosmetically acceptable medium may consist exclusively of water, a cosmetically acceptable solvent, or a blend of water and a cosmetically acceptable solvent, such as a lower alcohol composed of C1 to C4, such as ethanol, isopropanol, t-butanol, n-butanol, alkylene glycols such as propylene glycol, and glycol ethers.

In one of the embodiment, the compositions of the invention may be anhydrous.

Typically, sun care compositions may also comprise one or more UV actives, which include organic and inorganic materials that scatter, absorb, and/or reflect radiation having a wavelength from about 100 nm to about 400 nm.

In one particular embodiment, the sun care compositions protect against UV-A, UV-B, and/or UV-C radiation.

UV-A radiation, from about 320 nm to about 400 nm, has the longest wavelengths within the UV spectrum, and consequently is the least energetic. UV-A radiation includes UV-A1 (from about 340 nm to about 400 nm) and UV-A2 (from about 320 nm to about 340 nm). UV-B radiation has shorter wavelengths, from about 290 nm to about 320 nm. UV-C radiation has the shortest wavelengths from about 200 nm to about 290 nm.

In another embodiment, the sun care compositions may not contain UV actives, and may be regarded as tanning oils or tan promoters.

Sun care compositions may be formulated, for example, for application to the lips, hair, face, cheeks, neck, area around the eyes, full hands, and body area. Self-tanning compositions, which are products that color skin without requiring full sun exposure, also fit under the sun care umbrella.

Suitable UV absorber(s) that may be included in the personal care compositions most likely will depend on local regulations. As the rules governing the names and usage levels evolve over time, it is impossible to include every UV absorber that may be used with the invention.

Non-limiting examples of suitable UV absorbers include: octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomenthyl salicylate; bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis(octylthiomethyl)-o-cresol; CAS number 65447-77-0; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-25 PABA; 2-(1,1-dimethylethyl)-6-[[3-(1,1-demethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl)propionate]; 2,6-di-tert-butyl-4-[4,6-bis(octylthio)-1,3,5-triazin-2-ylamino]phenol; 2-(2H-benzotriazole-2-yl)-4,6-bis(1-methyl-1-phenylethyl)phenol; trolamine salicylate; diethylanolamine p-methoxycinnamate; polysilicone-15; CAS number 152261-33-1; 4-methylbenzylidene camphor; bisoctrizole; n-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl)aminobenzoate; 6-tert-butyl-2-(5-chloro-2H-benzotriazole-2-yl)-4-methylphenol; p-aminobenzoic acid; 3,3',3'',5,5',5''-hexa-tert-butyl-α-α'-α''-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N, N'-bis-(2,2,6,6-tetramethyl-4-piperidinyl)-; 3-benzylidene camphor; terephthalylidene dicamphor sulfonic acid; camphor benzalkonium methosulfate; bisdisulizole disodium; etocrylene; ferulic acid; 2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethylamine hydroxybenzoyl hexylbenzoate; 3',3'-diphenylacryloyl)oxy]methyl}-propane; ethylhexyl p-methoxycinnamate, and blends thereof.

Personal care compositions may comprise antioxidant(s) and/or antiradical protecting agent(s).

Non-limiting examples of suitable antioxidants and/or antiradical protecting agents include: BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, lactoferrin, and blends thereof.

Personal care compositions may comprise vitamin(s), provitamin(s), and/or mineral(s).

Non-limiting examples of suitable vitamins include: ascorbic acid (vitamin C), vitamin E, vitamin E acetate, vitamin E phosphate, B vitamins such as B3 and B5, niacin, vitamin A, derivatives thereof, and blends thereof.

Non-limiting examples of suitable provitamins include: panthenol, retinol, and blends thereof.

Non-limiting examples of suitable minerals include: talc, clay, calcium carbonate, silica, kaolin, mica, and blends thereof. Further examples of minerals that may be used in the personal care compositions may be found in a brochure titled *Minerals for personal care* from Imerys Performance Minerals, the disclosure of which is hereby incorporated in its entirety by reference.

Personal care compositions may comprise one or more surfactants. Surfactants serve in solubilizing, dispersing, emulsifying and/or reducing the interfacial tension. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants may act as germicides in the compositions disclosed herein.

Nonionic surfactants useful herein include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Also suitable as surfactants are the following commercial products:

(1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™, Schercotaine™ and Schercoteric™; imidazolines, under the trade name Schercozoline™; pearlizing agents, under the trade name Quickpearl™; performance concentrates, under the trade names Sulfochem™ and Chemoryl™; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from Lubrizol.

(2) Avaniel, Cremaphore®, Jordapan®, and Pluracare® from BASF Corp.

(3) Miracare® SLB, Mackam® Bab, Mackanate® Ultra SI, Miranol® Ultra, and
Miracare Plaisant from Rhodia.

(4) Stepan® Pearl 2, Stepan® Pearl 4, Stepan® Pearl Series, Neobee M-20, Stepan® PTC, Amphosol® 2CSF, Steol®, Stepan-Mild® GCC, Stepan® SLL-FB, Stepanol® AM, Stepanol® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book *Surfactants in Personal Care Products and Decorative Cosmetics*, Third Edition, 2006, CRC Press. The disclosure is incorporated hereby in its entirety by reference.

Personal care compositions may be also be formulated as detergent compositions, such as shampoos, bath gels, and bubble baths. Such compositions comprise water as a liquid carrier. The surfactant or surfactants that form the washing base may be chosen alone or in blends, from known anionic, amphoteric, zwitterionic and/or non-ionic surfactants. The quantity and quality of the washing base must be sufficient to impart a satisfactory foaming and/or detergent value to the final composition. The washing base may be present in an amount from about 4% to about 50% by weight, particularly from about 6% to about 35% by weight, and more particularly from about 8% to about 25% by weight of the final composition.

Personal care compositions may comprise one or more thickener(s) and/or viscosifier(s).

Non-limiting examples of suitable thickeners and/or viscosifiers include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; arachis hypogaea (peanut) flour; ascorbyl methylsilanol pectinate; astragalus gummifer gum; attapulgite; avena sativa (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked bacillus/glucose/sodium glutamate ferment; cyamopsis tetragonoloba (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine;

ethylene/sodium acrylate copolymer; gelatin; gellan gum; glyceryl alginate; glycine soja (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/1 aureth-50/™ MG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/™ MG copolymer; PEG-150 pentaerythrityl tetrastearate; PEG-4 rapeseedamide; PEG-150/stearyl alcohol/SMDI copolymer; phaseolus angularis seed powder; polianthes tuberosa extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; pyrus cydonia seed; pyrus malus (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; rosa multiflora flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; solanum tuberosum (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia urens gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; triticum vulgare (wheat) germ powder; triticum vulgare (wheat) kernel flour; triticum vulgare (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; zea mays (corn) starch; and blends thereof.

Also suitable as thickeners and/or viscosifiers are the following commercial products:

(1) Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurf™ cetyl modified hydroxyethylcellulose, n-Hance™ cationic guar, n-Hance™ HP Series hydroxypropyl guar, n-Hance™ SP-100 conditioning polymer, and Supercol™ guar gum from Ashland Specialty Ingredients (2) Carbopol® Polymers, Fixate™ PLUS Polymer, Glucamate™ Thickeners, Amidex™ Surfactants, Chembetaine™ Surfactants, Chemoxide™ Surfactants, Chemonic™ Surfactants, Chemccinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid™ Diethanolamides from The Lubrizol Corporation.

(3) Salcare® and Luvigel® from BASF Corporation.

(4) Aculyn™ 22, Aculyn™ 28, Aculyn™ 33, Aculyn™ 38, and Aculyn™ 44 from The Dow Chemical Company.

(5) Ammonyx® C and Stepan-Mild® GCC from Stepan Company.

(6) Stabileze™, Rapithix™ A-60, Rapithix™ A-100, Ultrathix™ P-100, Lubrajel™ and FlexiThix™ from Ashland Specialty Ingredients (Wayne, N.J.).

Also suitable as a thickener/rheology modifier are lightly- to moderately-crosslinked polyvinylpyrrolidones. Disclosures of these polymers are provided in the following publications, each of which is hereby incorporated in its entirety by reference: U.S. Pat. Nos. 5,073,614; 5,312,619; 5,139,770; 5,716,634; 5,470,884; 5,759,524; 5,997,887; 6,024,942; as well as international application PCT/US10/26973, PCT/US10/26976, PCT/US10/26940, PCT/US11/32993, and PCT/US11/34515.

Personal care compositions may comprise natural extracts and/or natural products. Extensive details on natural products that can be used in personal care compositions is provided in book chapter "Chemistry of Cosmetics, Comprehensive Natural Products II" in *Chemistry and Biology*; volume 3, 2010.

Oral Care Composition Ingredients

Oral care compositions may optionally contain one or more additional ingredients. Non-limiting examples of suitable ingredients include: carriers, dentifrices, cleaning agents, breath freshening actives, pain relievers, anesthetics, anti-inflammatory agents, antimicrobial agents, antibacterial agents, anti-calculus agents, anti-plaque agents, gums, thickeners, gelling agents, surfactants, flavors, warming or tingling agents, tooth bleaching agents, whiteners, stain removers, stain preventers, abrasives, adhesives, colors, emollients, emulsifiers, preservatives, solvents, binders, stimulants, depressants, diet aids, smoking cessation aides, vitamins, minerals, throat-soothing agents, spices, herbs, herbal extracts, alkaloids (such as caffeine and nicotine), and humectants.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, as disclosed in e.g., U.S. Pat. No. 3,988,433. Carrier materials for biphasic dentifrice formulations are disclosed in U.S. Pat. Nos. 5,213,790; 5,145,666; 5,281,410; 4,849,213; and 4,528,180. Mouthwash, rinse or mouth spray carrier materials typically include water, flavoring and sweetening agents, etc., as disclosed in, e.g., U.S. Pat. No. 3,988,433. Lozenge carrier materials typically include a candy base; chewing gum carrier materials include a gum base, flavoring and sweetening agents, as in, e.g., U.S. Pat. No. 4,083,955. Sachet carrier materials typically include a sachet bag, flavoring and sweetening agents. For sub-gingival gels used for delivery of actives into the periodontal pockets or around the periodontal pockets, a "sub-gingival gel carrier" is chosen as disclosed in, e.g., U.S. Pat. Nos. 5,198,220 and 5,242,910. The selection of a carrier will depend on secondary considerations like taste, cost, and shelf stability, and other factors.

Oral care compositions may comprise one or more dental abrasives. Dental abrasives useful in the compositions include many different materials. The material selected must be one which is compatible within the composition of interest and does not excessively abrade dentin.

Non-limiting examples of suitable abrasives include: silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, resinous abrasive materials such as particulate condensation products of urea and formaldehyde, and blends thereof.

Another class of abrasives is the particulate thermosetting polymerized resins as described in U.S. Pat. No. 3,070,510.

Non-limiting examples of suitable resins include: melamines, phenolics, ureas, melamine-ureas, melamine-formaldehydes, urea-formaldehyde, melamine-urea-formaldehydes, cross-linked epoxides, cross-linked polyesters, and blends thereof.

Silica dental abrasives of various types may be employed because of their unique benefits of exceptional dental cleaning and polishing performance without unduly abrading tooth enamel or dentine. The silica abrasive polishing materials herein, as well as other abrasives, generally have an average particle size ranging from about 0.1 to about 30 microns, and particularly from about 5 to about 15 microns. The abrasive can be precipitated silica or silica gels such as the silica xerogels described in U.S. Pat. Nos. 3,538,230, and 3,862,307.

Non-limiting examples of suitable silica abrasives include: silica xerogels marketed under the trade name "Syloid" by the W. R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the invention are described in more detail in U.S. Pat. Nos. 4,340,583; 5,603,920; 5,589,160; 5,658,553; 5,651,958; and 6,740,311. Each of these disclosures is hereby incorporated in its entirety by reference.

Mixtures of abrasives can be used such as mixtures of the various grades of Zeodent® silica abrasives listed above.

The total amount of abrasive(s) in the oral care compositions typically range from about 6% to about 70% by weight; toothpastes may contain from about 10% to about 50% of abrasives by weight of the composition. Dental solution, mouth spray, mouthwash and non-abrasive gel compositions typically contain little or no abrasives.

Oral care compositions may comprise polymeric mineral surface active agent(s) (PMSAs). PMSAs include any agent which will have a strong affinity for the tooth surface, deposit a polymer layer or coating on the tooth surface and produce the desired surface modification effects. The "mineral" descriptor is intended to convey that the surface activity or substantivity of the polymer is toward mineral surfaces such as calcium phosphate minerals or teeth.

Non-limiting examples of suitable PMSAs include: polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate), poly(vinyl benzyl chloride), polycarboxylates, carboxy-substituted polymers, and blends thereof. Also suitable as polymeric mineral surface active agents are the carboxy-substituted alcohol polymers described in U.S. Pat. Nos. 5,292,501; 5,213,789, 5,093,170; 5,009,882; and 4,939,284; and the diphosphonate-derivatized polymers in U.S. Pat. No. 5,011,913; the synthetic anionic polymers including polyacrylates and copolymers of maleic anhydride or acid and methyl vinyl ether (e.g., Gantrez®), as described, for example, in U.S. Pat. No. 4,627,977. Another example of a polymeric mineral surface active agent is a diphosphonate modified polyacrylic acid.

Polymers with activity must have sufficient surface binding propensity to desorb pellicle proteins and remain affixed to enamel surfaces. For tooth surfaces, polymers with end or side chain phosphate or phosphonate functions may be used, although other polymers with mineral binding activity may prove effective depending upon adsorption affinity.

PMSAs are useful in the compositions because of their stain prevention benefit. It is believed the PMSAs provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSAs on teeth can also prevent stains from accruing due to disruption of binding sites of color bodies on tooth surfaces.

The ability of PMSA to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers. The desired surface effects may include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

Oral care compositions may comprise additional anticalculus agent(s), such as a pyrophosphate salt as a source of pyrophosphate ion.

Non-limiting examples of suitable pyrophosphate salts include: dialkali metal pyrophosphate salts, tetraalkali metal pyrophosphate salts, and mixtures thereof. Particularly, disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms may find utility.

In compositions of the invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, particularly from about 1.5% to about 10%, and more particularly from about 2% to about 6%. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, particularly less than about 10% of the total pyrophosphate dissolved in the composition. Tetrasodium pyrophosphate salt may be one such pyrophosphate salt in these compositions. Tetrasodium pyrophosphate may be the anhydrous salt form or the decahydrate form, or any other species stable in solid form in the oral care compositions. The salt is in its solid particle form, which may be its crystalline and/or amorphous state, with the particle size of the salt being small enough to be aesthetically acceptable and readily soluble during use. The amount of pyrophosphate salt useful in making these compositions is any tartar control effective amount, generally from about 1.5% to about 15%, particularly from about 2% to about 10%, and more particularly from about 3% to about 8% by weight of the oral care composition.

The pyrophosphate salts are described in more detail in *Kirk-Othmer Encyclopedia of Chemical Technology*, third edition, volume 17, Wiley-Interscience Publishers (1982).

Oral care compositions may comprise peroxide compounds.

Non-limiting examples of suitable peroxide compounds include: hydrogen peroxide and organic peroxides including urea peroxide, carbamide peroxide, glyceryl peroxide, benzoyl peroxide, derivatives thereof, and blends thereof.

Typically, the peroxide compound can be employed in amounts so that at least about 1% by weight of the composition comprises peroxide. The peroxide compound may comprise from about 2% to about 30% by weight of the composition. More particularly, the peroxide comprises from about 3% to about 15% by weight of the composition. A typical peroxide concentration in the composition is generally from about 2% to about 7% by weight for home use products, and from about 15% to about 20% by weight for dental professional use.

Thickening or gelling agents used in dentifrice compositions may include nonionic polyoxyethylene polyoxypropylene block copolymers. Illustrative of polyoxyethylene polyoxypropylene block copolymers useful in the practice include block copolymers having the formula $HO(C_2H_4O)_b(C_3H_6O_6)_a(C_2H_4O)_bH$ wherein a is an integer such that the hydrophobic base represented by ($C_3H_6O_6$) has a molecular weight of about 2,750 Da to 4000 Da, b is an integer such that the hydrophilic portion (moiety) represented by ($C_2H_4O$) constitutes from about 70% to about 80% by weight of the copolymer. Block copolymers of this composition are available commercially under the trademark Pluronic® F type.

Pluronic® F127 has a molecular weight of 4,000 Da and contains 70% of the hydrophilic polyoxyethylene moiety.

Also suitable as a thickening agent is lightly- to moderately-crosslinked PVP, described in international application PCT/US11/30642.

The thickening agents may be present in an amount from about 15% to about 50% by weight, particularly from about 25% to about 45% by weight of the composition.

Surfactants may also be included in the oral care compositions of the invention, where they may serve in solubilizing, dispersing, emulsifying and/or reducing the surface tension of the teeth in order to increase the contact between the tooth and the peroxide. The compositions may also comprise surfactants, also commonly referred to as sudsing agents. Suitable surfactants are those which are reasonably stable and foam throughout a wide pH range. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type. Many suitable anionic surfactants are disclosed in U.S. Pat. No. 3,959,458. The compositions may comprise an anionic surfactant in an amount from about 0.025% to about 9% by weight, particularly from about 0.05% to about 5% by weight, and more particularly from about 0.1% to about 1% by weight of the composition.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate. The sarcosinate surfactant may be present in the compositions from about 0.1% to about 2.5%, particularly from about 0.5% to about 2.0% by weight of the total composition.

Non-limiting examples of suitable cationic surfactants include: derivatives of aliphatic quaternary ammonium compounds having at least one long alkyl chain containing from about 8 to about 18 carbon atoms such as lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Also suitable are the quaternary ammonium fluorides described in U.S. Pat. No. 3,535,421, where the quaternary ammonium fluorides have detergent properties. Certain cationic surfactants can also act as germicides in the compositions disclosed herein.

Nonionic surfactants that may be used in the compositions of the invention include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Oral care compositions may comprise flavor(s).

Non-limiting examples of suitable flavors include: methyl salicylate, ethyl salicylate, methyl cinnamate, ethyl cinnamate, butyl cinnamate, ethyl butyrate, ethyl acetate, methyl anthranilate, iso-amyl acetate, iso-armyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, α-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone, and blends thereof.

Generally suitable flavoring agents are those containing structural features and functional groups that are less prone to oxidation by peroxide. These include derivatives of flavor chemicals that are saturated or contain stable aromatic rings or ester groups.

Also suitable are flavor chemicals that may undergo some oxidation or degradation without resulting in a significant change in the flavor character or profile. The flavor chemicals, including menthol, may be provided as single or purified chemicals rather than supplied in the composition by addition of natural oils or extracts such as peppermint, spearmint, or wintergreen oils as these sources may contain other components that are relatively unstable and may degrade in the presence of peroxide. Flavoring agents are generally used in the compositions at levels of from about 0.001% to about 5% by weight of the composition.

The flavor system may typically include sweetening agent(s). Sweeteners include compounds of natural and artificial origin.

Non-limiting examples of suitable water-soluble natural sweeteners include: monosaccharides, disaccharides and polysaccharides, such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and blends thereof.

Non-limiting examples of suitable water-soluble artificial sweeteners include: soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-a-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, derivatives thereof, and blends thereof. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) may be used. The compositions may contain sweetener(s) in an amount from about 0.1% to about 10% by weight, in particular from about 0.1% to about 1% by weight of the composition.

In addition, the flavor system may include salivating agents, warming agents, and numbing agents. These agents are present in the compositions in an amount from about 0.001% to about 10% by weight, particularly from about 0.1% to about 1% by weight of the composition.

A non-limiting example of suitable salivating agent includes Jambus® manufactured by Takasago. Non-limiting examples of suitable warming agents include capsicum and nicotinate esters such as benzyl nicotinate. Non-limiting examples of suitable numbing agents include benzocaine, lidocaine, clove bud oil, ethanol, and blends thereof.

Oral care compositions may comprise chelating agent(s).

The chelating agents may include metal solubilizing agents and metal precipitating agents. The metal solubilizing agents include a condensed pyrophosphate compound. For purposes of this invention "condensed phosphate" relates to an inorganic phosphate composition containing two or more phosphate species in a linear or cyclic pyrophosphate form. The condensed phosphate may be sodium pyrophosphate, but may also include tripolyphosphate, hexametaphosphate, cyclic condensed phosphate or other similar phosphates well known in the field. The blend may also include an organic chelating agent. The term "organic phosphate" includes phosphonic acid, di and tri phosphonoc acid compound or its salts. An example of phosphonic acid is 1-hydroxyethylidene-1,1-diphosphonic acid that is sold under the trade name of Dequest®. The blend may also include a metal precipitating chelating agent. The term "metal precipitating chelating agent" is an agent that binds to metals and causes the metal to precipitate and includes halogens such as fluoride. The chelating agents are incorporated in the oral care compositions of the invention in an amount from about 0.1% to about 8.0% by weight, and particularly from about 0.5% to about 3.0% by weight of the composition, in a ratio of about 3:1:1 w/w organic chelating agent: condensed phosphate chelating agent: metal precipitating agent.

Another optional ingredient that may be used in oral care compositions is a humectant. For example, a humectant may be added to keep toothpaste compositions from hardening upon exposure to air, to give compositions a moist feel to the mouth, and, for particular humectants, to impart desirable sweetness of flavor to toothpaste compositions. The humectant, on a pure humectant basis, is generally present from about 0% to about 70%, particularly from about 5% to about 25% by weight of the composition.

Non-limiting examples of suitable humectants include: edible polyhydric alcohols such as glycerin, sorbitol, xylitol, butylene glycol, polyethylene glycol, propylene glycol, trimethyl glycine, and blends thereof.

The invention also contemplates oral care compositions comprising polymer(s) described herein complexed with hydrogen peroxide. A description of such complexes is present in international application WO 91/07184, the contents of which are hereby incorporated in their entirety by reference.

Also contemplated are oral care compositions such as those described in the following patents and patent applications, the contents of each are hereby incorporated in their entirety by reference: WO 2011/068514, WO 2011/053877, US 2010/0275394, US 2011/0076090, US 2008/091935, US 2008/0181716, US 2008/0014224, WO 2007/066837, US 2008/0292669, US 2007/0071696, US 2007/0154863, US 2008/0317797, US 2005/0249678, US 2007/0178055, US 2007/0189983, WO 2005/041910, U.S. Pat. No. 7,785,572, WO 1998/005749, WO 1997/022651, and U.S. Pat. No. 5,310,563.

Oral care compositions may comprise one or more denture adhesives.

Synthetic materials presently dominate the denture adhesive market. Such materials may consist of mixtures of the salts of short-acting polymers (e.g., carboxymethylcellulose or "CMC") and long-acting polymers (e.g., poly[lvinyl methyl ether maleate], or "Gantrez" and its salts). Polyvinylpyrrolidone (povidone) may also be used.

Other components of denture adhesive products impart particular physical attributes to the formulations. Petrolatum, mineral oil, and polyethylene oxide may be included in creams to bind the materials and to make their placement easier. Silicon dioxide and calcium stearate may be used in powders to minimize clumping. Menthol and peppermint oils may be used for flavoring, red dye for color, and sodium borate and methyl- or poly-paraben as preservatives.

It is also contemplated that the composition ingredients may be formulated in a single container, or the ingredients may be formulated in-part in two or more distinct containers of the same or different type, the contents of which may require mixing prior to use.

The UV-absorbing polymers according to the invention may be prepared according to the examples set out below. The examples are presented for purposes of demonstrating, but not limiting, the preparation of the compounds, polymers, and non-homopolymers according to the invention.

EXAMPLES

Example 1: Poly(IB/MA) Grafted with JT Benzone, Half Ethyl Ester and Sodium Salt Forms

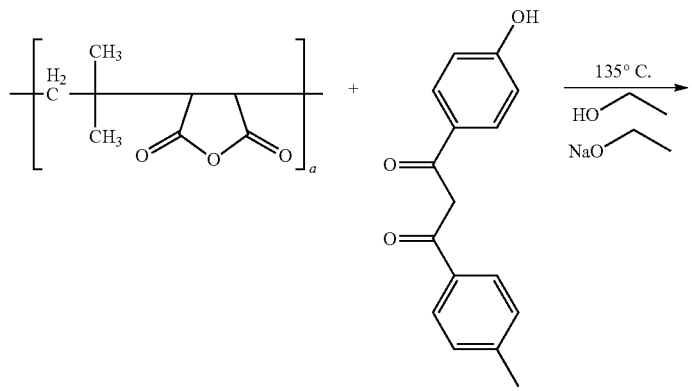

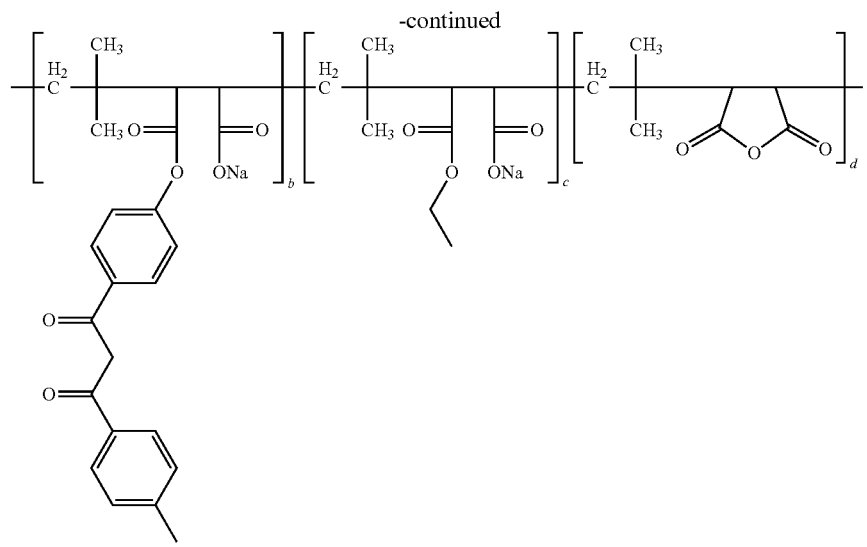

A premix was prepared having 0.8 g (3.25 mM) of JT benzone and 1.1 g (3.25 mM) NaOEt/EtOH, and then 1.0 7 of ethanol was added with stirring until the premix was thoroughly dissolved. Then, 5.0 g of poly(isobutylene-co-maleic anhydride) having a weight-average molecular weight ($M_w$) of 80,000 Da was added and the mixture heated to 135° C. for 10 hours. Afterward, the mixture was cooled to room temperature to obtain a clear dark yellow ethanol solution that was also soluble in ethanol/water solutions and oils, such di-isopropyl-adipate. The molar quantities are such that a=b+c+d.

This product can be used for personal care formulations, such as gels/emulsions for UV-A/B protection for hair and as a styling agent, and for UV-A/B suncare applications.

Example 2: Poly(IB/MA) Grafted with JT Benzone and Isobutylamine; Half Ethyl Ester, Amic Acid, and Imide Forms

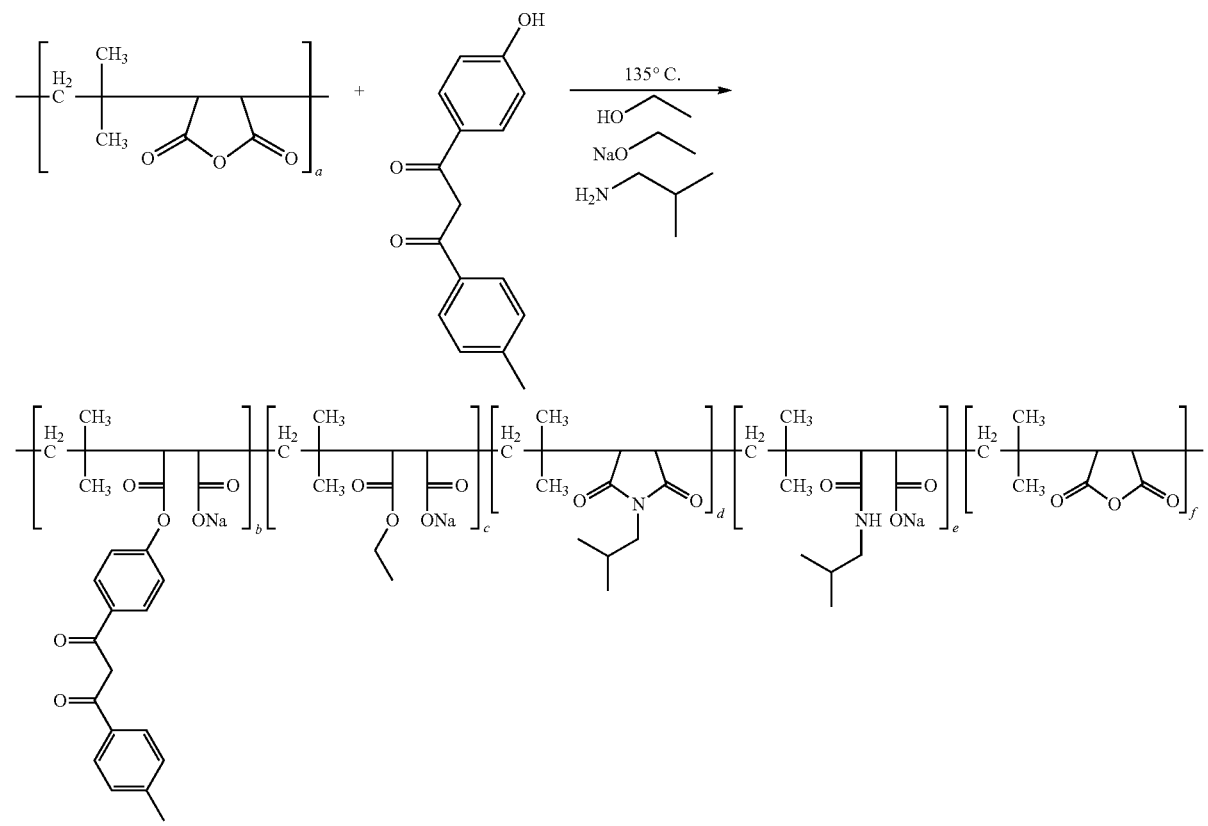

Example 1 was substantially repeated, except 1.9 g (26 mM) of isobutylamine was added to the premix, which was dissolved with 6.0 g ethanol. A clear dark yellow ethanol solution was obtained that was also soluble in ethanol/water solutions and oils like di-isopropyl-adipate. The molar quantities are such that a=b+c+d+e+f.

This product can be used for personal care formulations, such as gels/emulsions for UV-A/B protection for hair and as a styling agent, and for UV-A/B suncare applications.

Example 3: Poly(IB/MA) Grafted with JT Benzone and n-octylamine; Half Ethyl Ester, Amic Acid, Full Imide and Sodium Salt Forms

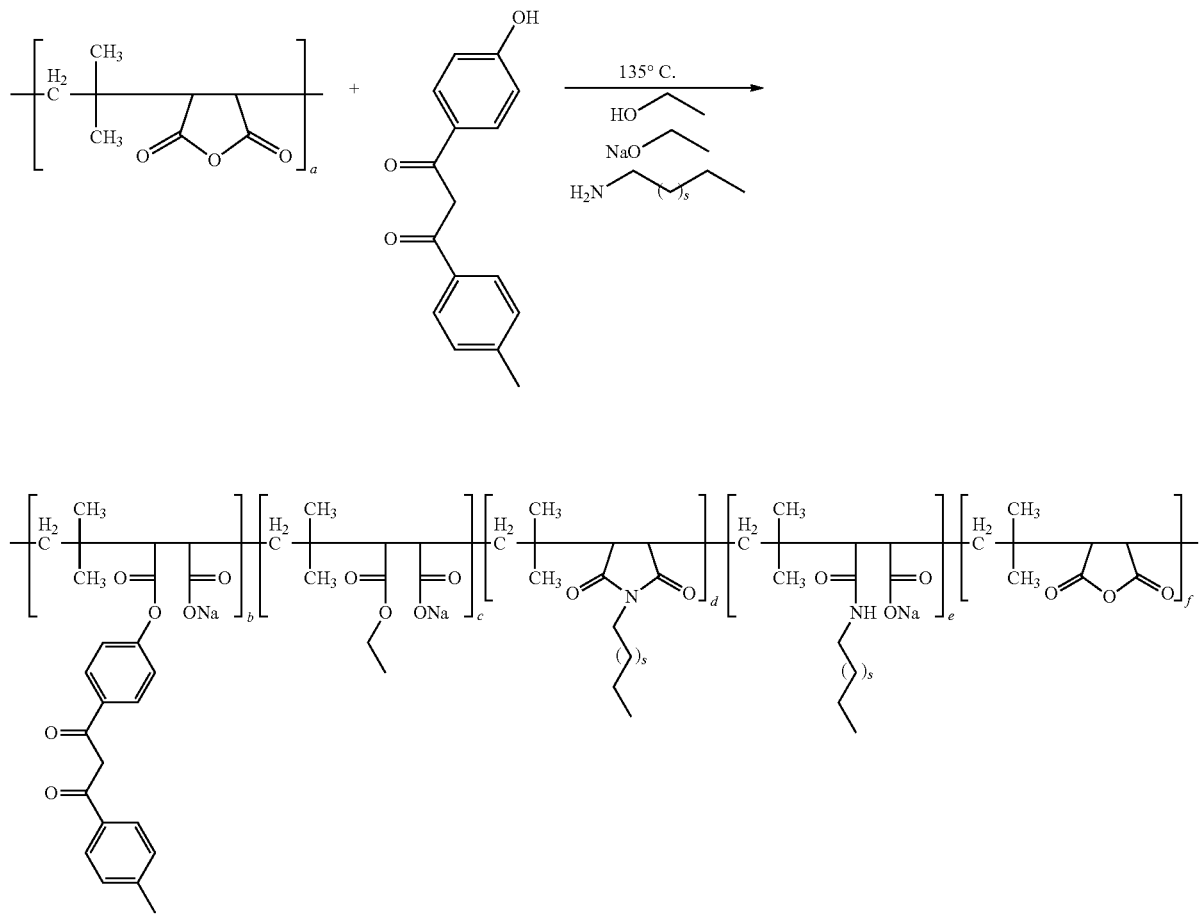

Example 2 was substantially repeated, except 3.3 g (26 mM) of n-octylamine was added to the premix, and it was dissolved with 6.0 g ethanol. A clear dark yellow ethanol solution was obtained that was also soluble in ethanol/water solutions and oils like di-isopropyl-adipate. The molar quantities are such that a=b+c+d+e+f.

This product can be used for personal care formulations, such as gels/emulsions for UV-A/B protection for hair and as a styling agent, and for UV-A/B suncare applications.

Example 4: Poly(IB/MA) Grafted with JT Benzone and n-dodecylamine; Half Ethyl Ester, Amic Acid, Full Imide and Sodium Salt Forms

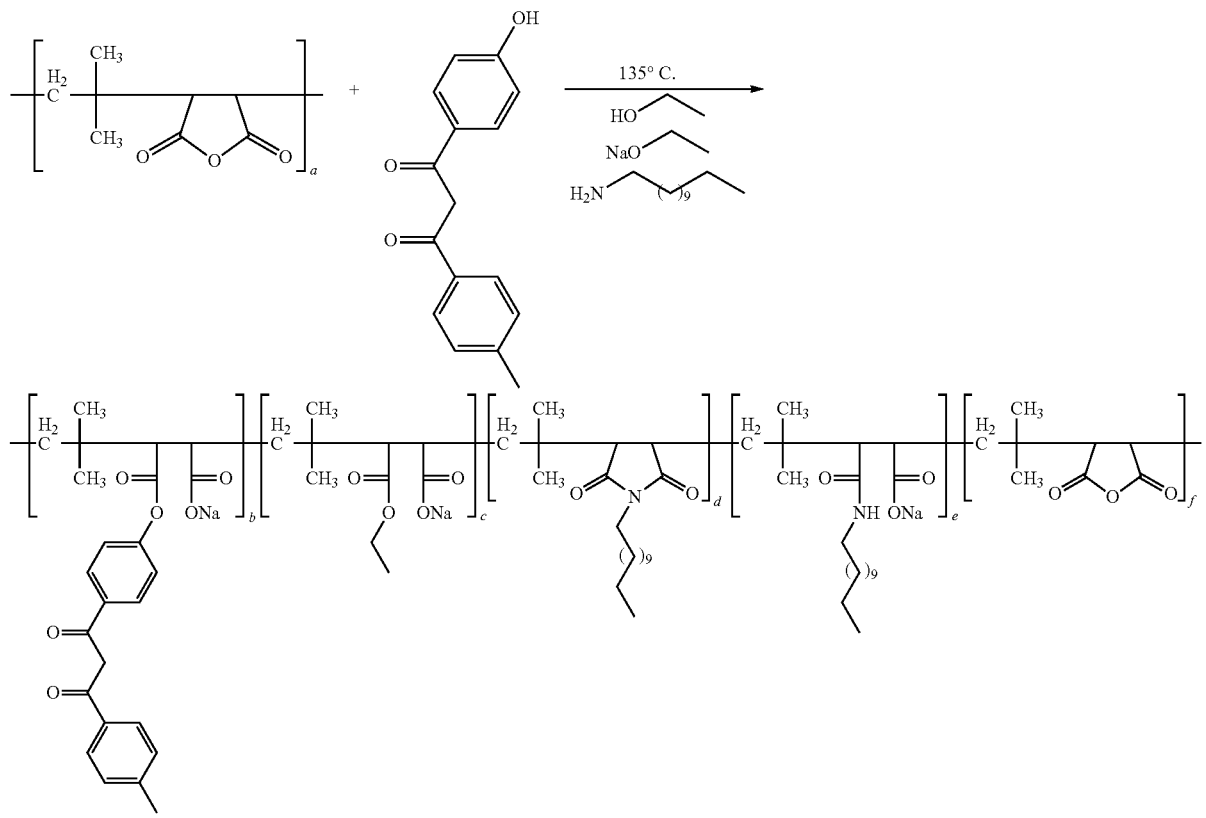

Example 2 was substantially repeated, except 4.8 g (26 mM) of n-dodecylamine was added to the premix, and it was dissolved with 6.0 g ethanol. A clear dark yellow ethanol solution was obtained that was also soluble in ethanol/water solutions and oils like di-isopropyl-adipate, or coconut, vegetable, or soybean oil. The molar quantities are such that a=b+c+d+e+f.

This product can be used for personal care formulations, such as gels/emulsions for UV-A/B protection for hair and as a styling agent, and for UV-A/B suncare applications.

Example 5: Poly(IB/MA) Grafted with JT Benzone and Dimethylaminopropylamine; Half Ethyl Ester, Amic Acid, Full Imide and Sodium Salt Forms

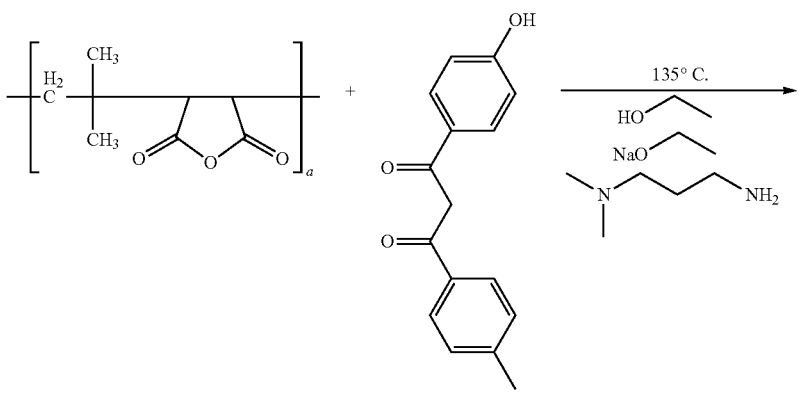

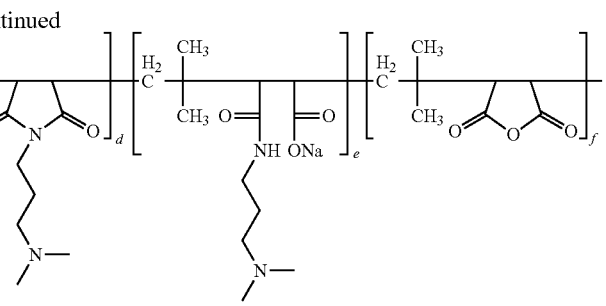
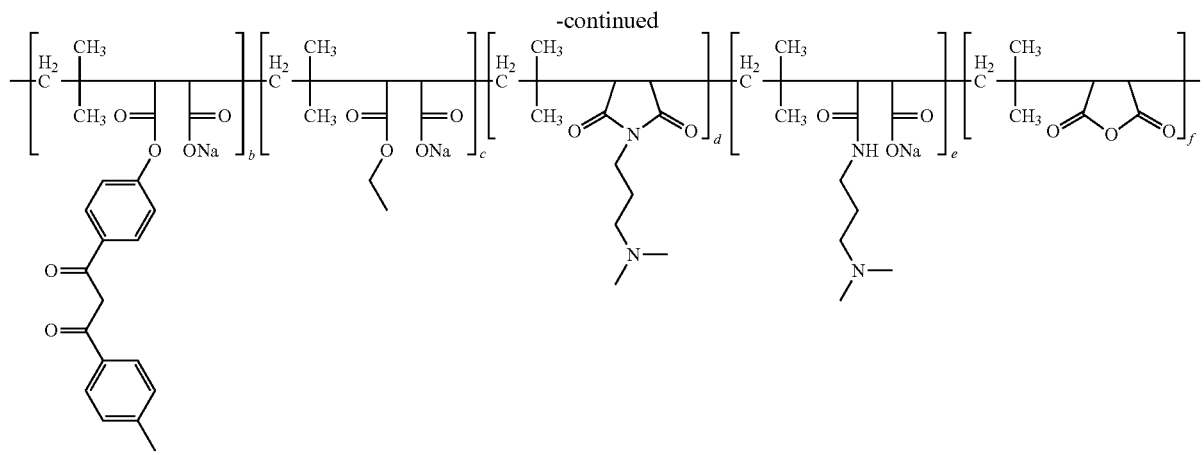

Example 2 was substantially repeated, except 2.7 g (26 mM) of dimethylaminopropylamine was added to the pre-mix, and it was dissolved with 9.0 g ethanol. A clear dark yellow ethanol solution was obtained that was also soluble in ethanol/water solutions and other alcohols. The molar quantities are such that a=b+c+d+e+f.

This product can be used for personal care formulations, such as gels/emulsions for UV-A/B protection for conditioning hair and/or skin applications.

Examples 6-10

Poly(IB/MA) Grafted with JT Benzone, Lower Molecular Weight Variants

Examples 1-5 are substantially repeated, in each case the poly(IB/MA) copolymer having a $M_w$, of 80,000 Da is replaced with the same copolymer having a $M_w$, of 6,000 Da. A clear dark yellow ethanol solution is obtained that is also soluble in ethanol/water solutions and other alcohols.

These products may be used for personal care formulations, such as gels/emulsions for UV-A/B protection for conditioning hair and/or skin applications.

Example 11: Poly(MVE/MA) Grafted with HE-JT Benzone; Half Ethyl Ester and Sodium Salt Forms

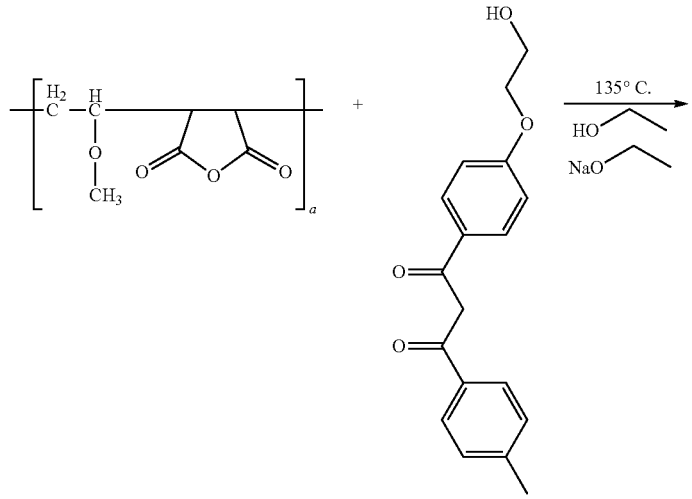

-continued

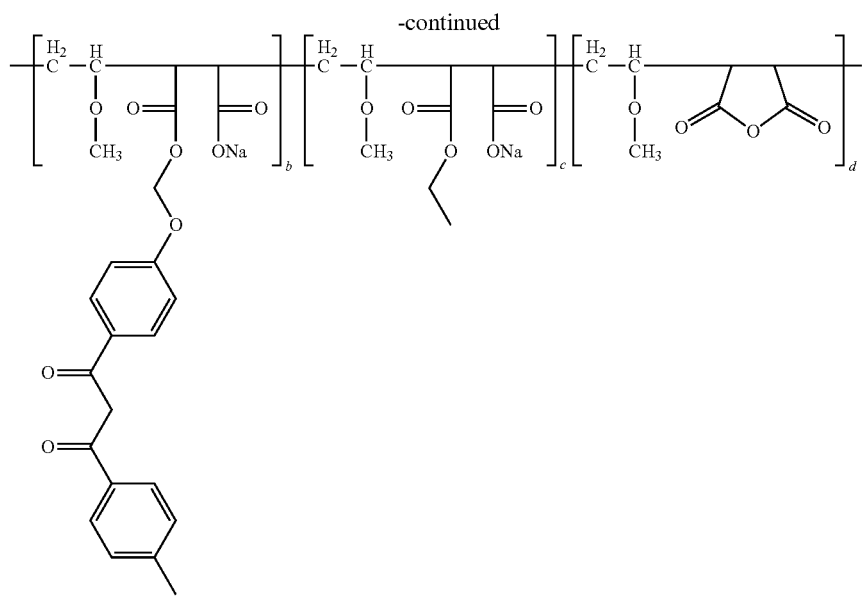

Example 1 was substantially repeated, replacing the poly(IB/MA) copolymer having a $M_w$, of 80,000 Da with a copolymer of methyl vinyl ether and maleic anhydride having a $M_w$, of 130,000 Da, and replacing the JT benzone with 0.94 g (3.25 mM) of HE-JT benzone. The clear, dark-colored product in ethanol solution was soluble in ethanol/water solutions and in oils like di-isopropyl adipate. The molar quantities are such that a=b+c+d.

This product can be used for personal care formulations, such as gels/emulsions for UV-A/B protection for hair and as a styling agent, and for UV-A/B suncare applications.

Example 12: Poly(MVE/MA) Grafted with HE-JT Benzone and Isobutylamine; Half Ethyl Ester, Amic Acid, Full Imide and Sodium Salt Forms

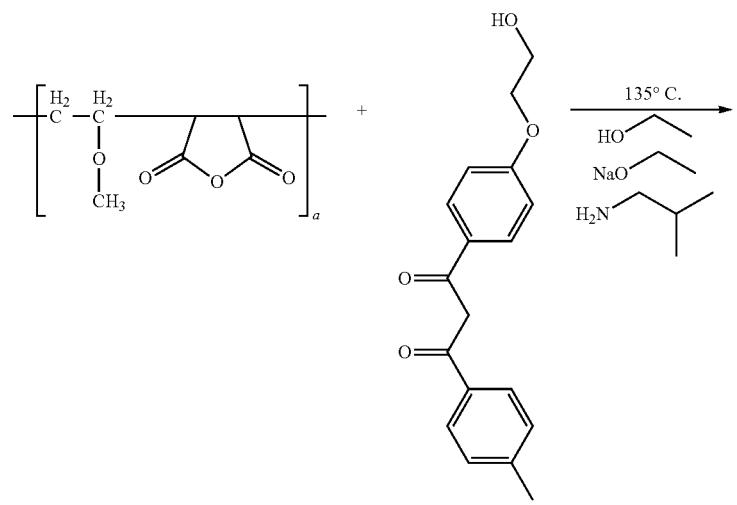

-continued

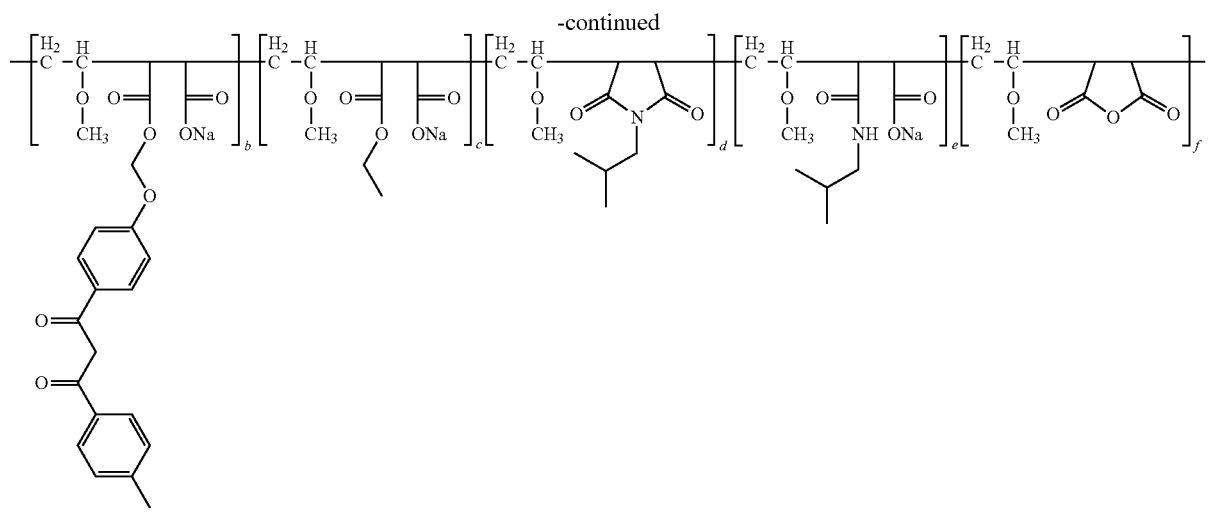

Example 11 is substantially repeated, except 1.9 g (26 mM) of isobutylamine is added to the premix, which is dissolved with 6.0 g ethanol. The molar quantities are such that a=b+c+d+e+f.

This product may be used for personal care gels/emulsions for UV-A/B protection for hair and as a styling agent, and for UV-A/B Skin sunscreen applications.

Example 13: Poly(MVE/MA) Grafted with HE-JT Benzone and n-octylamine; Half Ethyl Ester, Amic Acid, Full Imide and Sodium Salt Forms

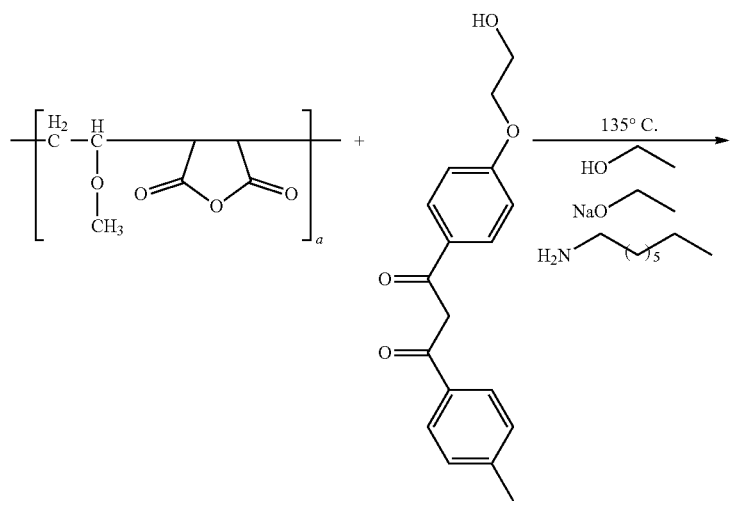

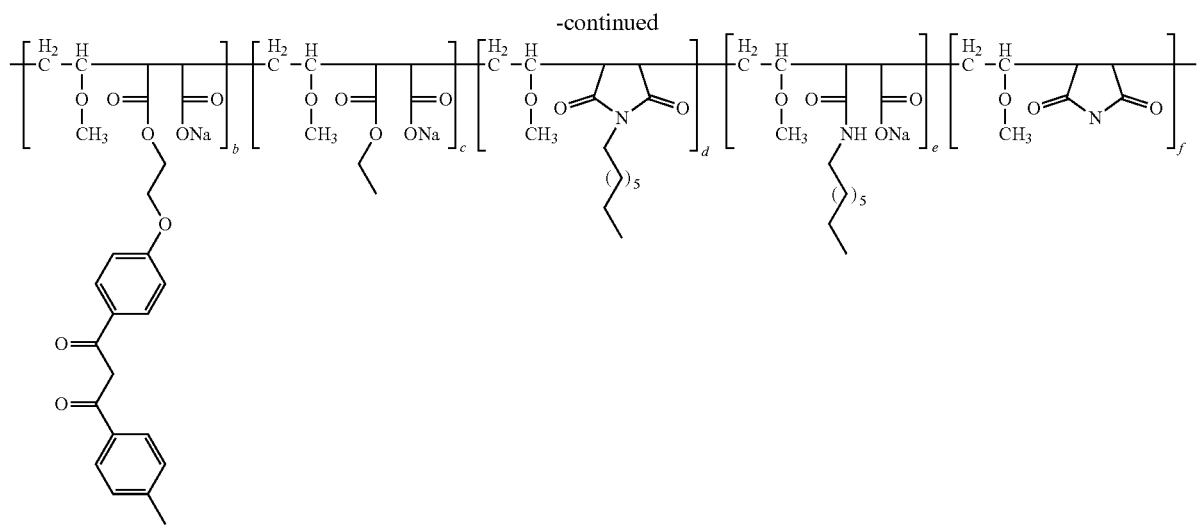

Example 11 is substantially repeated, except 3.3 g (26 mM) of n-octylamine is added to the premix, which is dissolved with 6.0 g ethanol. The product is cooled to room temperature to obtain a clear dark colored ethanol solution that is soluble in alcohols and in oils like di-isopropyl-adipate or coconut oil. The molar quantities are such that $a=b+c+d+e+f$.

This product may be used for personal care gels/emulsions for UV-A/B protection for hair and as a styling agent, and for UV-A/B suncare applications.

Example 14: Poly(MVE/MA) Grafted with HE-JT Benzone and n-dodecylamine; Half Ethyl Ester, Amic Acid, Full Imide and Sodium Salt Forms

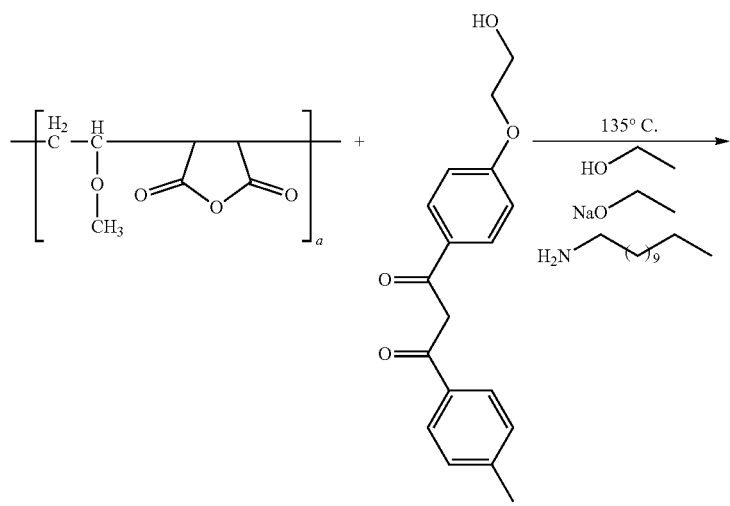

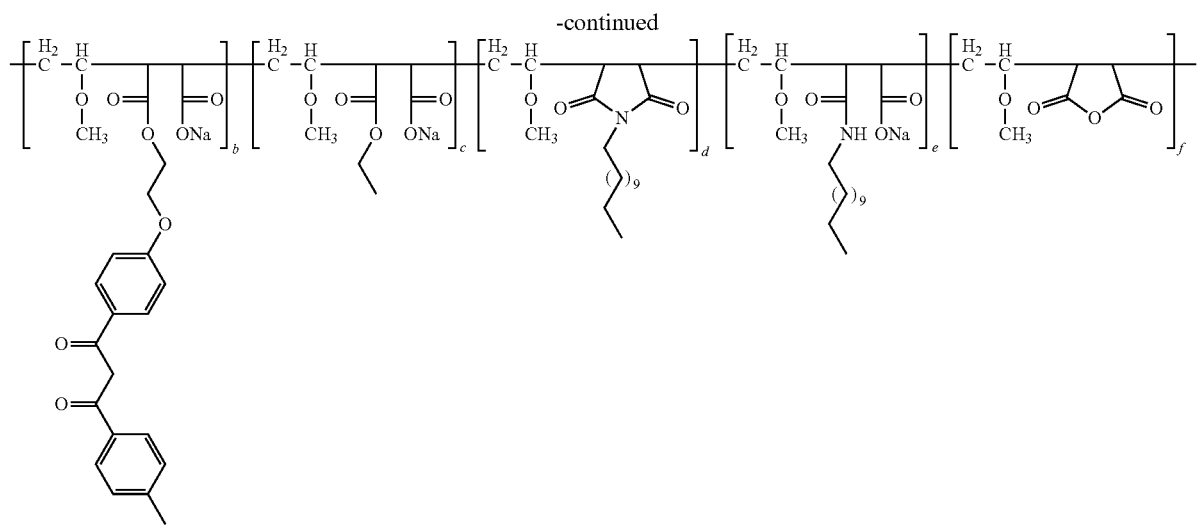

Example 11 is substantially repeated, except 4.8 g (26 mM) of n-dodecylamine is added to the premix, which is dissolved with 6.0 g ethanol. The product is cooled to room temperature to obtain a clear dark colored ethanol solution that is soluble in alcohols and in oils like di-isopropyl-adipate or coconut oil. The molar quantities are such that a=b+c+d+e+f.

This product may be used for personal care gels/emulsions for UV-A/B protection for hair and as a styling agent, and for UV-A/B suncare applications.

Example 15: Poly(MVE/MA) Grafted with HE-JT Benzone and Dimethylaminopropylamine; Half Ethyl Ester, Full Imide and Sodium Salt Forms

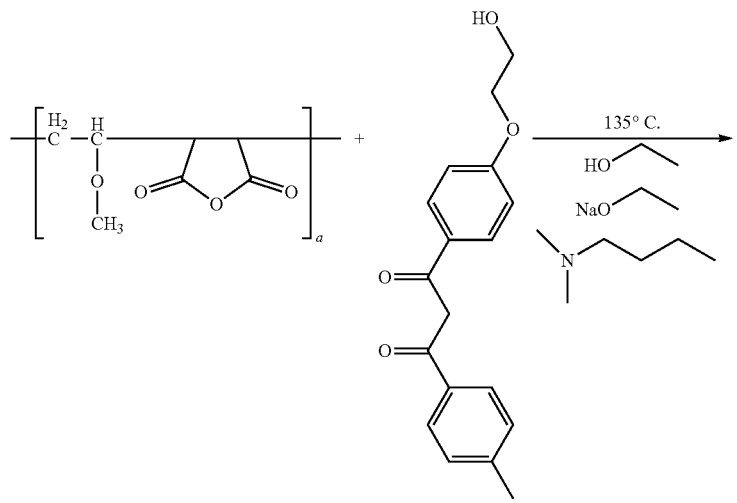

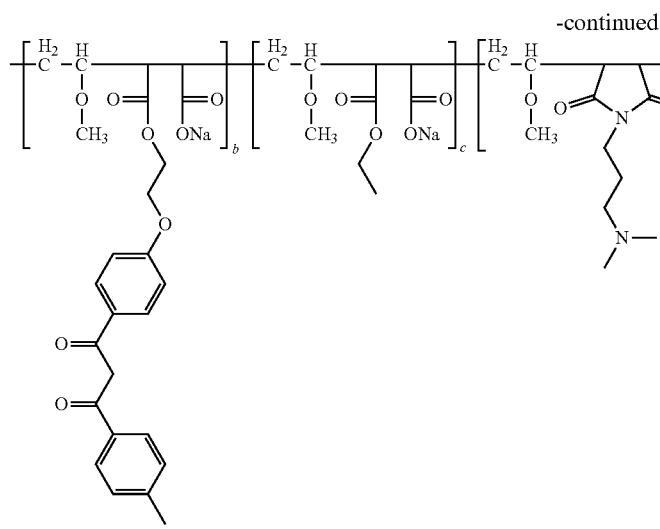

Example 11 is substantially repeated, except 3.3 g (26 mM) of n-dodecylamine is added to the premix, which was dissolved with 9.0 g ethanol. The product is cooled to room temperature to obtain a clear dark colored ethanol solution that is soluble in alcohols and in oils like di-isopropyl-adipate or coconut oil. The molar quantities are such that a=b+c+d+e+f.

This product may be used for personal care formulations, such as gels/emulsions for UV-A/B protection for conditioning hair and/or skin applications.

Examples 16-20

Poly(MVE/MA) Grafted with HE-JT Benzone, Lower Molecular Weight Variants

Examples 11-15 were substantially repeated, except the poly(MVE/MA) copolymer having a $M_w$, of 130,000 Da was replaced by an equal amount of the same copolymer having a $M_w$, of 2,500 Da. The products were cooled to room temperature to obtain clear dark colored ethanol solutions that was soluble in alcohols and in oils like di-isopropyl-adipate or coconut oil.

These products may be used for personal care formulations for hair and/or skin applications.

Example 21: Poly(Octadecene/MA) Grafted with HE-JT Benzone

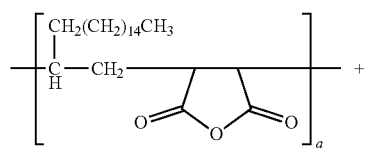

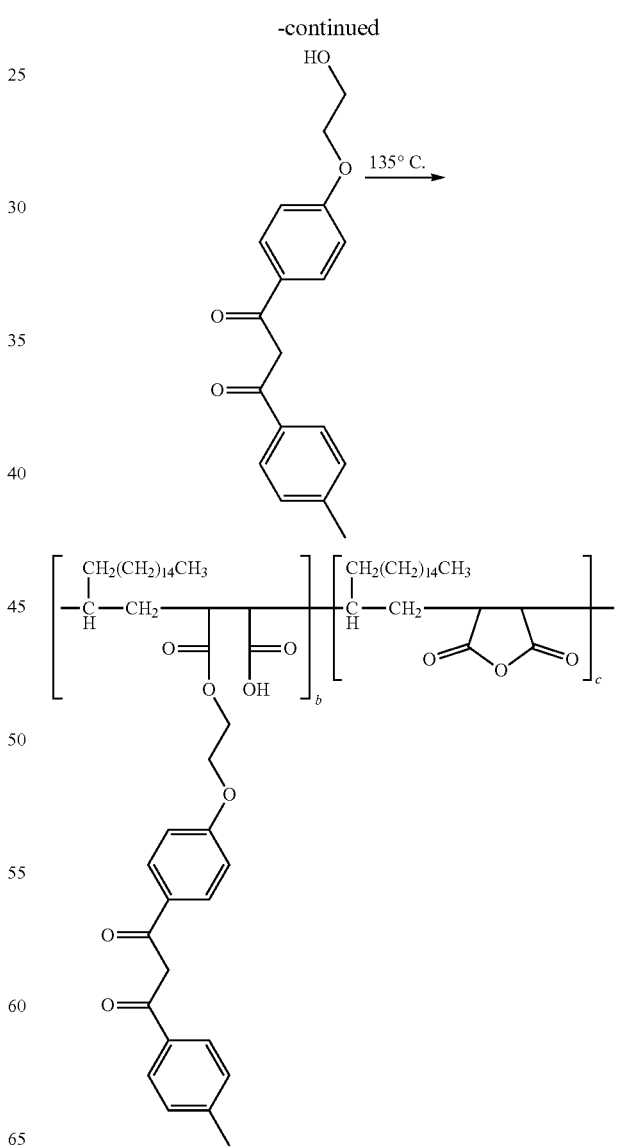

Example 11 was substantially repeated, replacing the poly(MVE/MA) copolymer having a Mw of 130,000 Da with a copolymer of octadecene and maleic anhydride having a Mw of 6,000 Da. Instead of ethanol, 24 g of cetyl alcohol was used to dissolve the HE-JT benzone, to which the copolymer was added and heated to 135° C. for 10 hours. The product was cooled to room temperature to obtain a creamy solid that was miscible in ethanol/water solutions and soluble in oils like di-isopropyl-adipate. The molar quantities are such that a=b+c.

This product can be used for personal care formulations, such as gels/emulsions for UV-A/B protection for hair and as a styling agent, and for UV-A/B suncare applications.

Example 22: Poly(Octadecene/MA) Grafted with HE-JT Benzone and Isobutylamine, Amic Acid and Full Imide Forms

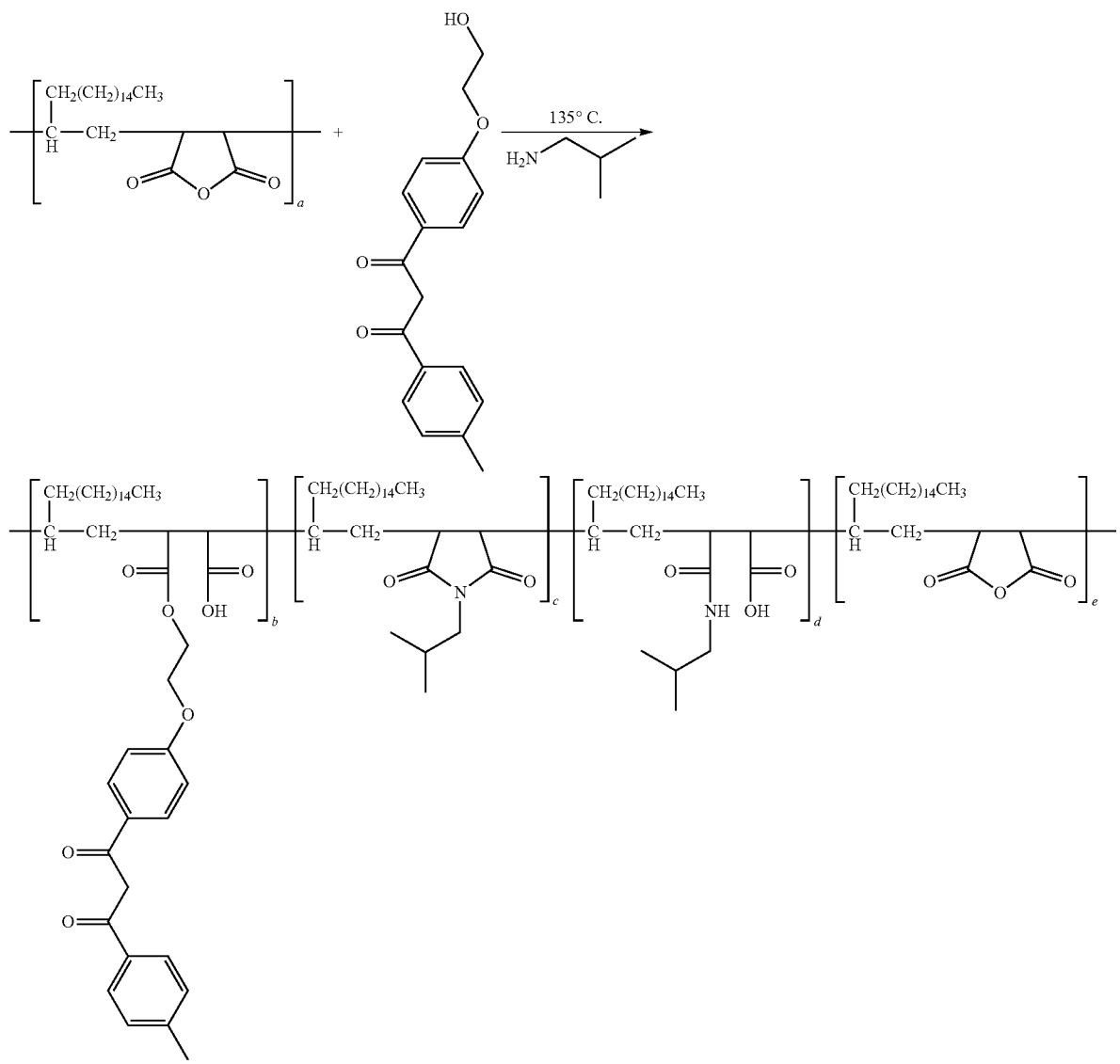

Example 21 was substantially repeated, except 1.9 g (26 mM) of isobutylamine was added to the HE-JT benzone and the cetyl alcohol. The product was cooled to room temperature to obtain a creamy solid that was miscible in ethanol/water solutions and soluble in oils like di-isopropyl-adipate. The molar quantities are such that a=b+c+d+e.

This product can be used for personal care formulations, such as gels/emulsions for UV-A/B protection for hair and as a styling agent, and for UV-A/B suncare applications.

Example 23: Poly(octadecene/MA) Grafted with HE-JT Benzone and n-octylamine, Amic Acid and Full Imide Forms

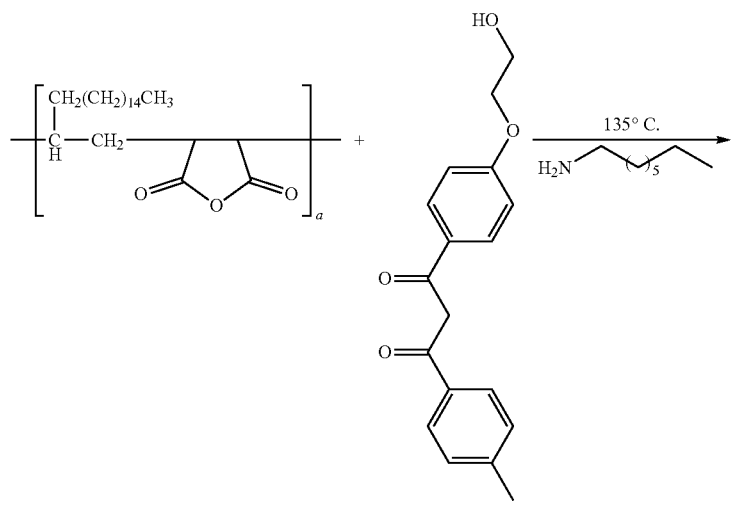

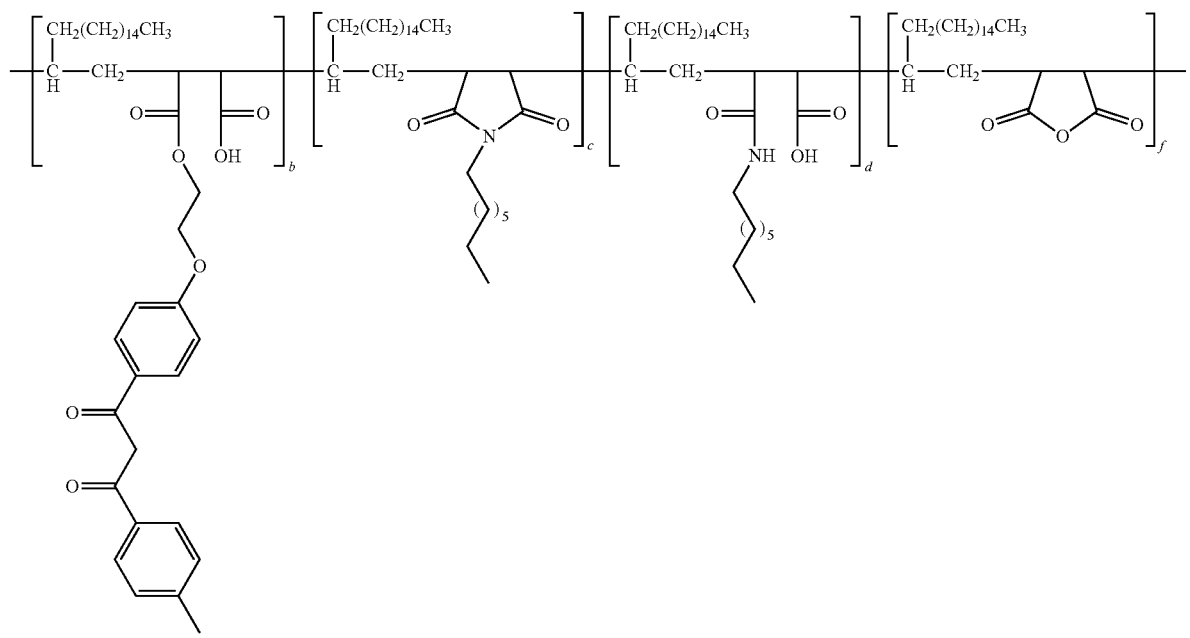

Example 22 was substantially repeated, except 3.3 g (26 mM) of n-octylamine replaced isobutylamine. The product was cooled to room temperature to obtain a creamy solid that was miscible in ethanol/water solutions and soluble in oils like di-isopropyl-adipate. The molar quantities are such that $a=b+c+d+e+f$.

Example 24: Poly(octadecene/MA) Grafted with HE-JT Benzone and n-dodecylamine, Amic Acid and Full Imide Forms

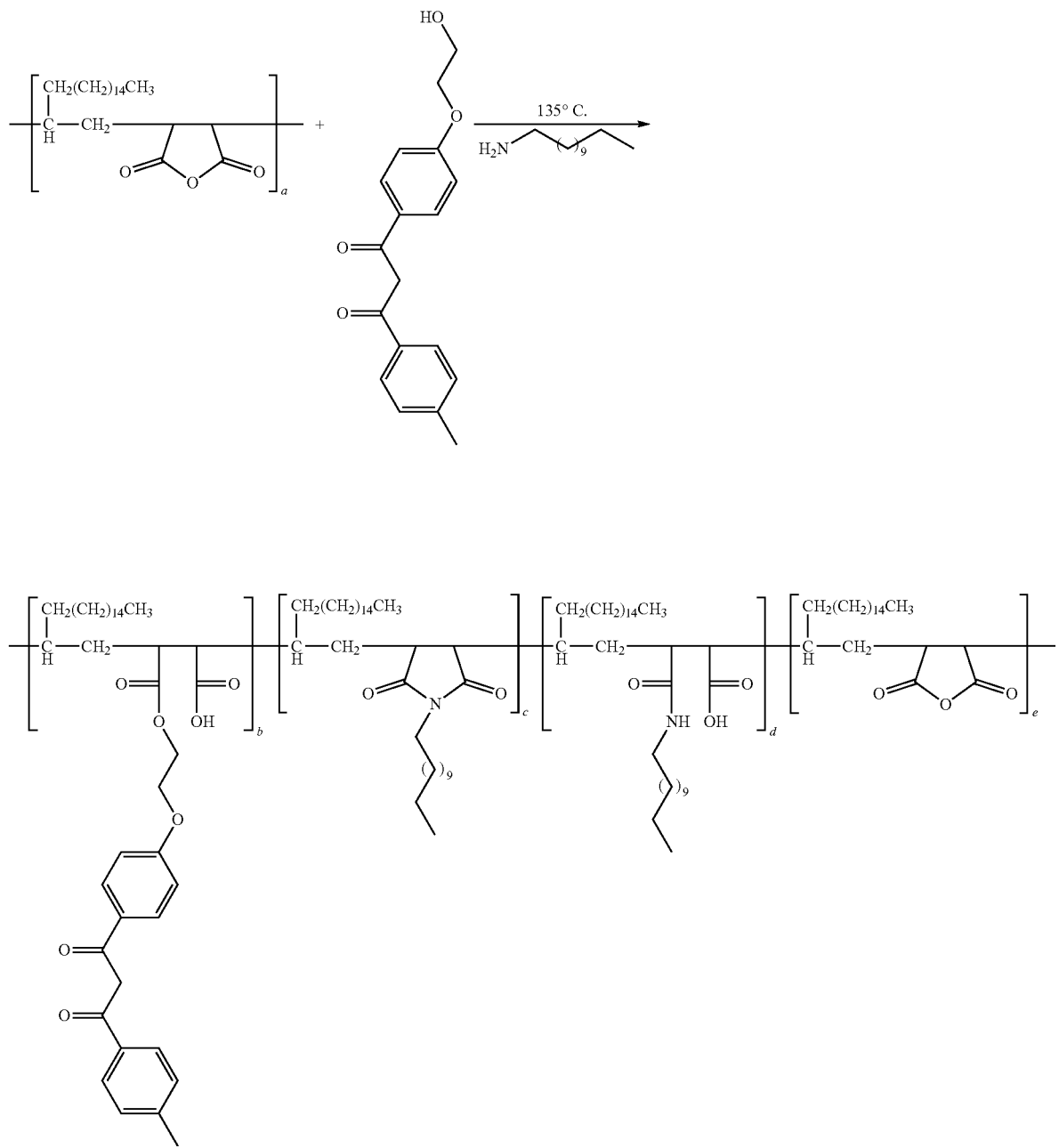

Example 22 was substantially repeated, except 1.9 g (26 mM) of n-dodecylamine replaced isobutylamine. The product was cooled to room temperature to obtain a creamy solid that was miscible in ethanol/water solutions and soluble in oils like di-isopropyl-adipate. The molar quantities are such that a=b+c+d+e.

Example 25: Poly(octadecene/MA) Grafted with HE-JT Benzone and Dimethylaminopropylamine, Amic Acid and Full Imide Forms
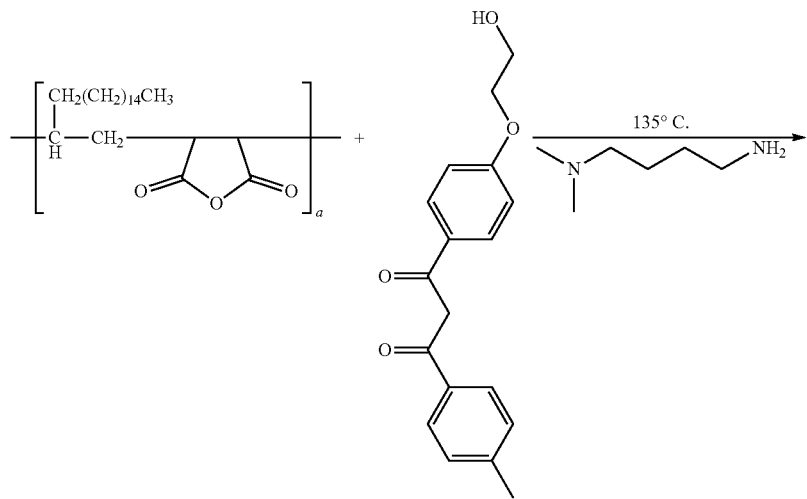
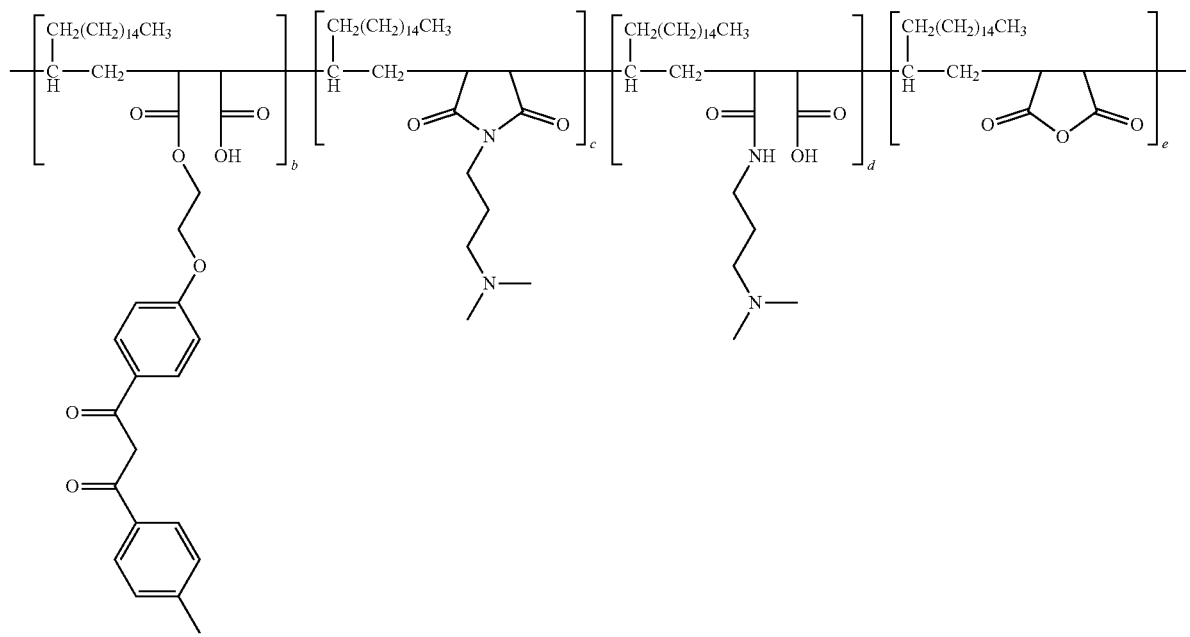

Example 22 was substantially repeated, except 2.7 g (26 mM) of dimethylpropylamine replaced isobutylamine. The product was cooled to room temperature to obtain a creamy solid that was miscible in ethanol/water solutions and soluble in oils like di-isopropyl-adipate. The molar quantities are such that a=b+c+d+e.

This product can be used for personal care formulations, such as gels/emulsions for UV-A/B protection for conditioning hair and/or skin applications.

Example 26: Poly(styrene/MA) Grafted with HE-JT Benzone

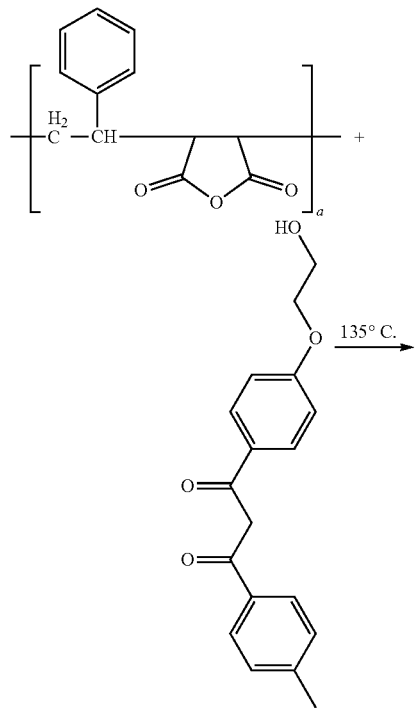

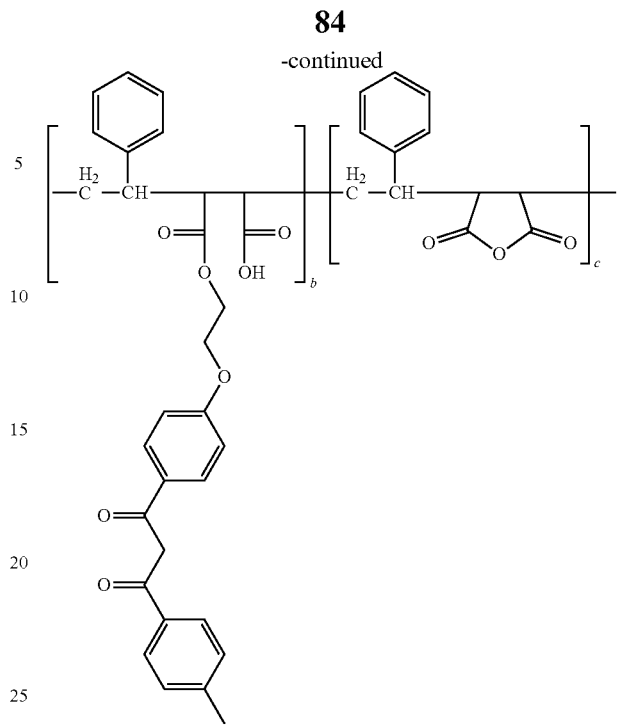

Example 21 was substantially repeated, replacing the poly(octadecene/maleic anhydride) copolymer having a $M_w$, of 6,000 Da with a copolymer of styrene and maleic anhydride having a $M_w$, of 6,000 Da, and replacing the JT benzone with 0.94 g (3.25 mM) of HE-JT benzone. The product was cooled to room temperature to obtain a creamy solid that was soluble in ethanol solutions and soluble in oils like di-isopropyl-adipate. The molar quantities are such that a=b+c.

This product can be used for personal care gels/emulsions for UV-A/B protection for hair and as a styling agent, and for UV-A/B suncare applications.

Example 27: Poly(styrene/MA) Grafted with HE-JT Benzone and Isobutylene, Amic Acid and Full Imide Forms

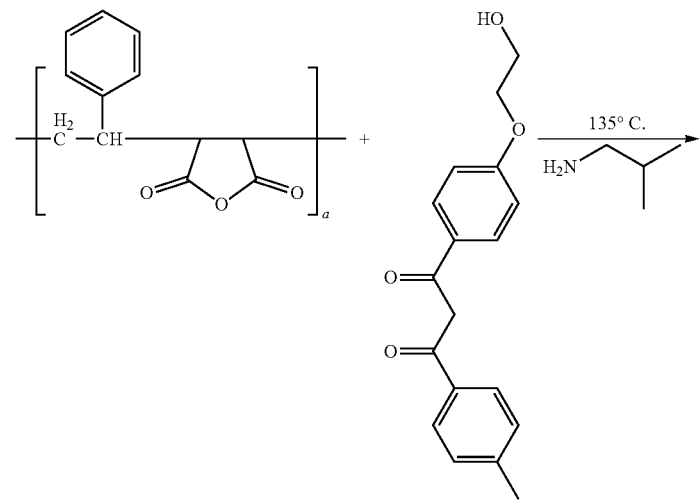

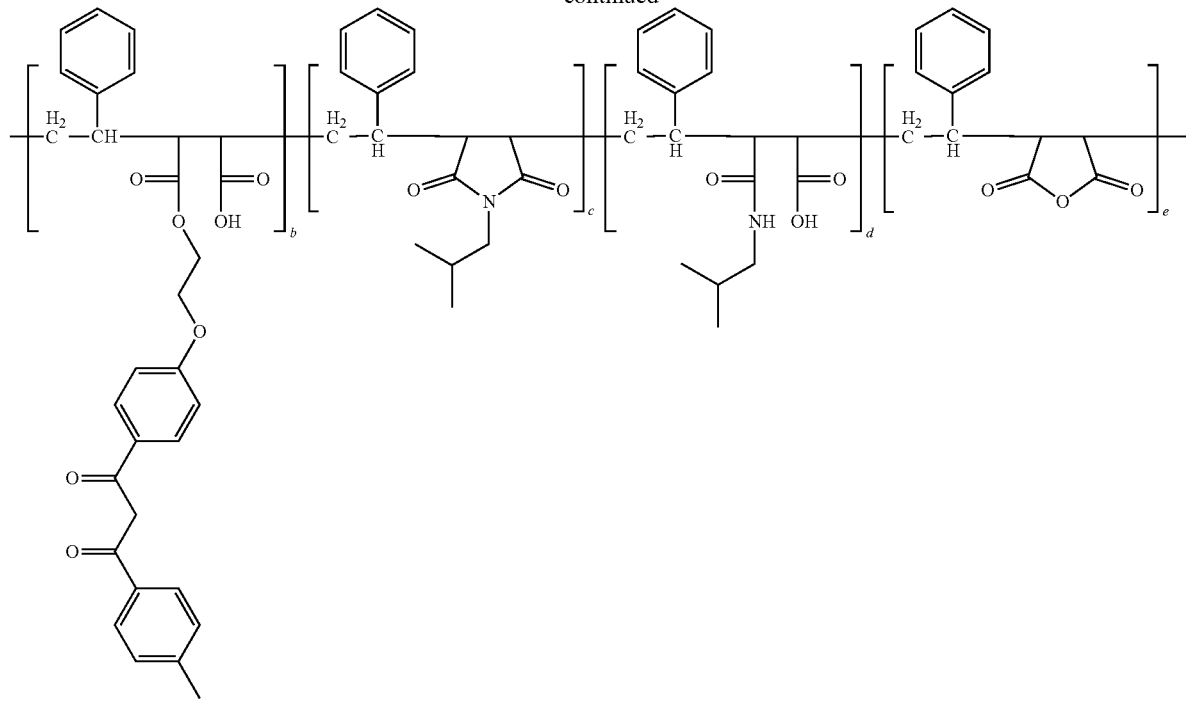

Example 26 was substantially repeated, except 1.9 g (26 mM) of isobutylamine was added to the HE-JT benzone and the cetyl alcohol. The product was cooled to room temperature to obtain a creamy solid that was soluble in ethanol solutions and soluble in oils like di-isopropyl-adipate. The molar quantities are such that a=b+c+d+e.

This product can be used for personal care gels/emulsions for UV-A/B protection for hair and as a styling agent, and for UV-A/B suncare applications.

Example 28: Poly(styrene/MA) Grafted with HE-JT Benzone and n-octylamine, Amic Acid and Full Imide Forms

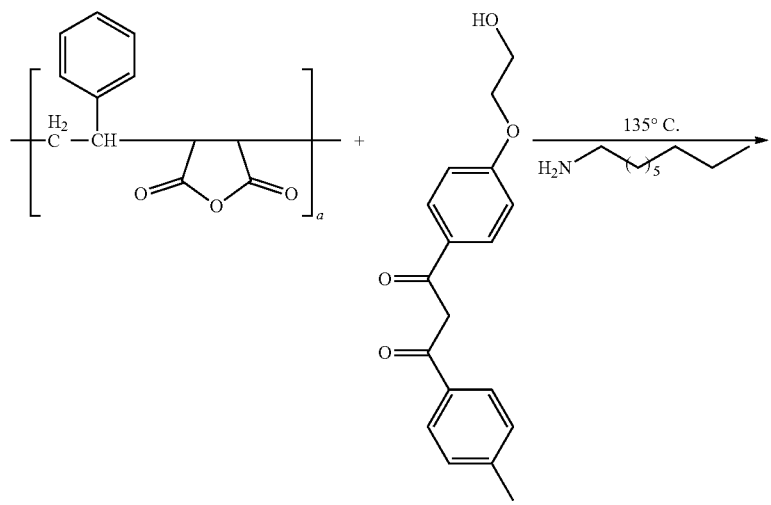

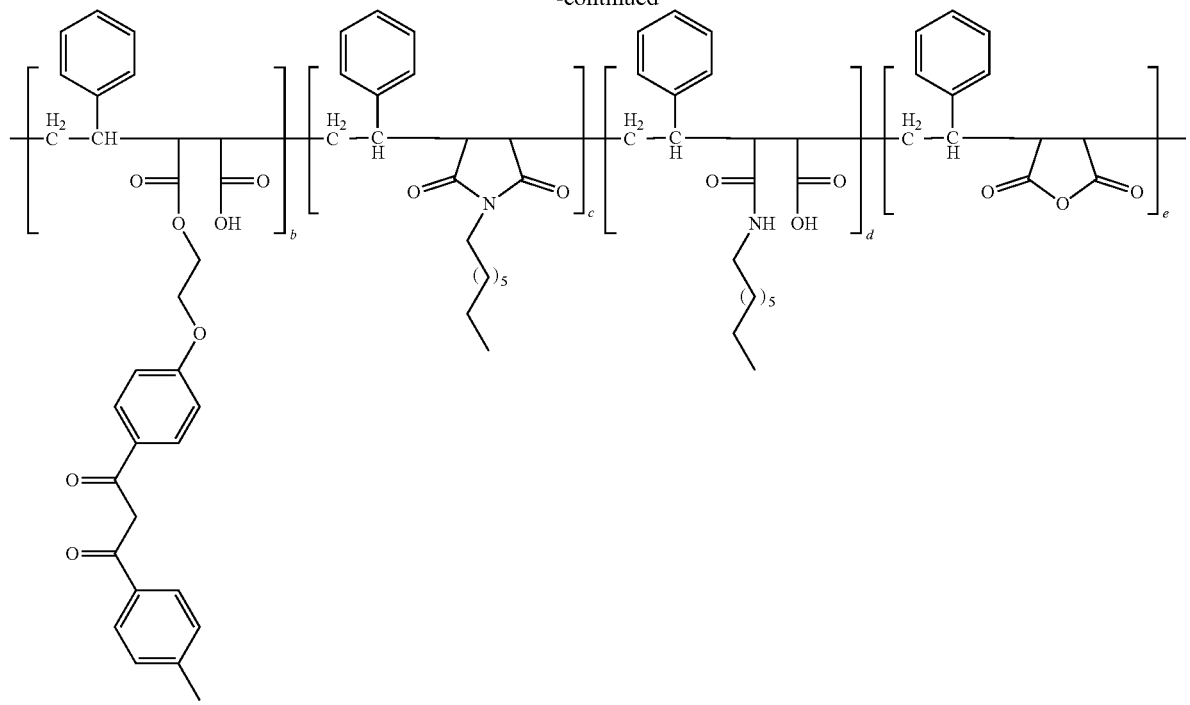

Example 26 was substantially repeated, except 3.3 g (26 mM) of n-octylamine replaced to isobutylene. The product was cooled to room temperature to obtain a creamy solid that was soluble in ethanol solutions and soluble in oils like di-isopropyl-adipate. The molar quantities are such that a=b+c+d+e.

This product can be used for personal care gels/emulsions for UV-A/B protection for hair and as a styling agent, and for UV-A/B suncare applications.

Example 29: Poly(styrene/MA) Grafted with HE-JT Benzone and n-dodecylamine, Amic Acid and Full Imide Forms

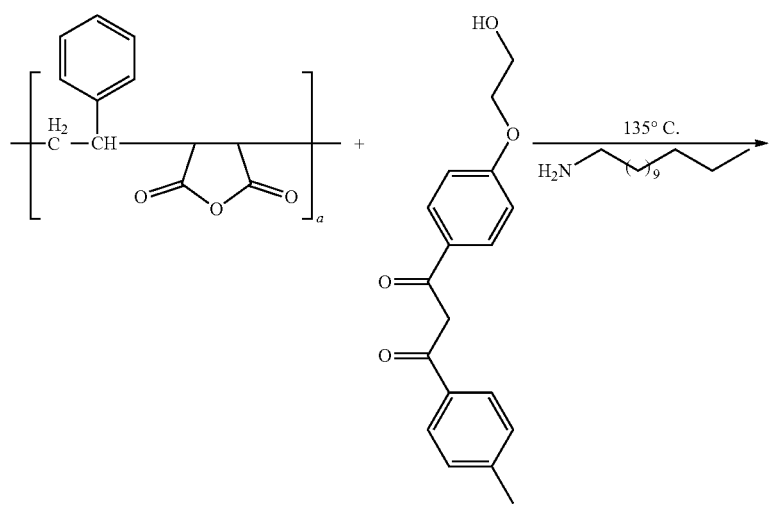

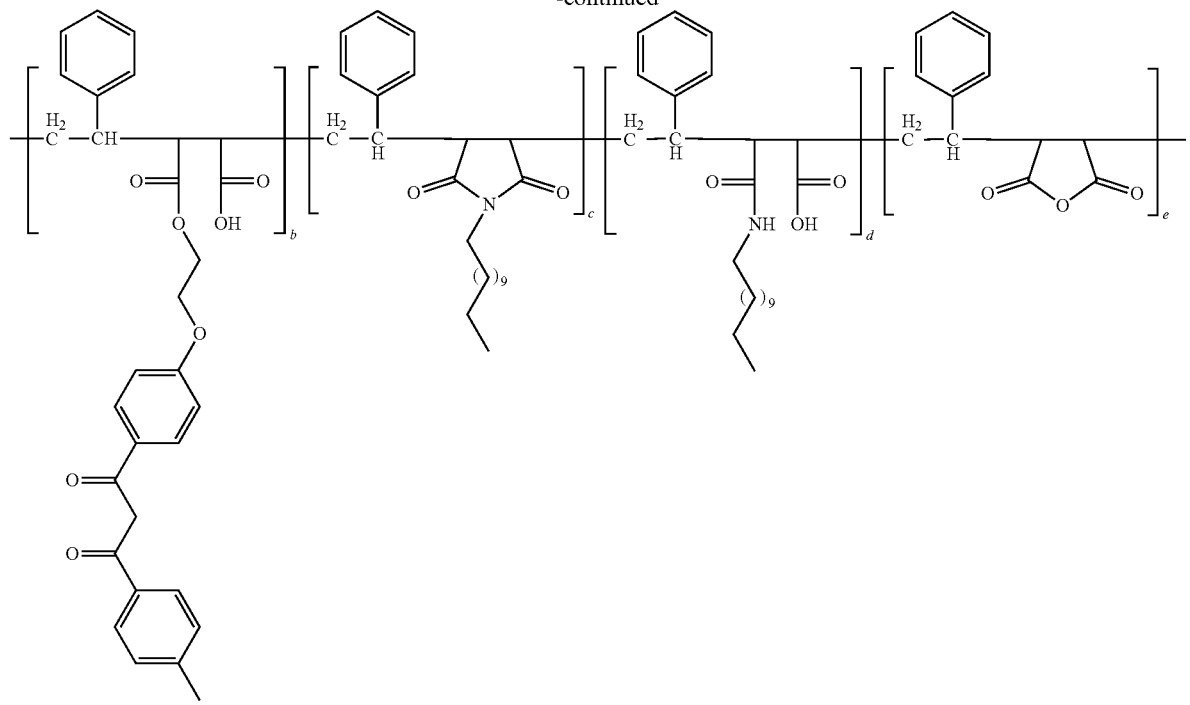

Example 26 was substantially repeated, except 4.8 g (26 mM) of n-dodecylamine replaced to isobutylene. The product was cooled to room temperature to obtain a creamy solid that was soluble in ethanol solutions and soluble in oils like di-isopropyl-adipate. The molar quantities are such that $a=b+c+d+e$.

This product can be used for personal care gels/emulsions for UV-A/B protection for hair and as a styling agent, and for UV-A/B suncare applications.

Example 30: Poly(styrene/MA) Grafted with HE-JT Benzone and Dimethylaminopropylamine, Amic Acid and Full Imide Forms

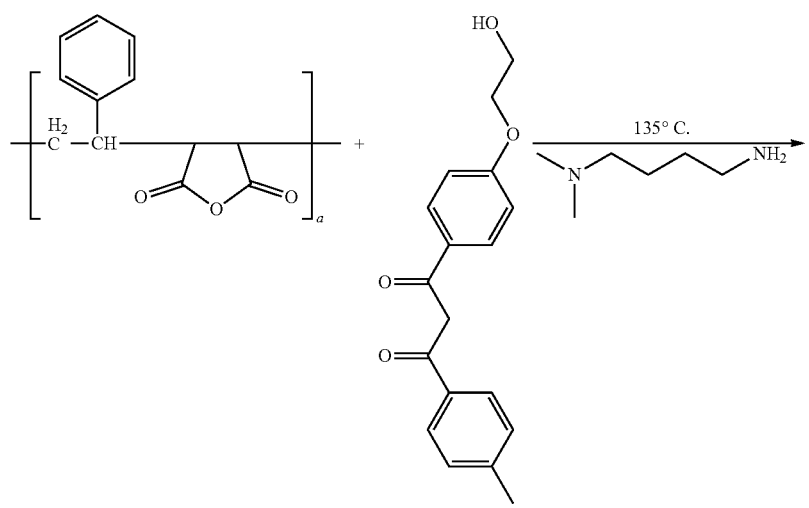

-continued

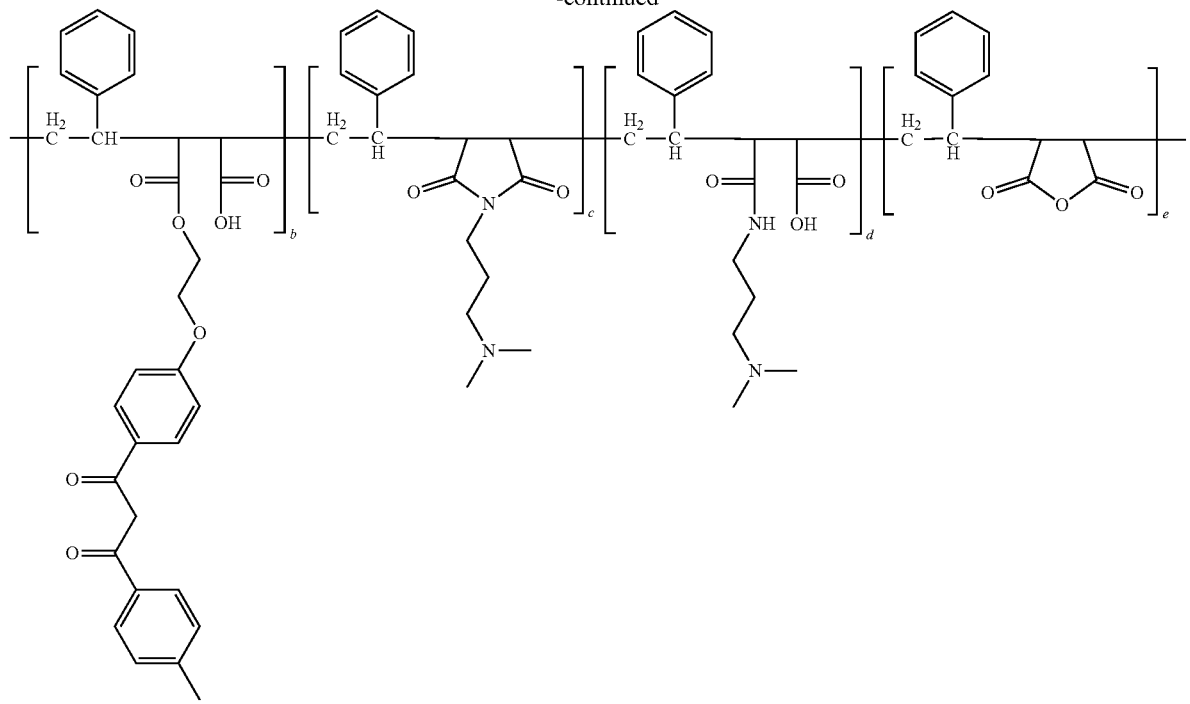

Example 26 was substantially repeated, except 4.8 g (26 mM) of dimethylaminopropylamine replaced to isobutylene. The product was cooled to room temperature to obtain a creamy solid that was soluble in ethanol solutions and soluble in oils like di-isopropyl-adipate. The molar quantities are such that a=b+c+d+e.

This product can be used for personal care formulations, such as gels/emulsions for UV-A/B protection for conditioning hair and/or skin applications.

Example 31: Poly(styrene/MA) Grafted with JT Benzone

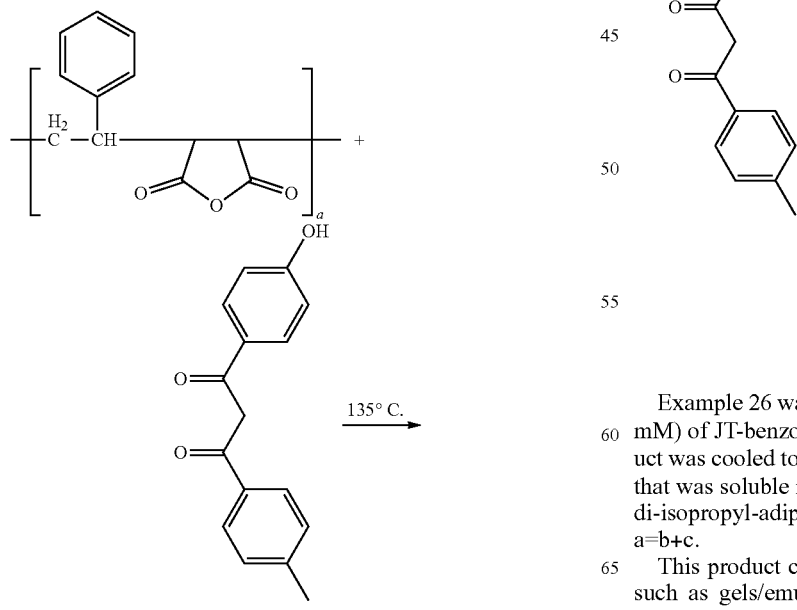

-continued

Example 26 was substantially repeated, except 0.8 g (3.25 mM) of JT-benzone replaced the HE-JT benzone. The product was cooled to room temperature to obtain a creamy solid that was soluble in ethanol solutions and soluble in oils like di-isopropyl-adipate. The molar quantities are such that a=b+c.

This product can be used for personal care formulations, such as gels/emulsions for UV-A/B protection for conditioning hair and/or skin applications.

Example 32: Poly(styrene/MA) Grafted with JT Benzone and Isobutylamine, Amic Acid and Full Imide Forms

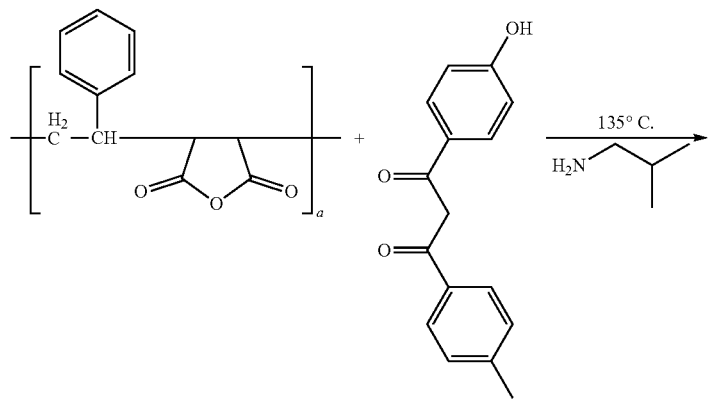

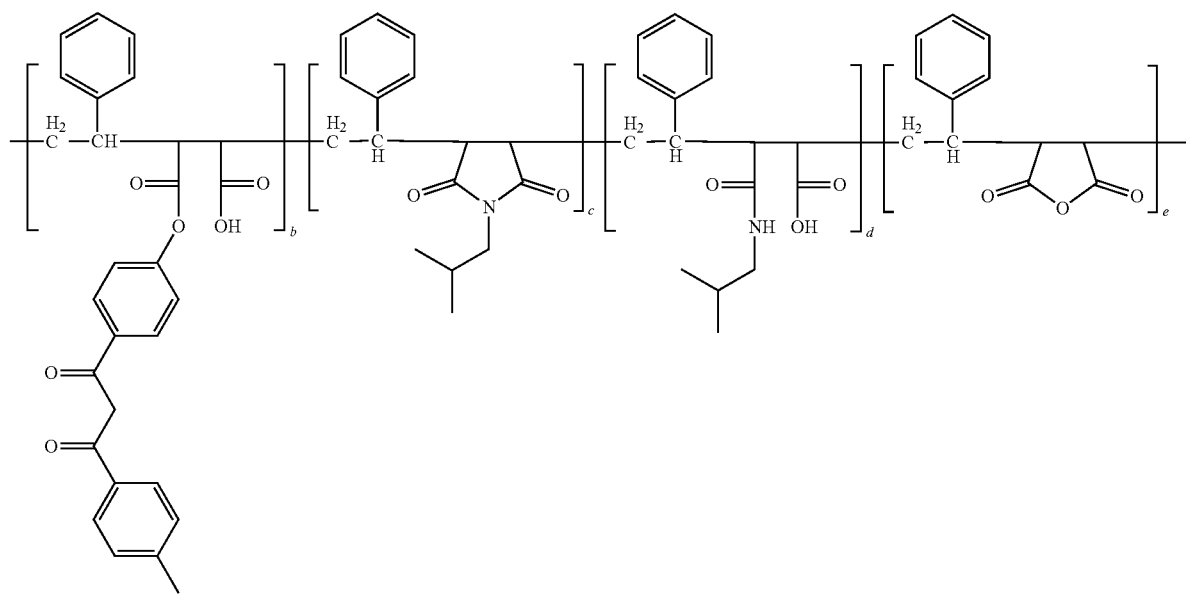

Example 31 was substantially repeated, except 1.9 g (26 mM) of isobutylamine was added to the mixture with JT benzone and the cetyl alcohol. The product was cooled to room temperature to obtain a creamy solid that was soluble in ethanol solutions and soluble in oils like di-isopropyl-adipate. The molar quantities are such that a=b+c+d+e.

This product can be used for personal care formulations, such as gels/emulsions for UV-A/B protection for conditioning hair and/or skin applications.

Example 33: Poly(styrene/MA) Grafted with JT Benzone and n-octylamine, Amic Acid and Full Imide Forms

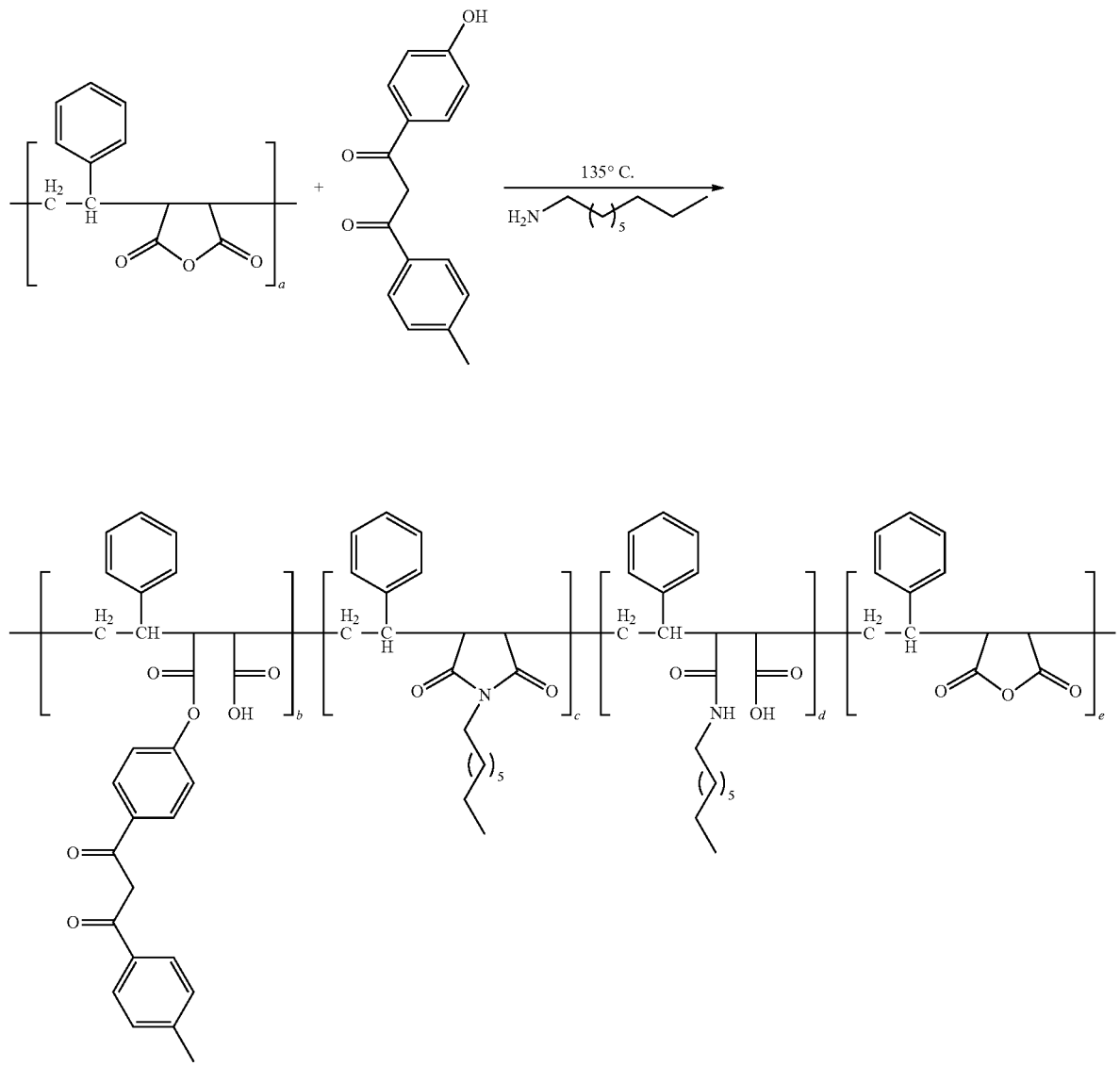

Example 31 was substantially repeated, except 3.3 g (26 mM) of n-octylamine replaced the isobutylamine. The product was cooled to room temperature to obtain a creamy solid that was soluble in ethanol solutions and soluble in oils like di-isopropyl-adipate. The molar quantities are such that a=b+c+d+e.

This product can be used for personal care formulations, such as gels/emulsions for UV-A/B protection for conditioning hair and/or skin applications.

Example 34: Poly(styrene/MA) Grafted with JT Benzone and n-dodecylamine, Amic Acid and Full Imide Forms

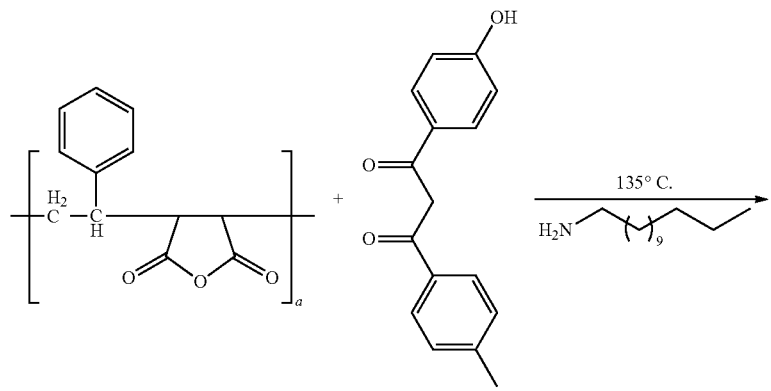

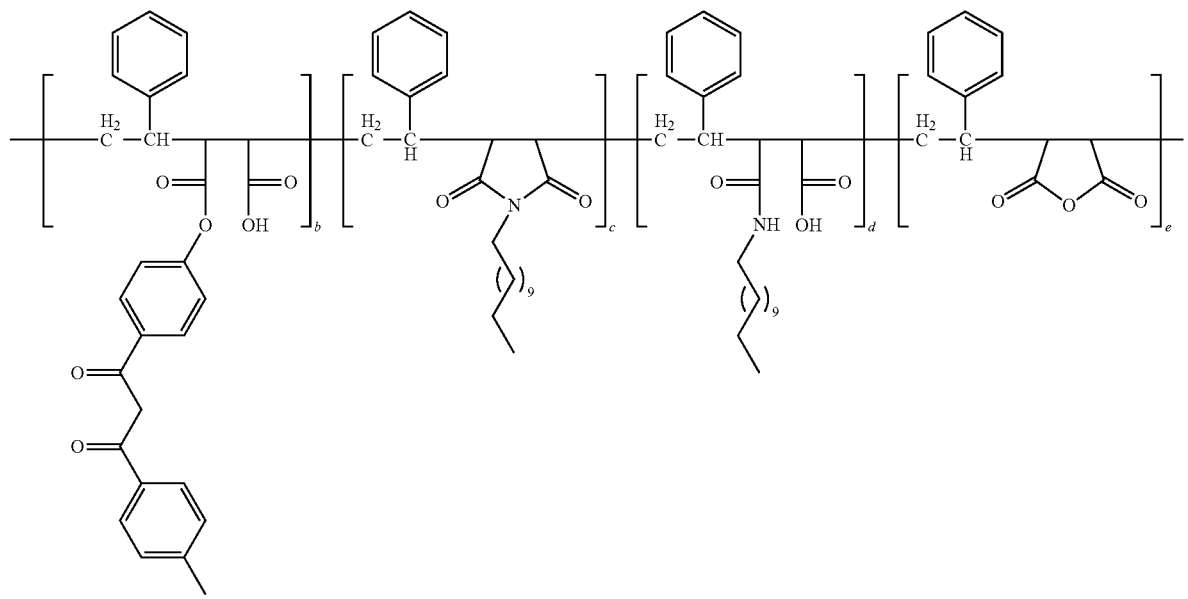

Example 31 was substantially repeated, except 4.8 g (26 mM) of n-dodecylamine replaced the isobutylamine. The product was cooled to room temperature to obtain a creamy solid that was soluble in ethanol solutions and soluble in oils like di-isopropyl-adipate. The molar quantities are such that a=b+c+d+e.

This product can be used for personal care formulations, such as gels/emulsions for UV-A/B protection for conditioning hair and/or skin applications.

Example 35: Poly(styrene/MA) Grafted with JT Benzone and Dimethylaminopropylamine, Amic Acid and Full Imide Forms

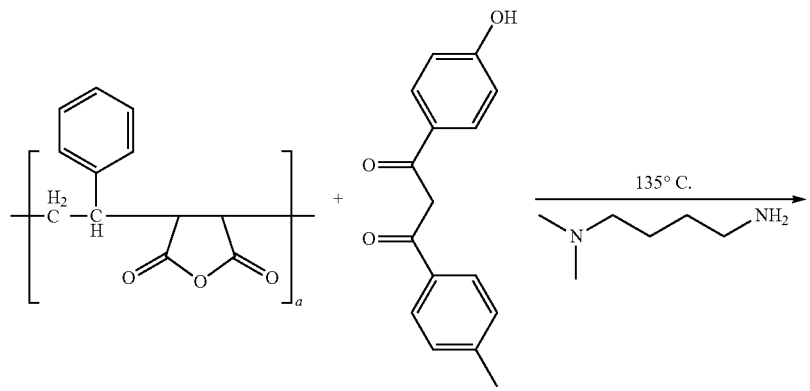

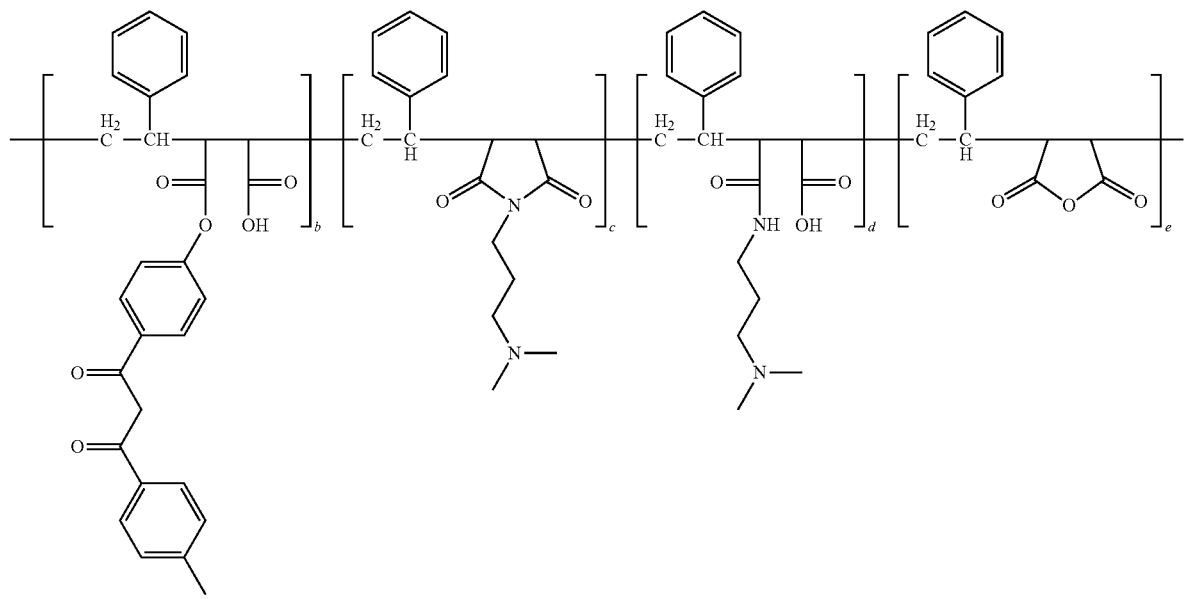

Example 31 was substantially repeated, except 2.7 g (26 mM) of dimethylaminopropylamine replaced the isobutylamine. The product was cooled to room temperature to obtain a creamy solid that was soluble in ethanol solutions and soluble in oils like di-isopropyl-adipate. The molar quantities are such that a=b+c+d+e.

This product can be used for personal care formulations, such as gels/emulsions for UV-A/B protection for conditioning hair and/or skin applications.

Example 36: Poly(IB/MA) Grafted with 577-Sulfanamide-propylenediamine, Half Ethyl Ester, Amic Acid, and Full Imide Forms

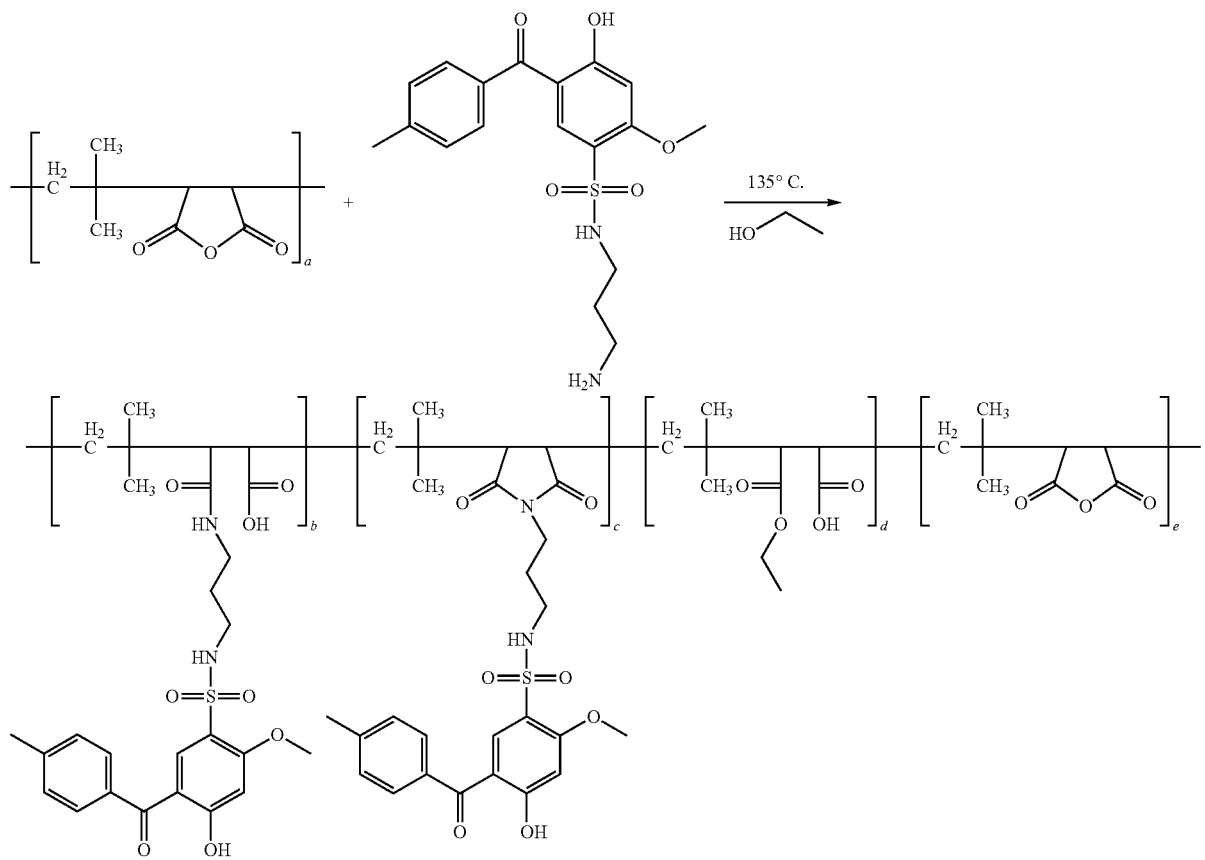

A premix was prepared having 1.2 g (3.25 mM) 577-sulfanamide-propylenediamine and 7 g ethanol until the UV active was thoroughly dissolved. Then, 5.0 g of poly(isobutylene-co-maleic anhydride) having a weight-average molecular weight ($M_w$) of 80,000 Da was added and the mixture heated to 135° C. for 10 hours. Afterward, the mixture was cooled to room temperature to obtain a clear dark yellow ethanol solution that was also soluble in ethanol/water solutions and oils, such di-isopropyl-adipate. The molar quantities are such that a=b+c+d+e.

This product can be used for personal care formulations, such as gels/emulsions for UV-A/B protection for hair and as a styling agent, and for UV-A/B suncare applications.

Example 37: Poly(IB/MA) Grafted with 577-Sulfanamide-Propylenediamine and Isobutylamine; Half Ethyl Ester, Amic Acid, and Full Imide Forms

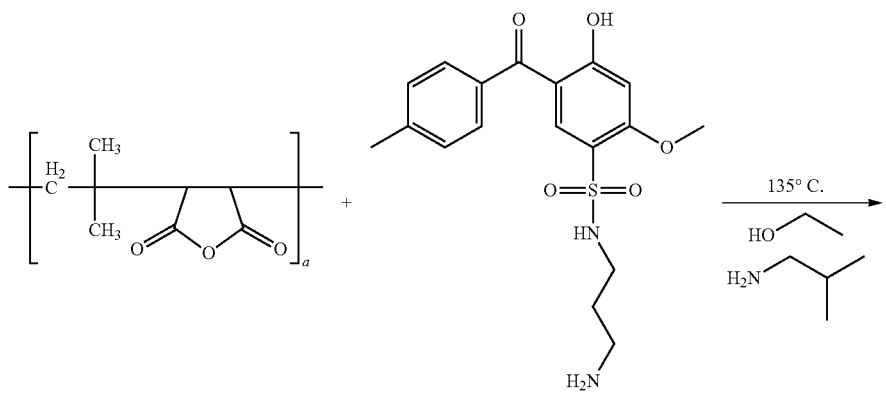

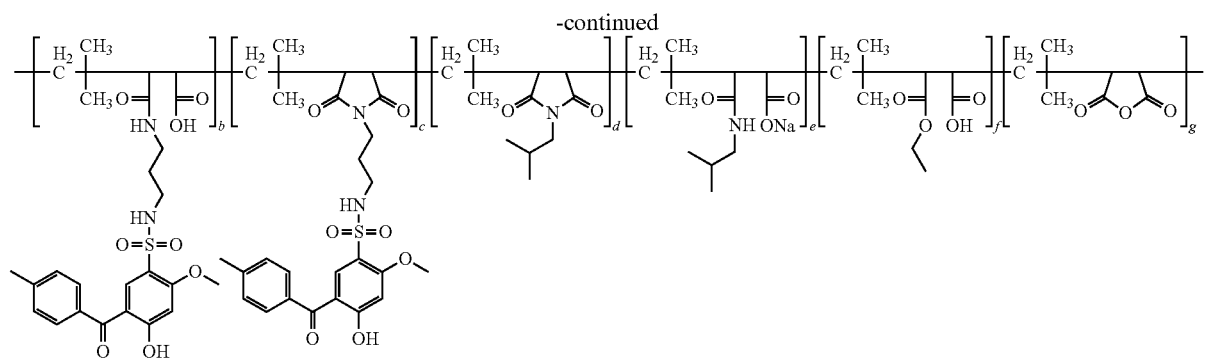

Example 36 was substantially repeated, except 1.9 g (26 mM) of isobutylamine was added to the premix, which was dissolved with 6.0 g ethanol. A clear dark yellow ethanol solution was obtained that was also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 38: Poly(IB/MA) Grafted with 577-Sulfanamide-Propylenediamine and n-octylamine; Half Ethyl Ester, Amic Acid, and Full Imide Forms

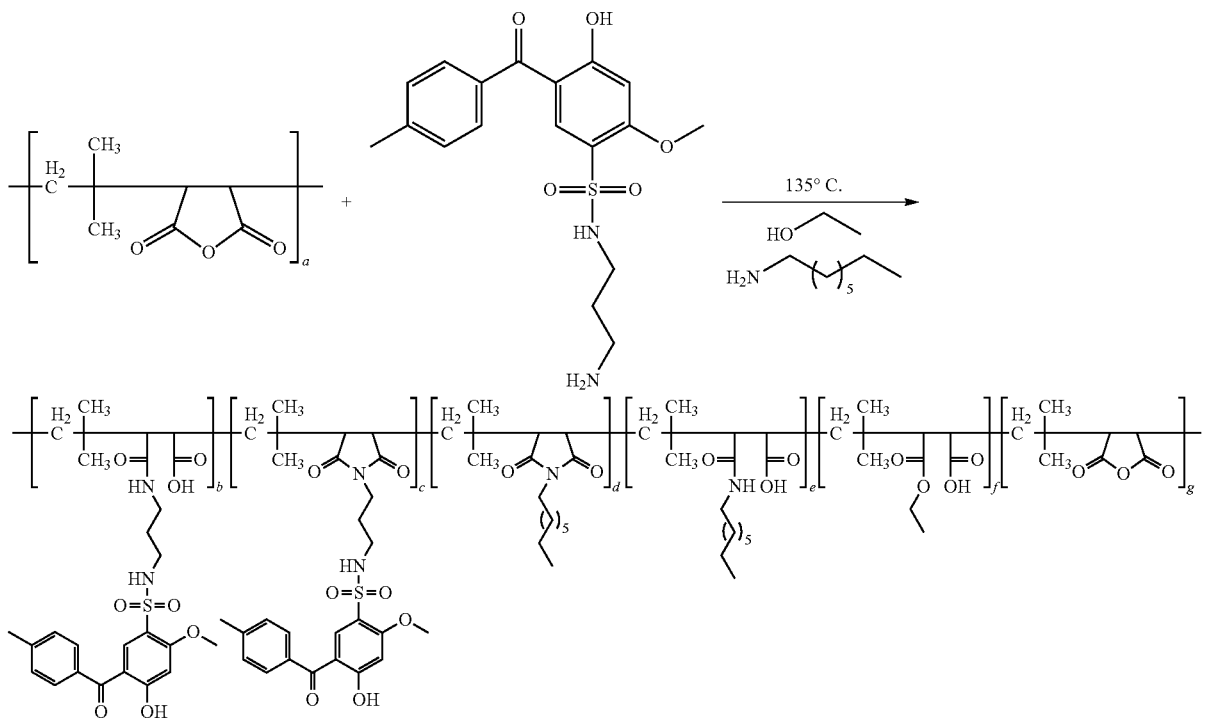

Example 36 was substantially repeated, except 3.3 g (26 mM) of n-octylamine was added to the premix, and it was dissolved with 6.0 g ethanol. A clear dark yellow ethanol solution was obtained that was also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 39: Poly(IB/MA) Grafted with 577-Sulfanamide-Propylenediamine and n-dodecylamine; Half Ethyl Ester, Amic Acid, and Full Imide Forms

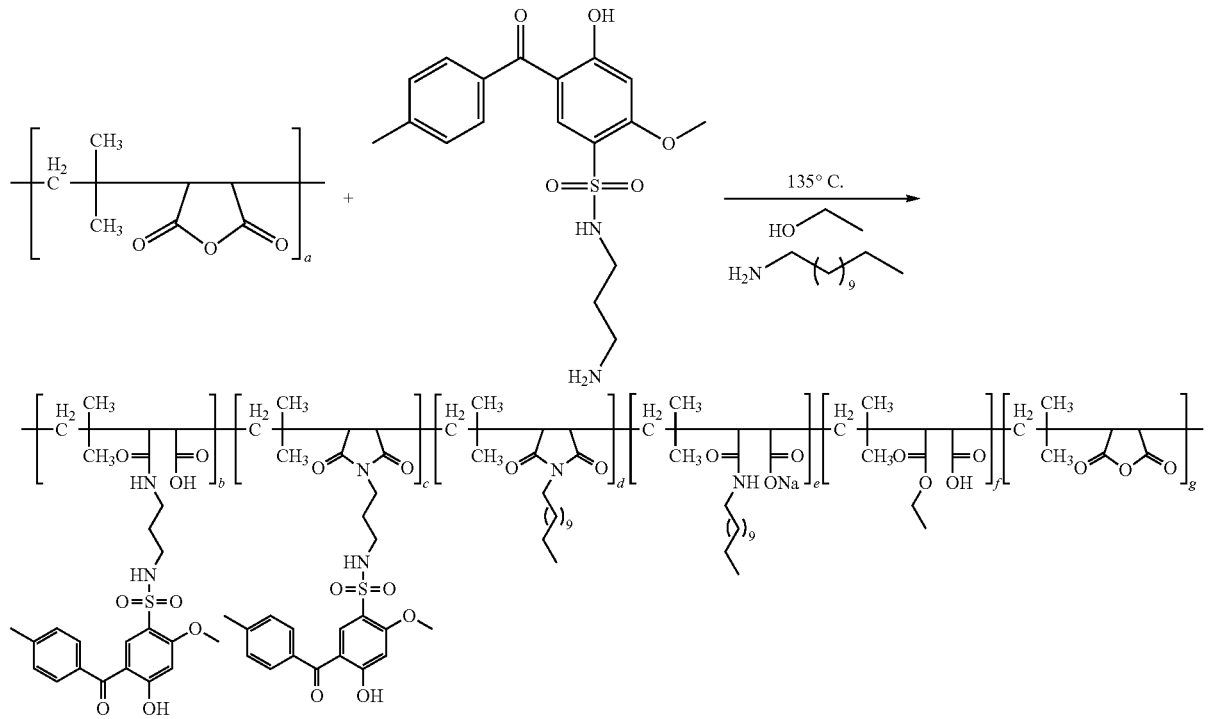

Example 36 was substantially repeated, except 4.8 g (26 mM) of n-dodecylamine was added to the premix, and it was dissolved with 6.0 g ethanol. A clear dark yellow ethanol solution was obtained that was also soluble in ethanol/water solutions and oils like di-isopropyl-adipate, or coconut, vegetable, or soybean oil. The molar quantities are such that a=b+c+d+e+f+g.

This product can be used for personal care formulations, such as gels/emulsions for UV-A/B protection for hair and as a styling agent, and for UV-A/B suncare applications.

Example 40: Poly(IB/MA) Grafted with 577-Sulfanamide-Propylenediamine and Dimethylaminopropylamine; Half Ethyl Ester, Amic Acid, and Full Imide Forms

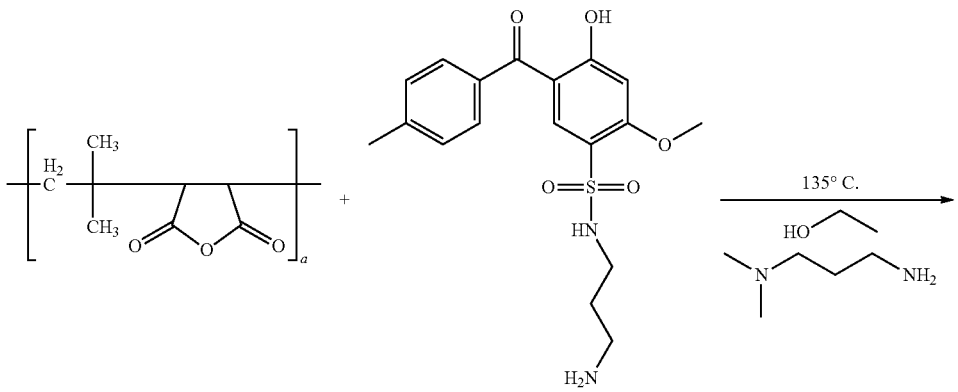

-continued

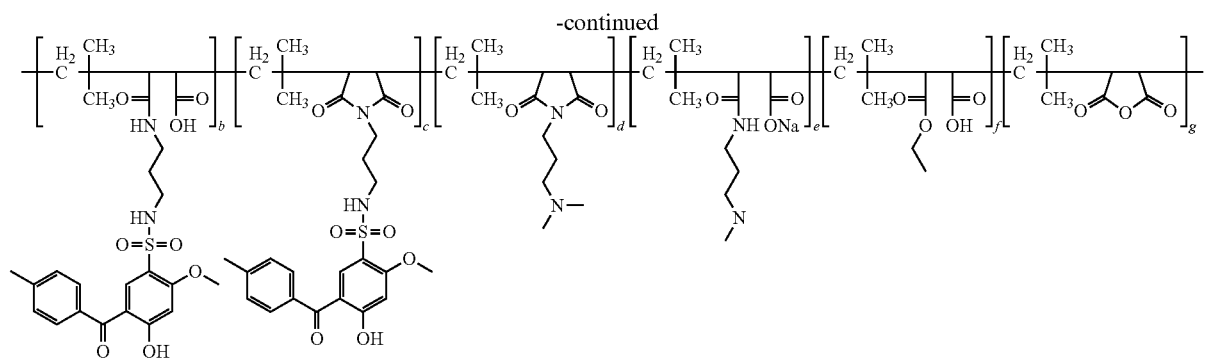

Example 36 was substantially repeated, except 2.7 g (26 mM) of dimethylaminopropylamine was added to the pre-mix, and it was dissolved with 9.0 g ethanol. A clear dark yellow ethanol solution was obtained that was also soluble in ethanol/water solutions and other alcohols. The molar quantities are such that a=b+c+d+e+f+g.

This product can be used for personal care formulations, such as gels/emulsions for UV-A/B protection for conditioning hair and/or skin applications.

Example 41: Poly(IB/MA) Grafted with 577-Sulfanamide-Ethanolamine, Half Ethyl Ester, Amic Acid, and Full Imide Forms Example 36 was substantially repeated, replacing the 1.2 g (3.25 mM) of 577-sulfanamide-propylenediamine with 1.15 g (3.25 mM) of 577-sulfanamide-ethanolamine. The product mixture was cooled to room temperature to obtain a clear dark yellow ethanol solution that was also soluble in ethanol/water solutions and oils, such di-isopropyl-adipate. The molar quantities are such that a=b+c+d.

This product can be used for personal care formulations, such as gels/emulsions for UV-A/B protection for hair and as a styling agent, and for UV-A/B suncare applications.

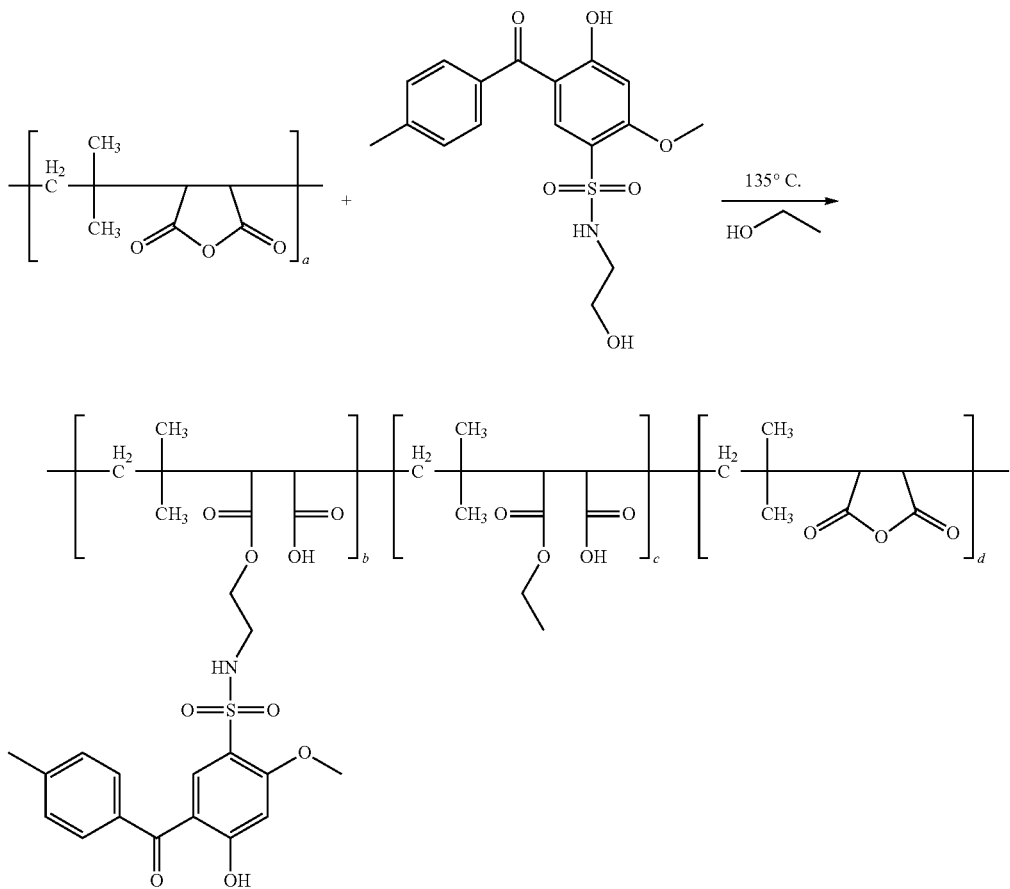

Example 42: Poly(IB/MA) Grafted with 577-Sulfanamide-Ethanolamine and Isobutylamine; Half Ethyl Ester, Amic Acid, and Full Imide Forms

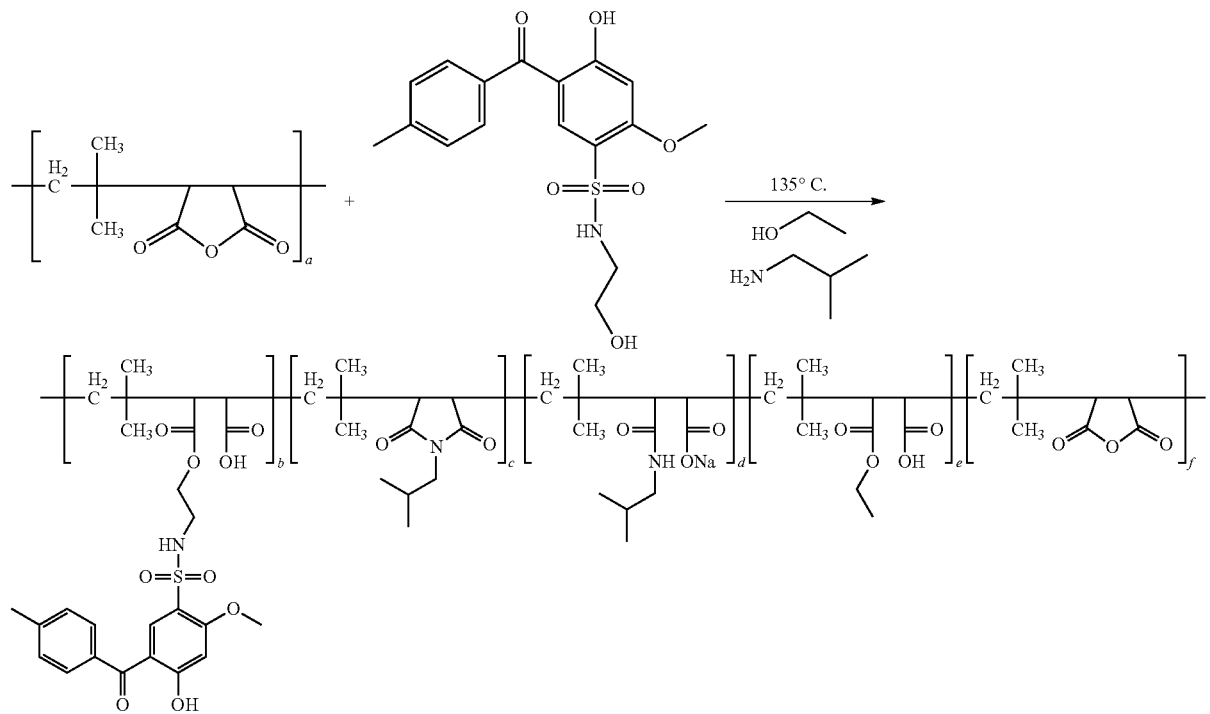

Example 41 is substantially repeated, except 1.9 g (26 mM) of isobutylamine is added to the premix, which was dissolved with 6.0 g ethanol. A clear dark yellow ethanol solution is obtained that is also soluble in ethanol/water solutions and oils like di-isopropyl-adipate. The molar quantities are such that a=b+c+d+e+f.

This product may be used for personal care formulations, such as gels/emulsions for UV-A/B protection for hair and as a styling agent, and for UV-A/B suncare applications.

Example 43: Poly(IB/MA) Grafted with 577-Sulfanamide-Ethanolamine and n-octylamine; Half Ethyl Ester, Amic Acid, and Full Imide Forms

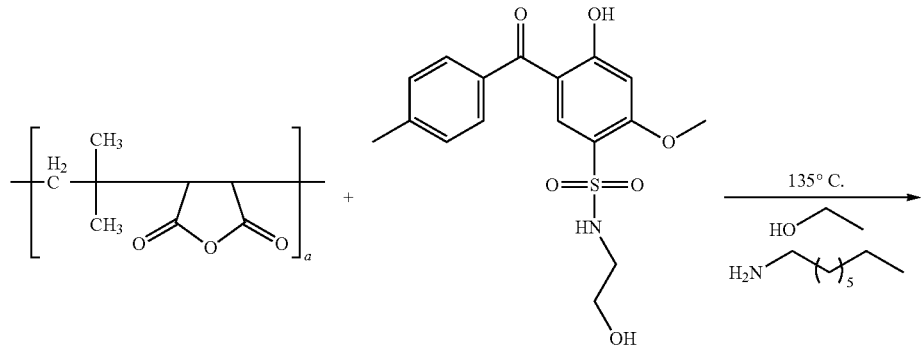

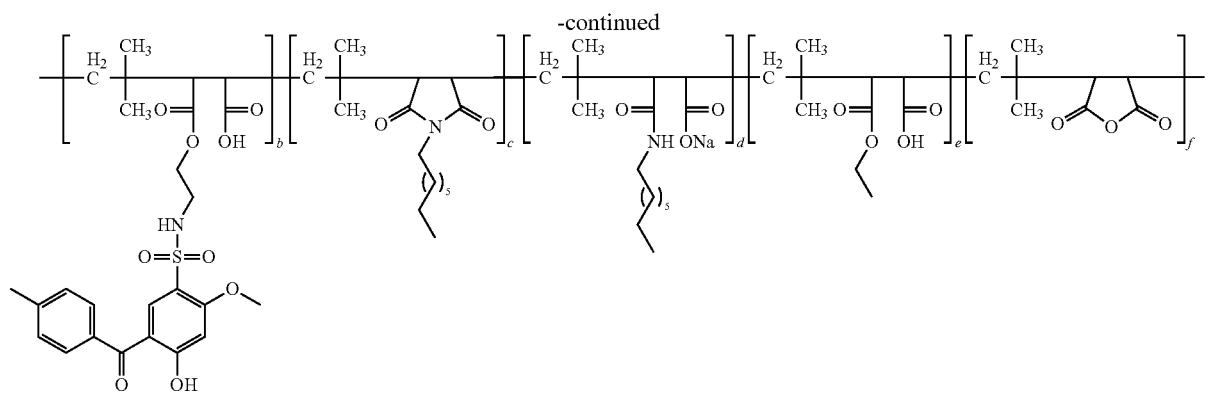

Example 41 is substantially repeated, except 3.3 g (26 mM) of n-octylamine is added to the premix, and it is dissolved with 6.0 g ethanol. A clear dark yellow ethanol solution is obtained that is also soluble in ethanol/water solutions and oils like di-isopropyl-adipate. The molar quantities are such that $a=b+c+d+e+f$.

This product may be used for personal care formulations, such as gels/emulsions for UV-A/B protection for hair and as a styling agent, and for UV-A/B suncare applications.

Example 44: Poly(IB/MA) Grafted with 577-Sulfanamide-Ethanolamine and n-dodecylamine; Half Ethyl Ester, Amic Acid, and Full Imide Forms

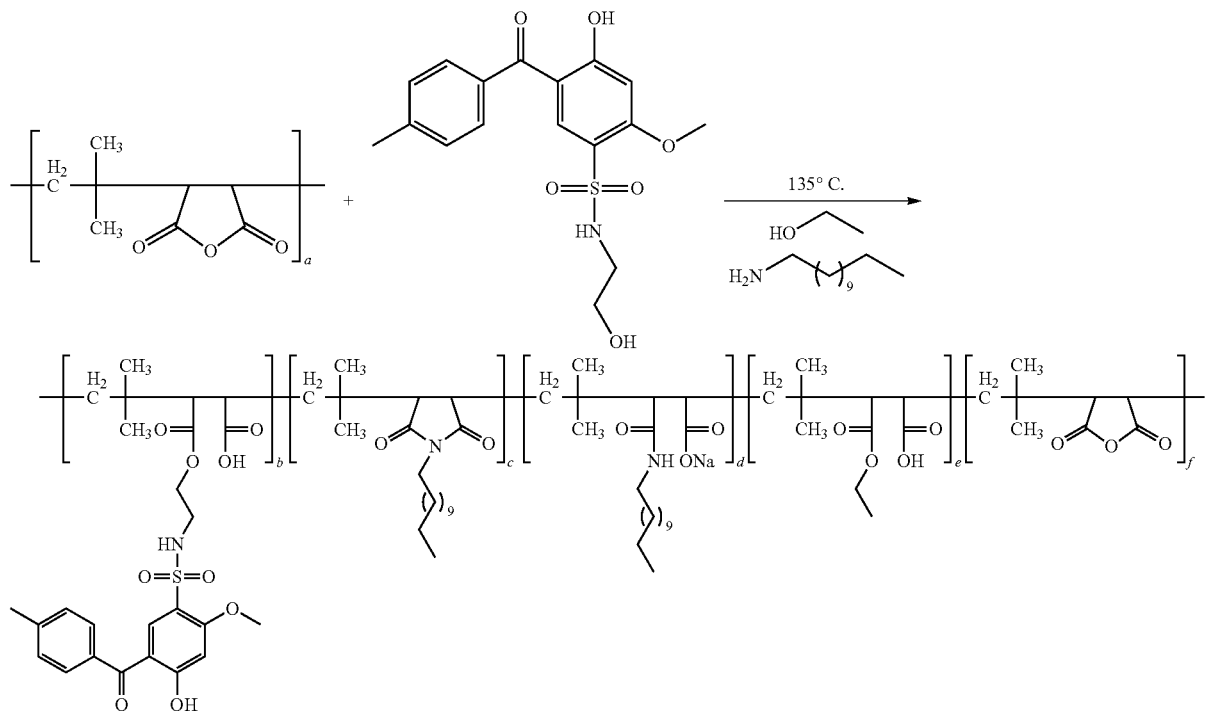

Example 41 is substantially repeated, except 4.8 g (26 mM) of n-dodecylamine is added to the premix, and it is dissolved with 6.0 g ethanol. A clear dark yellow ethanol solution is obtained that is also soluble in ethanol/water solutions and oils like di-isopropyl-adipate, or coconut, vegetable, or soybean oil. The molar quantities are such that $a=b+c+d+e+f$.

This product may be used for personal care formulations, such as gels/emulsions for UV-A/B protection for hair and as a styling agent, and for UV-A/B suncare applications.

Example 45: Poly(IB/MA) Grafted with 577-Sulfanamide-Ethanolamine and Dimethylaminopropylamine; Half Ethyl Ester, Amic Acid, and Full Imide Forms

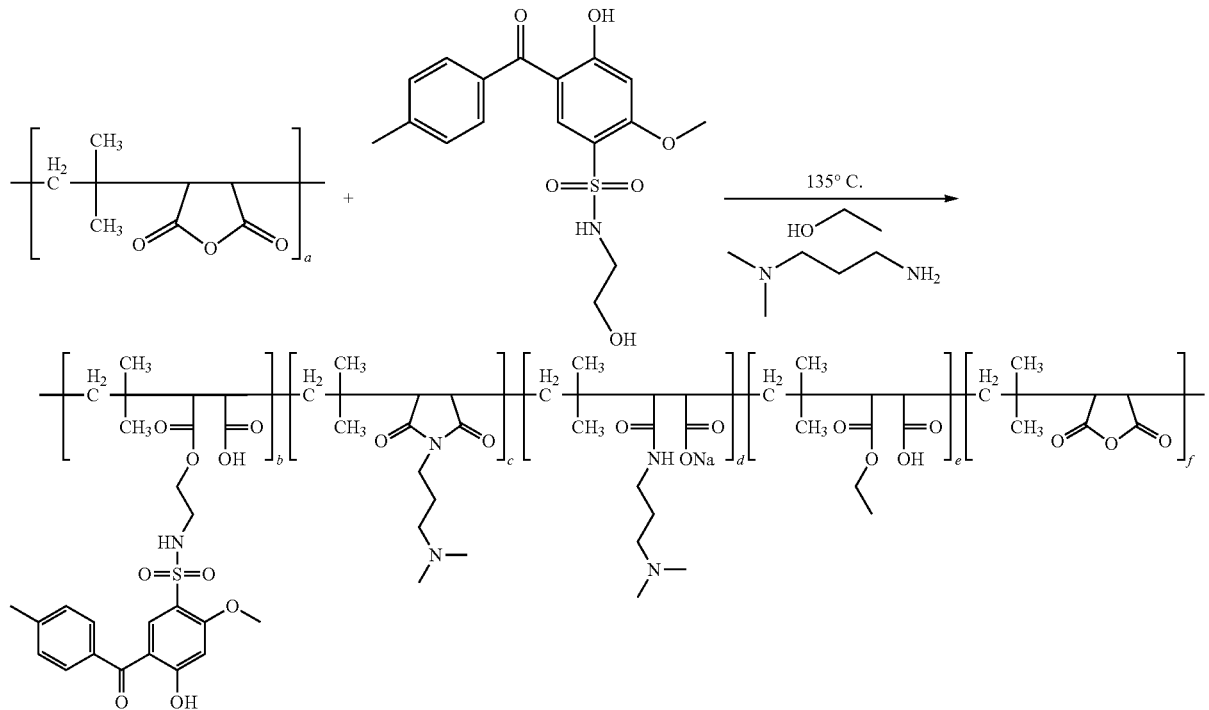

Example 41 is substantially repeated, except 2.7 g (26 mM) of dimethylaminopropylamine is added to the premix, and it is dissolved with 9.0 g ethanol. A clear dark yellow ethanol solution is obtained that is also soluble in ethanol/water solutions and other alcohols. The molar quantities are such that a=b+c+d+e+f.

This product may be used for personal care formulations, such as gels/emulsions for UV-A/B protection for conditioning hair and/or skin applications.

Example 46: Poly(IB/MA) Grafted with 577-Sulfanamide-Hexylenediamine, Half Ethyl Ester, Amic Acid, and Full Imide Forms

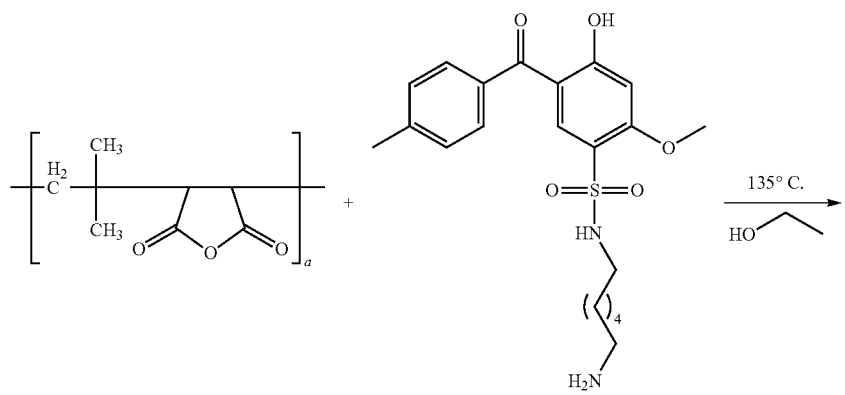

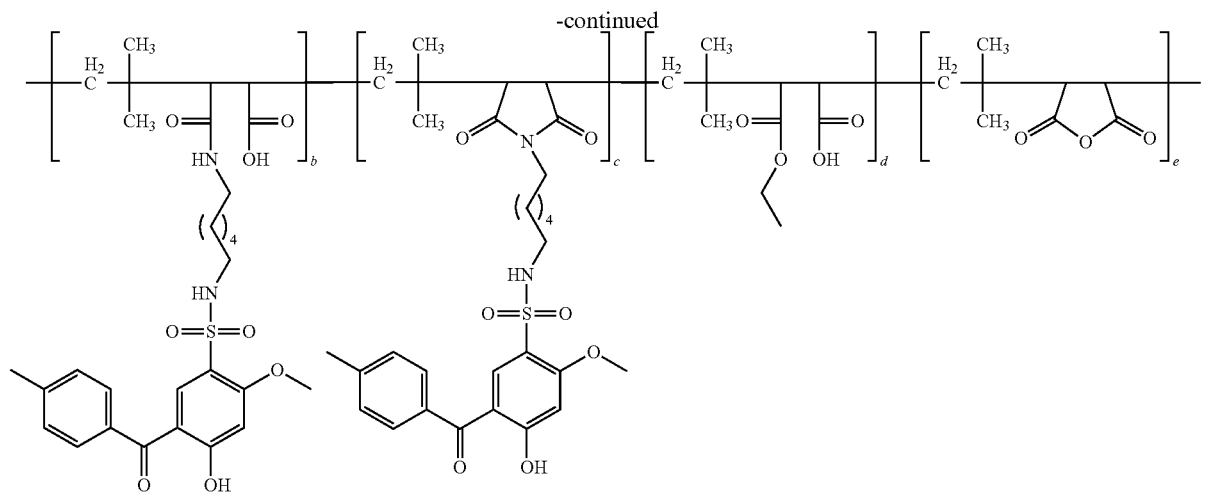

Example 36 was substantially repeated, replacing the 1.2 g (3.25 mM) of 577-sulfanamide-propylenediamine with 1.15 g (3.25 mM) of 577-sulfanamide-hexylenediamine. The product mixture was cooled to room temperature to obtain a clear dark yellow ethanol solution that was also soluble in ethanol/water solutions and oils, such di-isopropyl-adipate. The molar quantities are such that $a=b+c+d+e$.

This product can be used for personal care formulations, such as gels/emulsions for UV-A/B protection for hair and as a styling agent, and for UV-A/B suncare applications.

Example 47: Poly(IB/MA) Grafted with 577-Sulfanamide-Hexylenediamine and Isobutylamine; Half Ethyl Ester, Amic Acid, and Full Imide Forms

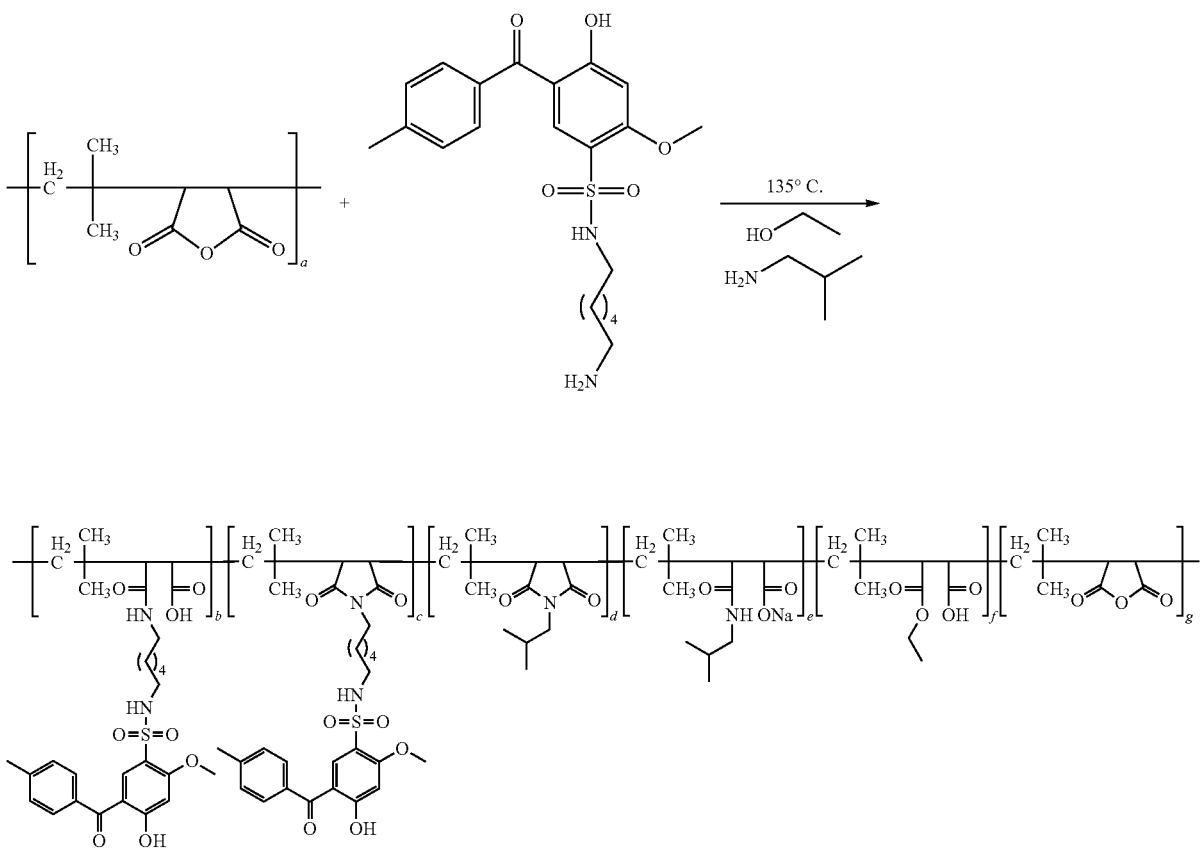

Example 46 was substantially repeated, except 1.9 g (26 mM) of isobutylamine was added to the premix, which was dissolved with 6.0 g ethanol. A clear dark yellow ethanol solution was obtained that was also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 48: Poly(IB/MA) Grafted with 577-Sulfanamide-Hexylenediamine and n-octylamine; Half Ethyl Ester, Amic Acid, and Full Imide Forms

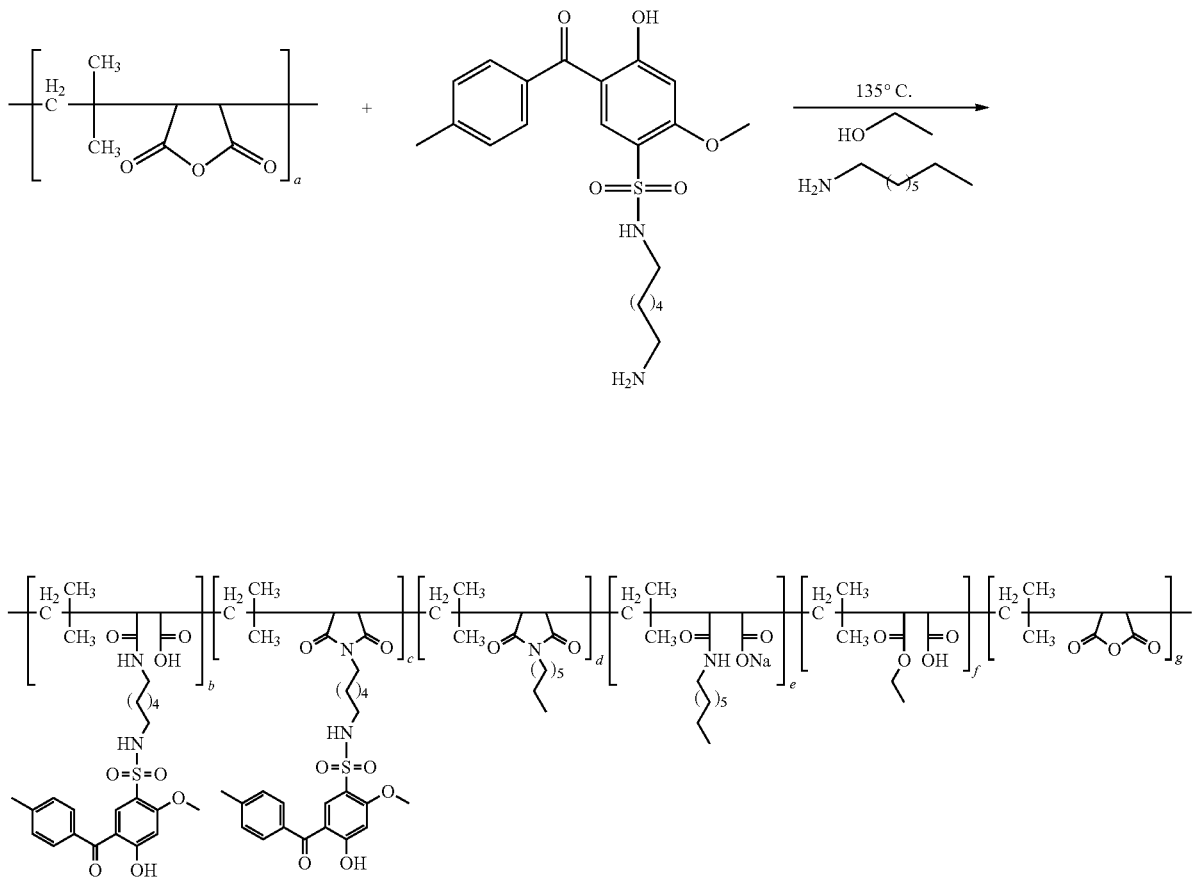

Example 46 was substantially repeated, except 3.3 g (26 mM) of n-octylamine was added to the premix, and it was dissolved with 6.0 g ethanol. A clear dark yellow ethanol solution was obtained that was also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 49: Poly(IB/MA) Grafted with 577-Sulfanamide-Hexylenediamine and n-dodecylamine; Half Ethyl Ester, Amic Acid, and Full Imide Forms

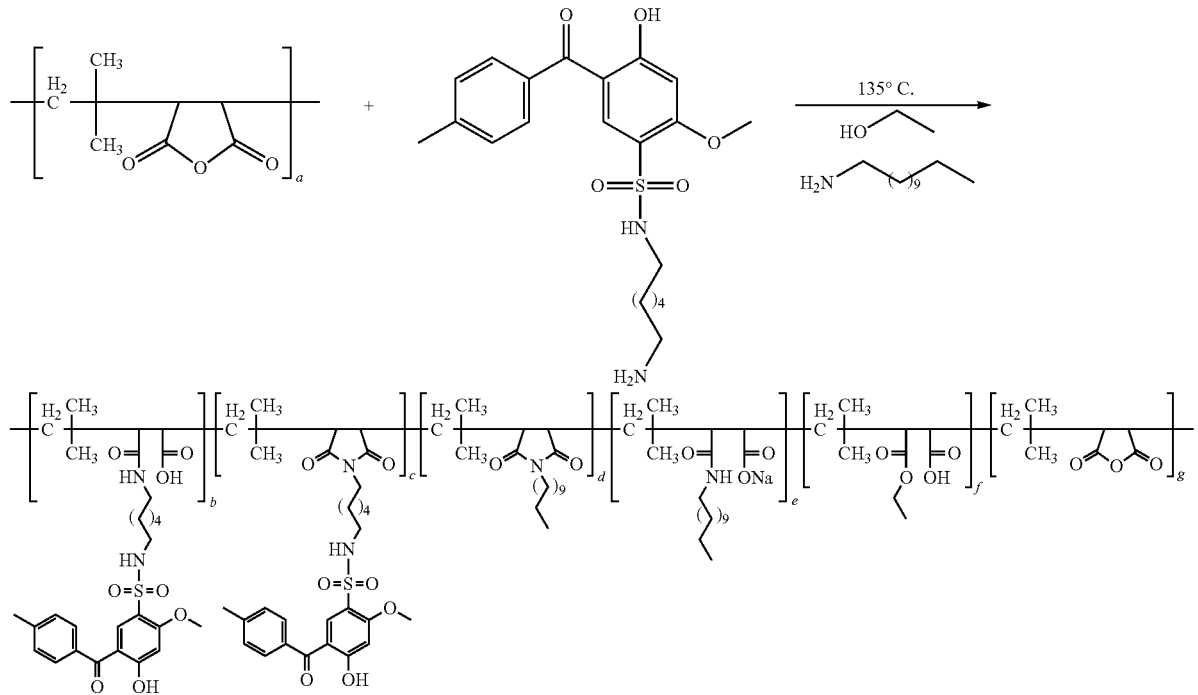

Example 46 was substantially repeated, except 4.8 g (26 mM) of n-dodecylamine was added to the premix, and it was dissolved with 6.0 g ethanol. A clear dark yellow ethanol solution was obtained that was also soluble in ethanol/water solutions and oils like di-isopropyl-adipate, or coconut, vegetable, or soybean oil. The molar quantities are such that a=b+c+d+e+f+g.

This product can be used for personal care formulations, such as gels/emulsions for UV-A/B protection for hair and as a styling agent, and for UV-A/B suncare applications.

Example 50: Poly(IB/MA) Grafted with 577-Sulfanamide-Hexylenediamine and Dimethylaminopropylamine; Half Ethyl Ester, Amic Acid, and Full Imide Forms

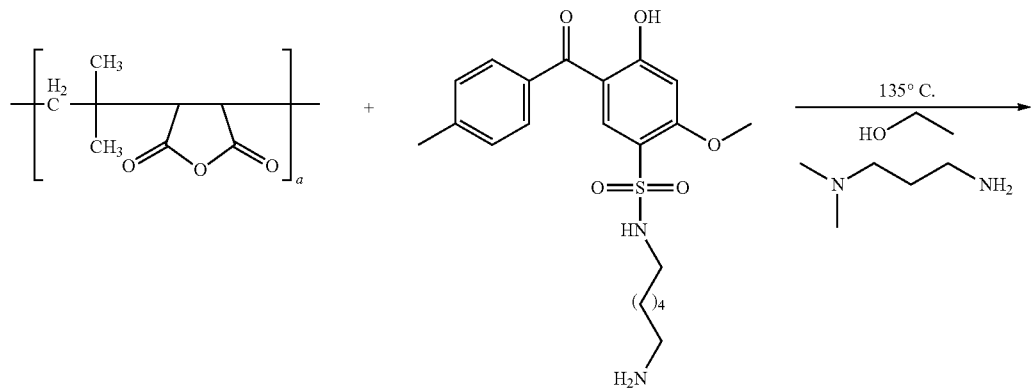

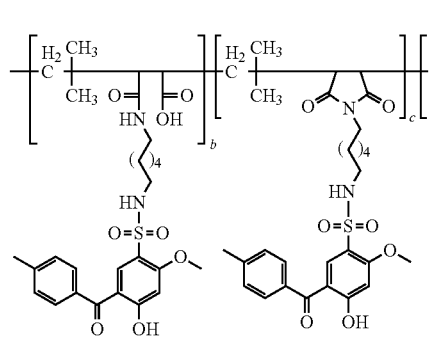
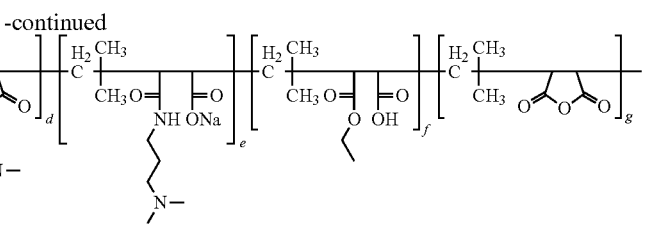

Example 46 was substantially repeated, except 2.7 g (26 mM) of dimethylaminopropylamine was added to the premix, and it was dissolved with 9.0 g ethanol. A clear dark yellow ethanol solution was obtained that was also soluble in ethanol/water solutions and other alcohols. The molar quantities are such that a=b+c+d+e+f+g.

This product can be used for personal care formulations, such as gels/emulsions for UV-A/B protection for conditioning hair and/or skin applications.

Examples 51-55

Poly(IB/MA) Grafted with
577-Sulfanamide-Propylenediamine, Lower
Molecular Weight Variants Examples 36-40 were substantially repeated, replacing the poly(IB/MA) having a $M_w$, of 80,000 Da by the same copolymer having a $M_w$, of 6,000 Da.

Examples 56-60

Poly(IB/MA) Grafted with
577-Sulfanamide-Hexylenediamine, Lower
Molecular Weight Variants Examples 46-50 are substantially repeated, replacing the poly(IB/MA) having a $M_w$, of 80,000 Da by the same copolymer having a $M_w$, of 6,000 Da.

Examples 61-65

Poly(IB/MA) Grafted with
577-Sulfanamide-Ethanolamine, Lower Molecular
Weight Variants Examples 41-45 are substantially repeated, replacing the poly(IB/MA) having a $M_w$, of 80,000 Da by the same copolymer having a $M_w$, of 6,000 Da.

Example 66: Poly(MVE/MA) Grafted with
577-Sulfanamide-Propylenediamine, Half Ethyl
Ester, Amic Acid, and Full Imide Forms

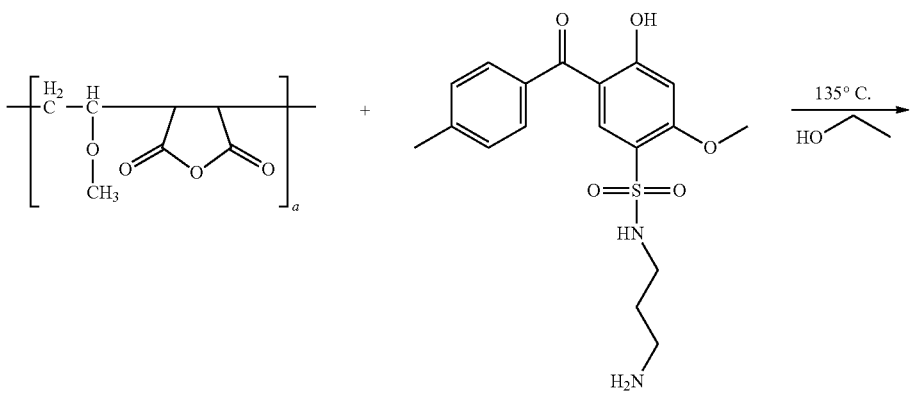

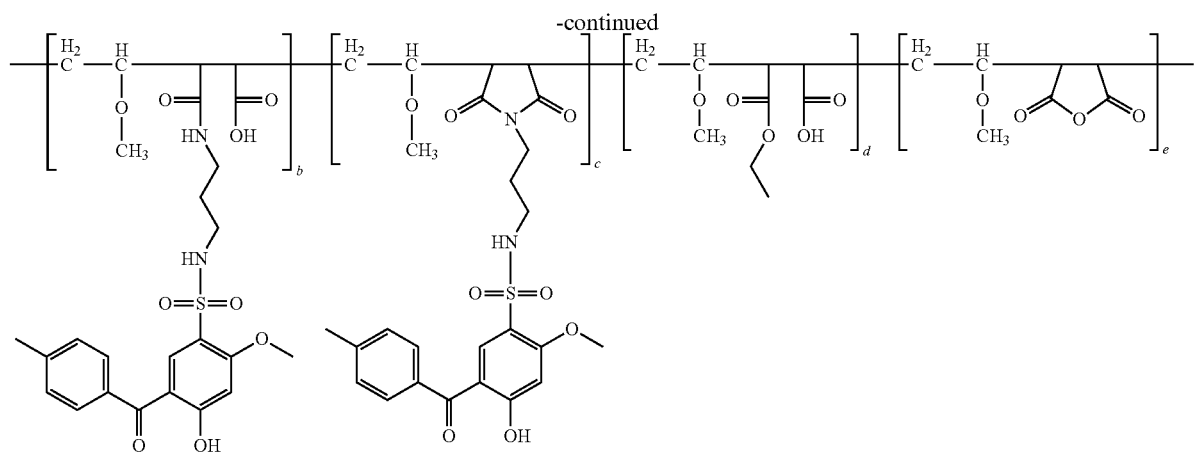

Example 36 is substantially repeated, replacing the poly(IB/MA) copolymer with an equal amount of poly(methyl vinyl ether/MA) having a $M_w$, of 130,000 Da. The molar quantities are such that a=b+c+d+e.

This product can be used for personal care formulations, such as gels/emulsions for UV-A/B protection for hair and as a styling agent, and for UV-A/B suncare applications.

Example 67: Poly(MVE/MA) Grafted with 577-Sulfanamide-Propylenediamine and Isobutylamine; Half Ethyl Ester, Amic Acid, and Full Imide Forms

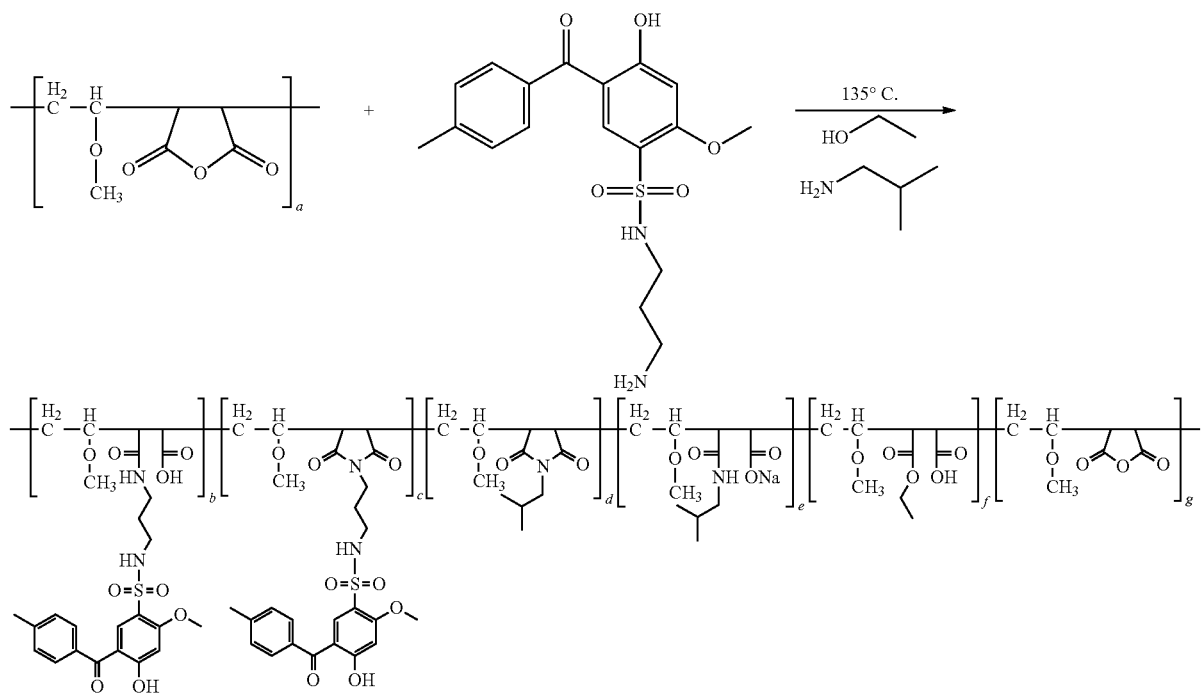

Example 66 is substantially repeated, except 1.9 g (26 mM) of isobutylamine was added to the premix, which was dissolved with 6.0 g ethanol. A clear dark yellow ethanol solution is obtained that was also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 68: Poly(MVE/MA) Grafted with 577-Sulfanamide-Propylenediamine and n-octylamine; Half Ethyl Ester, Amic Acid, and Full Imide Forms

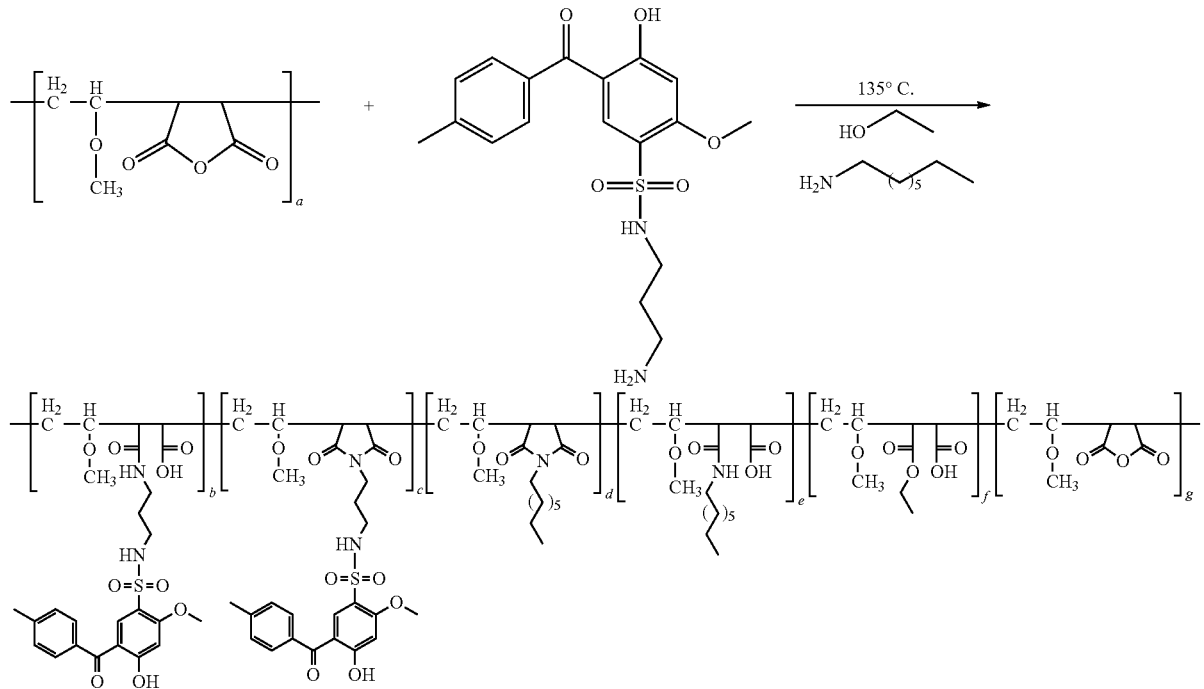

Example 66 is substantially repeated, except 3.3 g (26 mM) of n-octylamine was added to the premix, and it was dissolved with 6.0 g ethanol. A clear dark yellow ethanol solution is obtained that is also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 69: Poly(MVE/MA) Grafted with 577-Sulfanamide-Propylenediamine and n-dodecylamine; Half Ethyl Ester, Amic Acid, and Full Imide Forms

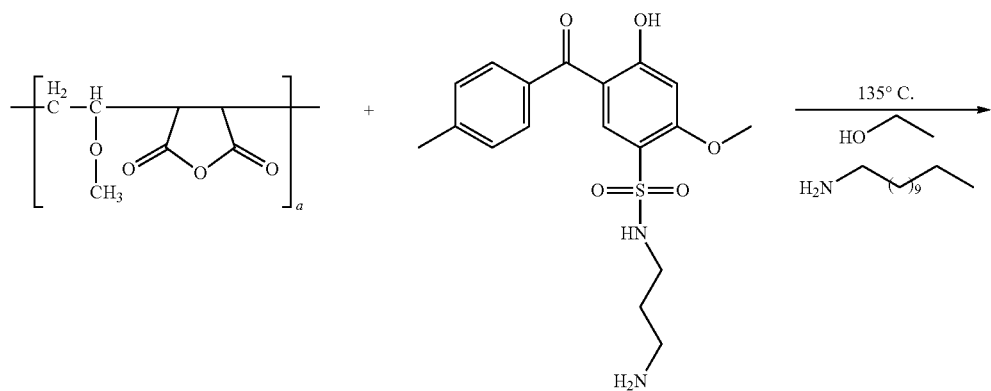

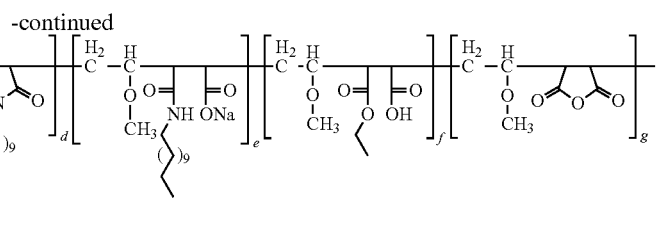

Example 66 is substantially repeated, except 4.8 g (26 mM) of n-dodecylamine is added to the premix, and it was dissolved with 6.0 g ethanol. A clear dark yellow ethanol solution is obtained that is also soluble in ethanol/water solutions and oils like di-isopropyl-adipate, or coconut, vegetable, or soybean oil. The molar quantities are such that a=b+c+d+e+f+g.

This product can be used for personal care formulations, such as gels/emulsions for UV-A/B protection for hair and as a styling agent, and for UV-A/B suncare applications.

Example 70: Poly(MVE/MA) Grafted with 577-Sulfanamide-Propylenediamine and Dimethylaminopropylamine; Half Ethyl Ester, Amic Acid, and Full Imide Forms

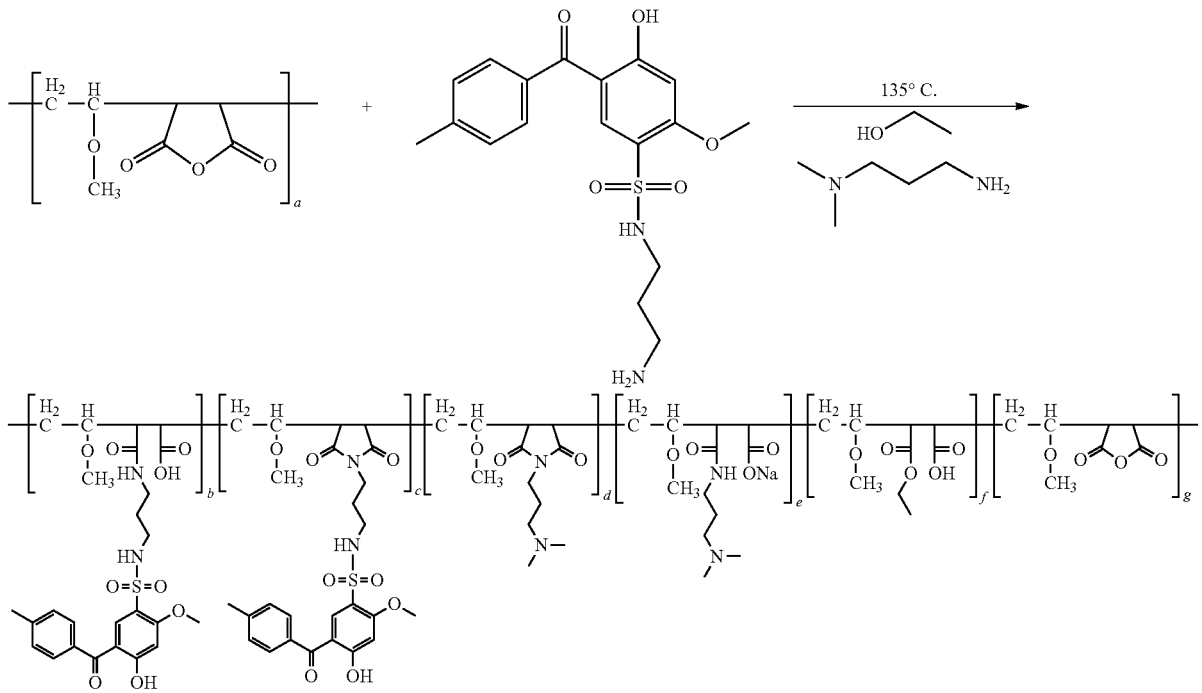

Example 66 is substantially repeated, except 2.7 g (26 mM) of dimethylaminopropylamine is added to the premix, and it is dissolved with 9.0 g ethanol. A clear dark yellow ethanol solution is obtained that is also soluble in ethanol/water solutions and other alcohols. The molar quantities are such that a=b+c+d+e+f+g.

This product can be used for personal care formulations, such as gels/emulsions for UV-A/B protection for conditioning hair and/or skin applications.

Examples 71-75

Poly(MVE/MA) Grafted with 577-Sulfanamide-Propylenediamine, Higher Molecular Weight Variants Examples 66-70 are substantially repeated, replacing the poly(MVE/MA) having a $M_w$, of 130,000 Da by the same copolymer having a $M_w$, of 2,500,000 Da.

Example 76: Poly(octadecene/MA) Grafted with 577-Sulfanamide-Propylenediamine; Half Ethyl Ester, Amic Acid, and Full Imide Forms

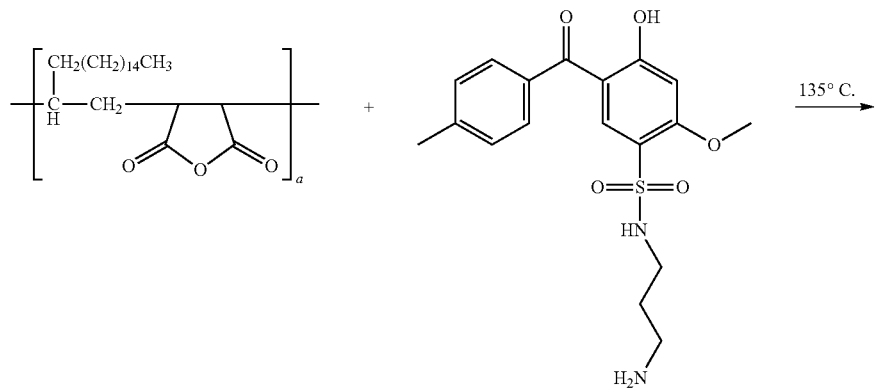

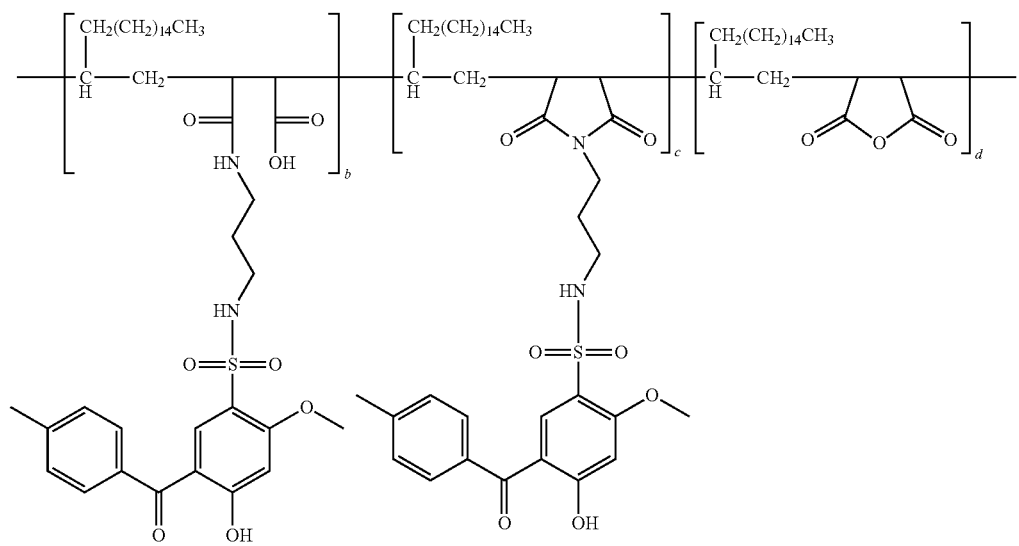

Example 66 was substantially repeated, replacing the poly(MVE/MA) having a $M_w$ of 130,000 Da by the copolymer of octadecene and maleic anhydride having a $M_w$ of 6,000 Da. Cetyl alcohol (17 g) was used instead of ethanol. A creamy solid was obtained that was miscible in ethanol/water solutions and soluble in oils like di-isopropyl-adipate. The molar quantities are such that a=b+c+d.

This product can be used for personal care formulations for UV-A/B protection for hair and as a styling agent, and for UV-A/B suncare applications.

Example 77: Poly(MVE/MA) Grafted with 577-Sulfanamide-Propylenediamine and Isobutylamine; Half Ethyl Ester, Amic Acid, and Full Imide Forms

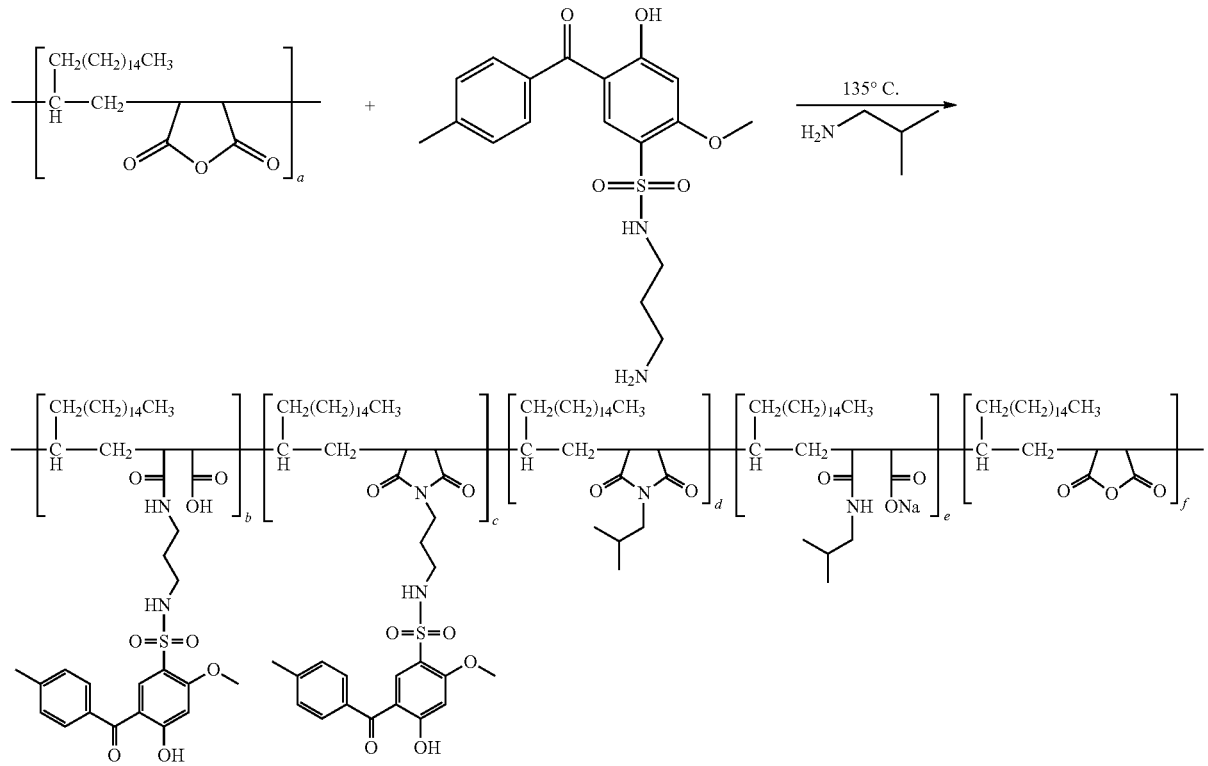

Example 76 was substantially repeated, except 1.9 g (26 mM) of isobutylamine was added to the premix, which was dissolved with 6.0 g ethanol. A creamy solid was obtained that was miscible in ethanol/water solutions and soluble in oils like di-isopropyl-adipate. The molar quantities are such that a=b+c+d+e+f.

This product can be used for personal care formulations for UV-A/B protection for hair and as a styling agent, and for UV-A/B suncare applications.

Example 78: Poly(MVE/MA) Grafted with 577-Sulfanamide-Propylenediamine and n-octylamine; Half Ethyl Ester, Amic Acid, and Full Imide Forms

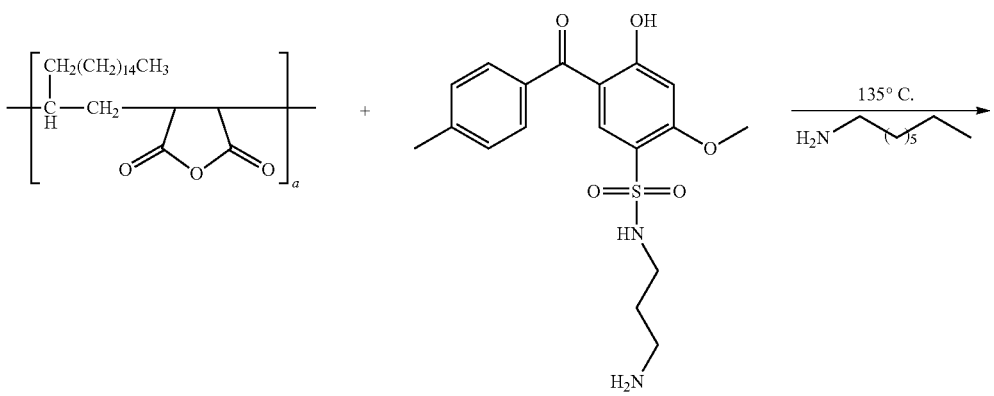

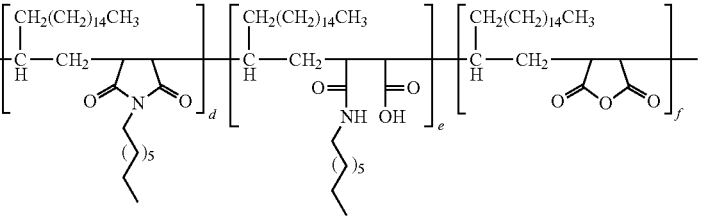

Example 76 was substantially repeated, except 3.3 g (26 mM) of n-octylamine was added to the premix, and it was dissolved with 6.0 g ethanol. A creamy solid was obtained that was miscible in ethanol/water solutions and soluble in oils like di-isopropyl-adipate. The molar quantities are such that a=b+c+d+e+f.

This product can be used for personal care formulations for UV-A/B protection for hair and as a styling agent, and for UV-A/B suncare applications.

Example 79: Poly(MVE/MA) Grafted with 577-Sulfanamide-Propylenediamine and n-dodecylamine; Half Ethyl Ester, Amic Acid, and Full Imide Forms

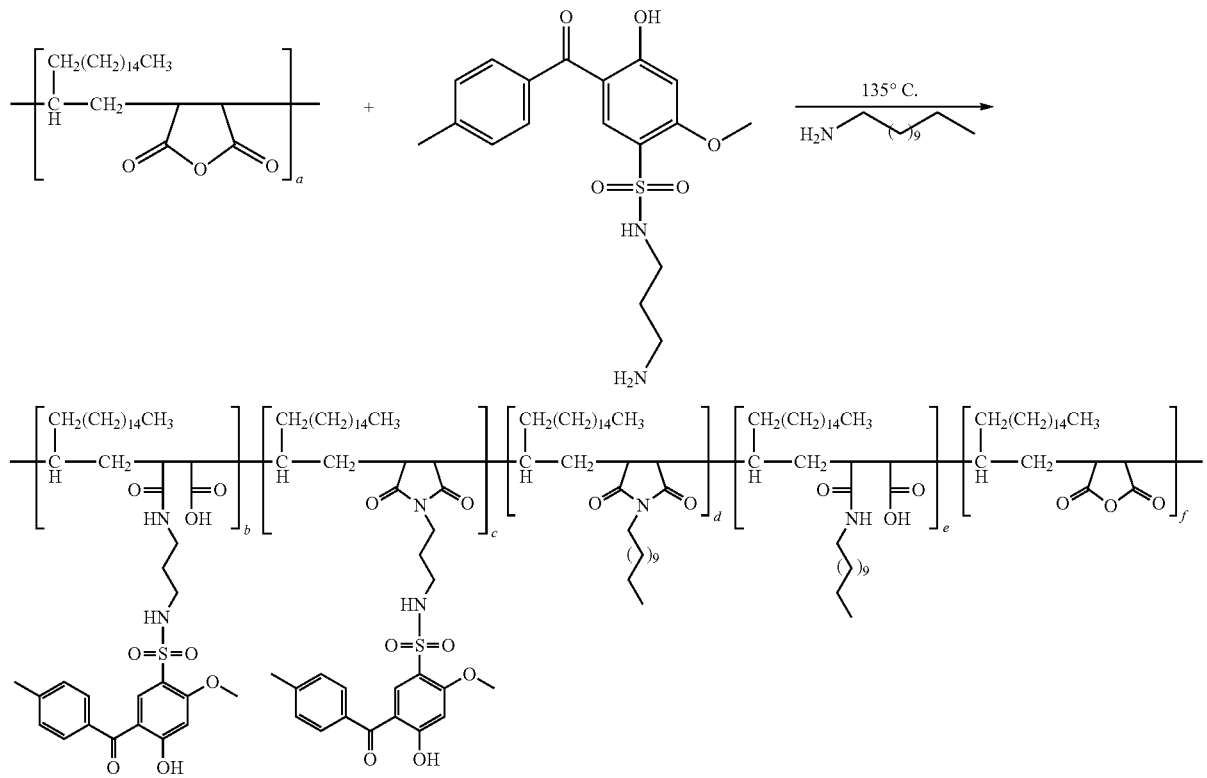

Example 76 was substantially repeated, except 4.8 g (26 mM) of n-dodecylamine was added to the premix, and it was dissolved with 6.0 g ethanol. A creamy solid was obtained that was miscible in ethanol/water solutions and soluble in oils like di-isopropyl-adipate. The molar quantities are such that a=b+c+d+e+f.

This product can be used for personal care formulations for UV-A/B protection for hair and as a styling agent, and for UV-A/B suncare applications.

Example 80: Poly(MVE/MA) Grafted with 577-Sulfanamide-Propylenediamine and Dimethylaminopropylamine; Half Ethyl Ester, Amic Acid, and Full Imide Forms

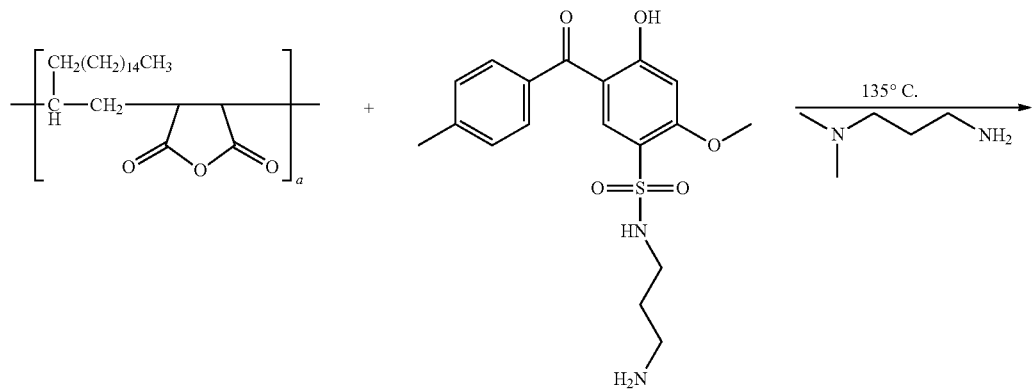

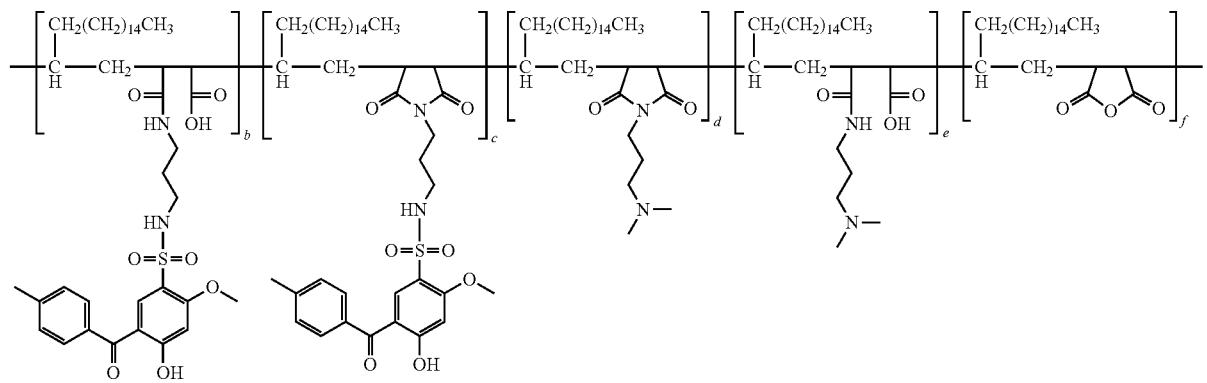

Example 76 was substantially repeated, except 2.7 g (26 mM) of dimethylaminopropylamine was added to the premix, and it was dissolved with 9.0 g ethanol. A creamy solid was obtained that was miscible in ethanol/water solutions and soluble in oils like di-isopropyl-adipate. The molar quantities are such that a=b+c+d+e+f.

This product can be used for personal care formulations, such as gels/emulsions for UV-A/B protection for conditioning hair and/or skin applications.

Example 81: Poly(styrene/MA) Grafted with 577-Sulfanamide-Propylenediamine; Half Ethyl Ester, Amic Acid, and Full Imide Forms

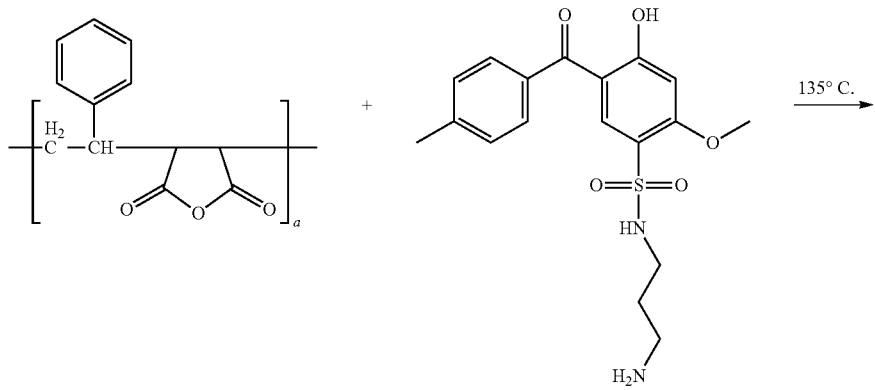

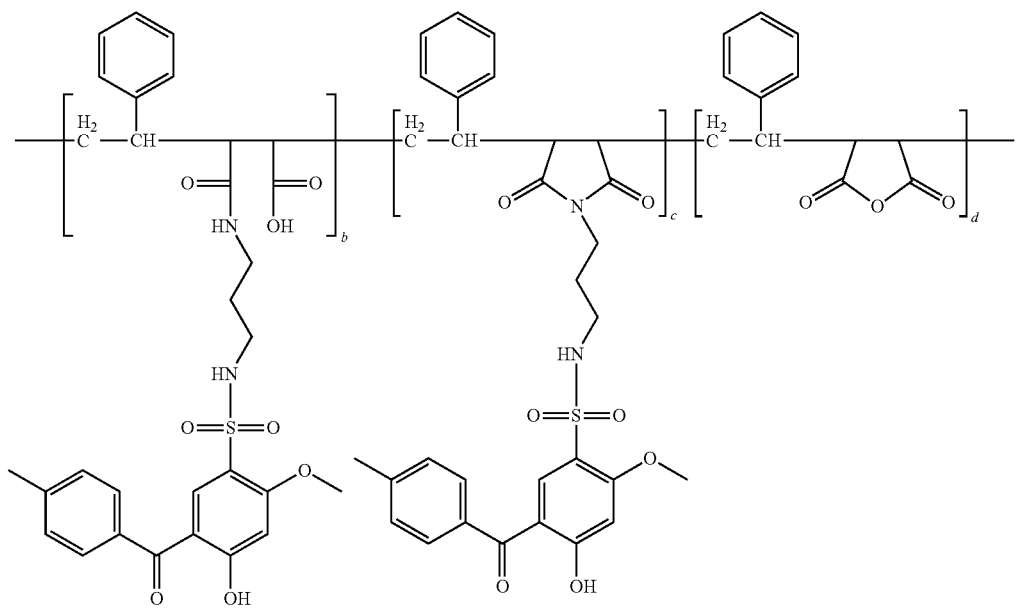

Example 66 was substantially repeated, replacing the poly(styrene/MA) having a $M_w$ of 130,000 Da by the copolymer of octadecene and maleic anhydride having a $M_w$ of 6,000 Da. Cetyl alcohol (17 g) was used instead of ethanol. A creamy solid was obtained that was miscible in ethanol/water solutions and soluble in oils like di-isopropyl-adipate. The molar quantities are such that a=b+c+d.

This product can be used for personal care formulations for UV-A/B protection for hair and as a styling agent, and for UV-A/B suncare applications.

Example 82: Poly(styrene/MA) Grafted with 577-Sulfanamide-Propylenediamine and Isobutylamine; Half Ethyl Ester, Amic Acid, and Full Imide Forms

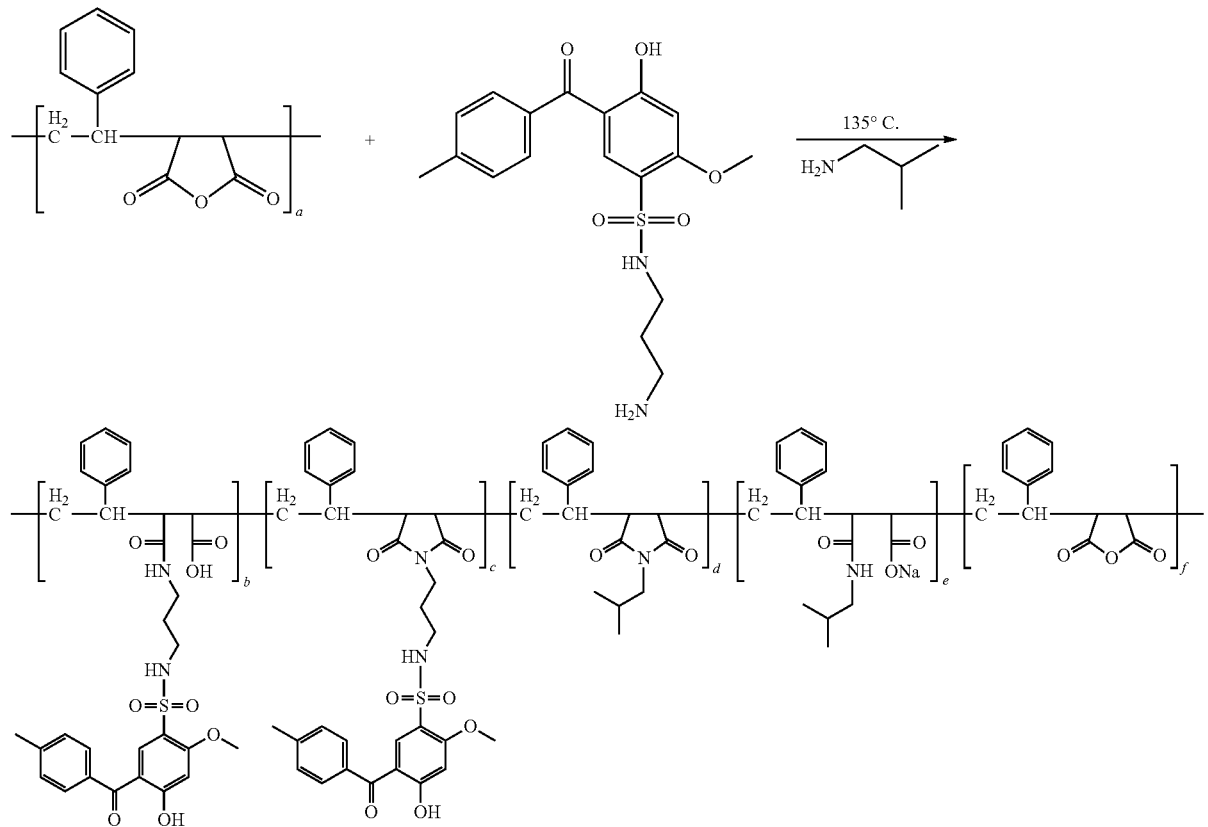

Example 81 was substantially repeated, except 1.9 g (26 mM) of isobutylamine was added to the premix, which was dissolved with 6.0 g ethanol. A creamy solid was obtained that was miscible in ethanol/water solutions and soluble in oils like di-isopropyl-adipate. The molar quantities are such that a=b+c+d+e+f.

This product can be used for personal care formulations for UV-A/B protection for hair and as a styling agent, and for UV-A/B suncare applications.

Example 83: Poly(styrene/MA) Grafted with 577-Sulfanamide-Propylenediamine and n-octylamine; Half Ethyl Ester, Amic Acid, and Full Imide Forms

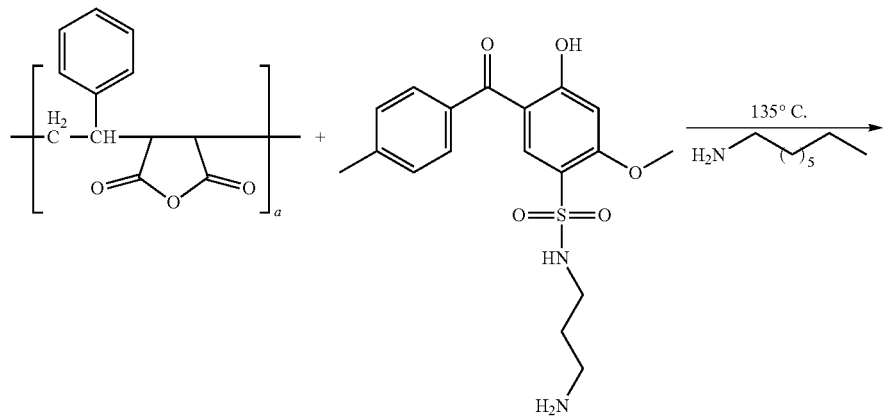

-continued

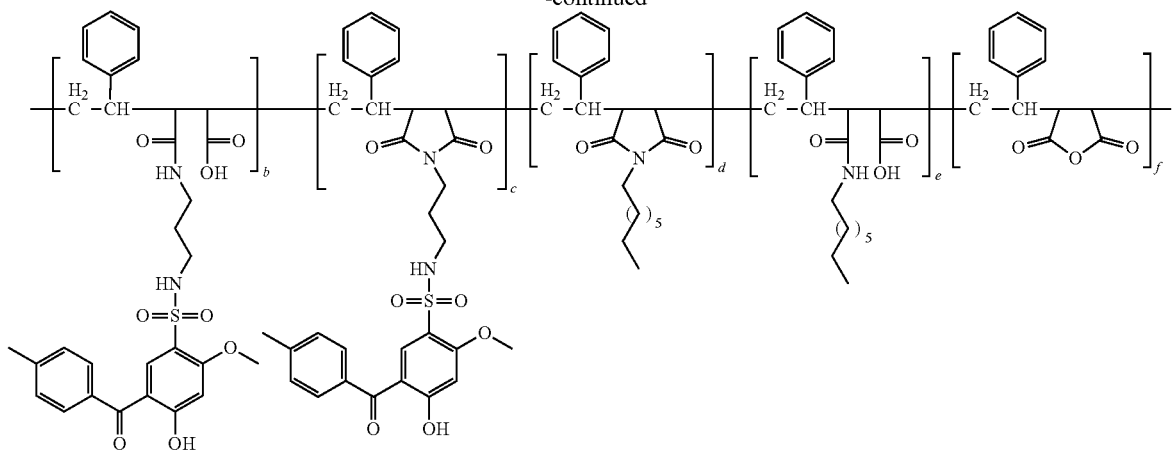

Example 81 was substantially repeated, except 3.3 g (26 mM) of n-octylamine was added to the premix, and it was dissolved with 6.0 g ethanol. A creamy solid was obtained that was miscible in ethanol/water solutions and soluble in oils like di-isopropyl-adipate. The molar quantities are such that a=b+c+d+e+f.

This product can be used for personal care formulations for UV-A/B protection for hair and as a styling agent, and for UV-A/B suncare applications.

Example 84: Poly(styrene/MA) Grafted with 577-Sulfanamide-Propylenediamine and n-dodecylamine; Half Ethyl Ester, Amic Acid, and Full Imide Forms

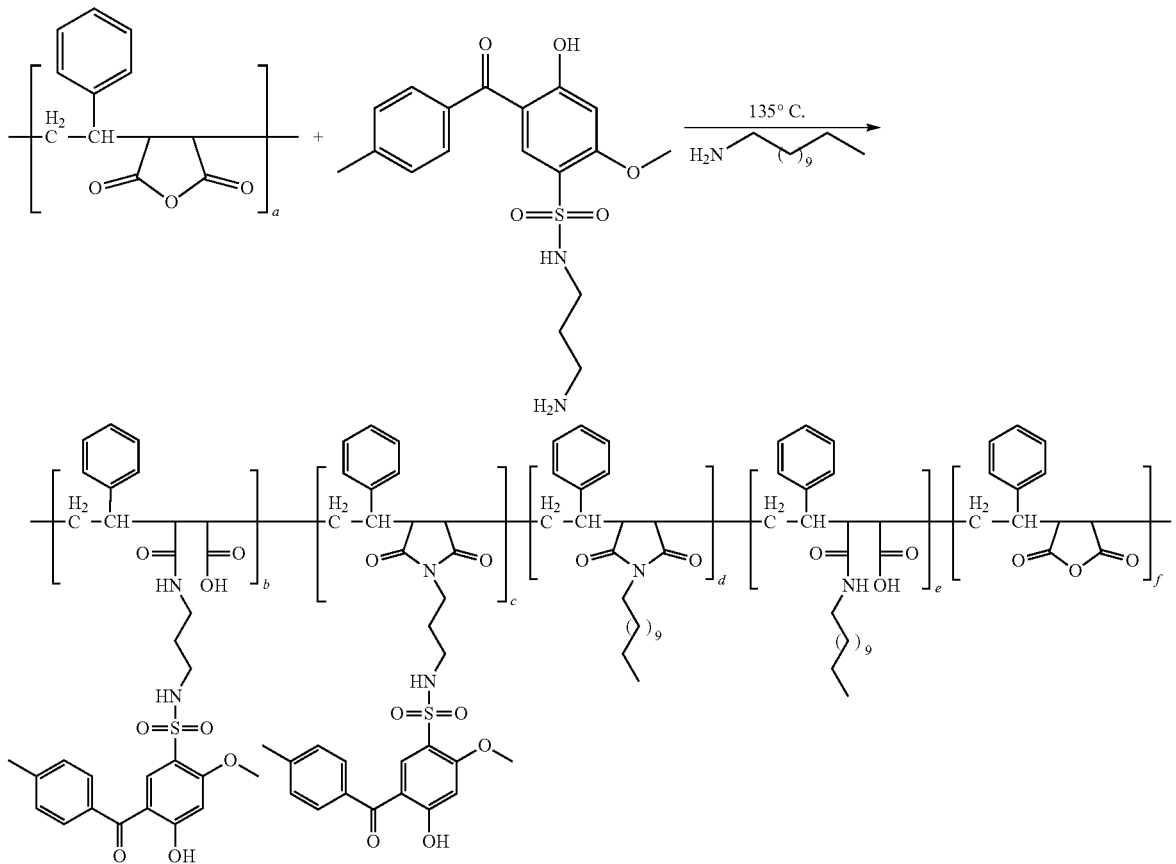

Example 81 was substantially repeated, except 4.8 g (26 mM) of n-dodecylamine was added to the premix, and it was dissolved with 6.0 g ethanol. A creamy solid was obtained that was miscible in ethanol/water solutions and soluble in oils like di-isopropyl-adipate. The molar quantities are such that $a=b+c+d+e+f$.

This product can be used for personal care formulations for UV-A/B protection for hair and as a styling agent, and for UV-A/B suncare applications.

Example 85: Poly(styrene/MA) Grafted with 577-Sulfanamide-Propylenediamine and Dimethylaminopropylamine; Half Ethyl Ester, Amic Acid, and Full Imide Forms

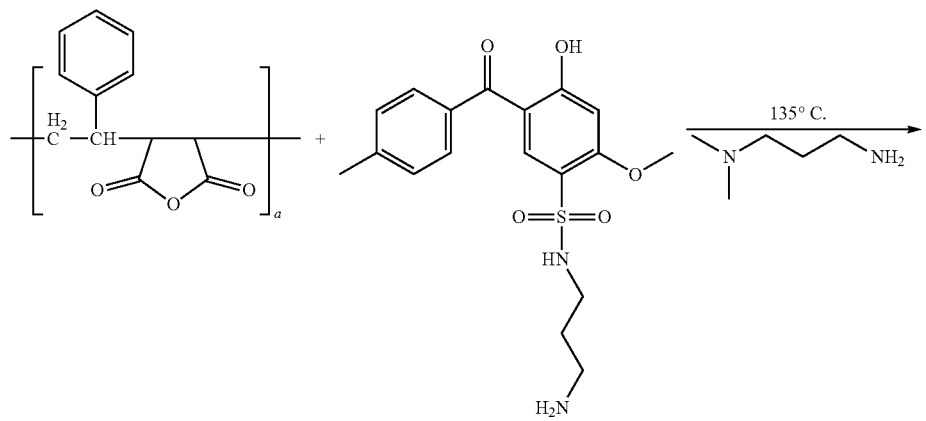

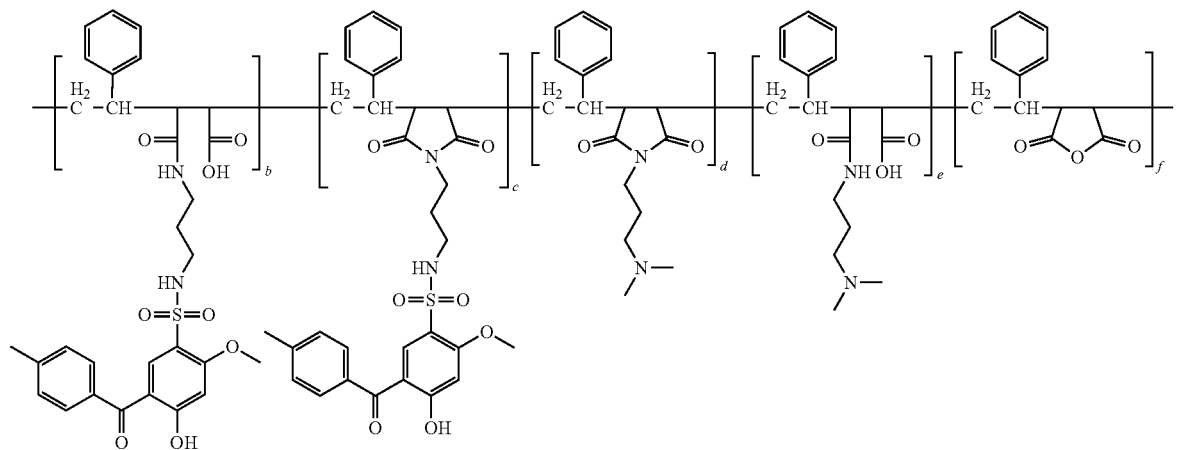

Example 81 was substantially repeated, except 2.7 g (26 mM) of dimethylaminopropylamine was added to the premix, and it was dissolved with 9.0 g ethanol. A creamy solid was obtained that was miscible in ethanol/water solutions and soluble in oils like di-isopropyl-adipate. The molar quantities are such that $a=b+c+d+e+f$.

This product can be used for personal care formulations, such as gels/emulsions for UV-A/B protection for conditioning hair and/or skin applications.

Example 86: Poly(styrene/MA) Grafted with 577-Sulfanamide-Hexylenediamine; Half Ethyl Ester, Amic Acid, and Full Imide Forms

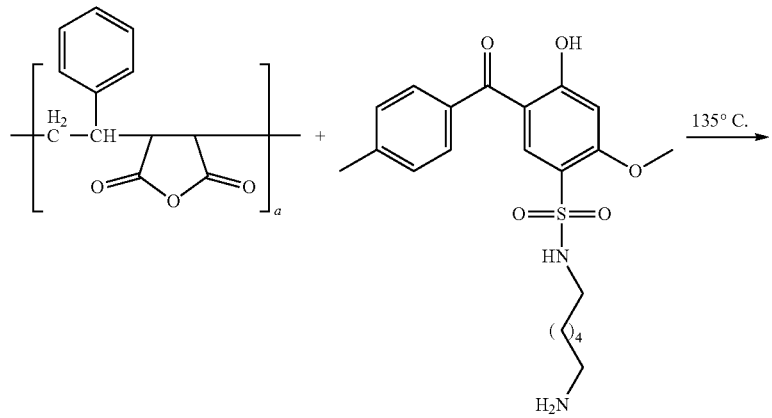

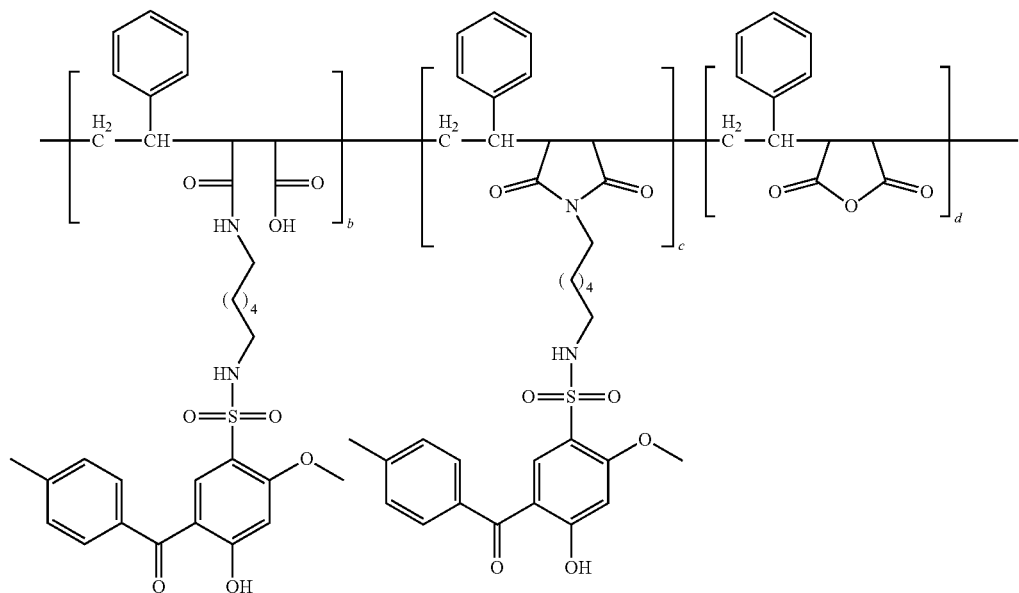

Example 66 is substantially repeated, replacing the poly(styrene/MA) having a $M_w$, of 130,000 Da by the copolymer of octadecene and maleic anhydride having a $M_w$, of 6,000 Da. Cetyl alcohol (17 g) is used instead of ethanol. A creamy solid is obtained that is miscible in ethanol/water solutions and soluble in oils like di-isopropyl-adipate. The molar quantities are such that a=b+c+d.

This product can be used for personal care formulations for UV-A/B protection for hair and as a styling agent, and for UV-A/B suncare applications.

Example 87: Poly(styrene/MA) Grafted with 577-Sulfanamide-Hexylenediamine and Isobutylamine; Half Ethyl Ester, Amic Acid, and Full Imide Forms

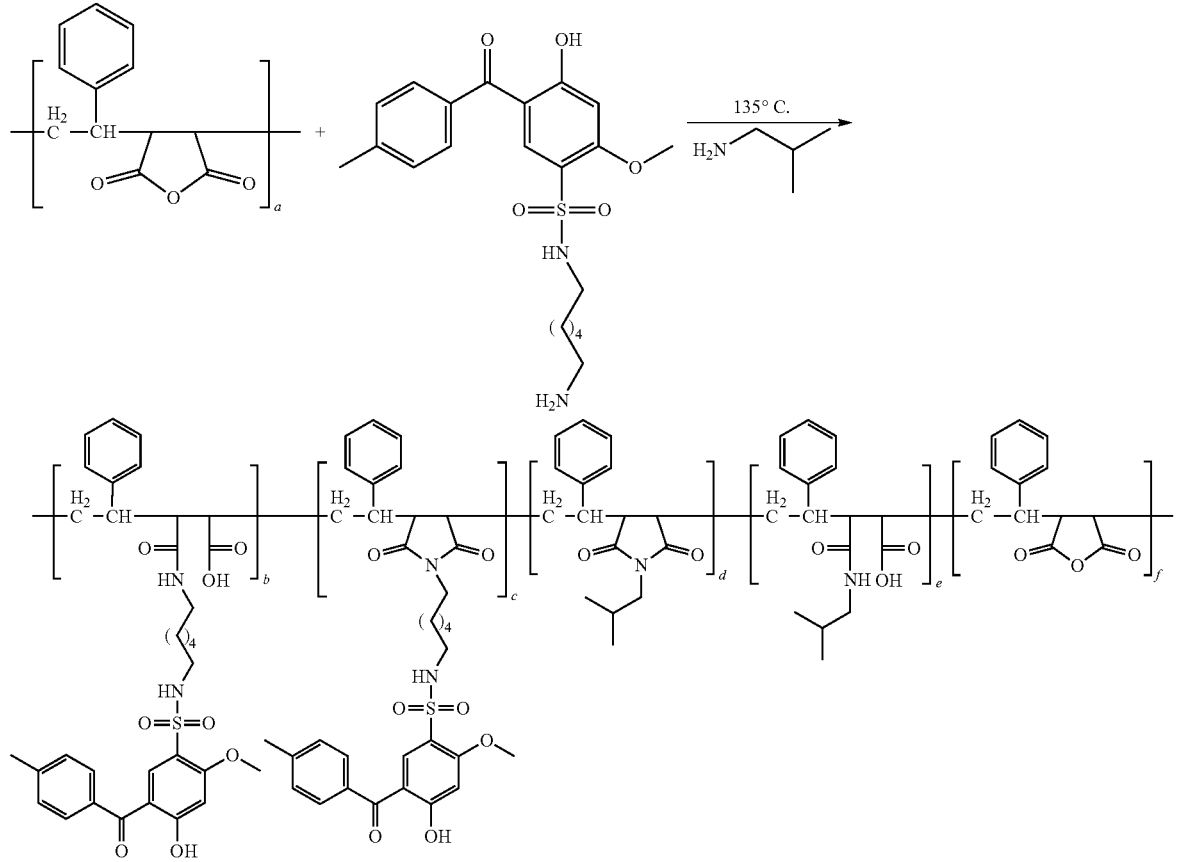

Example 86 is substantially repeated, except 1.9 g (26 mM) of isobutylamine is added to the premix, which is dissolved with 6.0 g ethanol. A creamy solid is obtained that is miscible in ethanol/water solutions and soluble in oils like di-isopropyl-adipate. The molar quantities are such that a=b+c+d+e+f.

This product can be used for personal care formulations for UV-A/B protection for hair and as a styling agent, and for UV-A/B suncare applications.

Example 88: Poly(styrene/MA) Grafted with 577-Sulfanamide-Hexylenediamine and n-octylamine; Half Ethyl Ester, Amic Acid, and Full Imide Forms

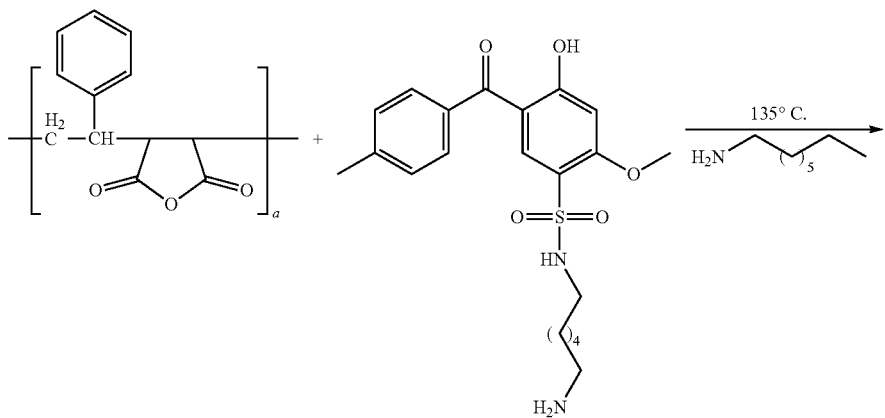

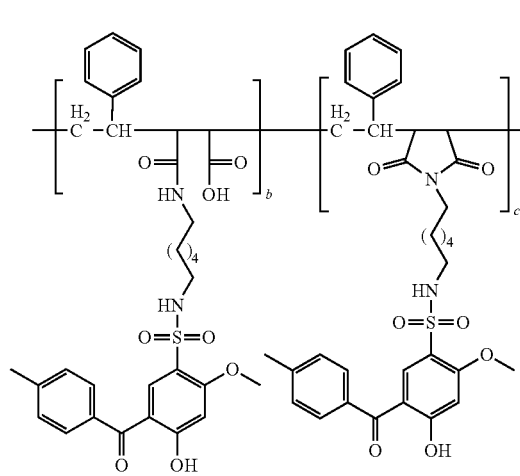

Example 86 is substantially repeated, except 3.3 g (26 mM) of n-octylamine is added to the premix, and it is dissolved with 6.0 g ethanol. A creamy solid is obtained that is miscible in ethanol/water solutions and soluble in oils like di-isopropyl-adipate. The molar quantities are such that a=b+c+d+e+f.

This product can be used for personal care formulations for UV-A/B protection for hair and as a styling agent, and for UV-A/B suncare applications.

Example 89: Poly(styrene/MA) Grafted with 577-Sulfanamide-Hexylenediamine and n-dodecylamine; Half Ethyl Ester, Amic Acid, and Full Imide Forms

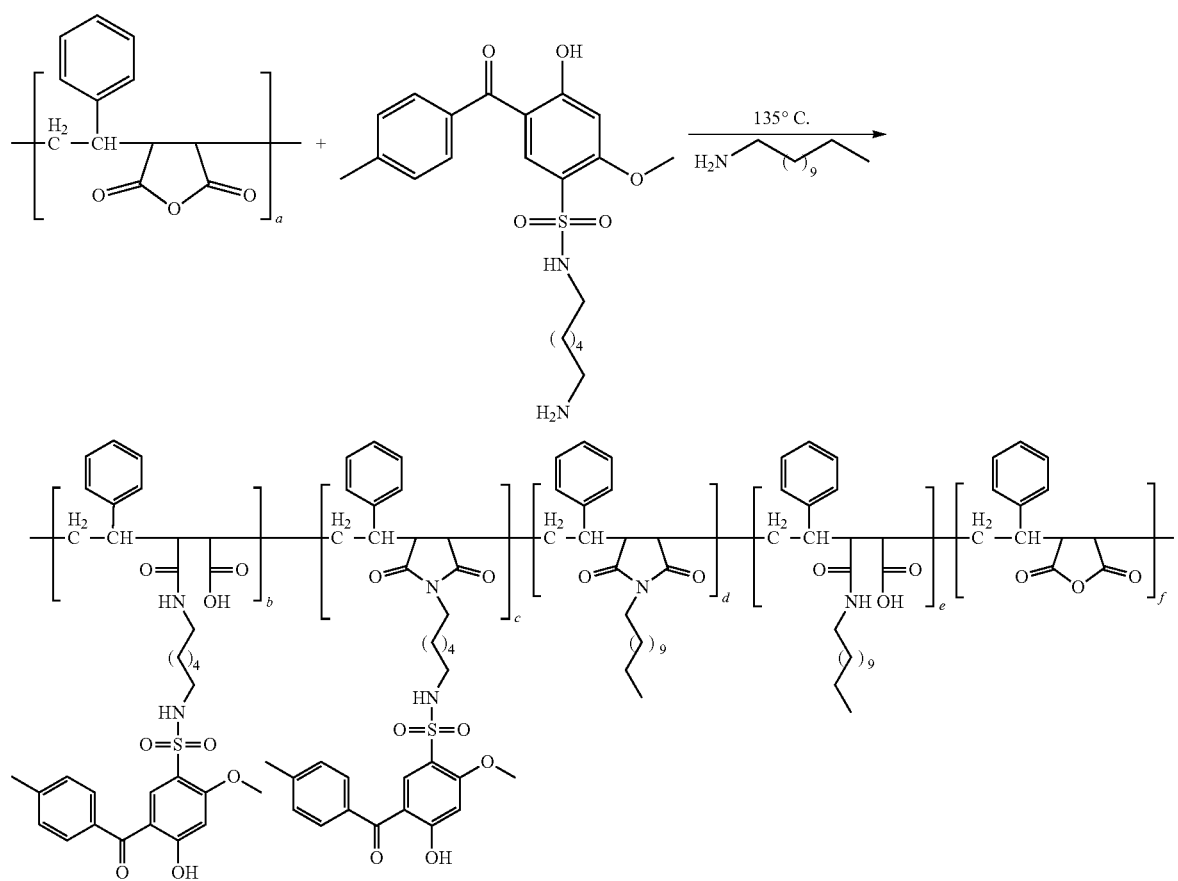

Example 86 is substantially repeated, except 4.8 g (26 mM) of n-dodecylamine is added to the premix, and it is dissolved with 6.0 g ethanol. A creamy solid is obtained that is miscible in ethanol/water solutions and soluble in oils like di-isopropyl-adipate. The molar quantities are such that $a=b+c+d+e+f$.

This product can be used for personal care formulations for UV-A/B protection for hair and as a styling agent, and for UV-A/B suncare applications.

Example 90: Poly(styrene/MA) Grafted with 577-Sulfanamide-Hexylenediamine and Dimethylaminopropylamine; Half Ethyl Ester, Amic Acid, and Full Imide Forms

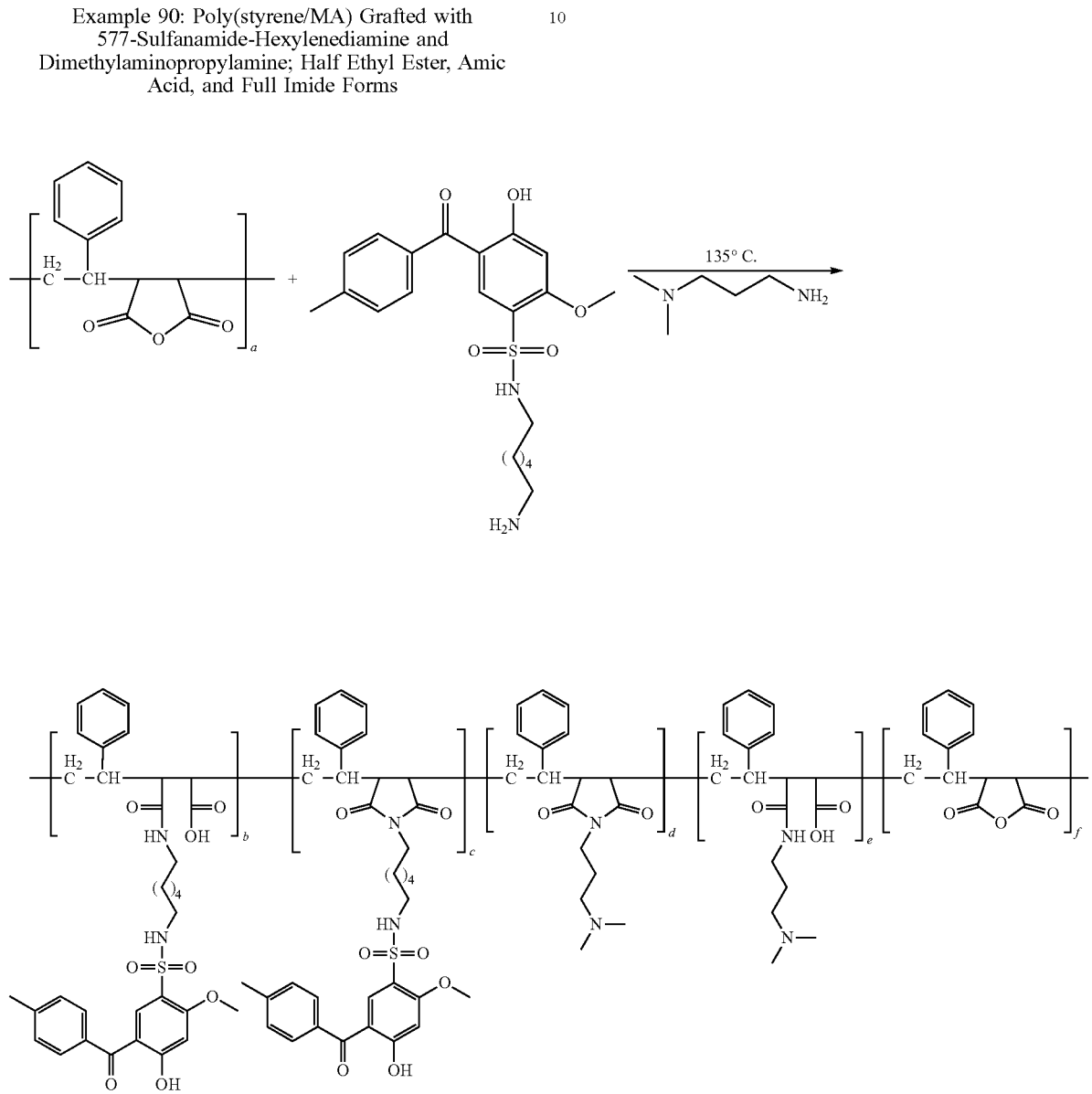

Example 86 is substantially repeated, except 2.7 g (26 mM) of dimethylaminopropylamine is added to the premix, and it is dissolved with 9.0 g ethanol. A creamy solid is obtained that is miscible in ethanol/water solutions and soluble in oils like di-isopropyl-adipate. The molar quantities are such that $a=b+c+d+e+f$.

This product can be used for personal care formulations, such as gels/emulsions for UV-A/B protection for conditioning hair and/or skin applications.

Example 91: Poly(IB/MA) Grafted with DMABPD, Half Ethyl Ester, Amic Acid, and Full Imide Forms

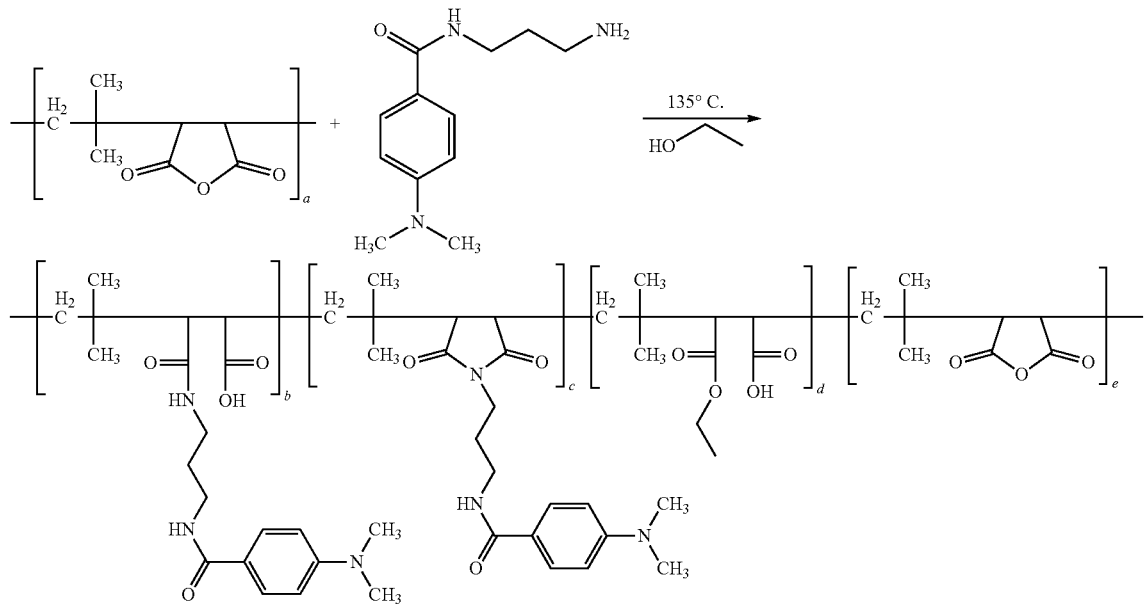

Example 46 was substantially repeated, replacing the 1.2 g (3.25 mM) of 577-sulfanamide-hexylenediamine with 0.71 g (3.25 mM) of DMABPD. The product mixture was cooled to room temperature to obtain a clear dark yellow ethanol solution that was also soluble in ethanol/water solutions and oils, such di-isopropyl-adipate. The molar quantities are such that a=b+c+d+e.

This product can be used for personal care formulations, such as gels/emulsions for UV-A/B protection for hair and as a styling agent, and for UV-A/B suncare applications.

Example 92: Poly(IB/MA) Grafted with DMABPD and Isobutylamine; Half Ethyl Ester, Amic Acid, and Full Imide Forms

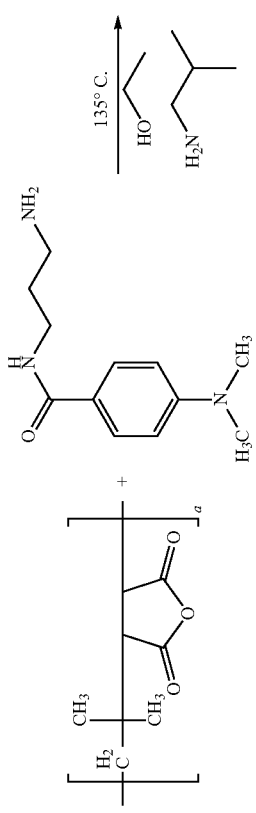
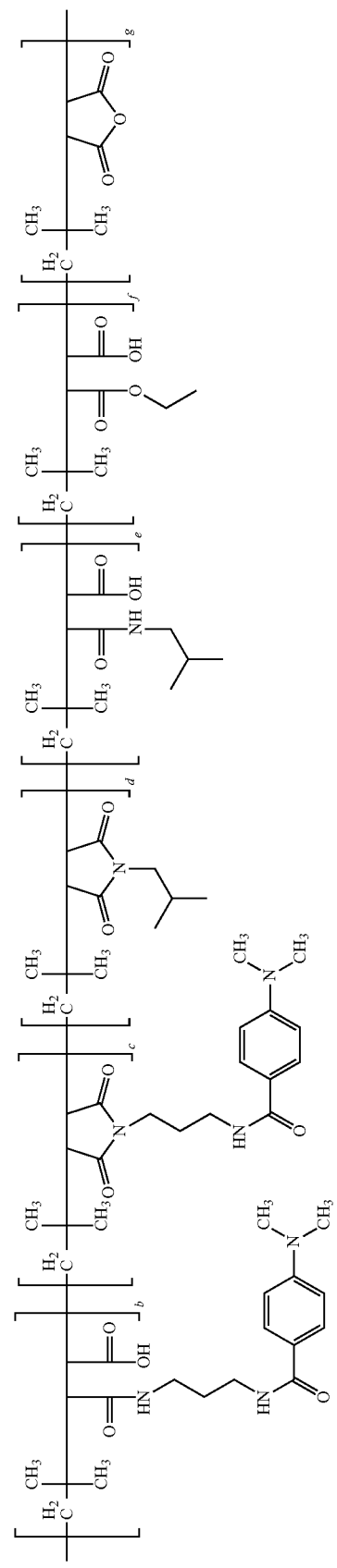

Example 91 was substantially repeated, except 1.9 g (26 mM) of isobutylamine was added to the premix, which was dissolved with 6.0 g ethanol. A clear dark yellow ethanol solution was obtained that was also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 93: Poly(IB/MA) Grafted with DMABPD and n-octylamine; Half Ethyl Ester, Amic Acid, and Full Imide Forms

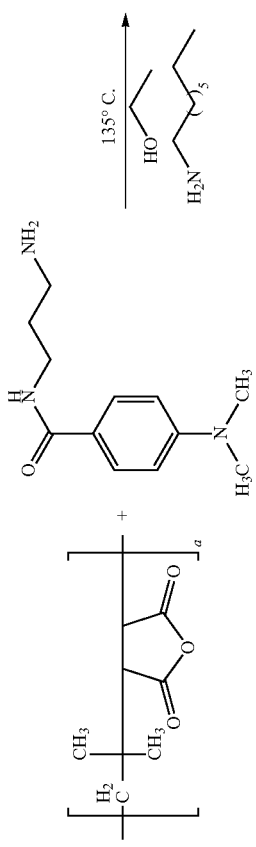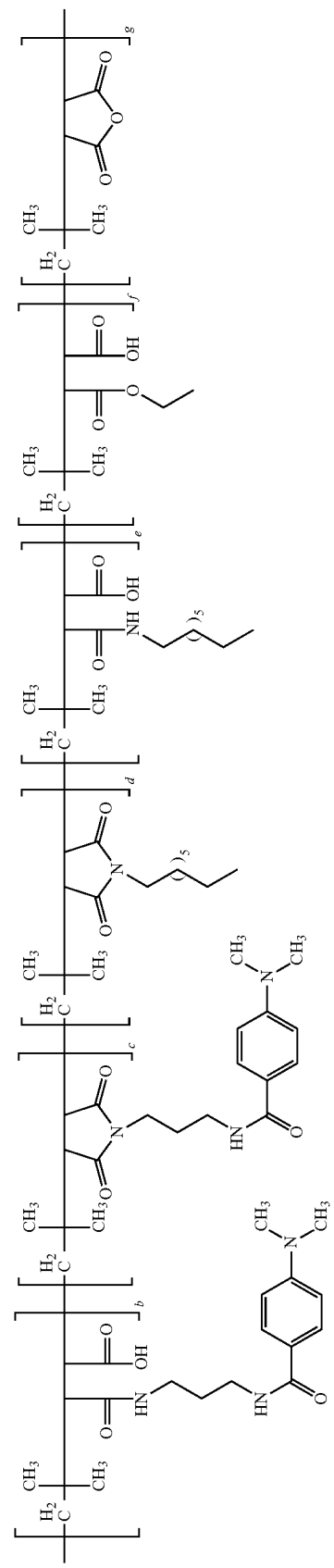

Example 91 was substantially repeated, except 3.3 g (26 mM) of n-octylamine was added to the premix, and it was dissolved with 6.0 g ethanol. A clear dark yellow ethanol solution was obtained that was also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 94: Poly(IB/MA) Grafted with DMABPD and n-dodecylamine; Half Ethyl Ester, Amic Acid, and Full Imide Forms

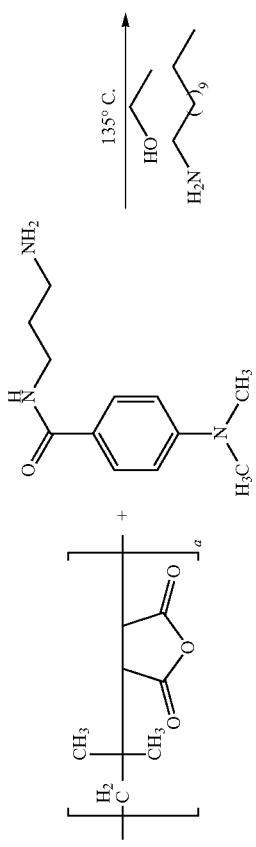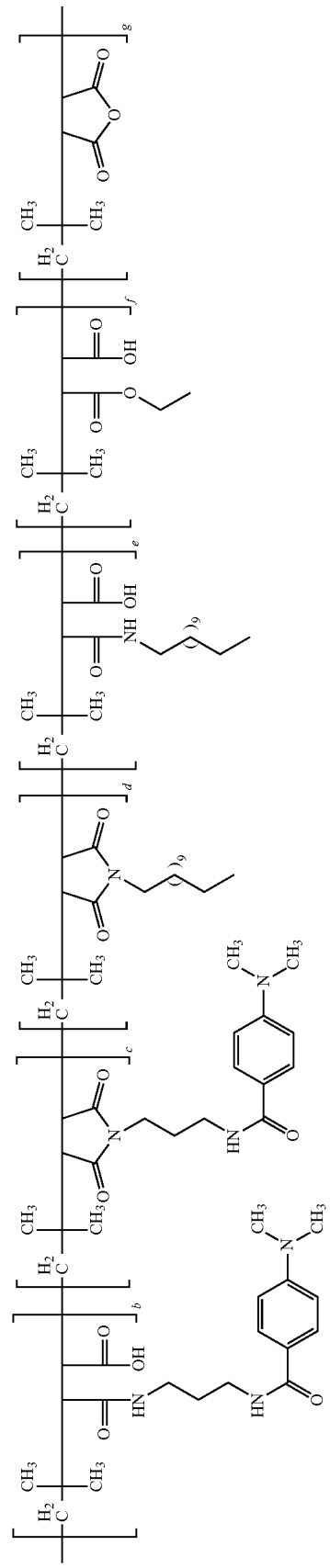

Example 91 was substantially repeated, except 4.8 g (26 mM) of n-dodecylamine was added to the premix, and it was dissolved with 6.0 g ethanol. A clear dark yellow ethanol solution was obtained that was also soluble in ethanol/water solutions and oils like di-isopropyl-adipate, or coconut, vegetable, or soybean oil. The molar quantities are such that $a=b+c+d+e+f+g$.

This product can be used for personal care formulations, such as gels/emulsions for UV-A/B protection for hair and as a styling agent, and for UV-A/B suncare applications.

Example 95: Poly(IB/MA) Grafted with DMABPD and Dimethylaminopropylamine; Half Ethyl Ester, Amic Acid, and Full Imide Forms

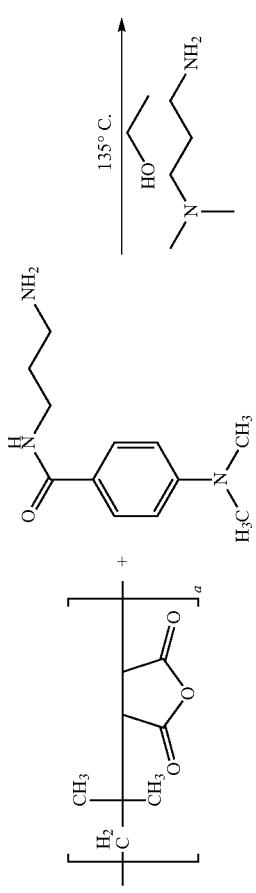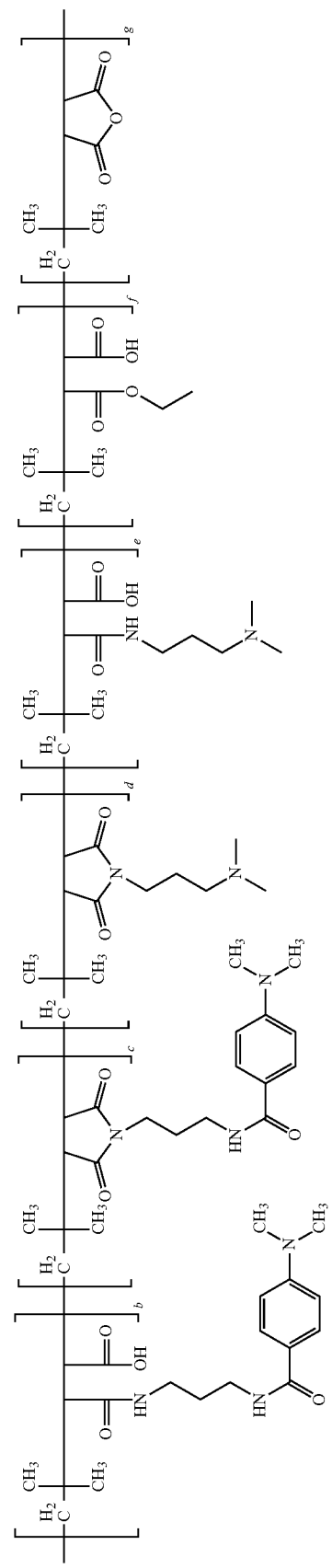

Example 91 was substantially repeated, except 2.7 g (26 mM) of dimethylaminopropylamine was added to the premix, and it was dissolved with 9.0 g ethanol. A clear dark yellow ethanol solution was obtained that was also soluble in ethanol/water solutions and other alcohols. The molar quantities are such that a=b+c+d+e+f+g.

This product can be used for personal care formulations, such as gels/emulsions for UV-A/B protection for conditioning hair and/or skin applications.

Example 96: Poly(IB/MA) Grafted with DMABHD, Half Ethyl Ester, Amic Acid, and Full Imide Forms

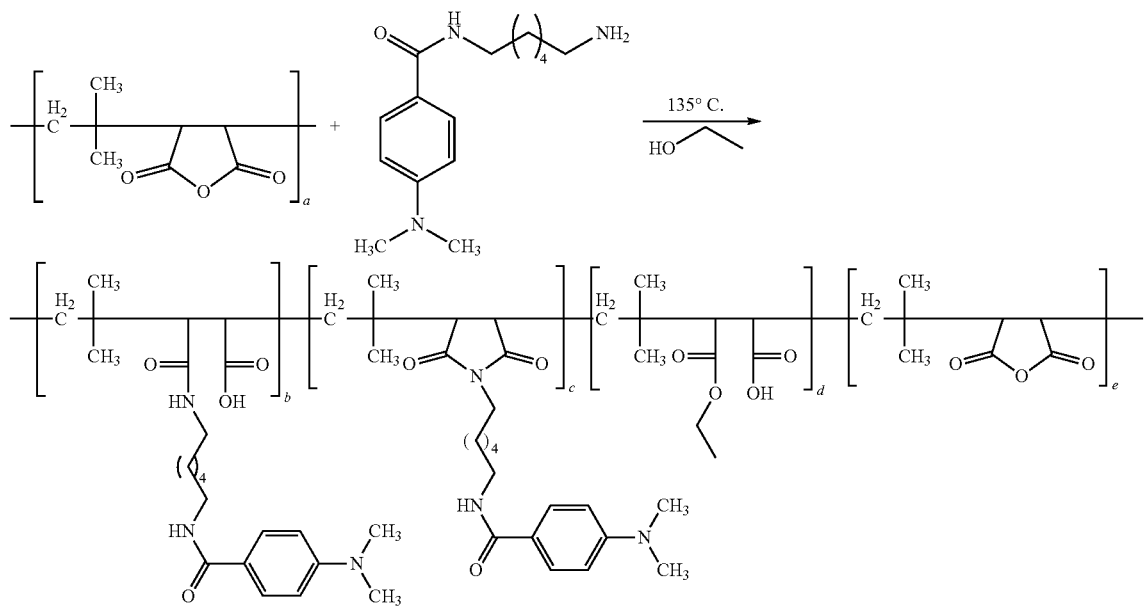

Example 46 is substantially repeated, replacing the 1.2 g (3.25 mM) of 577-sulfanamide-hexylenediamine with 0.71 g (3.25 mM) of DMABHD. The product mixture is cooled to room temperature to obtain a clear dark yellow ethanol solution that is also soluble in ethanol/water solutions and oils, such di-isopropyl-adipate. The molar quantities are such that a=b+c+d+e.

This product can be used for personal care formulations, such as gels/emulsions for UV-A/B protection for hair and as a styling agent, and for UV-A/B suncare applications.

Example 97: Poly(IB/MA) Grafted with DMABHD and Isobutylamine; Half Ethyl Ester, Amic Acid, and Full Imide Forms

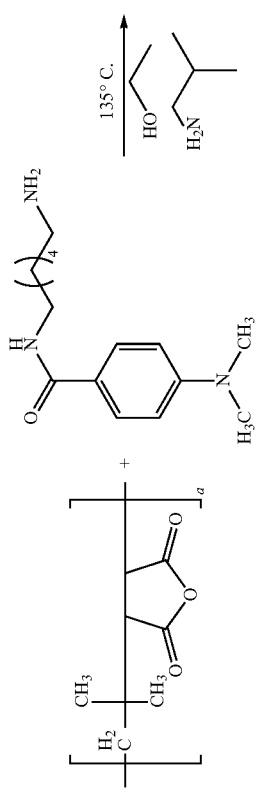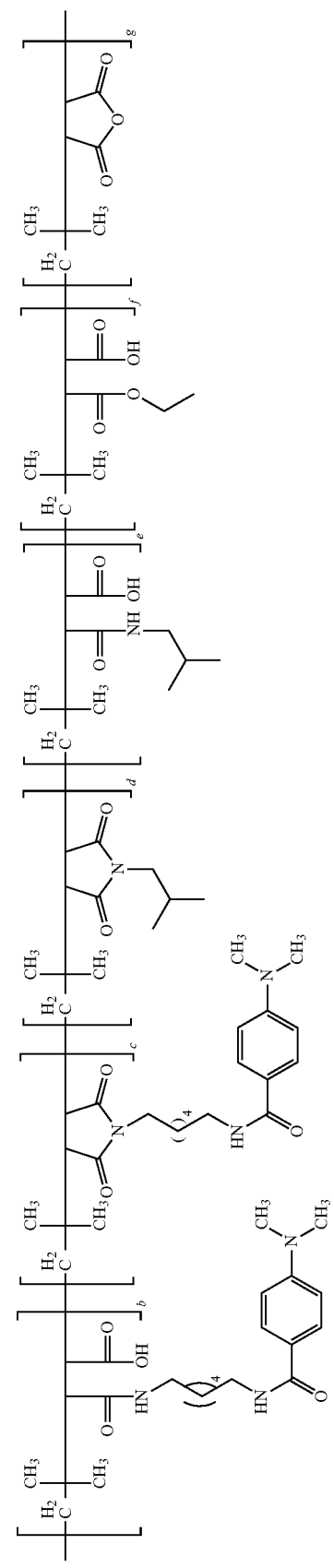

Example 96 is substantially repeated, except 1.9 g (26 mM) of isobutylamine is added to the premix, which is dissolved with 6.0 g ethanol. A clear dark yellow ethanol solution is obtained that is also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 98: Poly(IB/MA) Grafted with DMABHD and n-octylamine; Half Ethyl Ester, Amic Acid, and Full Imide Forms

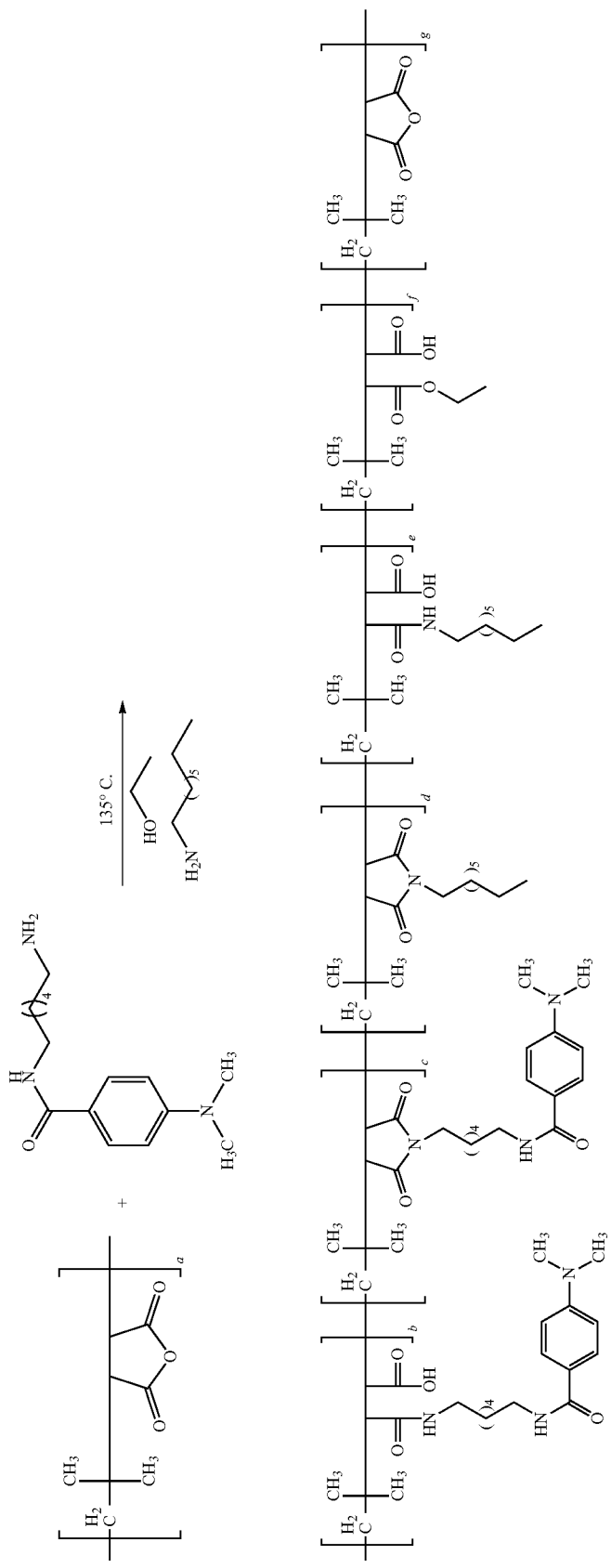

Example 96 is substantially repeated, except 3.3 g (26 mM) of n-octylamine is added to the premix, and it is dissolved with 6.0 g ethanol. A clear dark yellow ethanol solution is obtained that is also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 99: Poly(IB/MA) Grafted with DMABHD and n-dodecylamine; Half Ethyl Ester, Amic Acid, and Full Imide Forms

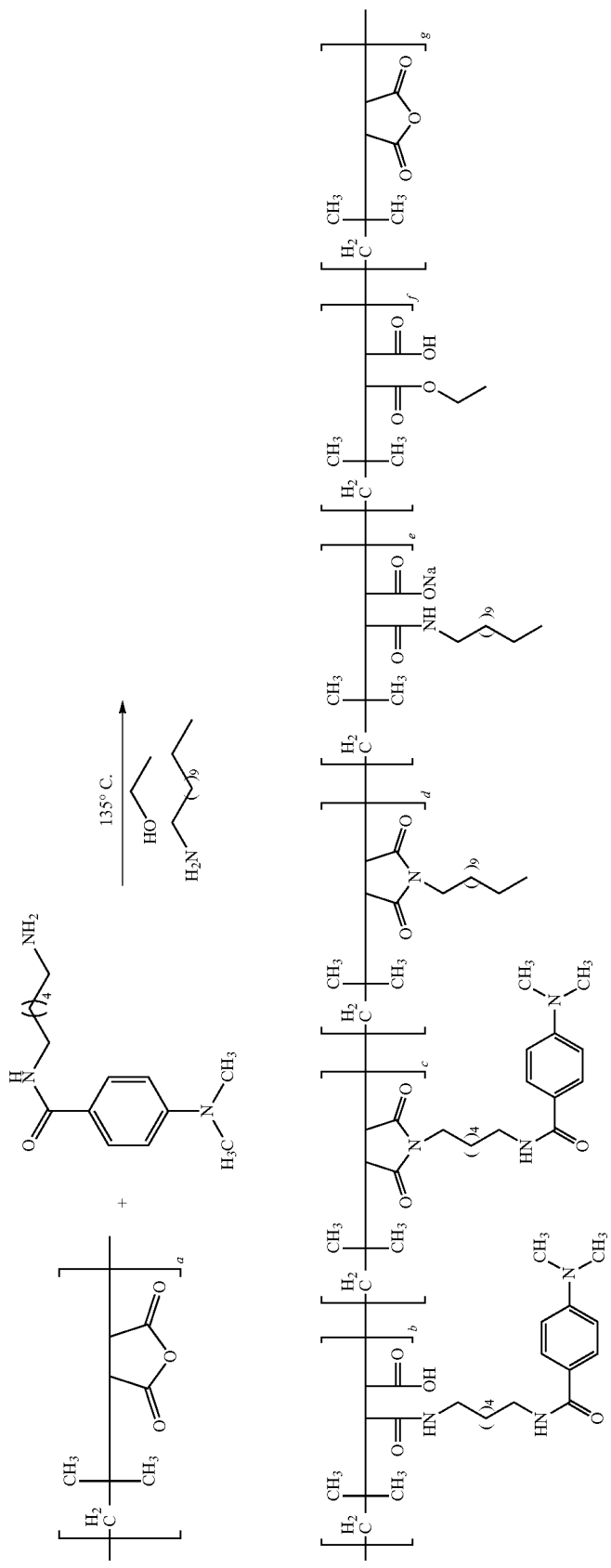

Example 96 is substantially repeated, except 4.8 g (26 mM) of n-dodecylamine is added to the premix, and it is dissolved with 6.0 g ethanol. A clear dark yellow ethanol solution is obtained that is also soluble in ethanol/water solutions and oils like di-isopropyl-adipate, or coconut, vegetable, or soybean oil. The molar quantities are such that a=b+c+d+e+f+g.

This product can be used for personal care formulations, such as gels/emulsions for UV-A/B protection for hair and as a styling agent, and for UV-A/B suncare applications.

Example 100: Poly(IB/MA) Grafted with DMABHD and Dimethylaminopropylamine; Half Ethyl Ester, Amic Acid, and Full Imide Forms

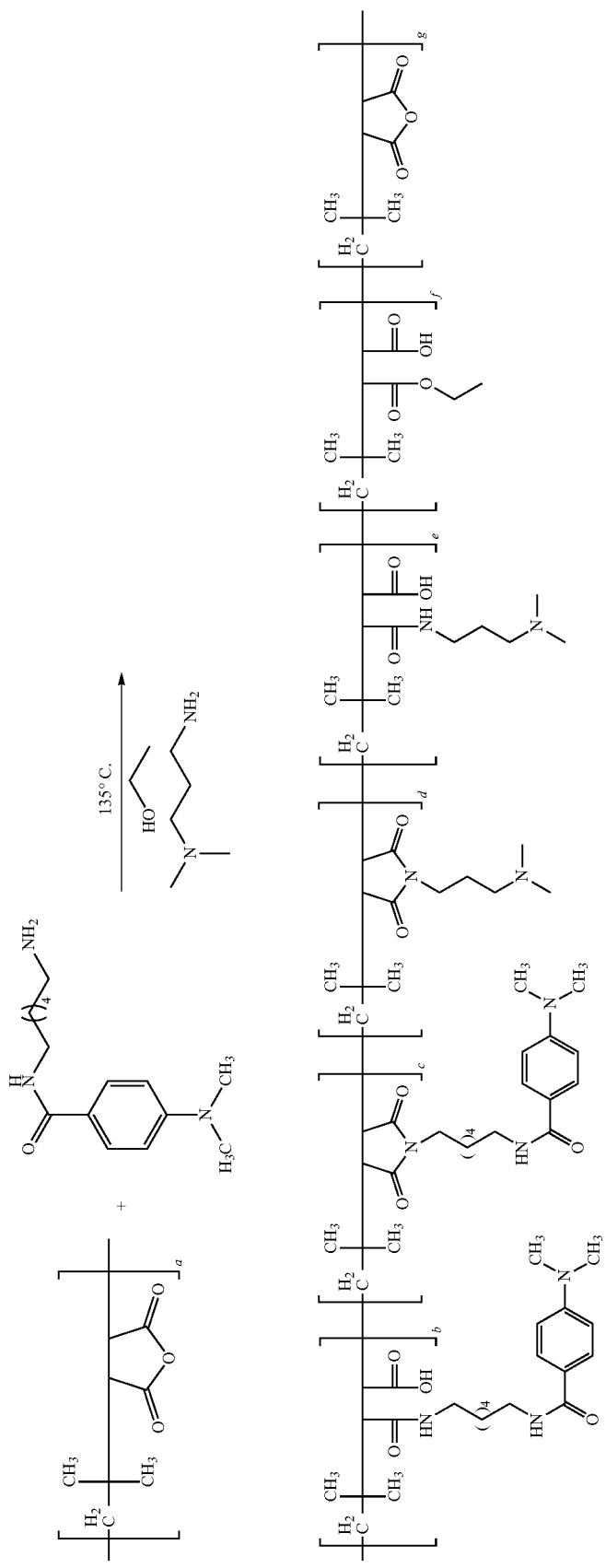

Example 96 is substantially repeated, except 2.7 g (26 mM) of dimethylaminopropylamine is added to the premix, and it is dissolved with 9.0 g ethanol. A clear dark yellow ethanol solution is obtained that is also soluble in ethanol/water solutions and other alcohols. The molar quantities are such that a=b+c+d+e+f+g.

This product can be used for personal care formulations, such as gels/emulsions for UV-A/B protection for conditioning hair and/or skin applications.

Example 101: Poly(IB/MA) Grafted with DMABEA, Half Ethyl Ester, Amic Acid, and Full Imide Forms

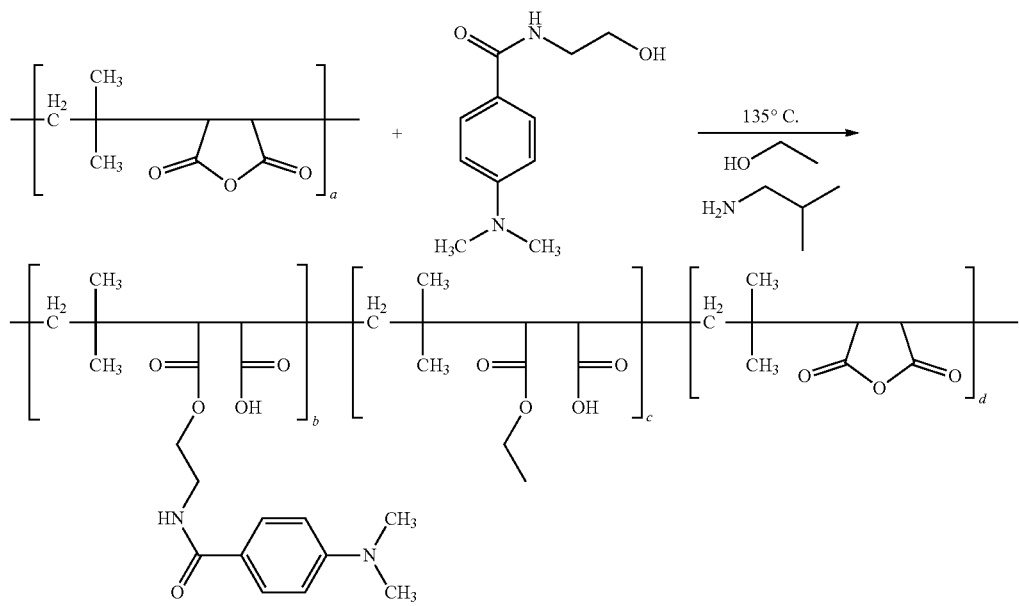

Example 46 is substantially repeated, replacing the 1.2 g (3.25 mM) of 577-sulfanamide-hexylenediamine with 0.71 g (3.25 mM) of DMABEA. The product mixture is cooled to room temperature to obtain a clear dark yellow ethanol solution that is also soluble in ethanol/water solutions and oils, such di-isopropyl-adipate. The molar quantities are such that a=b+c+d.

This product can be used for personal care formulations, such as gels/emulsions for UV-A/B protection for hair and as a styling agent, and for UV-A/B suncare applications.

Example 102: Poly(IB/MA) Grafted with DMABEA and Isobutylamine; Half Ethyl Ester, Amic Acid, and Full Imide Forms

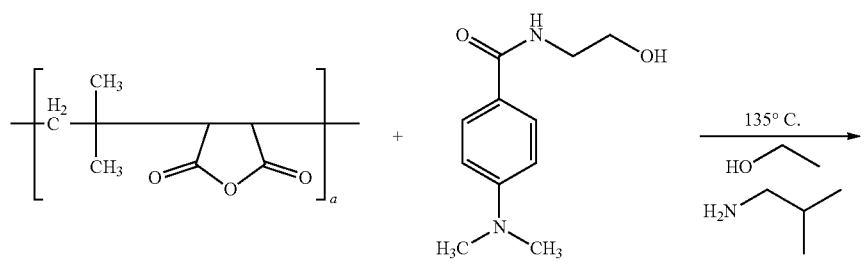

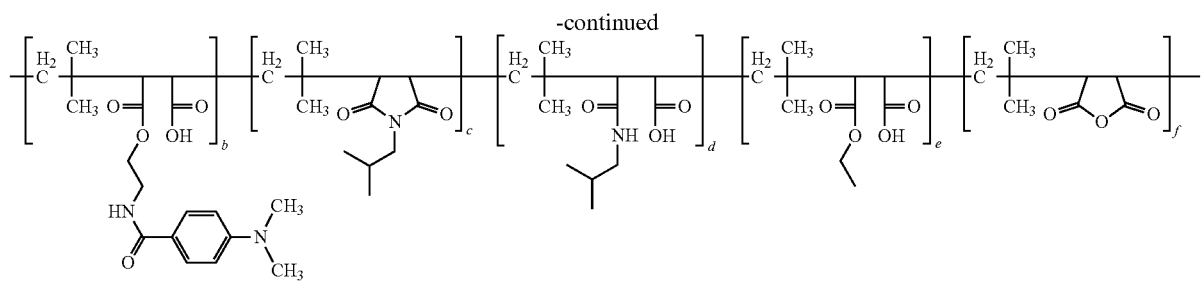

Example 101 is substantially repeated, except 1.9 g (26 mM) of isobutylamine is added to the premix, which is dissolved with 6.0 g ethanol. A clear dark yellow ethanol solution is obtained that is also soluble in ethanol/water solutions and oils like di-isopropyl-adipate. The molar quantities are such that a=b+c+d+e+f.

This product can be used for personal care formulations, such as gels/emulsions for UV-A/B protection for hair and as a styling agent, and for UV-A/B suncare applications.

Example 103: Poly(IB/MA) Grafted with DMABEA and n-octylamine; Half Ethyl Ester, Amic Acid, and Full Imide Forms

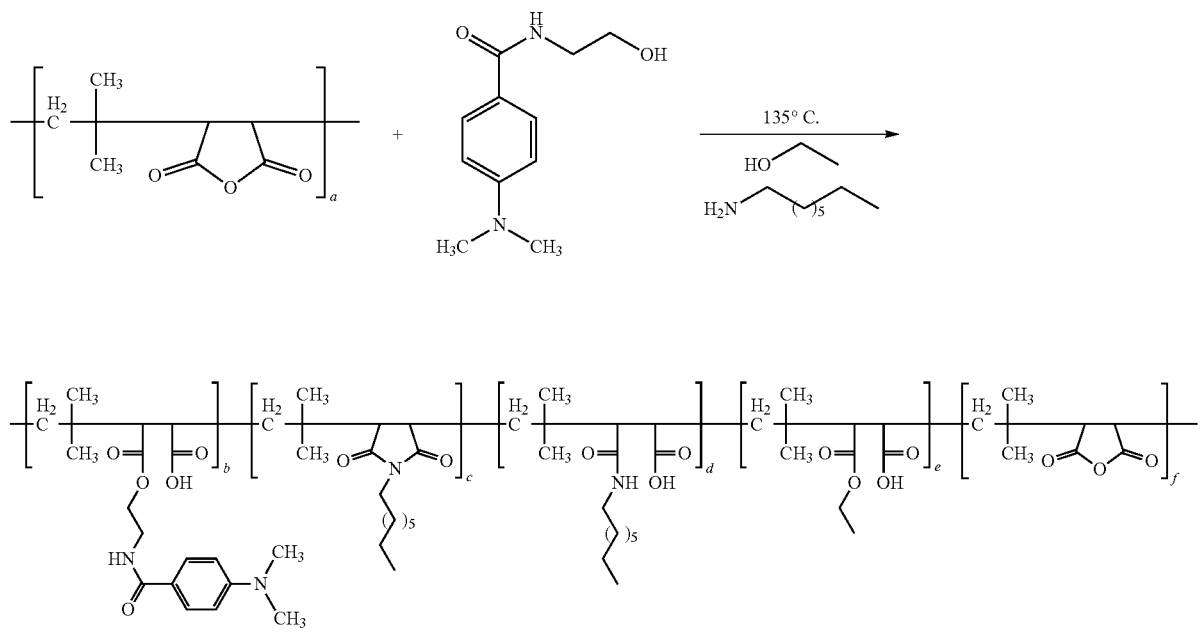

Example 101 is substantially repeated, except 3.3 g (26 mM) of n-octylamine is added to the premix, and it is dissolved with 6.0 g ethanol. A clear dark yellow ethanol solution is obtained that is also soluble in ethanol/water solutions and oils like di-isopropyl-adipate. The molar quantities are such that a=b+c+d+e+f.

This product can be used for personal care formulations, such as gels/emulsions for UV-A/B protection for hair and as a styling agent, and for UV-A/B suncare applications.

Example 104: Poly(IB/MA) Grafted with DMABEA and n-dodecylamine; Half Ethyl Ester, Amic Acid, and Full Imide Forms

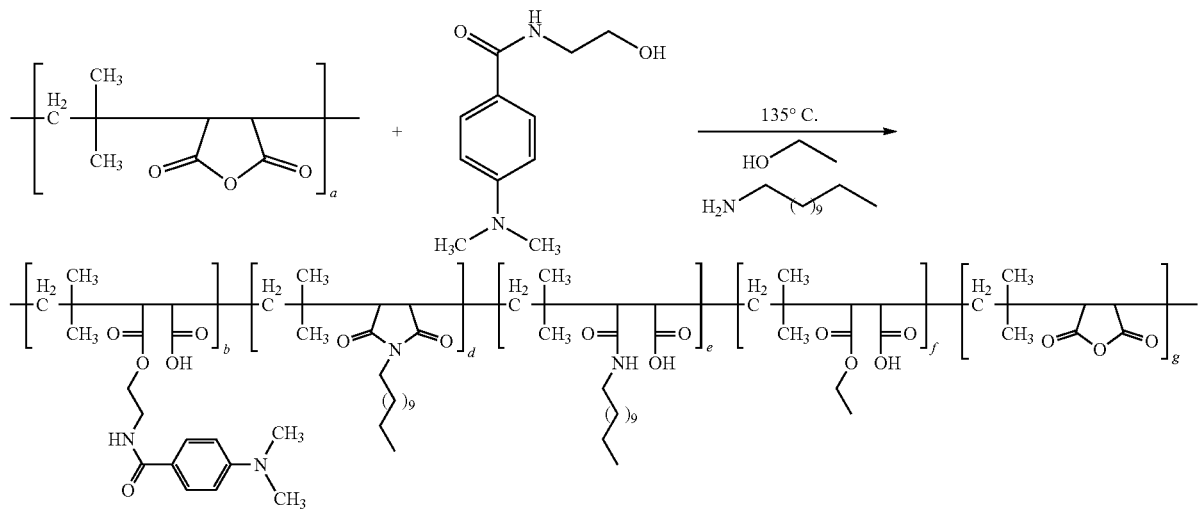

Example 101 is substantially repeated, except 4.8 g (26 mM) of n-dodecylamine is added to the premix, and it is dissolved with 6.0 g ethanol. A clear dark yellow ethanol solution is obtained that is also soluble in ethanol/water solutions and oils like di-isopropyl-adipate, or coconut, vegetable, or soybean oil. The molar quantities are such that a=b+c+d+e+f+g.

This product can be used for personal care formulations, such as gels/emulsions for UV-A/B protection for hair and as a styling agent, and for UV-A/B suncare applications.

Example 105: Poly(IB/MA) Grafted with DMABEA and Dimethylaminopropylamine; Half Ethyl Ester, Amic Acid, and Full Imide Forms

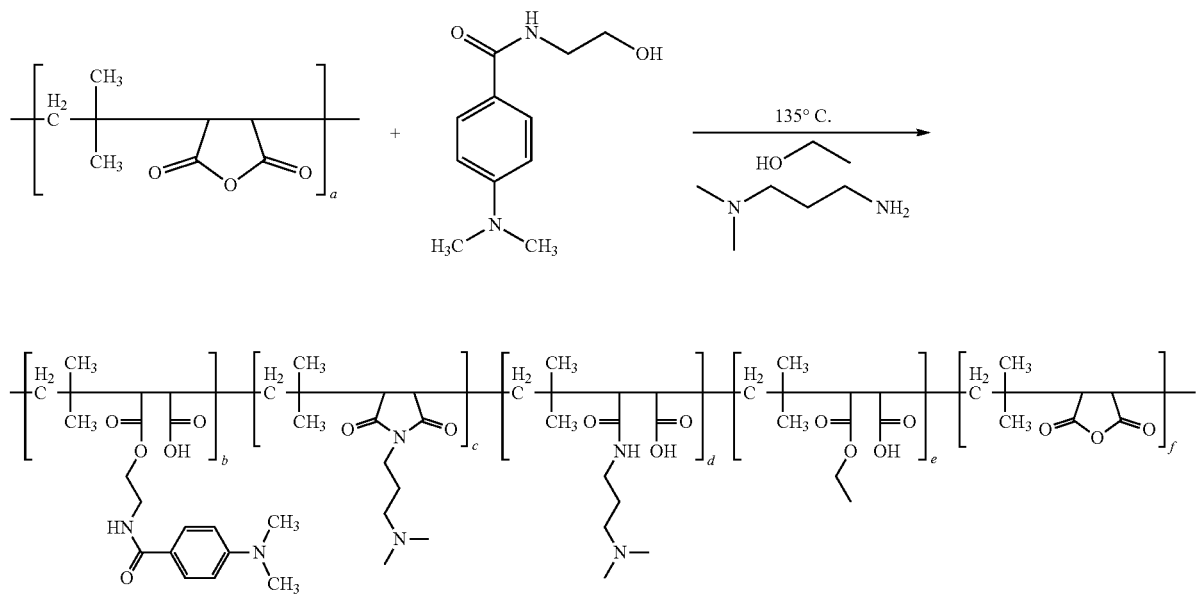

Example 101 is substantially repeated, except 2.7 g (26 mM) of dimethylaminopropylamine is added to the premix, and it is dissolved with 9.0 g ethanol. A clear dark yellow ethanol solution is obtained that was also soluble in ethanol/water solutions and other alcohols. The molar quantities are such that a=b+c+d+e+f+g.

This product can be used for personal care formulations, such as gels/emulsions for UV-A/B protection for conditioning hair and/or skin applications.

Examples 106-110

Poly(IB/MA) Grafted with DMABPD, Lower Molecular Weight Variants

Examples 91-95 were substantially repeated, in each case the poly(IB/MA) copolymer having a $M_w$, of 80,000 Da was replaced with the same copolymer having a $M_w$, of 6,000 Da. A clear dark yellow ethanol solution was obtained that was also soluble in ethanol/water solutions and other alcohols.

Examples 110-115

Poly(IB/MA) Grafted with DMABEA, Higher Molecular Weight Variants

Examples 91-95 were substantially repeated, in each case the poly(IB/MA) copolymer having a $M_w$, of 6,000 Da was replaced with the same copolymer having a $M_w$, of 80,000 Da. A clear dark yellow ethanol solution was obtained that was also soluble in ethanol/water solutions and other alcohols.

Example 116: Poly(MVE/MA) Grafted with DMABPD, Half Ethyl Ester, Amic Acid, and Full Imide Forms

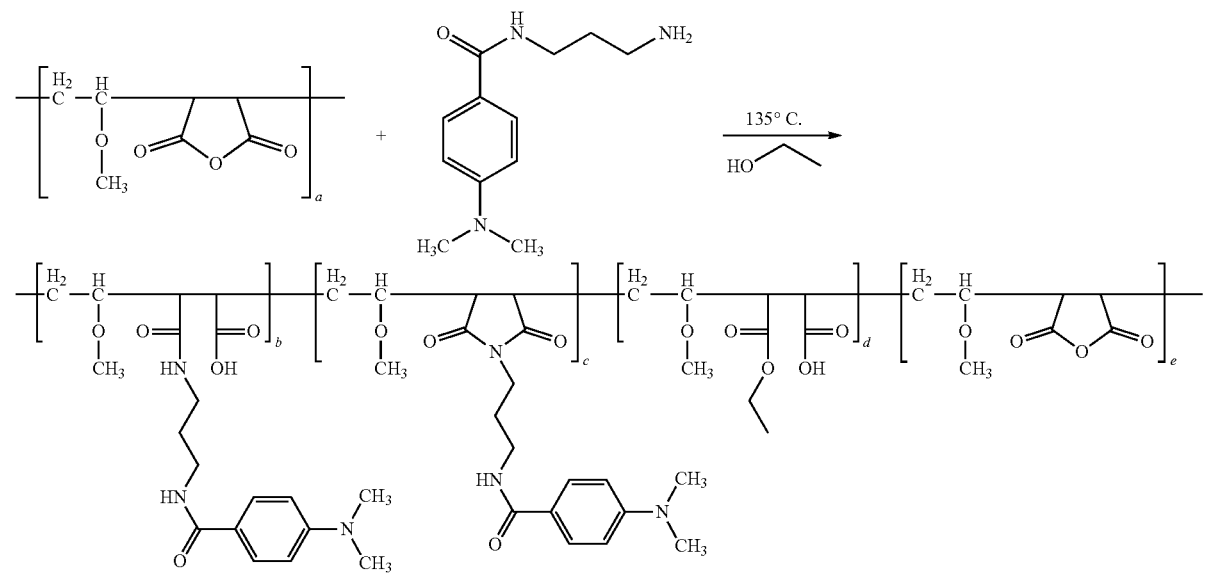

Example 91 was substantially repeated, replacing the poly(IB/MA) copolymer with a copolymer of methyl vinyl ether and maleic anhydride having a $M_w$, of 130,000 Da. The product mixture was cooled to room temperature to obtain a clear dark yellow ethanol solution that was also soluble in ethanol/water solutions and oils, such di-isopropyl-adipate. The molar quantities are such that a=b+c+d+e.

This product can be used for personal care formulations, such as gels/emulsions for UV-A/B protection for hair and as a styling agent, and for UV-A/B suncare applications.

Example 117: Poly(MVE/MA) Grafted with DMABPD and Isobutylamine; Half Ethyl Ester, Amic Acid, and Full Imide Forms

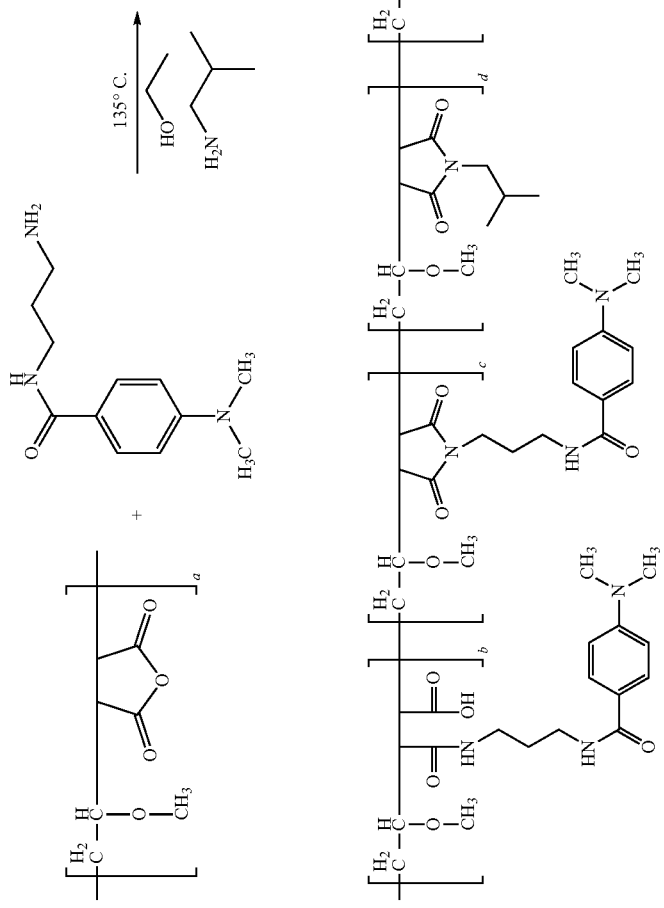

Example 116 was substantially repeated, except 1.9 g (26 mM) of isobutylamine was added to the premix, which was dissolved with 6.0 g ethanol. A clear dark yellow ethanol solution was obtained that was also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 118: Poly(MVE/MA) Grafted with DMABPD and n-octylamine; Half Ethyl Ester, Amic Acid, and Full Imide Forms

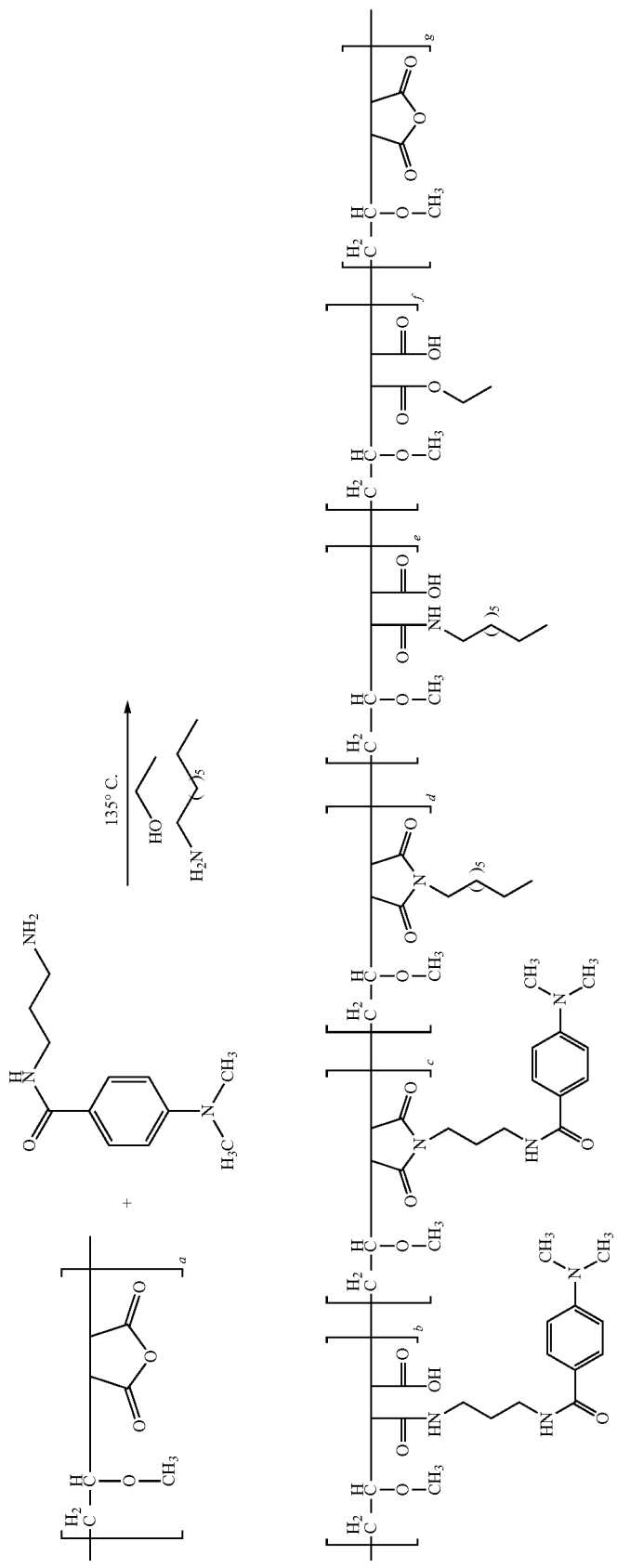

Example 116 was substantially repeated, except 3.3 g (26 mM) of n-octylamine was added to the premix, and it was dissolved with 6.0 g ethanol. A clear dark yellow ethanol solution was obtained that was also soluble in ethanol/water solutions and oils like di-isopropyl-adipate. The molar quantities are such that a=b+c+d+e+f+g.

This product can be used for personal care formulations, such as gels/emulsions for UV-A/B protection for hair and as a styling agent, and for UV-A/B suncare applications.

Example 119: Poly(MVE/MA) Grafted with DMABPD and n-dodecylamine; Half Ethyl Ester, Amic Acid, and Full Imide Forms

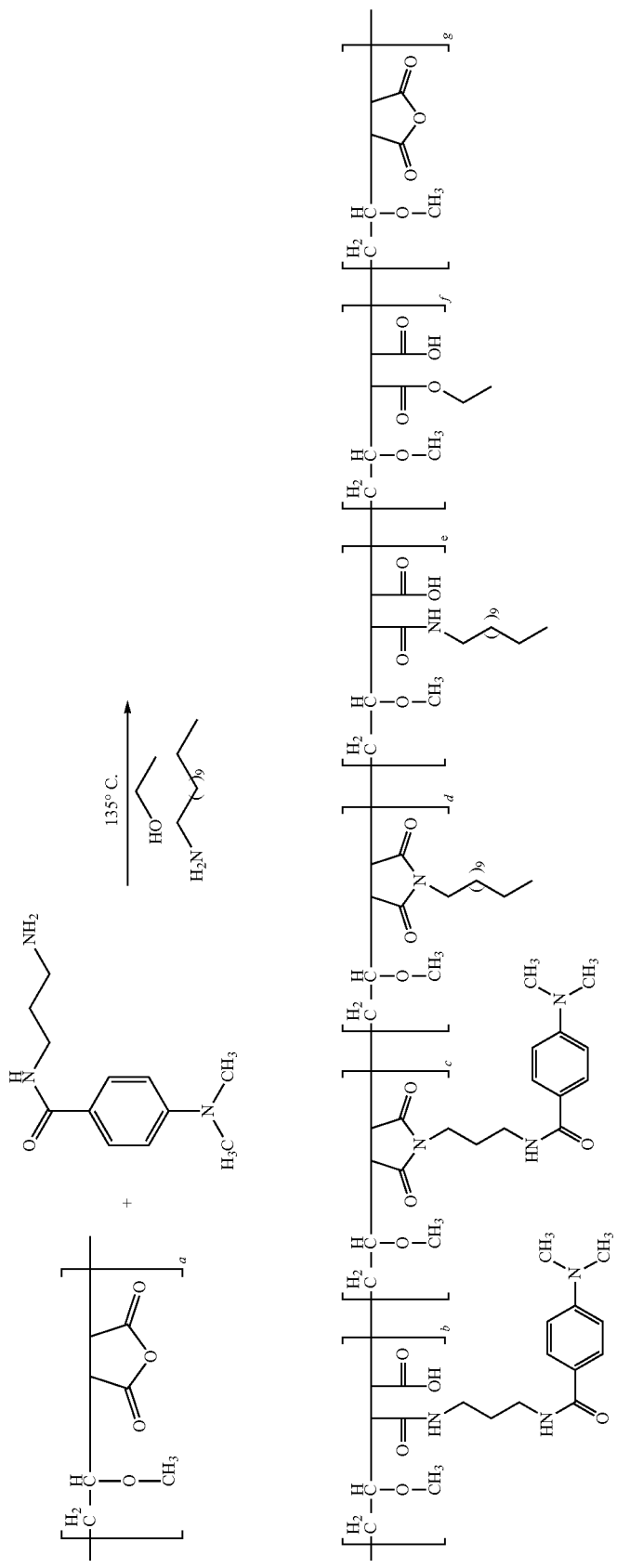

Example 116 was substantially repeated, except 4.8 g (26 mM) of n-dodecylamine was added to the premix, and it was dissolved with 6.0 g ethanol. A clear dark yellow ethanol solution was obtained that was also soluble in ethanol/water solutions and oils like di-isopropyl-adipate, or coconut, vegetable, or soybean oil. The molar quantities are such that a=b+c+d+e+f+g.

This product can be used for personal care formulations, such as gels/emulsions for UV-A/B protection for hair and as a styling agent, and for UV-A/B suncare applications.

Example 120: Poly(MVE/MA) Grafted with DMABPD and Dimethylaminopropylamine; Half Ethyl Ester, Amic Acid, and Full Imide Forms

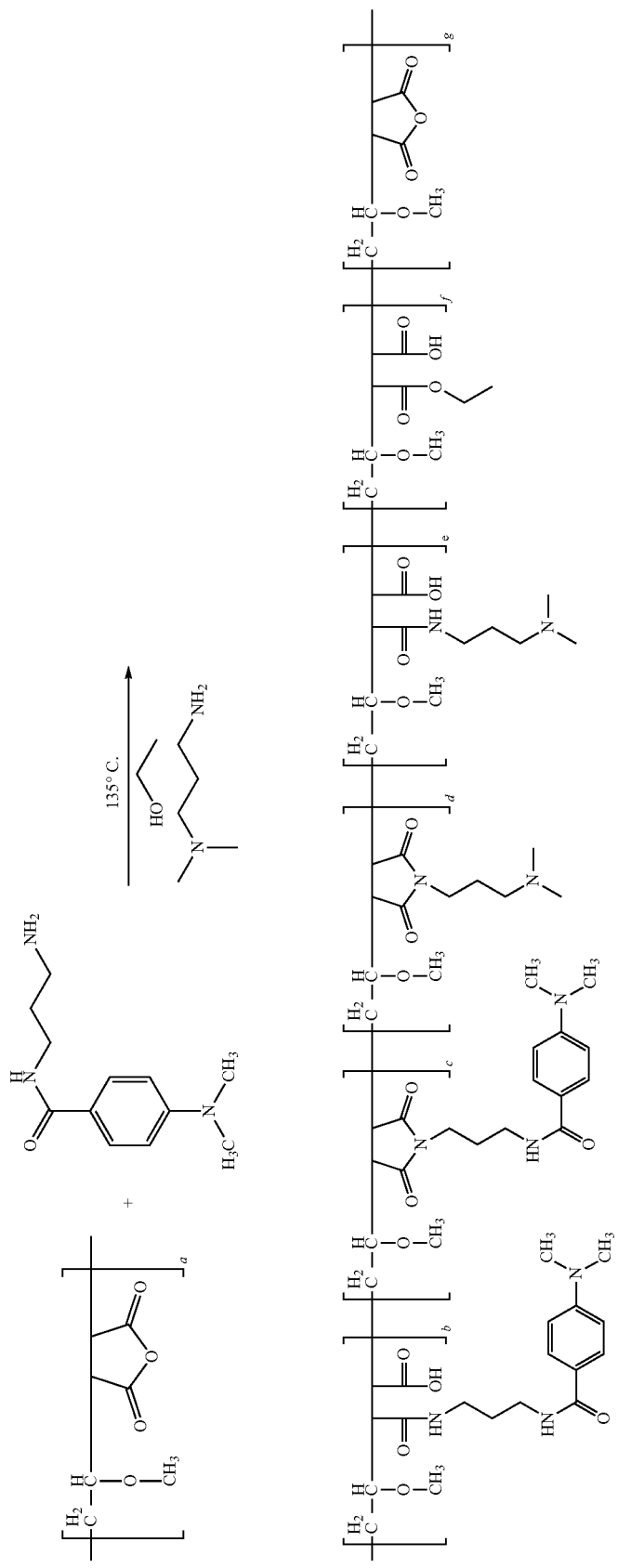

Example 116 was substantially repeated, except 2.7 g (26 mM) of dimethylaminopropylamine was added to the premix, and it was dissolved with 9.0 g ethanol. A clear dark yellow ethanol solution was obtained that was also soluble in ethanol/water solutions and other alcohols. The molar quantities are such that a=b+c+d+e+f+g.

This product can be used for personal care formulations, such as gels/emulsions for UV-A/B protection for conditioning hair and/or skin applications.

Example 121: Poly(MVE/MA) Grafted with DMABEA, Half Ethyl Ester, Amic Acid, and Full Imide Forms

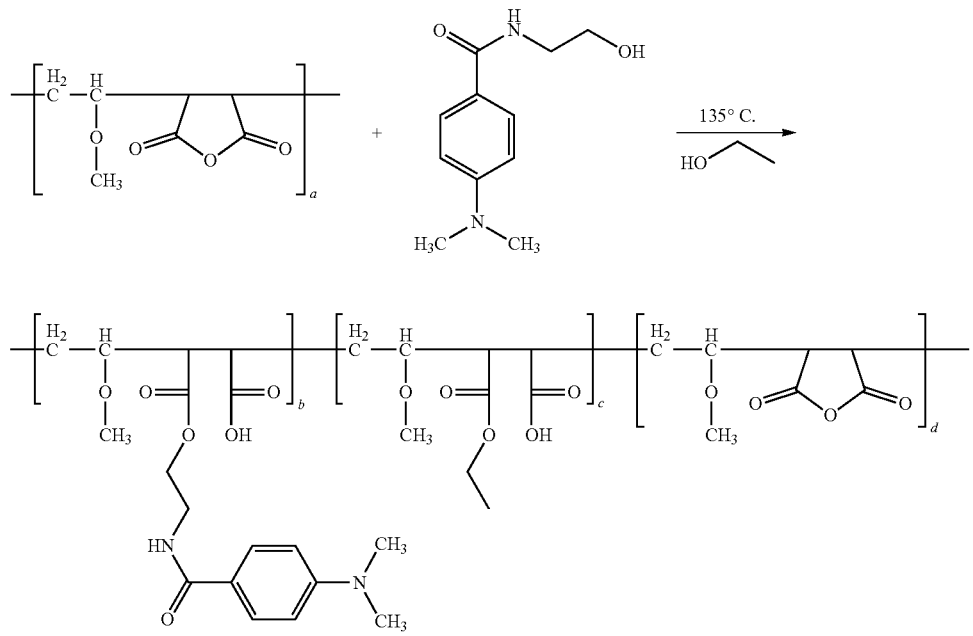

Example 116 was substantially repeated, replacing DMABPD with 0.67 g (3.25 mM) of DMABEA, and replacing the poly(MVE/MA) copolymer having a $M_w$, of 130,000 Da with the same copolymer having a $M_w$, of 2,500,000 Da. The product mixture was cooled to room temperature to obtain a clear dark yellow ethanol solution that was also soluble in ethanol/water solutions and oils, such di-isopropyl-adipate. The molar quantities are such that a=b+c+d.

This product can be used for personal care formulations, such as gels/emulsions for UV-A/B protection for hair and as a styling agent, and for UV-A/B suncare applications.

Example 122: Poly(MVE/MA) Grafted with DMABEA and Isobutylamine; Half Ethyl Ester, Amic Acid, and Full Imide Forms

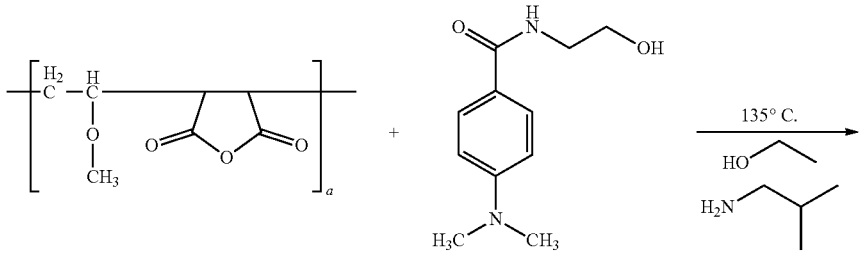

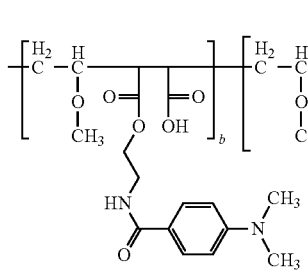 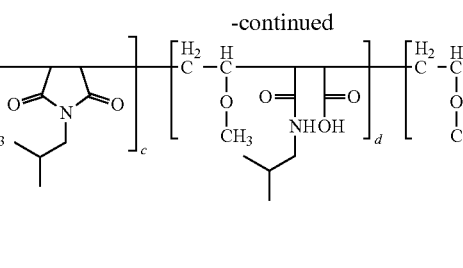 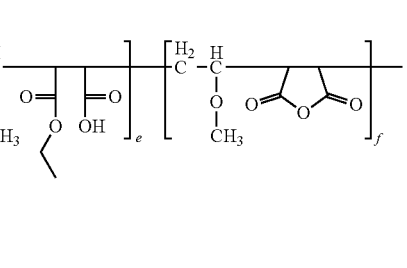

-continued

Example 121 is substantially repeated, except 1.9 g (26 mM) of isobutylamine is added to the premix, which is dissolved with 6.0 g ethanol. A clear dark yellow ethanol solution is obtained that is also soluble in ethanol/water solutions and oils like di-isopropyl-adipate. The molar quantities are such that $a=b+c+d+e+f$.

This product can be used for personal care formulations, such as gels/emulsions for UV-A/B protection for hair and as a styling agent, and for UV-A/B suncare applications.

Example 123: Poly(MVE/MA) Grafted with DMABEA and n-octylamine; Half Ethyl Ester, Amic Acid, and Full Imide Forms

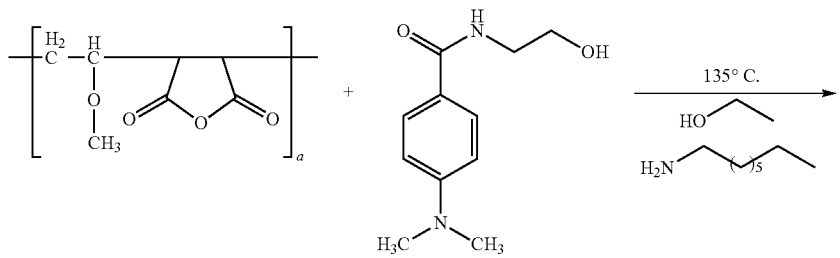

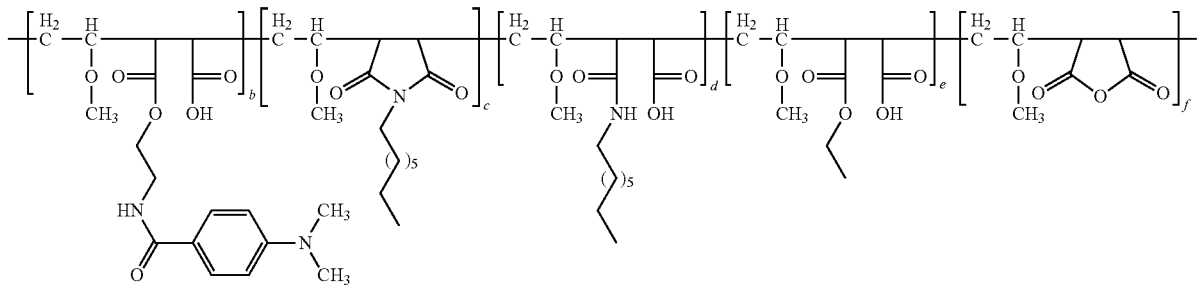

Example 121 is substantially repeated, except 3.3 g (26 mM) of n-octylamine is added to the premix, and it is dissolved with 6.0 g ethanol. A clear dark yellow ethanol solution is obtained that is also soluble in ethanol/water solutions and oils like di-isopropyl-adipate. The molar quantities are such that $a=b+c+d+e+f$.

This product can be used for personal care formulations, such as gels/emulsions for UV-A/B protection for hair and as a styling agent, and for UV-A/B suncare applications.

Example 124: Poly(MVE/MA) Grafted with DMABEA and n-dodecylamine; Half Ethyl Ester, Amic Acid, and Full Imide Forms

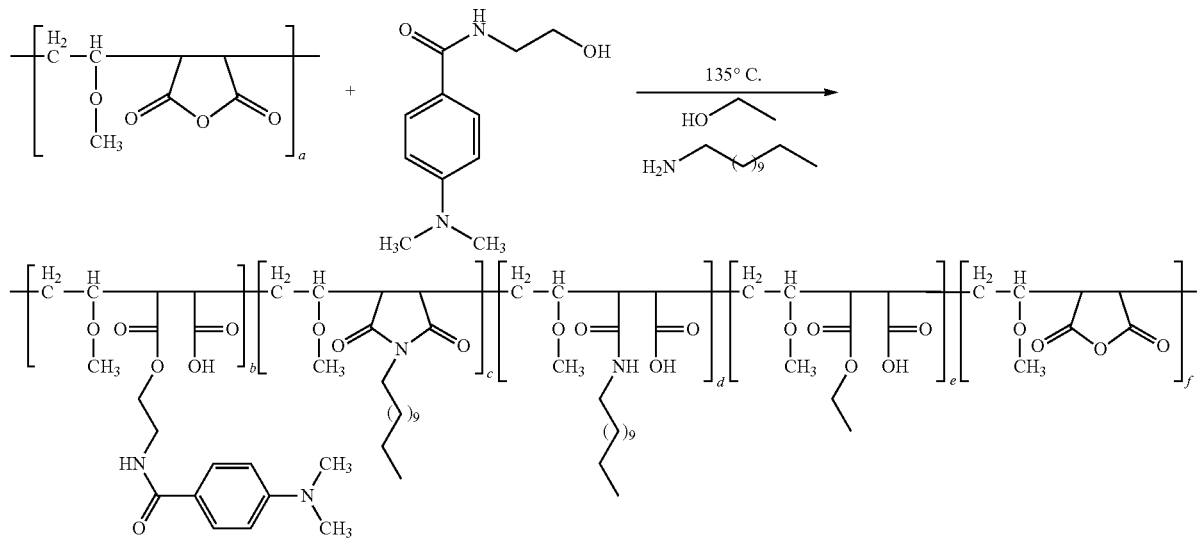

Example 121 is substantially repeated, except 4.8 g (26 mM) of n-dodecylamine is added to the premix, and it is dissolved with 6.0 g ethanol. A clear dark yellow ethanol solution is obtained that is also soluble in ethanol/water solutions and oils like di-isopropyl-adipate, or coconut, vegetable, or soybean oil. The molar quantities are such that a=b+c+d+e+f+g.

This product can be used for personal care formulations, such as gels/emulsions for UV-A/B protection for hair and as a styling agent, and for UV-A/B suncare applications.

Example 125: Poly(MVE/MA) Grafted with DMABEA and Dimethylaminopropylamine; Half Ethyl Ester, Amic Acid, and Full Imide Forms

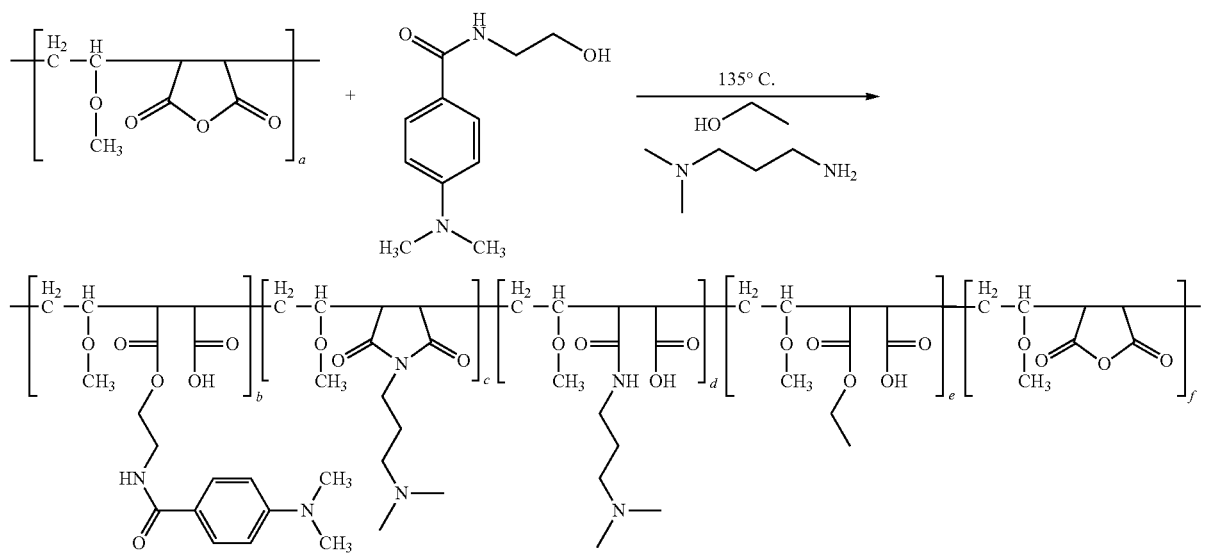

Example 121 is substantially repeated, except 2.7 g (26 mM) of dimethylaminopropylamine is added to the premix, and it is dissolved with 9.0 g ethanol. A clear dark yellow ethanol solution is obtained that is also soluble in ethanol/water solutions and other alcohols. The molar quantities are such that a=b+c+d+e+f.

This product can be used for personal care formulations, such as gels/emulsions for UV-A/B protection for conditioning hair and/or skin applications.

Example 126: Poly(octadecene/MA) Grafted with DMABPD, Half Ethyl Ester, Amic Acid, and Full Imide Forms

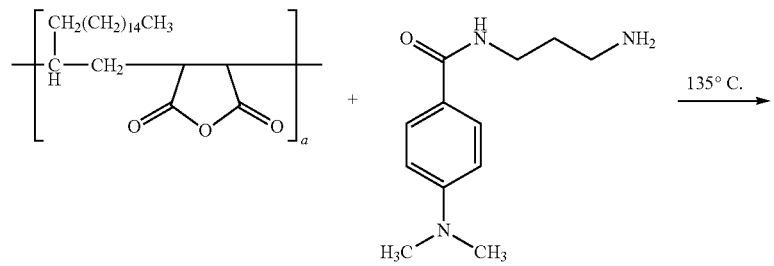

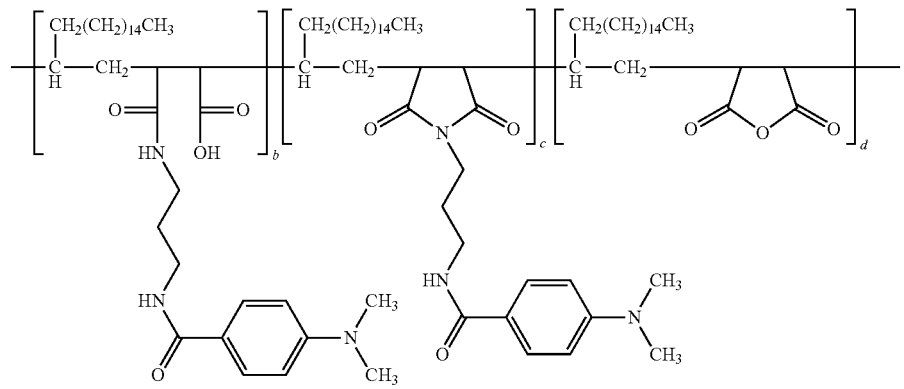

Example 116 was substantially repeated, replacing the poly(MVE/MA) copolymer with a copolymer of octadecene and maleic anhydride having a $M_w$, of 6,000 Da. Cetyl alcohol (24 g) was used instead of ethanol. The product mixture was cooled to room temperature to obtain a clear dark yellow ethanol solution that was also soluble in ethanol/water solutions and oils, such di-isopropyl-adipate. The molar quantities are such that a=b+c+d.

This product can be used for personal care formulations, such as gels/emulsions for UV-A/B protection for hair and as a styling agent, and for UV-A/B suncare applications.

Example 127: Poly(octadecene/MA) Grafted with DMABPD and Isobutylamine; Half Ethyl Ester, Amic Acid, and Full Imide Forms

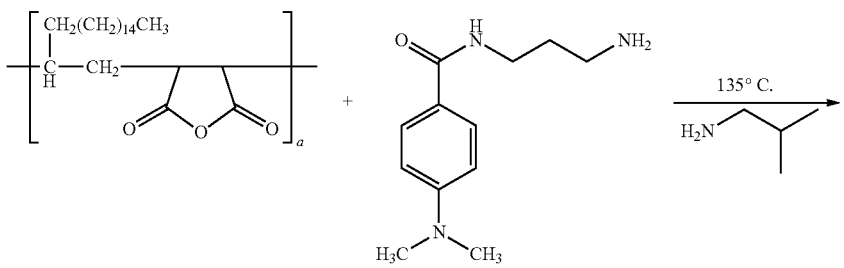

-continued

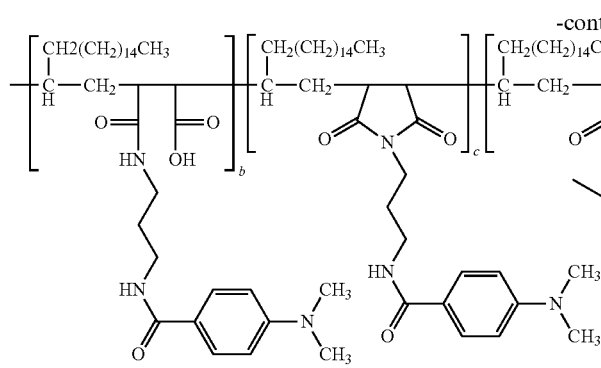
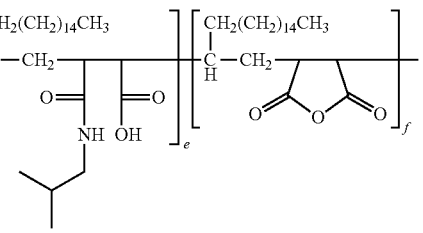

Example 126 was substantially repeated, except 1.9 g (26 mM) of isobutylamine was added to the premix, which was dissolved with 6.0 g ethanol. A clear dark yellow ethanol solution was obtained that was also soluble in ethanol/water solutions and oils like di-isopropyl-adipate. The molar quantities are such that a=b+c+d+e+f.

This product can be used for personal care formulations, such as gels/emulsions for UV-A/B protection for hair and as a styling agent, and for UV-A/B suncare applications.

Example 128: Poly(octadecene/MA) Grafted with DMABPD and n-octylamine; Half Ethyl Ester, Amic Acid, and Full Imide Forms

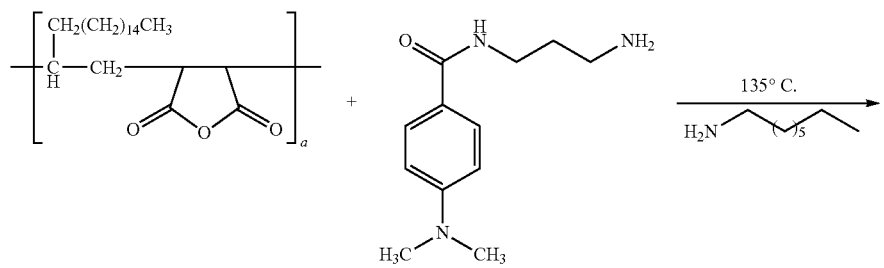

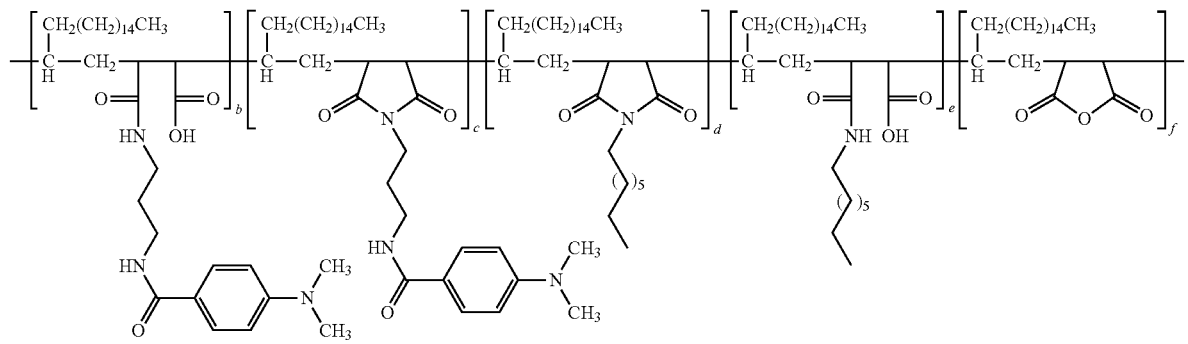

Example 126 was substantially repeated, except 3.3 g (26 mM) of n-octylamine was added to the premix, and it was dissolved with 6.0 g ethanol. A clear dark yellow ethanol solution was obtained that was also soluble in ethanol/water solutions and oils like di-isopropyl-adipate. The molar quantities are such that a=b+c+d+e+f.

This product can be used for personal care formulations, such as gels/emulsions for UV-A/B protection for hair and as a styling agent, and for UV-A/B suncare applications.

Example 129: Poly(octadecene/MA) Grafted with DMABPD and n-dodecylamine; Half Ethyl Ester, Amic Acid, and Full Imide Forms

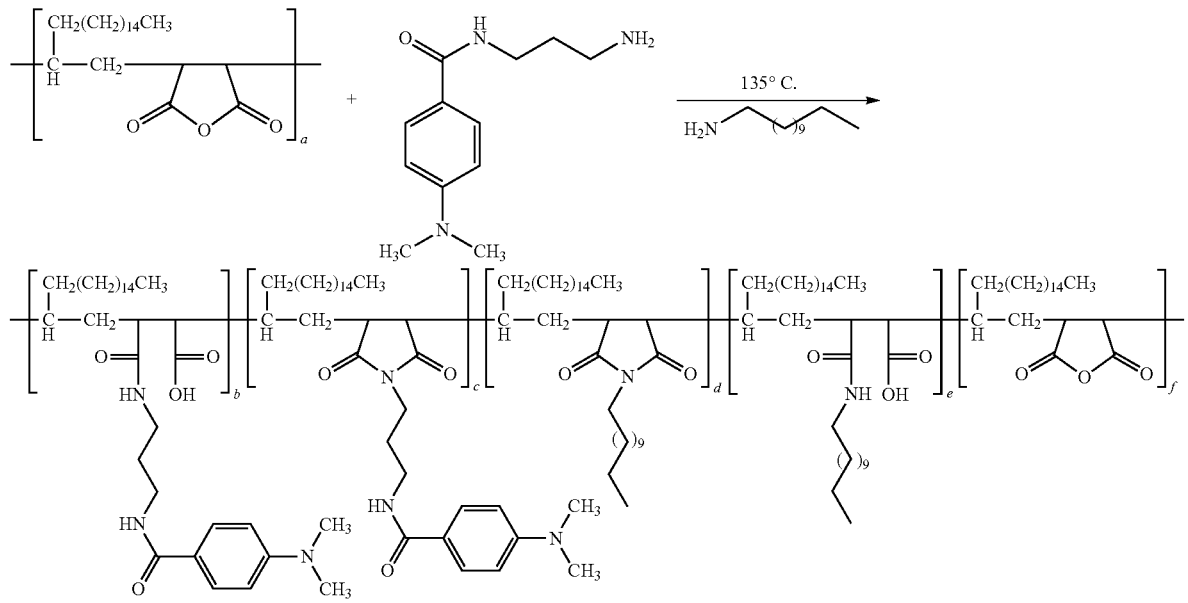

Example 126 was substantially repeated, except 4.8 g (26 mM) of n-dodecylamine was added to the premix, and it was dissolved with 6.0 g ethanol. A clear dark yellow ethanol solution was obtained that was also soluble in ethanol/water solutions and oils like di-isopropyl-adipate, or coconut, vegetable, or soybean oil. The molar quantities are such that a=b+c+d+e+f.

This product can be used for personal care formulations, such as gels/emulsions for UV-A/B protection for hair and as a styling agent, and for UV-A/B suncare applications.

Example 130: Poly(octadecene/MA) Grafted with DMABPD and Dimethylaminopropylamine; Half Ethyl Ester, Amic Acid, and Full Imide Forms

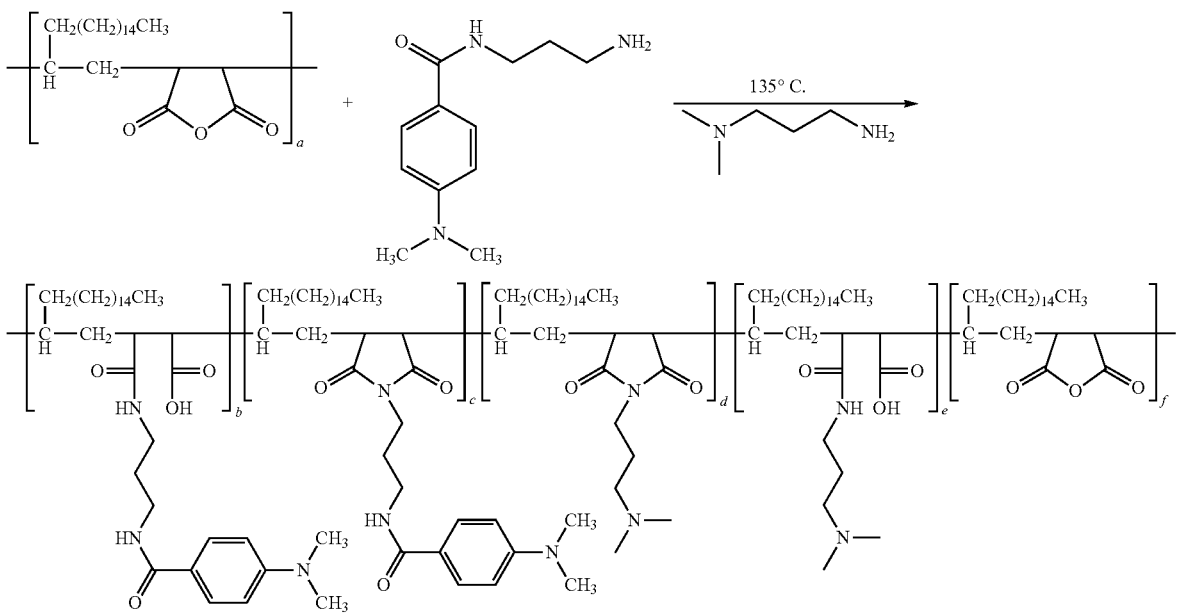

Example 126 was substantially repeated, except 2.7 g (26 mM) of dimethylaminopropylamine was added to the premix, and it was dissolved with 9.0 g ethanol. A clear dark yellow ethanol solution was obtained that was also soluble in ethanol/water solutions and other alcohols. The molar quantities are such that a=b+c+d+e+f.

This product can be used for personal care formulations, such as gels/emulsions for UV-A/B protection for conditioning hair and/or skin applications.

Example 131: Poly(octadecene/MA) Grafted with DMABEA, Half Ethyl Ester, Amic Acid, and Full Imide Forms

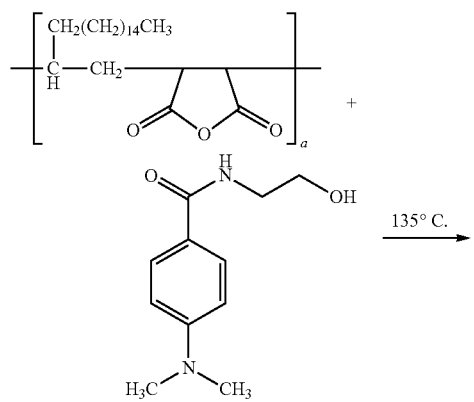

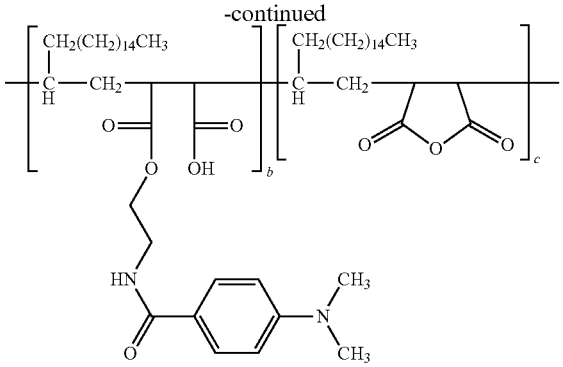

Example 126 is substantially repeated, replacing DMABPD with 0.67 g (3.25 mM) DMABEA. Cetyl alcohol (24 g) is used instead of ethanol. The product mixture is cooled to room temperature to obtain a clear dark yellow ethanol solution that is also soluble in ethanol/water solutions and oils, such di-isopropyl-adipate. The molar quantities are such that a=b+c.

This product can be used for personal care formulations, such as gels/emulsions for UV-A/B protection for hair and as a styling agent, and for UV-A/B suncare applications.

Example 132: Poly(octadecene/MA) Grafted with DMABEA and Isobutylamine; Half Ethyl Ester, Amic Acid, and Full Imide Forms

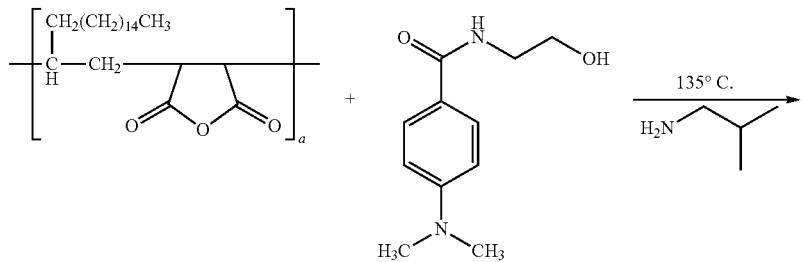

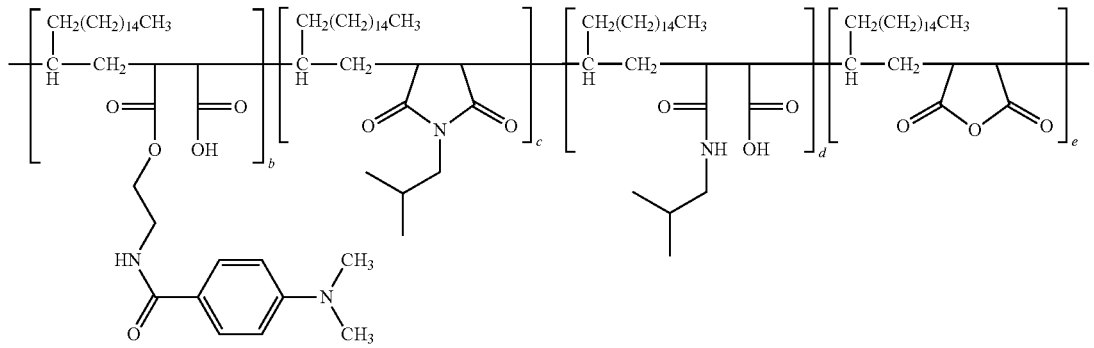

Example 131 is substantially repeated, except 1.9 g (26 mM) of isobutylamine is added to the premix, which is dissolved with 6.0 g ethanol. A clear dark yellow ethanol solution is obtained that is also soluble in ethanol/water solutions and oils like di-isopropyl-adipate. The molar quantities are such that a=b+c+d+e.

This product can be used for personal care formulations, such as gels/emulsions for UV-A/B protection for hair and as a styling agent, and for UV-A/B suncare applications.

Example 133: Poly(octadecene/MA) Grafted with DMABEA and n-octylamine; Half Ethyl Ester, Amic Acid, and Full Imide Forms

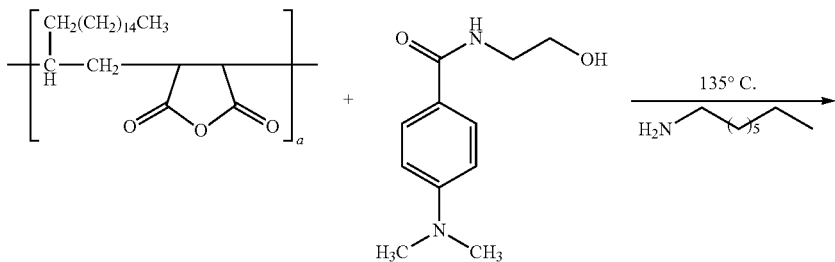

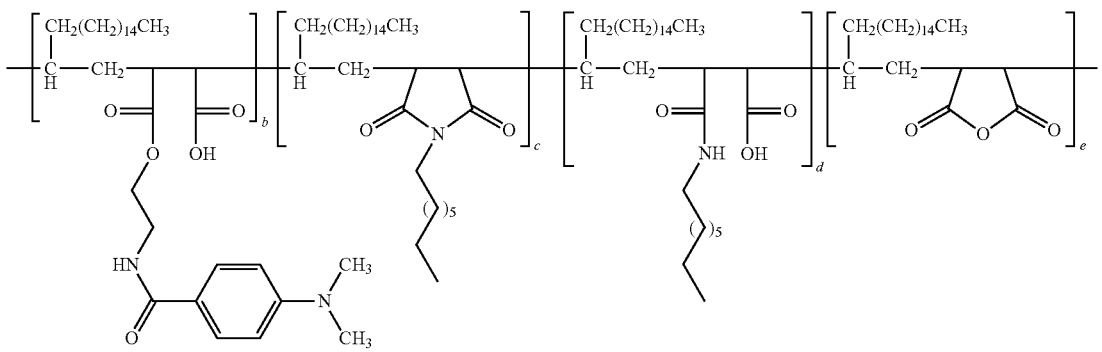

Example 131 is substantially repeated, except 3.3 g (26 mM) of n-octylamine is added to the premix, and it is dissolved with 6.0 g ethanol. A clear dark yellow ethanol solution is obtained that is also soluble in ethanol/water solutions and oils like di-isopropyl-adipate. The molar quantities are such that a=b+c+d+e.

This product can be used for personal care formulations, such as gels/emulsions for UV-A/B protection for hair and as a styling agent, and for UV-A/B suncare applications.

Example 134: Poly(octadecene/MA) Grafted with DMABEA and n-dodecylamine; Half Ethyl Ester, Amic Acid, and Full Imide Forms

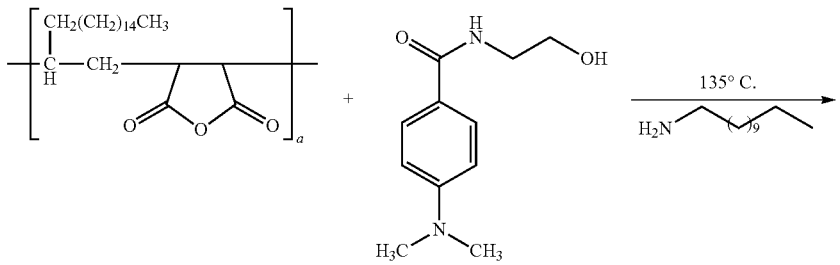

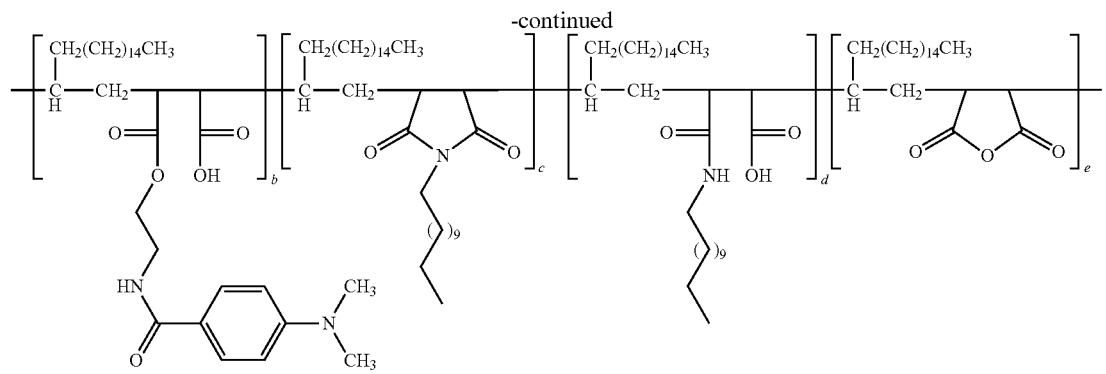

Example 131 is substantially repeated, except 4.8 g (26 mM) of n-dodecylamine is added to the premix, and it is dissolved with 6.0 g ethanol. A clear dark yellow ethanol solution is obtained that is also soluble in ethanol/water solutions and oils like di-isopropyl-adipate, or coconut, vegetable, or soybean oil. The molar quantities are such that a=b+c+d+e.

This product can be used for personal care formulations, such as gels/emulsions for UV-A/B protection for hair and as a styling agent, and for UV-A/B suncare applications.

Example 135: Poly(octadecene/MA) Grafted with DMABEA and Dimethylaminopropylamine; Half Ethyl Ester, Amic Acid, and Full Imide Forms

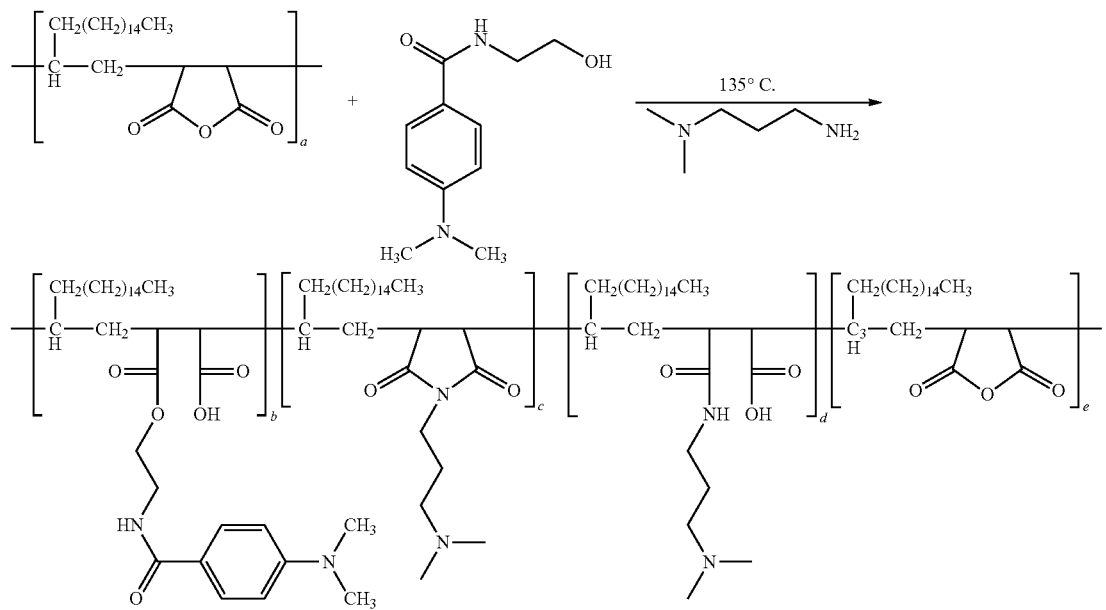

Example 131 is substantially repeated, except 2.7 g (26 mM) of dimethylaminopropylamine is added to the premix, and it is dissolved with 9.0 g ethanol. A clear dark yellow ethanol solution is obtained that is also soluble in ethanol/water solutions and other alcohols. The molar quantities are such that a=b+c+d+e.

This product can be used for personal care formulations, such as gels/emulsions for UV-A/B protection for conditioning hair and/or skin applications.

Example 136: Poly(styrene/MA) Grafted with DMABEA, Half Ethyl Ester, Amic Acid, and Full Imide Forms

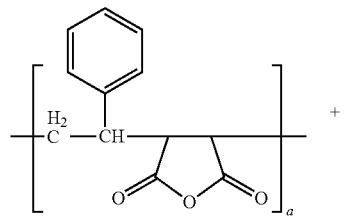
+
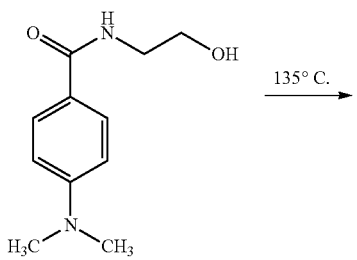
→ 135° C.

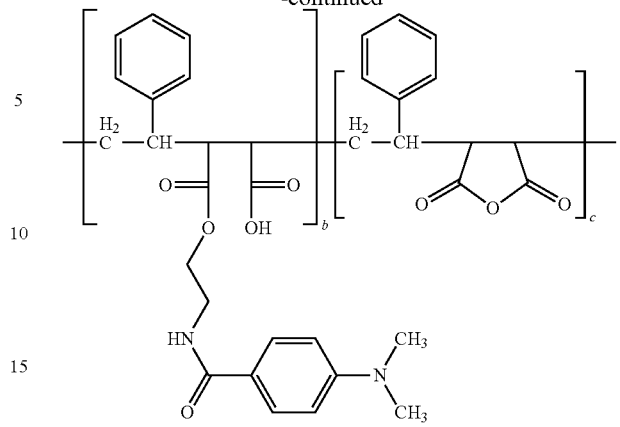

Example 131 is substantially repeated, replacing poly (octadecene/MA) with the copolymer of styrene and maleic anhydride having $M_w$, of 6,000 Da. Cetyl alcohol (24 g) is used instead of ethanol. The product mixture is cooled to room temperature to obtain a clear dark yellow ethanol solution that is also soluble in ethanol/water solutions and oils, such di-isopropyl-adipate. The molar quantities are such that a=b+c.

This product can be used for personal care formulations, such as gels/emulsions for UV-A/B protection for hair and as a styling agent, and for UV-A/B suncare applications.

Example 137: Poly(styrene/MA) Grafted with DMABEA and Isobutylamine; Half Ethyl Ester, Amic Acid, and Full Imide Forms

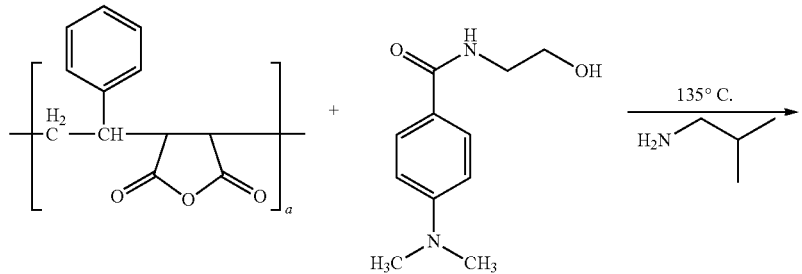

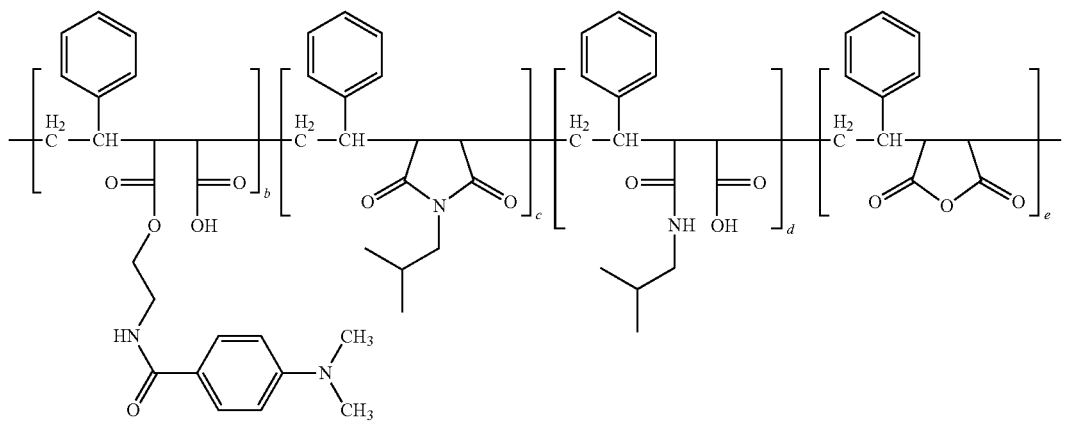

Example 136 is substantially repeated, except 1.9 g (26 mM) of isobutylamine is added to the premix, which is dissolved with 6.0 g ethanol. A clear dark yellow ethanol solution is obtained that is also soluble in ethanol/water solutions and oils like di-isopropyl-adipate. The molar quantities are such that a=b+c+d+e.

This product can be used for personal care formulations, such as gels/emulsions for UV-A/B protection for hair and as a styling agent, and for UV-A/B suncare applications.

Example 138: Poly(styrene/MA) Grafted with DMABEA and n-octylamine; Half Ethyl Ester, Amic Acid, and Full Imide Forms

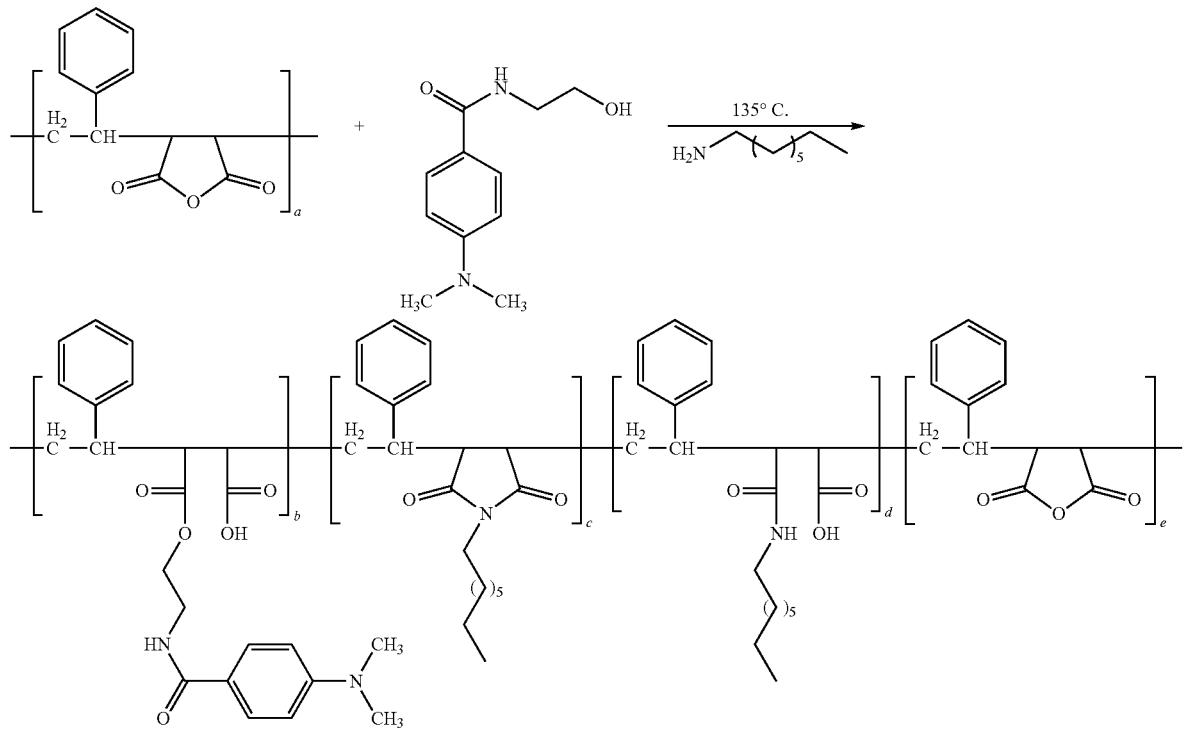

Example 137 is substantially repeated, except 3.3 g (26 mM) of n-octylamine is added to the premix, and it is dissolved with 6.0 g ethanol. A clear dark yellow ethanol solution is obtained that is also soluble in ethanol/water solutions and oils like di-isopropyl-adipate. The molar quantities are such that a=b+c+d+e.

This product can be used for personal care formulations, such as gels/emulsions for UV-A/B protection for hair and as a styling agent, and for UV-A/B suncare applications.

Example 139: Poly(styrene/MA) Grafted with DMABEA and n-dodecylamine; Half Ethyl Ester, Amic Acid, and Full Imide Forms

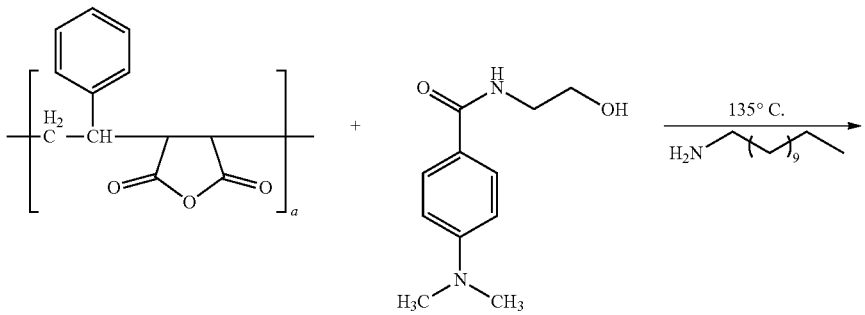

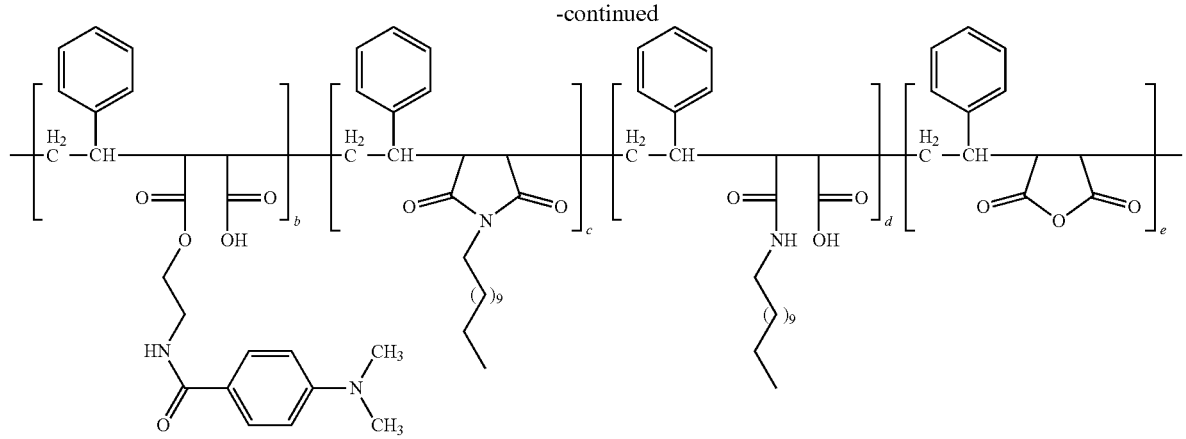

Example 137 is substantially repeated, except 4.8 g (26 mM) of n-dodecylamine is added to the premix, and it is dissolved with 6.0 g ethanol. A clear dark yellow ethanol solution is obtained that is also soluble in ethanol/water solutions and oils like di-isopropyl-adipate, or coconut, vegetable, or soybean oil. The molar quantities are such that a=b+c+d+e.

This product can be used for personal care formulations, such as gels/emulsions for UV-A/B protection for hair and as a styling agent, and for UV-A/B suncare applications.

Example 140: Poly(styrene/MA) Grafted with DMABEA and Dimethylaminopropylamine; Half Ethyl Ester, Amic Acid, and Full Imide Forms

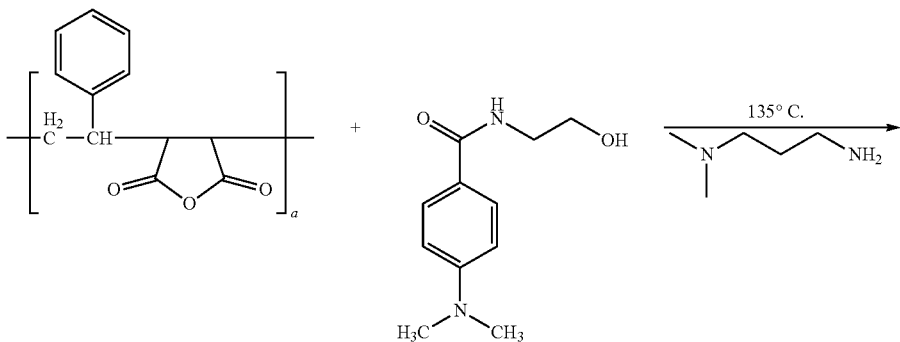

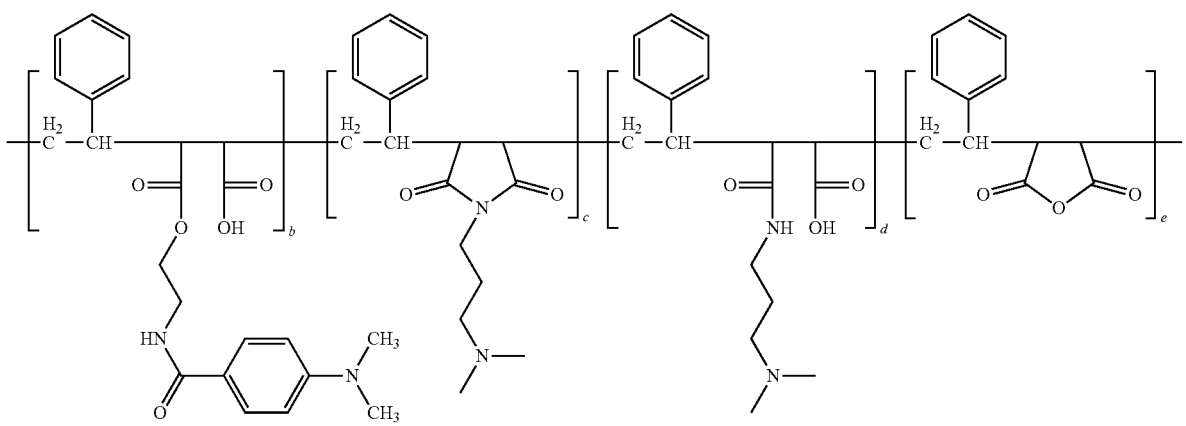

Example 137 is substantially repeated, except 2.7 g (26 mM) of dimethylaminopropylamine is added to the premix, and it is dissolved with 9.0 g ethanol. A clear dark yellow ethanol solution is obtained that is also soluble in ethanol/water solutions and other alcohols. The molar quantities are such that a=b+c+d+e.

This product can be used for personal care formulations, such as gels/emulsions for UV-A/B protection for conditioning hair and/or skin applications.

Example 141: Poly(styrene/MA) Grafted with DMABPD, Half Ethyl Ester, Amic Acid, and Full Imide Forms

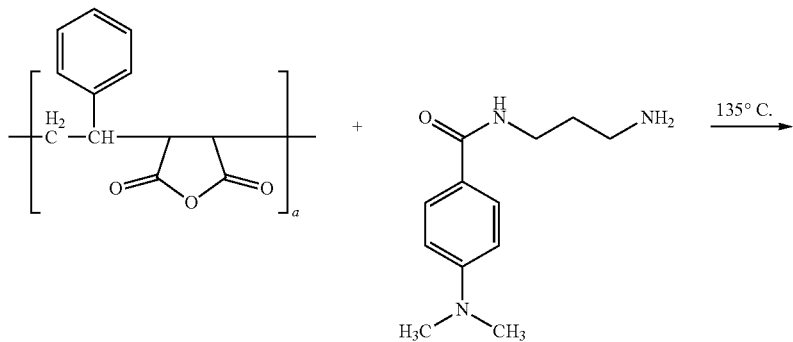

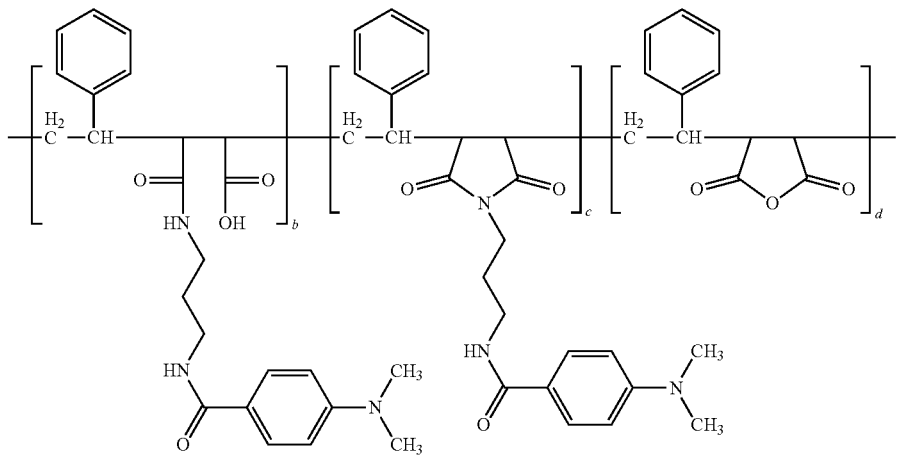

Example 136 was substantially repeated, replacing DMA-BEA with 0.71 g (3.25 mM) of DMABPD. Cetyl alcohol (24 g) was used instead of ethanol. The product mixture was cooled to room temperature to obtain a clear dark yellow ethanol solution that was also soluble in ethanol/water solutions and oils, such di-isopropyl-adipate. The molar quantities are such that a=b+c+d.

This product can be used for personal care formulations, such as gels/emulsions for UV-A/B protection for hair and as a styling agent, and for UV-A/B suncare applications.

Example 142: Poly(styrene/MA) Grafted with DMABPD and Isobutylamine; Half Ethyl Ester, Amic Acid, and Full Imide Forms

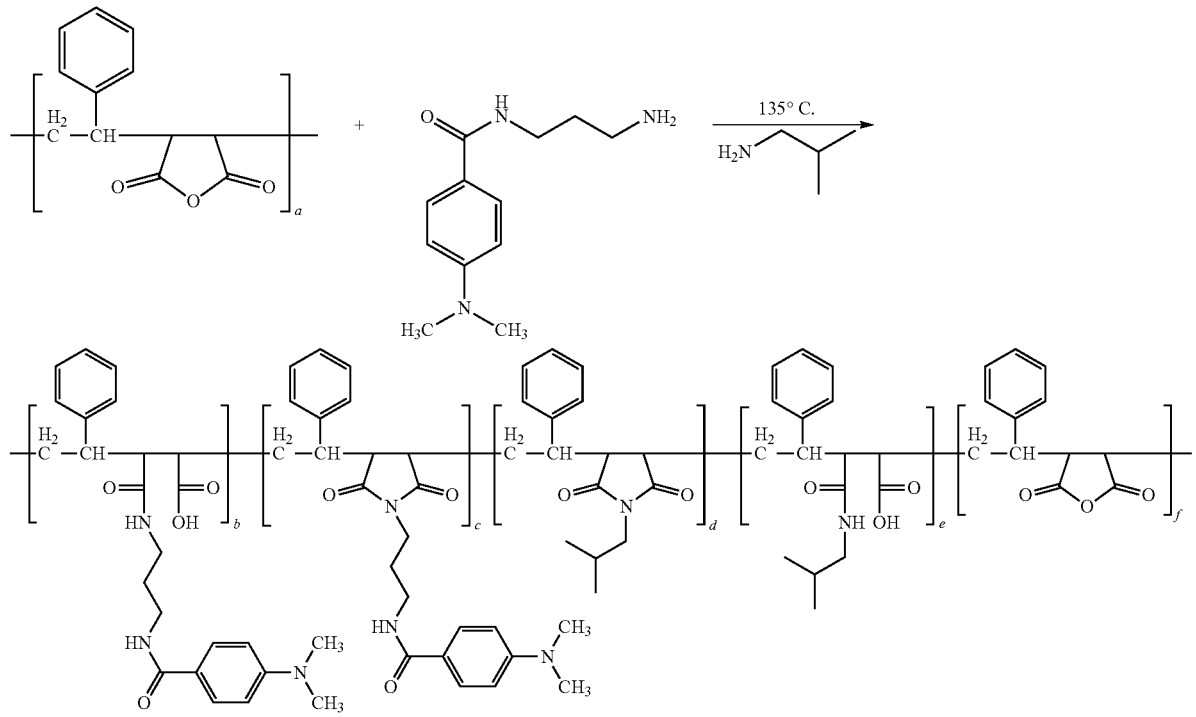

Example 141 was substantially repeated, except 1.9 g (26 mM) of isobutylamine was added to the premix, which was dissolved with 6.0 g ethanol. A clear dark yellow ethanol solution was obtained that was also soluble in ethanol/water solutions and oils like di-isopropyl-adipate. The molar quantities are such that a=b+c+d+e+f.

This product can be used for personal care formulations, such as gels/emulsions for UV-A/B protection for hair and as a styling agent, and for UV-A/B suncare applications.

Example 143: Poly(styrene/MA) Grafted with DMABPD and n-octylamine; Half Ethyl Ester, Amic Acid, and Full Imide Forms

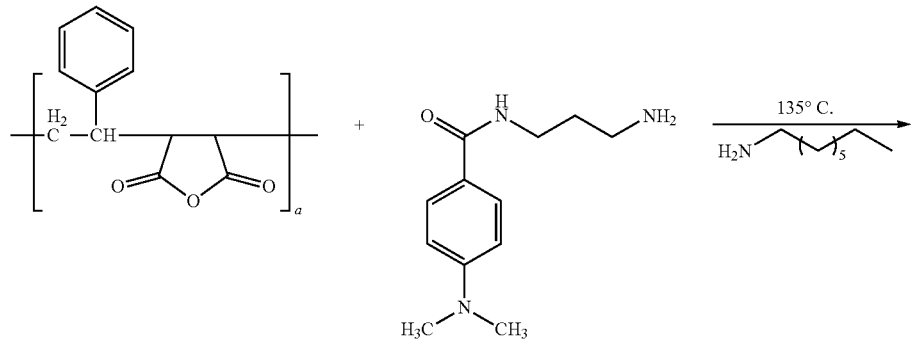

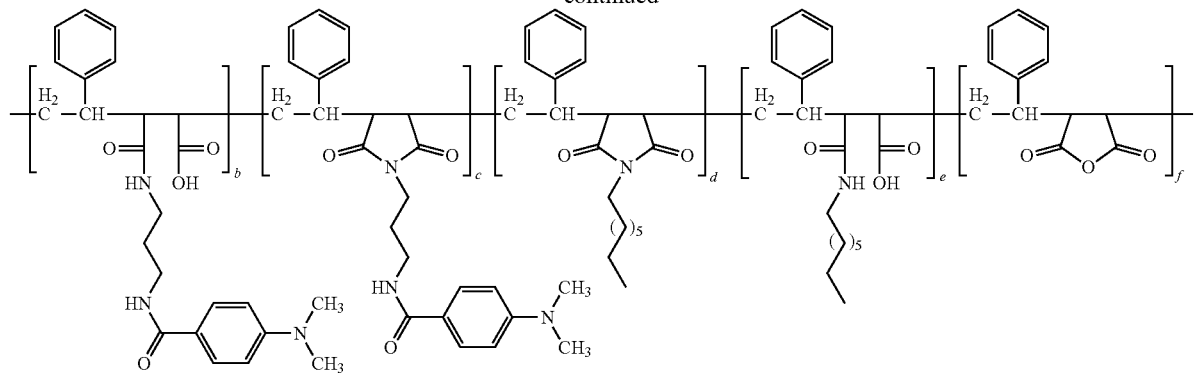

Example 141 was substantially repeated, except 3.3 g (26 mM) of n-octylamine was added to the premix, and it was dissolved with 6.0 g ethanol. A clear dark yellow ethanol solution was obtained that was also soluble in ethanol/water solutions and oils like di-isopropyl-adipate. The molar quantities are such that a=b+c+d+e+f.

This product can be used for personal care formulations, such as gels/emulsions for UV-A/B protection for hair and as a styling agent, and for UV-A/B suncare applications.

Example 144: Poly(styrene/MA) Grafted with DMABPD and n-dodecylamine; Half Ethyl Ester, Amic Acid, and Full Imide Forms

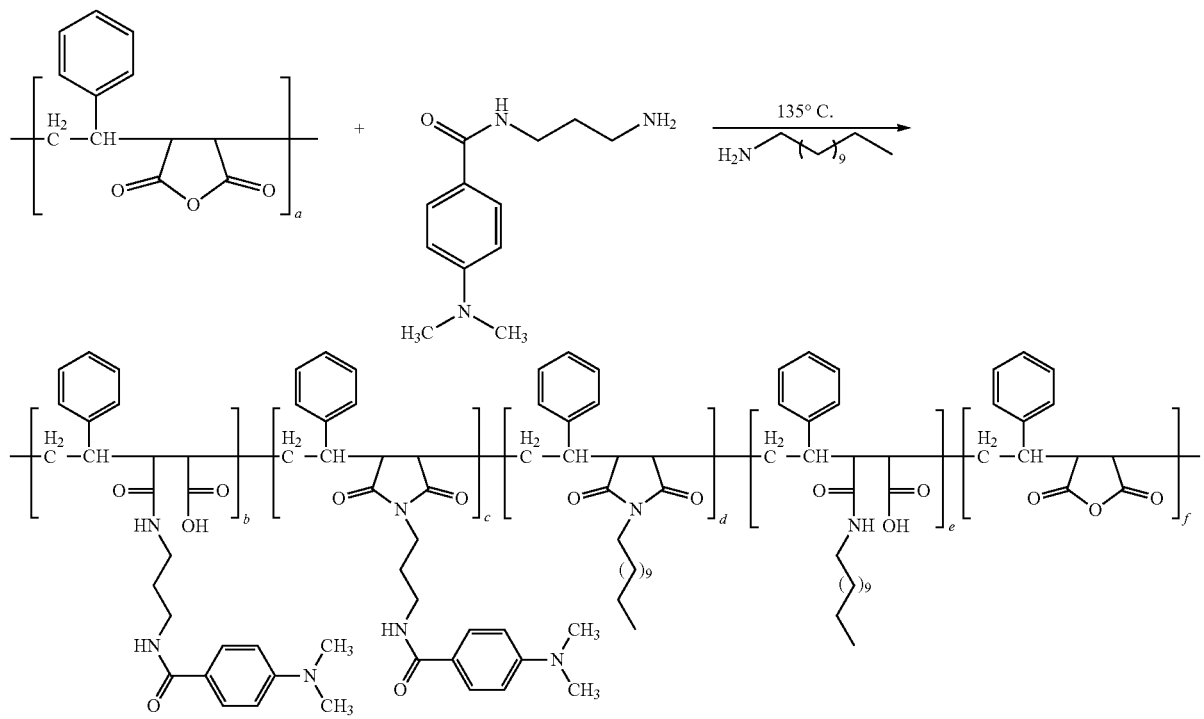

Example 141 was substantially repeated, except 4.8 g (26 mM) of n-dodecylamine was added to the premix, and it was dissolved with 6.0 g ethanol. A clear dark yellow ethanol solution was obtained that was also soluble in ethanol/water solutions and oils like di-isopropyl-adipate, or coconut, vegetable, or soybean oil. The molar quantities are such that a=b+c+d+e+f.

Example 145: Poly(styrene/MA) Grafted with DMABPD and Dimethylaminopropylamine; Half Ethyl Ester, Amic Acid, and Full Imide Forms

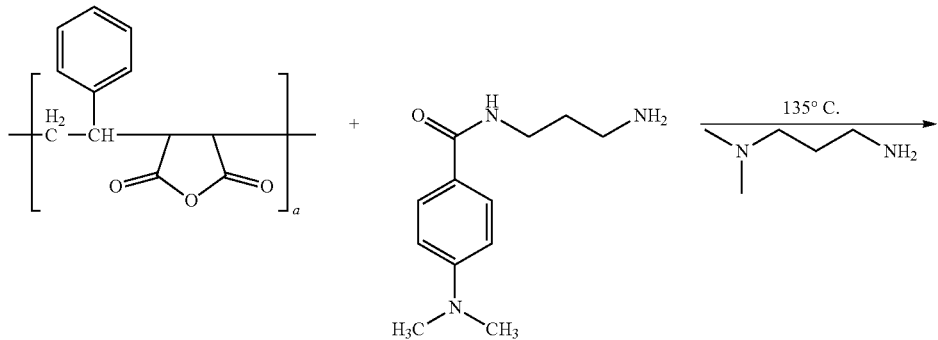

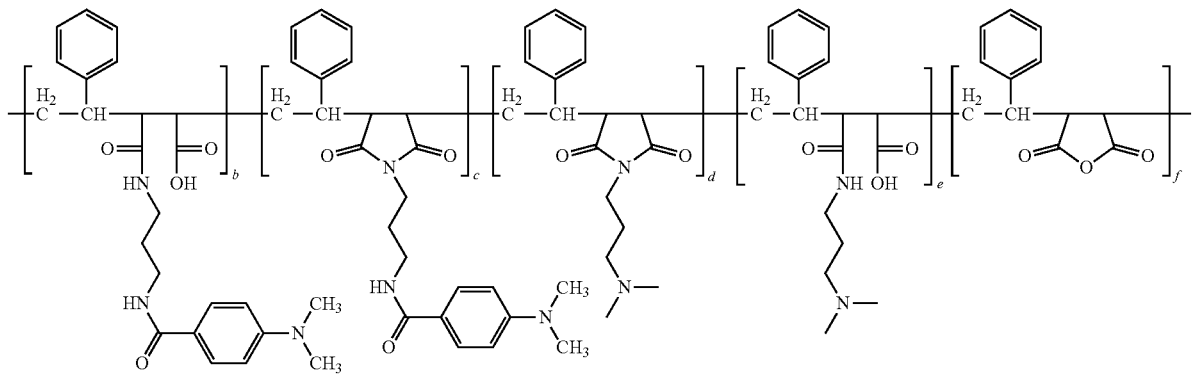

Example 141 was substantially repeated, except 2.7 g (26 mM) of dimethylaminopropylamine was added to the premix, and it was dissolved with 9.0 g ethanol. A clear dark yellow ethanol solution was obtained that was also soluble in ethanol/water solutions and other alcohols. The molar quantities are such that a=b+c+d+e+f.

This product can be used for personal care formulations, such as gels/emulsions for UV-A/B protection for hair and as a styling agent, and for UV-A/B suncare applications.

This product can be used for personal care formulations, such as gels/emulsions for UV-A/B protection for conditioning hair and/or skin applications.

Example 146: Poly(styrene/MA) Grafted with JT Benzone and DMABEA; Half Ethyl Ester, Amic Acid, and Full Imide Forms

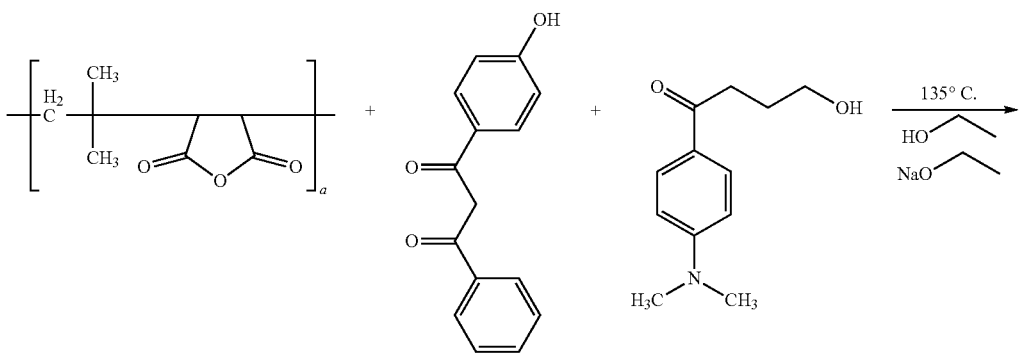

-continued

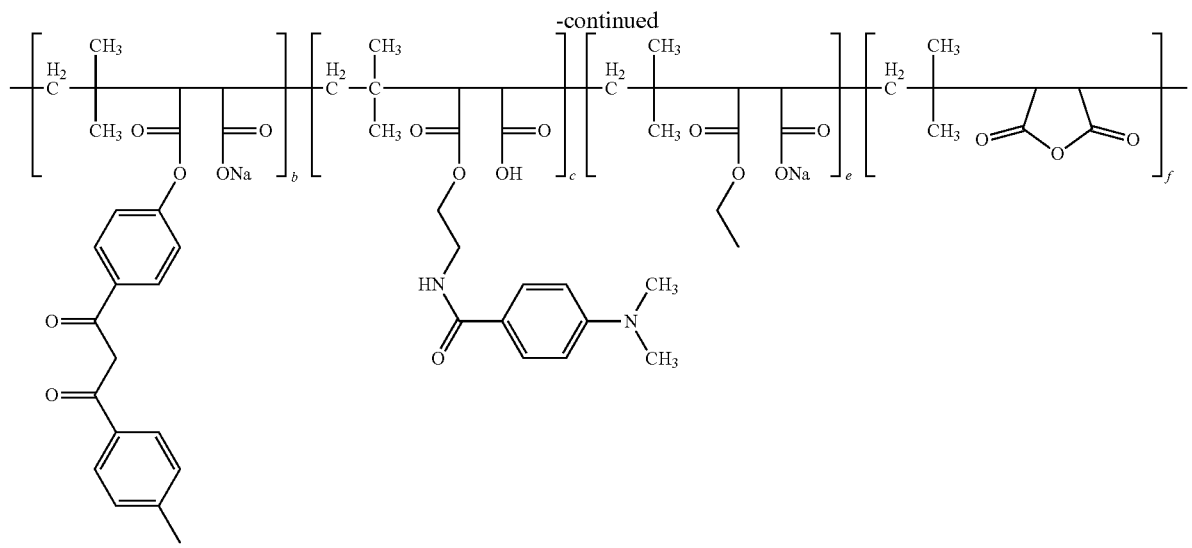

Example 101 is substantially repeated, reacting 0.8 g (3.25 mM) of JT benzone and 0.71 g (3.25 mM) of DMA-BEA with 1.1 g (3.25 mM) NaOH/EtOH and 5.0 g of poly(isobutylene-co-maleic anhydride) have a $M_w$, of 80,000 Da. A clear dark yellow ethanol solution is obtained that also is soluble in ethanol/water solutions and other alcohols. The molar quantities are such that a=b+c+d+e+f.

This product can be used for personal care formulations, such as gels/emulsions for UV-A/B protection for hair and as a styling agent, and for UV-A/B suncare applications.

Example 147: Poly(MVE/MA) Grafted with HE-JT Benzone, DMABEA and Isobutylamine; Half Ethyl Ester, Amic Acid, and Full Imide Forms

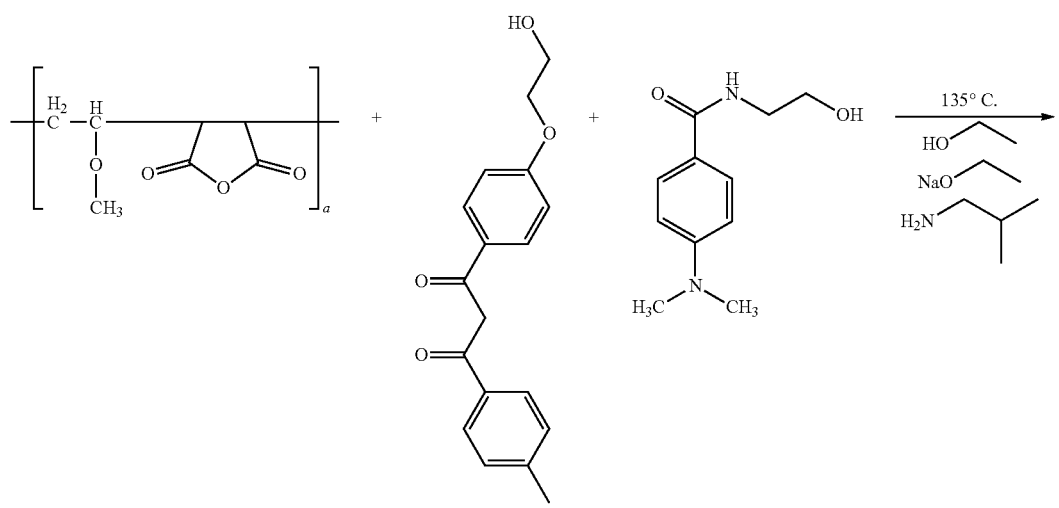

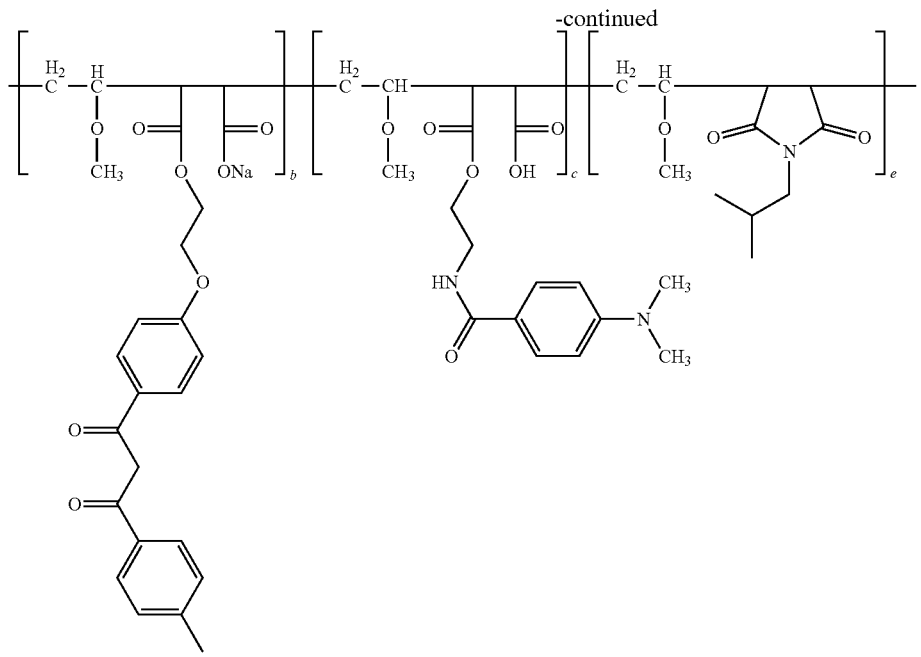

-continued

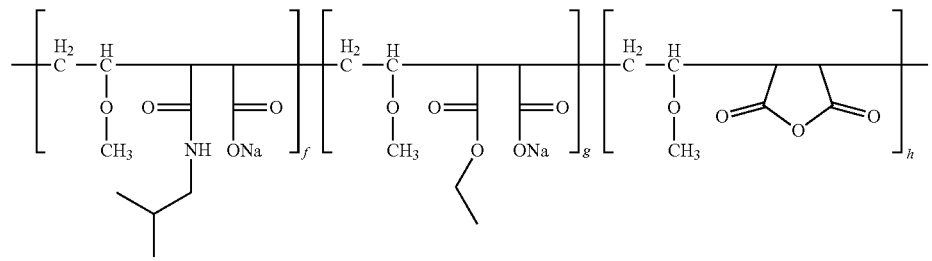

Example 12 is substantially repeated, adding 0.71 g (3.25 mM) of DMABEA to the reactive mixture and removing the sodium ethanol. A clear dark yellow ethanol solution is obtained that also is soluble in ethanol/water solutions and other alcohols. The molar quantities aresuchthat a=b+c+d+e+f+g+h.

This product can be used for personal care formulations, such as gels/emulsions for UV-A/B protection for hair and as a styling agent, and for UV-A/B suncare applications.

Example 148: Poly(IB/MA) Grafted with Sulfanamide-PD and HE-JT Benzone; Half Ethyl Ester, Amic Acid, and Full Imide Forms

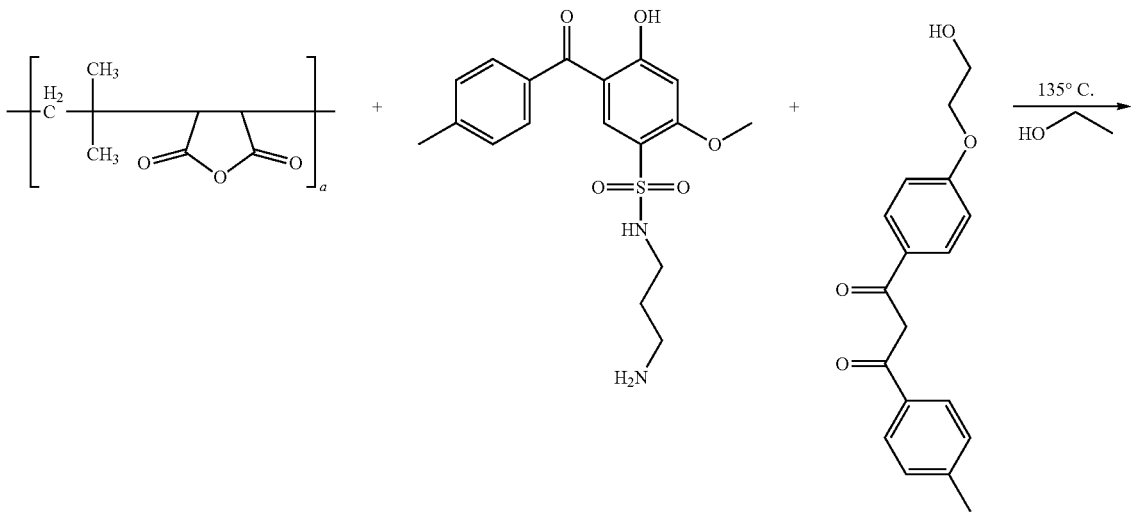

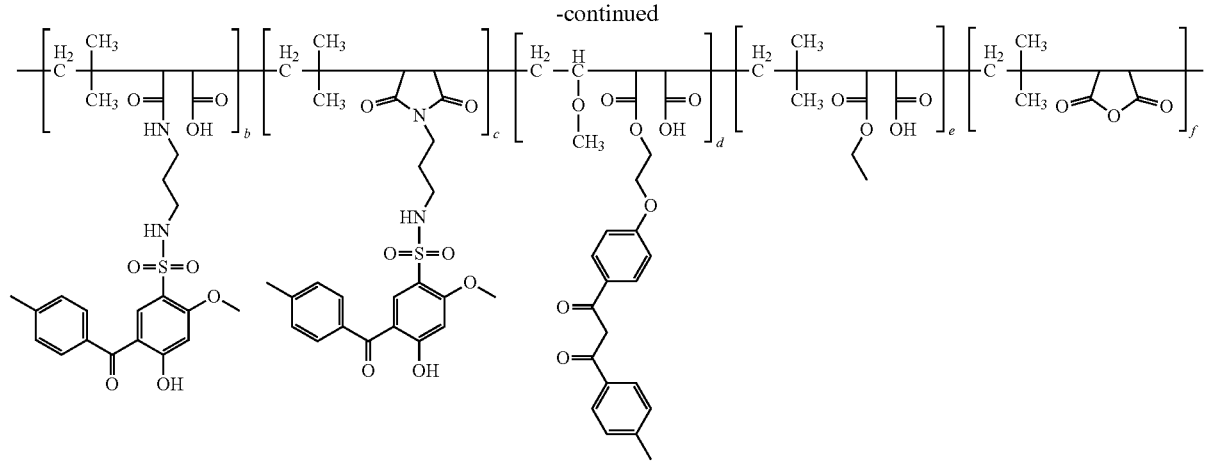

Example 36 is substantially repeated, adding 0.94 g (3.25 mM) of HE-JT benzone to the reactive mixture. A clear dark yellow ethanol solution is obtained that also is soluble in ethanol/water solutions and other alcohols. The molar quantities are such that a=b+c+d+e+f.

This product can be used for personal care formulations, such as gels/emulsions for UV-A/B protection for hair and as a styling agent, and for UV-A/B suncare applications.

Example 149: Poly(MVE/MA) Grafted with Sulfanamide-EA, HE-JT Benzone, and Dimethylaminopropylamine; Half Ethyl Ester, Amic Acid, and Full Imide Forms

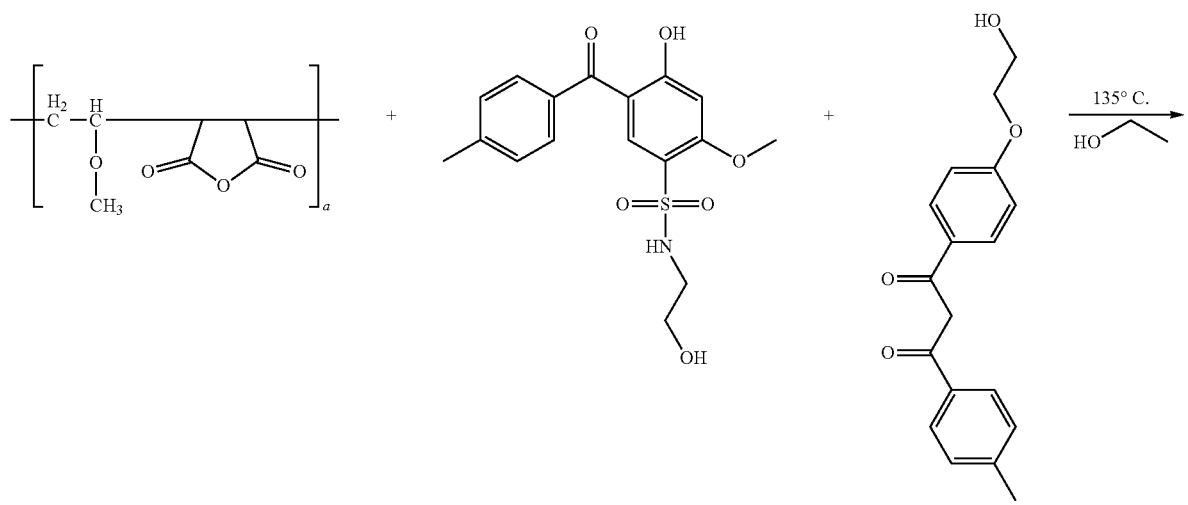

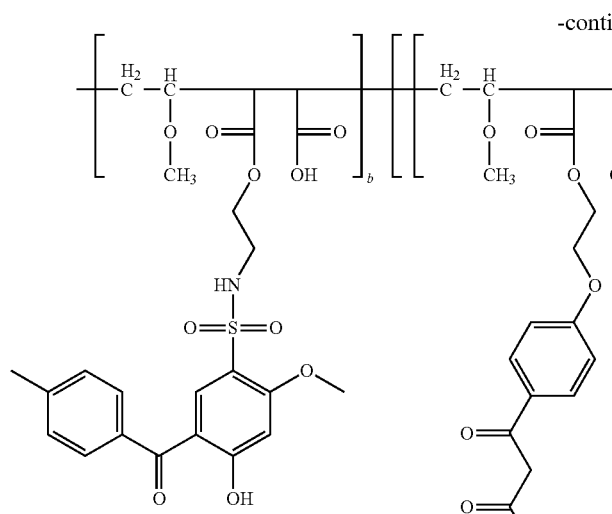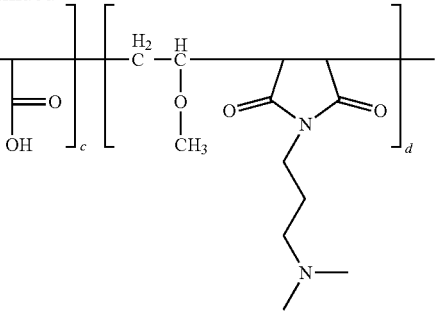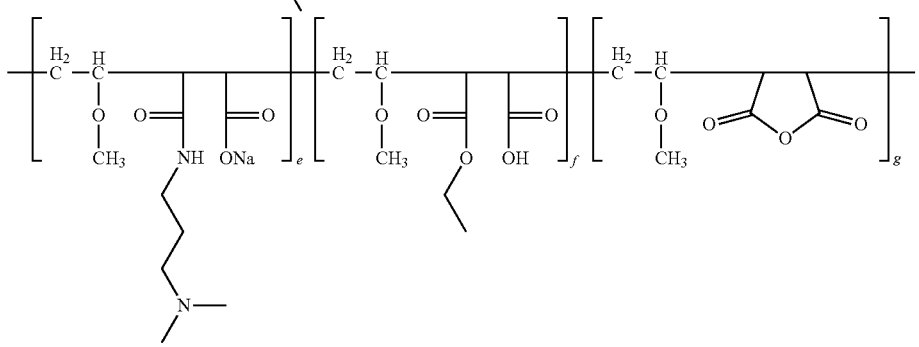

Example 75 is substantially repeated, replacing the 1.2 g (3.25 mM) of 577-sulfanamide-propylenediamine with 1.15 g (3.25 mM) of 577-sulfanamide-ethanolamine, and adding 0.94 g (3.25 mM) of HE-JT benzone to the reactive mixture. A clear dark yellow ethanol solution is obtained that also is soluble in ethanol/water solutions and other alcohols. The molar quantities are such that a=b+c+d+e+f+g.

This product can be used for personal care formulations, such as gels/emulsions for UV-A/B protection for hair and skin as a conditioning agent, and for UV-A/B suncare applications.

Example 150: Poly(IB/MA) Grafted with JT Benzone and Methyl-2-Aminobenzoate; Amic Acid, Imide, Half Ethyl Ester and Sodium Salt Forms

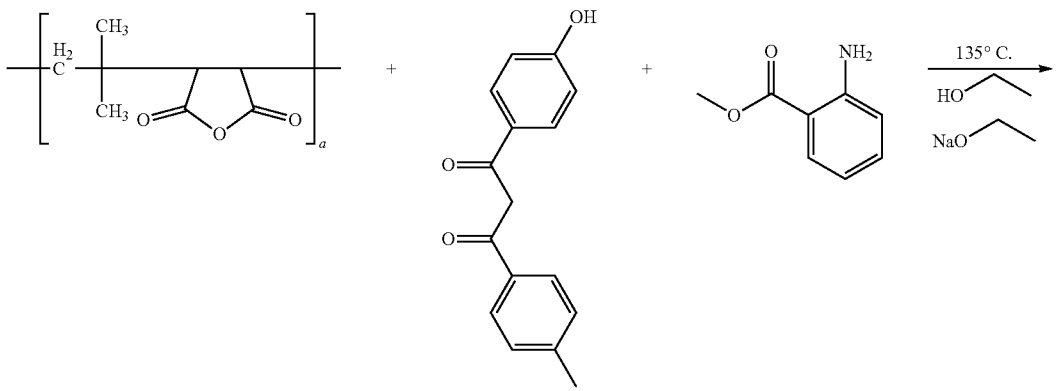

-continued

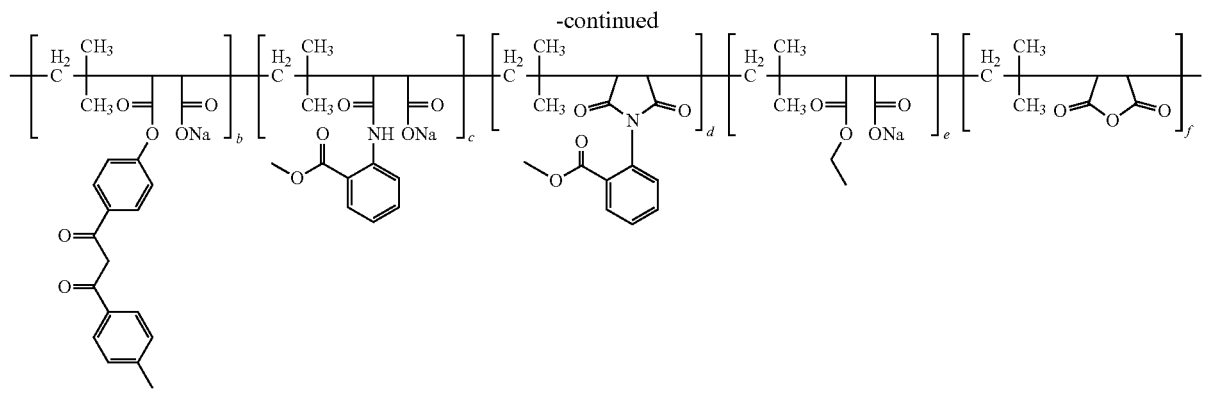

Example 1 is substantially repeated, adding 0.49 g (3.25 mM) methyl-2-aminobenzoate to the reactive mix. A clear dark yellow ethanol solution is obtained that also is soluble in ethanol/water solutions and other alcohols. The molar quantities are such that a=b+c+d+e+f.

This product can be used for personal care formulations, such as gels/emulsions for UV-A/B protection for hair and as a styling agent, and for UV-A/B suncare applications.

Example 151: Poly(MVE/MA) Grafted with DMABPD, Methyl-2-Aminobenzoate, and 2-Aminobenzophenone; Half Ethyl Ester, Amic Acid, Imide, and Sodium Salt Forms

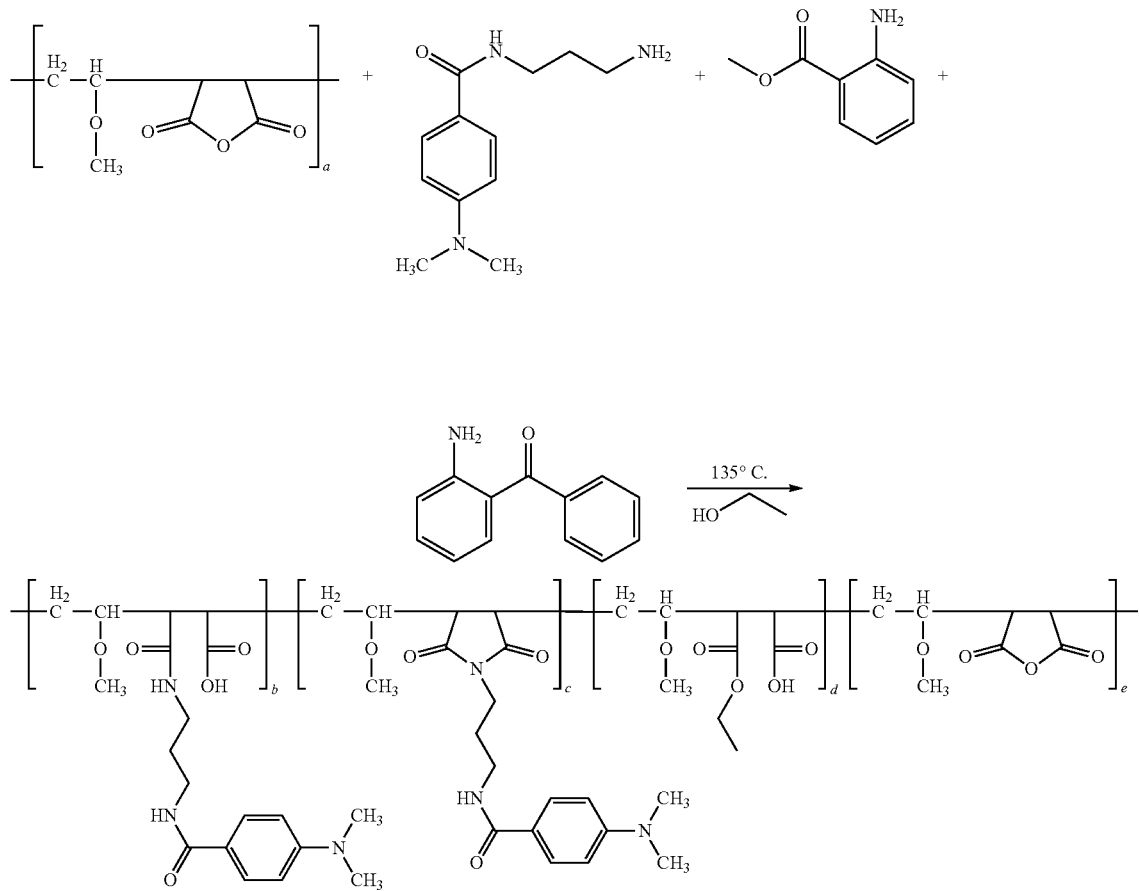

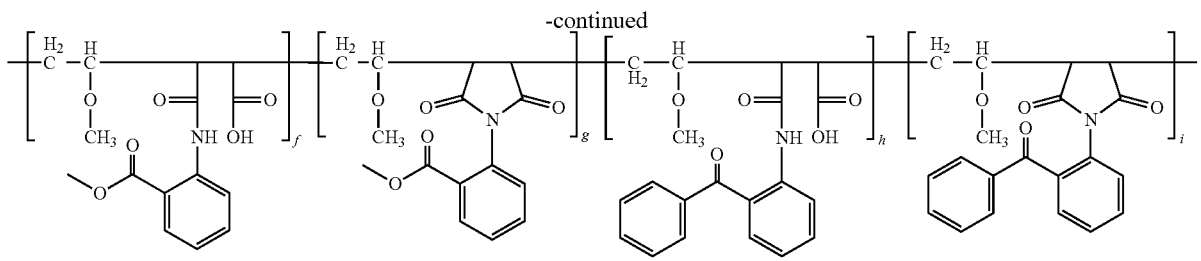

Example 116 is substantially repeated, adding 0.49 g (3.25 mM) methyl-2-aminobenzoate and 0.64 g (3.25 mM) 2-aminobenzophenone to the reactive mix. A clear dark yellow ethanol solution is obtained that also is soluble in ethanol/water solutions and other alcohols. The molar quantities are such that a=b+c+d+e+f+g+h+i.

Example 152: Poly(IB/MA) Grafted with DIOPAT, Dimethylaminopropylamine; Full Imide Form

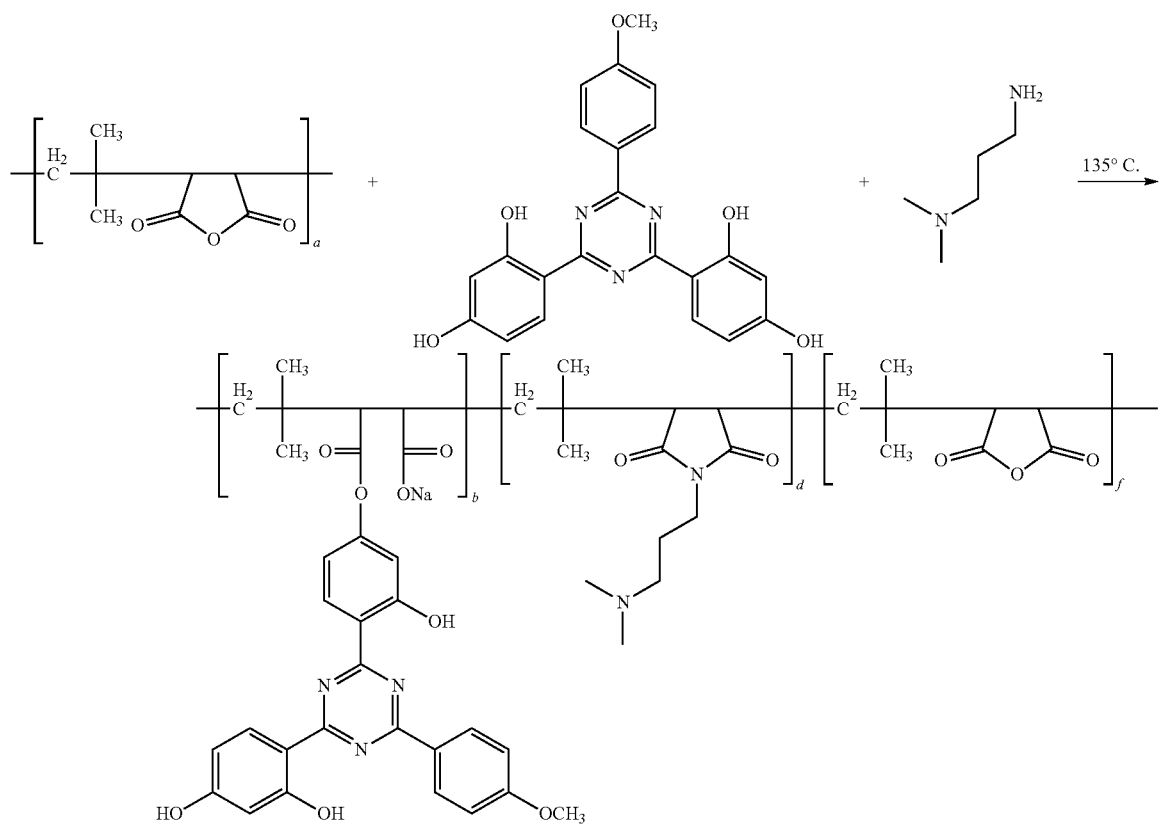

A 1-L, 4-neck round-bottom flask was charged with ethanol (250 mL), 37.5 g 2,4-bis-(2,4-dihydroxyphenyl)-6-(4-methoxyphenyl)-s-triazine (DIOPAT) and 85.0 g (0.657 mol) of dimethylaminopropylamine, and a yellow-gold slurry formed with mixing. A KOH/water solution was then added that formed a loose light orange mixture after one hour of mixing. During this time, the reaction temperature increased from 25 to 30° C. A doughy sample was collected and submitted for $_1$HNMR analysis. The balance of the product was collected from the flask and charged to a PARR reactor. The PARR heating schedule was programmed to ramp from 25° C. to 100° C. in 30 min. Temperature was held at 100° C. for 3 hours, ramped to 145° C. and held at 145° C. for 4 hours. Finally, the reactor was cooled to 50° C. and maintained over night. The next morning, the product was discharged as 200 g total solids. The solids were charged to a clean PARR reactor with 500 mL ethanol. The reactor was twice-purged with pressurized nitrogen which swept oxygen from the reactor to eliminate amine-oxide formation. A gold-colored liquid was discharged from the reactor. The solvent was stripped at 70° C. and the viscous liquid poured into a Pyrex dish and heated in a vacuum oven at 70-80° C. to obtain a vacuum dried solid.

Example 153: Other DIOPAT-Grafted Polymers

Example 152 is substantially repeated to create other product lines. First, poly(IB/MA) is grafted with DIOPAT and dimethylaminopropylamine is replaced by at least one other hydrophobic grafting reactant (e.g., n-butylamine, iso-butylamine, n-octylamine, tert-octylamide, and/or n-do-decylamine). Second, poly(IB/MA) is replaced by other polymers having at least one anhydride moiety [e.g., poly(MVE/MA), poly(styrene/MA), of varying weight-average molecular weights], which is used for the grafting reaction comprising DIOPAT and other hydrophobic grafting reactant(s) (e.g., dimethylaminopropylamine, n-butylamine, iso-butylamine, n-octylamine, tert-octylamide, and/or n-dodecylamine).

What is claimed is:

1. A polymer comprising: a first repeating unit selected from the group consisting of:

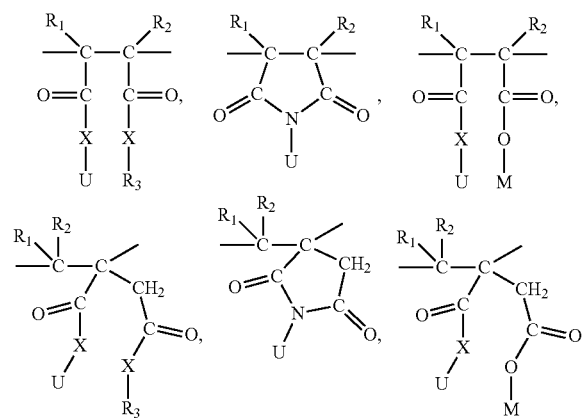

and combinations thereof, wherein each X is independently selected from the group consisting of O, $NR_1$, and combinations thereof;

each $R_1$ and $R_2$ is independently selected from the group consisting of hydrogen, halogen, and functionalized and unfunctionalized hydrocarbyl optionally having one or more heteroatoms;

each $R_3$ is independently selected from the group consisting of hydrogen, U, and functionalized and unfunctionalized hydrocarbyl optionally having one or more heteroatoms;

each M is independently selected from the group consisting of alkali metal ion, alkaline earth metal ion, ammonium ion, and combinations thereof;

each U has a structure independently selected from the group consisting of:

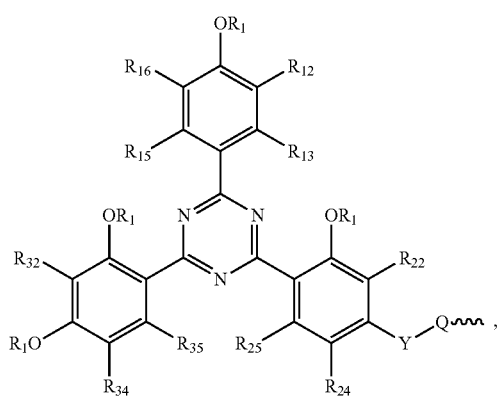

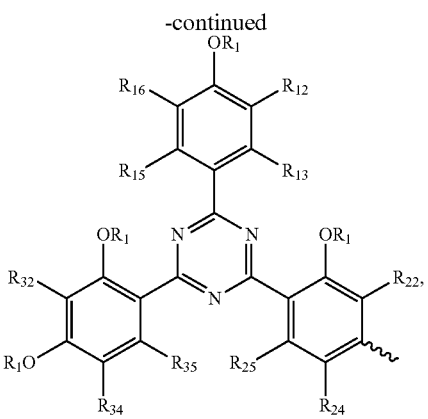

and combinations thereof, wherein each $R_{12}$, $R_{13}$, $R_{15}$, $R_{16}$, $R_{22}$, $R_{24}$, $R_{25}$, $R_{32}$, $R_{34}$ and $R_{35}$ is independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof;

each Y is independently selected from the group consisting of O, $NR_1$, S, and combinations thereof;

each Q is independently selected from the group consisting of functionalized and unfunctionalized hydrocarbylene optionally having one or more heteroatoms; and each ～ (wavy bond) indicates the point of attachment for each said U.

2. The polymer according to claim 1 wherein said first repeating unit is selected from the group consisting of:

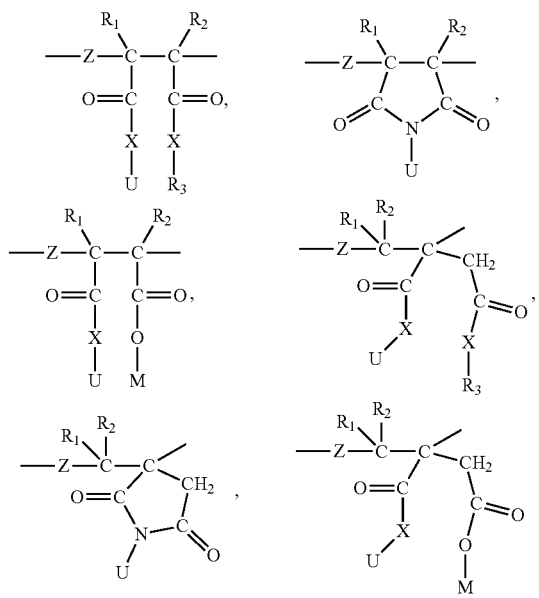

and combinations thereof, wherein each Z is a residue of a monomer independently selected from the group consisting of functionalized and unfunctionalized alpha-olefins, maleimides, maleamic acids, maleic anhydride, 4-vinyl-1,2,3-triazoles, 5-vinyl-1,2,3-triazoles, (meth)acrylamides, (meth)acrylates, vinyls, allyls, α,β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, allyl ethers, and combinations thereof, and wherein said X, Y, Q, $R_1$, $R_2$, $R_3$, M, U, $R_{12}$, $R_{13}$, $R_{15}$, $R_{16}$, $R_{22}$, $R_{24}$, $R_{25}$, $R_{32}$, $R_{34}$ and $R_{35}$ retain their definitions according to claim 1.

3. The polymer according to claim 2 wherein said vinyl ether is selected from the group consisting of: methyl vinyl ether, ethyl vinyl ether, isobutyl vinyl ether, octyl vinyl ether, ethyl hexyl vinyl ether, decyl vinyl ether, dodecyl vinyl ether, tetradecyl vinyl ether, octadecyl vinyl ether, and combinations thereof.

4. The polymer according to claim 2 wherein said alpha-olefin is selected from the group consisting of: isobutylene, octadecene, and combinations thereof.

5. The polymer according to claim 1 wherein each said U has an independently selected structure:

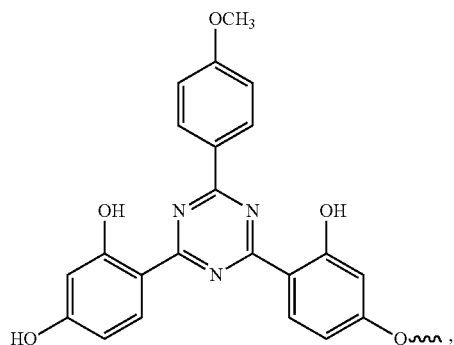

wherein each ⁓ (wavy bond) indicates the point of attachment for said U.

6. The polymer according to claim 2 having a structure selected from the group consisting of:

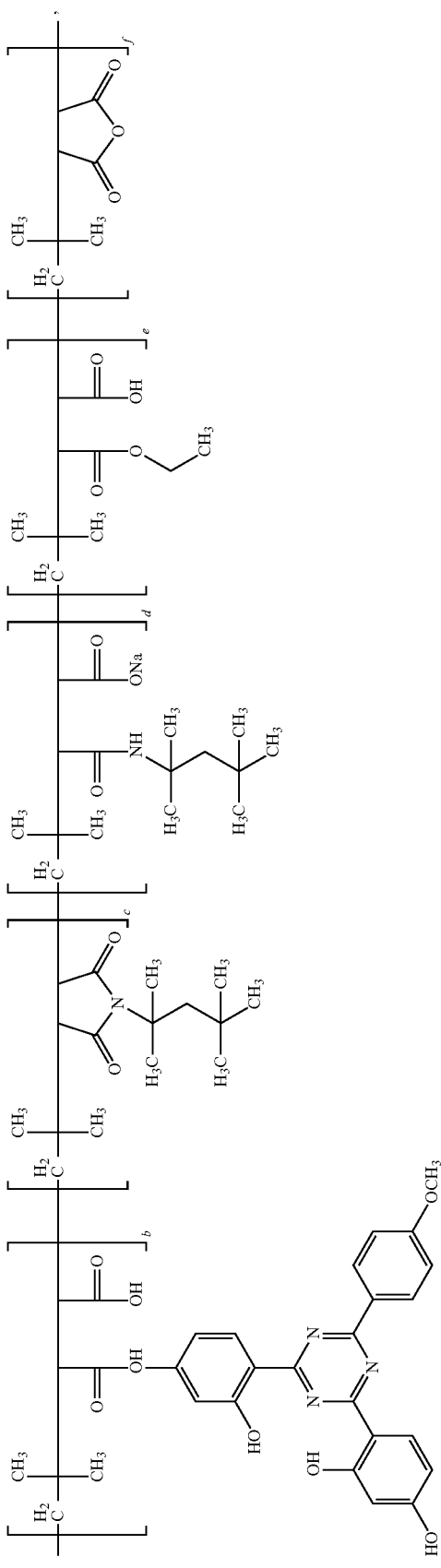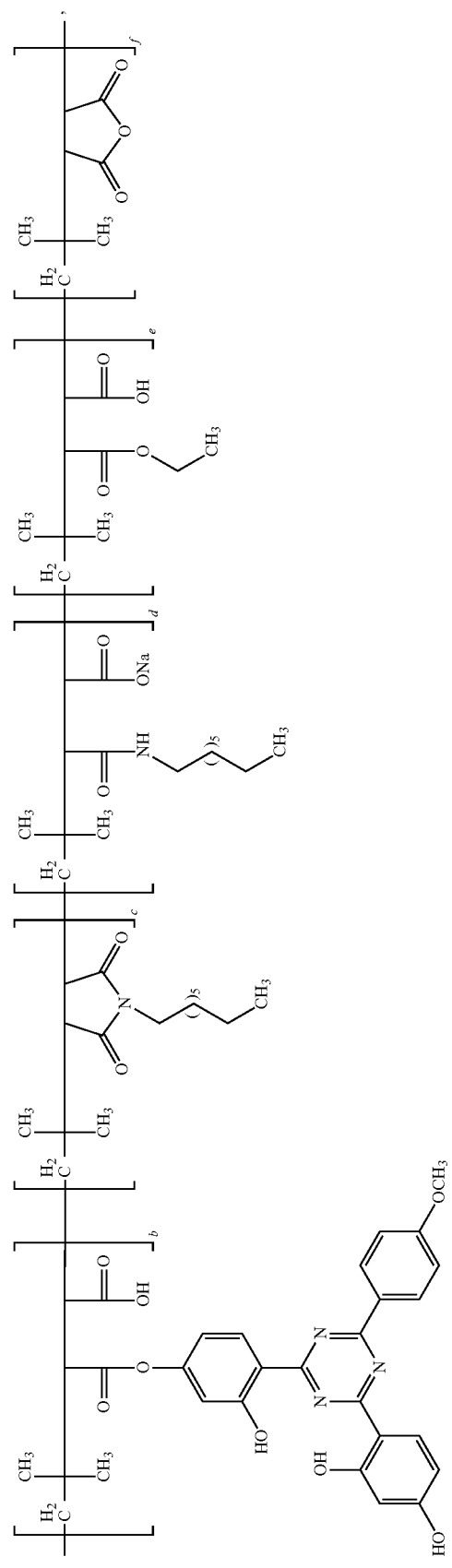

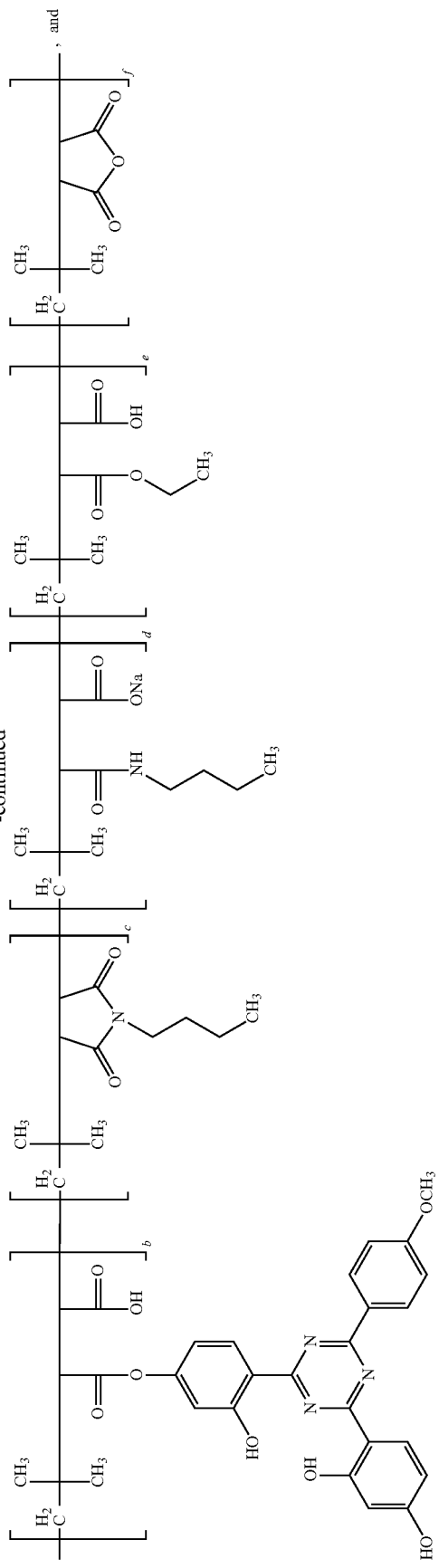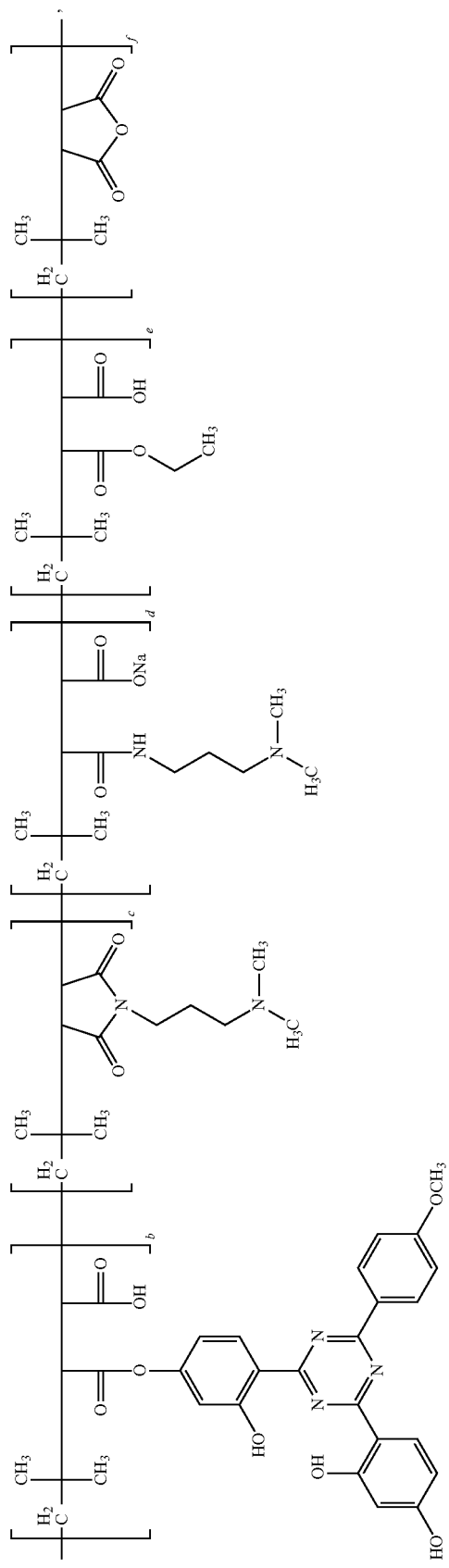

wherein b, c, d, e, and f are mole fractions such that sum of said mole fractions for each said polymer equals to 1.0.

7. A polymer comprising: a first repeating unit selected from the group consisting of:

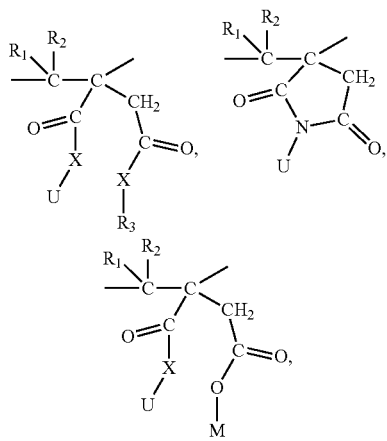

and combinations thereof, wherein each X is independently selected from the group consisting of O, $NR_1$, and combinations thereof;

each $R_1$ and $R_2$ is independently selected from the group consisting of hydrogen, halogen, and functionalized and unfunctionalized hydrocarbyl optionally having one or more heteroatoms;

$R_3$ is selected from the group consisting of hydrogen, U, and functionalized and unfunctionalized hydrocarbyl optionally having one or more heteroatoms;

M is selected from the group consisting of alkali metal ion, alkaline earth metal ion, and ammonium ion;

each U has an independently selected structure:

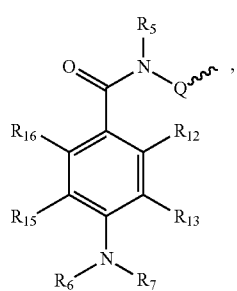

and combinations thereof, wherein each $R_{12}$, $R_{13}$, $R_{15}$, and $R_{16}$ is independently selected from the group consisting of hydrogen, halogen, amino, alkyl amino, hydroxyl, alkoxyl, sulfonyl, carboxyl, functionalized and unfunctionalized hydrocarbyl optionally having one or more heteroatoms, and combinations thereof;

each $R_5$ is independently selected from the group consisting of hydrogen and functionalized and unfunctionalized hydrocarbyl optionally having one or more heteroatoms;

each $R_6$ and $R_7$ is independently selected from the group consisting of functionalized and unfunctionalized hydrocarbyl optionally having one or more heteroatoms;

each Q is independently selected from the group consisting of functionalized and unfunctionalized hydrocarbylene optionally having one or more heteroatoms; and each ∼∼∼ (wavy bond) indicates the point of attachment for each said U.

8. The polymer according to claim 7 wherein said first repeating unit is selected from the group consisting of:

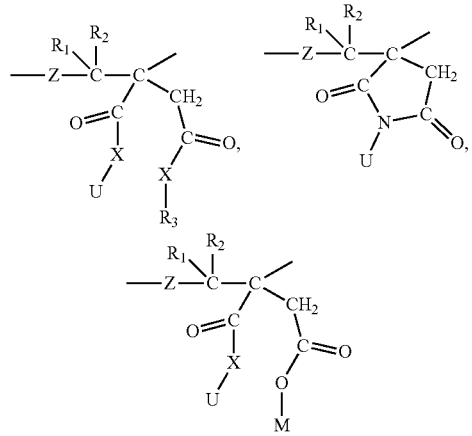

and combinations thereof, wherein each Z is a residue of a monomer independently selected from the group consisting of functionalized and unfunctionalized alpha-olefins, maleimides, maleamic acids, maleic anhydride, 4-vinyl-1,2,3-triazoles, 5-vinyl-1,2,3-triazoles, (meth)acrylamides, (meth)acrylates, vinyls, allyls, α,β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, allyl ethers, and combinations thereof, and wherein said X, Q, $R_1$, $R_2$, $R_3$, M, U, $R_{12}$, $R_{13}$, $R_{15}$, $R_{16}$, $R_5$, $R_6$, and $R_7$ retain their definitions according to claim 7.

9. The polymer according to claim 8 wherein said vinyl ether is selected from the group consisting of: methyl vinyl ether, ethyl vinyl ether, isobutyl vinyl ether, octyl vinyl ether, ethyl hexyl vinyl ether, decyl vinyl ether, dodecyl vinyl ether, tetradecyl vinyl ether, octadecyl vinyl ether, and combinations thereof.

10. The polymer according to claim 8 wherein said alpha-olefin is selected from the group consisting of: isobutylene, octadecene, and combinations thereof.

11. The polymer according to claim 7 wherein each said U is independently selected from the group consisting of:

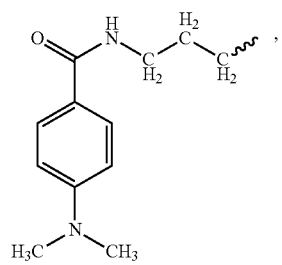

-continued
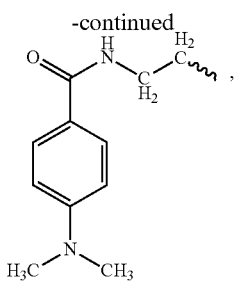
and combinations thereof, wherein each ~~ (wavy bond) indicates the point of attachment for each said U.
* * * * *